United States Patent
Armstrong

(10) Patent No.: US 10,407,732 B2
(45) Date of Patent: Sep. 10, 2019

(54) METHODS FOR THE DETECTION AND TREATMENT OF LEUKEMIAS THAT ARE RESPONSIVE TO DOT1L INHIBITION

(71) Applicant: MEMORIAL SLOAN-KETTERING CANCER CENTER, New York, NY (US)

(72) Inventor: Scott A. Armstrong, New York, NY (US)

(73) Assignee: Memorial Sloan Kettering Cancer Center, New York, NY (US)

( * ) Notice: Subject to any disclaimer, the term of this patent is extended or adjusted under 35 U.S.C. 154(b) by 0 days.

(21) Appl. No.: 14/909,713

(22) PCT Filed: Aug. 4, 2014

(86) PCT No.: PCT/US2014/049641
§ 371 (c)(1),
(2) Date: Feb. 2, 2016

(87) PCT Pub. No.: WO2015/017863
PCT Pub. Date: Feb. 5, 2015

(65) Prior Publication Data
US 2016/0298195 A1    Oct. 13, 2016

Related U.S. Application Data

(60) Provisional application No. 61/861,923, filed on Aug. 2, 2013, provisional application No. 61/885,947, filed on Oct. 2, 2013.

(51) Int. Cl.
| C12Q 1/68 | (2018.01) |
| C12Q 1/6886 | (2018.01) |
| A61K 31/5377 | (2006.01) |
| A61K 31/7064 | (2006.01) |

(52) U.S. Cl.
CPC ........ *C12Q 1/6886* (2013.01); *A61K 31/5377* (2013.01); *A61K 31/7064* (2013.01); *C12Q 2600/106* (2013.01); *C12Q 2600/156* (2013.01); *C12Q 2600/158* (2013.01)

(58) Field of Classification Search
None
See application file for complete search history.

(56) References Cited

FOREIGN PATENT DOCUMENTS

WO    WO 2007/087015 A1    8/2007

OTHER PUBLICATIONS

International Search Report and Written Opinion dated Nov. 12, 2014, from the Korean Intellectual Property Office, for International Patent Application No. PCT/US2014/049641 (filed Aug. 4, 2014), 13 pgs.
Daigle; et al., "Selective killing of mixed lineage leukemia cells by a potent small-molecule DOT1L inhibitor", Cancer Cell (Jul. 2011), 20(1):53-65.
Bernt; et al., "A role for DOT1L in MLL-rearranged leukemias", Epigenomics (Dec. 2011), 3(6):667-70.
Deshpande; et al., "Leukemic transformation by the MLL-AF6 fusion oncogene requires the H3K79 methyltransferase Dot1l", Blood (Mar. 2013), 121(13):2533-41.
Hollink; et al., "NUP98/NSD1 characterizes a novel poor prognostic group in acute myeloid leukemia with a distinct HOX gene expression pattern", Blood (Sep. 2011), 118(13):3645-56.
Deshpande; et al., "Chromatin modifications as therapeutic targets in MLL-rearranged leukemia", Trends Immunol (Nov. 2012), 33(11):563-70.
Hollink et al., "NUP98/NSD1 characterizes a novel poor prognostic group in acute myeloid leukemia with a distinct *HOX* gene expression pattern," Blood, vol. 118, No. 13, pp. 3645-3656 (Aug. 2, 2011).
Mullighan et al., "Pediatric acute myeloid leukemia with NPM1 mutations is characterized by a gene expression profile with dysregulated *HOX* gene expression distinct from MLL-rearranged leukemias," Leukemia, (21), pp. 2000-2009 (Jun. 28, 2007).
Chen et al., "Abrogation of MLL-AF10 and CALM-AF10-mediated transformation through genetic inactivation or pharmacological inhibition of the H3K79 methyltransferase Dot1L," Leukemia, vol. 27, No. 4, pp. 813-822 (Nov. 9, 2012).
Krivtsov et al., "MLL translocations, histone modifications and leukemia stem-cell development," Nature Reviews—Cancer, vol. 7, No. 11, pp. 823-833 (Nov. 1, 2007).
Daigle et al., "Potent inhibition of DOT1L as treatment of MLL-fusion leukemia," Blood, vol. 122, No. 6, pp. 1017-1025 (Jun. 25, 2013).
Chen et al., "Abrogation of MLL-AF10 and CALM-AF10-mediated transformation through genetic inactivation or pharmacological inhibition of the H3K79 methyltransferase Dot1L," Blood; 54th Annual Meeting and Exposition of the American Society of Hematology (Atlanta, GA), vol. 120, No. 21, pp. 1-2 (Nov. 1, 2012).
Brunangelo et al., "Acute myeloid leukemia with mutated nucleophosmin (NPM1): is it a distinct entity?," Blood, pp. 1109-1120 (Jan. 1, 2011) DOI: 10.1182/blood-2010-, retrieved from http://www.bloodjournal.org/content/bloodjournal/117/4/1109.full.pdf.

*Primary Examiner* — Celine X Qian
(74) *Attorney, Agent, or Firm* — Foley & Lardner LLP

(57) ABSTRACT

Disclosed are: (i) methods for identifying leukemia patients who (or leukemia cells that) do not exhibit an MLL-translocation, rearrangement or MLL-partial tandem duplication but who are nonetheless susceptible to treatment with DOT1L inhibitors; and (ii) methods for treating leukemia patients who (or inhibiting proliferation or inducing apoptosis of leukemia cells that) do not exhibit an MLL-translocation, rearrangement or MLL-partial tandem duplication with DOT1L inhibitors. The patients identified as susceptible and the patients (or cells) treated exhibit elevated expression of a HOX cluster gene or of a HOX cluster-associated gene. Elevated expression of such genes can be measured, e.g., by quantitating the relevant RNA and comparing it to that of a healthy individual (or cell) or to a predetermined standard or it can be inferred by determining whether the patient or cell possesses a mutation that is associated with elevated HOX cluster gene or HOX cluster associated gene expression and thereby inferring that the relevant expression with be elevated.

4 Claims, 11 Drawing Sheets

Specification includes a Sequence Listing.

A. Primary Transplantation

B. Secondary Transplantation

METHODS FOR THE DETECTION AND TREATMENT OF LEUKEMIAS THAT ARE
RESPONSIVE TO DOT1L INHIBITION

CROSS REFERENCE TO RELATED
APPLICATIONS

This application claims priority to U.S. Provisional Patent Application No. 61/885,947 filed Oct. 2, 2013 and No. 61/861,923 filed Aug. 2, 2013 the contents of each of which are incorporated by reference herein.

GOVERNMENT SPONSORED RESEARCH OR DEVELOPMENT

The work described in this disclosure was funded in part by grants from the National Cancer Institute (U01CA105423). The U.S. government may have certain rights in this disclosure.

REFERENCE TO SEQUENCE LISTING

The present application includes a Sequence Listing as a txt file in electronic ASCII format titled "8540231_1.txt," created on 1 Aug. 2014 and having a size of 206202 bytes. The contents of txt file "8540231_1.txt" are incorporated by reference herein.

BACKGROUND OF THE DISCLOSURE

1. Field of the Disclosure

The present disclosure relates, generally, to the detection and treatment of cancer. More specifically, this disclosure provides: (i) methods for identifying leukemia patients that are susceptible to treatment with a DOT1L inhibitor by detecting one or more mutation(s) in a tissue sample or cell that are associated with elevated HOX cluster and/or HOX cluster-associated gene expression or by detecting elevated HOX cluster gene expression or elevated HOX cluster-associated gene expression; (ii) methods for identifying mutations in a leukemia patient tissue sample or cell that are predictive of the therapeutic efficacy of a DOT1L inhibitor because of their association with elevated HOX cluster and/or HOX cluster-associated gene expression; and (iii) methods for treating a leukemia patient, including an acute lymphoblastic leukemia (ALL) patient and/or an acute myelogenous leukemia (AML) leukemia patient, who has been determined to exhibit elevated HOX cluster and/or HOX cluster associated gene expression or to possess a mutation that is associated with elevated gene expression of either or both gene types by administering a DOT1L inhibitor. Additionally, the disclosure provides methods for identifying patients at high risk for developing ALL or AML who are susceptible to treatment with a DOT1L inhibitor. This disclosure also provides treatment for ALL and AML with a DOT1L inhibition in combination with another therapeutic agent, such as an FLT3 inhibitor, ATR inhibitor or CDK4/CDK6 inhibitor, and IDH1/2 inhibitor.

2. Description of the Related Art

The treatment for patients with acute myelogenous leukemia (AML) has not changed in over 20 years, and AML survival rates remain significantly below 50% for adults and around 60-70% for children. Even if patients are cured of their disease, there is often significant morbidity from conventional chemotherapy regimens and from bone marrow transplantation. More effective, less toxic therapies are clearly needed.

Enhanced understanding of the genes and mechanisms that lead to leukemogenesis has led to the development of a number of new therapeutic approaches that target the underlying genetic abnormalities responsible for leukemia cell survival and proliferation. See, e.g., U.S. Patent Publication Nos. 2009/026951, 2005/048634, and 2009/061443. The most prominent examples of the success of such therapies are the development of all trans-retinoic acid (ATRA), which targets the genetic abnormality that drives acute pro-myelocytic leukemia, and Imatinib, which targets the genetic abnormality that drives chronic myelogenous leukemia and certain subtypes of acute lymphoblastic leukemias, such as Philadelphia chromosome positive ALL. Those therapies have significantly improved the outcome for patients with those diseases, and are significantly less toxic than standard chemotherapy and radiation. Continued development of novel targeted approaches is critical.

Recently identified classes of proteins that control gene expression via histone and DNA modification are driving the development of new therapeutics that modulate chromatin structure. Genetic mutations responsible for leukemogenesis frequently use those proteins to reprogram normal cells into cancer cells. Recent experiments show that inhibitors of this process relieve the block in differentiation that is a hallmark of cancer cells and reactivate gene expression programs that drive cellular differentiation. This inhibits the growth of cancer cells and ultimately causes them to die. Drugs that target histone modifications, such as the histone deacetylase (HDAC) inhibitors Vorinostat and Romidepsin, have recently been approved for the treatment of cutaneous T-cell lymphoma, which demonstrates the feasibility of such approaches.

Translocations involving the Mixed Lineage Leukemia (MLL) gene are found in >70% of infant leukemias, whether they are acute myelogenous leukemias (AMLs) or acute lymphoblastic leukemias (ALLs), and approximately 10% of AML cases in older children. Biondi et al., *Blood* 96(1): 24-33 (2000). Translocations involving MLL are also found in many cases of adult and therapy-related leukemias (B-ALL, T-ALL, and AML) and, as with infant leukemias, are frequently associated with a poor prognosis as compared to MLL-germline leukemias. In contrast to the high overall success rate in treating childhood ALL, where 5-year survival rates have reached ~80-90%, the genetically-defined subset of MLL-translocated ALL continues to predict poor survival rates of around 50%.

At the molecular level, MLL-translocated leukemias display characteristic gene expression profiles that are characterized by high level expression of the posterior homeobox-A (HOXA) gene cluster. Armstrong et al., *Nat. Genet.* J. Qill:41-47 (2002) and Ferrando et al., *Blood* 102(1):262-268 (2003).

Several HOX cluster genes are known to be regulated by MLL (Yu et al., *Nature* 378:505-508 (1995)), which has prompted a detailed comparison of the patterns of HOX gene expression in ALL and AML. HOXA4, HOXA5, and HOXA9 genes are not expressed, or are rarely expressed, in conventional ALL but are expressed, often at high levels, in most samples from leukemia patients exhibiting an MLL-translocation, an MLL rearrangement, or an MLL-primary tandem duplication (PTD). HOXC6 shows mildly elevated levels of expression in MLL-associated leukemias. MEIS 1, a HOX cluster associated cofactor for HOX proteins, which can accelerate HOXA9-dependent leukemia (Nakamura et al., *Nat. Genet.* 19:149-153 (1996)), is also significantly overexpressed in MLL-associated leukemias. Rozovskaia et al., *Oncogene* 20:874-878 (2001).

Several groups have demonstrated that HOXA cluster gene expression is necessary for proliferation and survival of MLL fusion driven leukemia cells and thus therapeutic approaches that suppress HOXA cluster gene expression should be efficacious against MLL-translocated leukemias.

Significant effort has been directed toward defining a unified mechanism of oncogenesis for the expressed chimeric MLL fusion proteins, including MLL translocations, MLL-rearrangements, and MLL-partial tandem duplications, since it would facilitate pharmacologic targeting of those shared leukemogenic mechanisms. Some broad patterns have emerged that are based on mechanisms that control MLL-target gene expression. The most commonly occurring MLL-translocations generate chimeric fusion proteins that harbor the NH3-terminus of MLL fused to proteins that are normally part of nuclear complexes, the function of which is now emerging. MLL fusions with nuclear proteins such as AF4, AF9, ENL, ELL, AFI0, AFI7, and AFF4, which collectively account for the vast majority of MLL leukemias, are all found to directly or indirectly recruit components of the transcriptional elongation machinery. Bitoun et al., *Hum. Mol. Genet.* 16(I):92-106 (2007); Mueller et al., *Blood* 110(13):4445-4454 (2007); Mueller et al., *PLoS Biol.*, 7(II): e1000249 (2009); Mohan et al., *Nat. Rev. Cancer* 10(10): 721-728 (2010); Yokoyama et al., *Cancer Cell* 17(2):198-212 (2010); and Lin et al., *Molecular Cell* 37(3):429-437 (2010).

A number of complexes linked to transcriptional elongation have been reported, often with overlapping protein components, such as the ENL-associated protein (EAP) complex (Mueller (2009)), the AF4/ENLIP-TEFb (AEP) complex (Yokoyama (2010)), the super elongation complex (SEC) (Lin (2010)), and the complex comprising the histone 3 lysine 79 (H3K79) methyltransferase DOT1L (DotCom) (Mohan (2010)). These data point to aberrant control of transcriptional elongation as being involved for MLL fusion-mediated oncogenesis.

The wild type MLL protein is a histone 3 lysine 4 (H3K4) methyltransferase that methylates H3K4 near gene promoters. This modification imparts the potential for the gene to be activated during hematopoietic development. DOT1L is a histone 3 lysine 79 (H3K79) methyltransferase that modifies H3K79 within the body and promoters of actively-transcribed genes, including genes that are highly expressed in hematopoietic cells. Thus, MLL-mediated H3K4 methylation prepares genes for expression, which gene expression is promoted by DOT1L-mediated H3K79 methylation.

Studies in yeast have shown that the two complexes are regulated similarly and simultaneously, which suggests that H3K4 and H3K79 methylation work in concert in a highly regulated fashion during gene transcription. Lee et al., *Cell* 131: 1084-1096 (2007). Genome wide studies have demonstrated elevated H3K79 methylation at MLL-target genes in MLL-translocated ALL and AML cells. Krivtsov et al., *Cancer Cell* 15(5):355-368 (2008); Guenther et al., *Genes Dev.* 22(24):3403-3408 (2008); Bernt et al., *Cancer Cell* 20(1):66-78 (2011); Copeland et al., *Oncogene* 32:939-946 (2013); Krivtsov et al., *Nat. Rev. Cancer* 1:823-833 (2007); and Monroe et al., *Exp Hematol* 39: 77-86 e71-75 (2011).

Several studies using conditional loss-of-function mouse models and RNAi approaches have formally demonstrated a critical role for DOT1L in MLL fusion-driven leukemias. Bernt (2011); Jo et al., *Blood* 117(18):4759-4768 (2011); Nguyen et al., *Blood* 117(25):6912-6922 (2011); and Chang et al., *Cancer Res.* 70(24):10234-10242 (2010). These studies demonstrate that genetic inactivation of DOT1L, or small molecule-mediated inhibition of DOT1L, leads to a decrease in MLL fusion target gene expression, including a rapid decrease in HOX cluster gene expression, which is correlated with an anti-proliferative response.

It has been hypothesized that translocations of MLL express aberrant MLL-fusion proteins that mistarget DOT1L to MLL target genes thereby disrupting the normal interplay between H3K79 and H3K4 methylation, which results in elevated gene expression, including elevated HOX cluster gene expression. Based upon this hypothesis, it has been suggested that DOT1L inhibitors might block the mistargeting of DOT1L to MLL-target genes in those leukemias that exhibit an MLL gene abnormalities thereby reducing the level of deregulated H3K79 and H3K4 methylation and the resulting elevation in gene expression.

Remarkably, inactivation of DOT1L does not affect the transformation potential of HOXA9 when it is expressed from a retroviral promoter. Expression of HOXA9 and its heterodimerizing partner MEIS1a, an example of a HOX cluster-associated gene expression product, rescues the anti-proliferative effect of DOT1L inhibitors on MLL-translocated leukemias. Furthermore, microarray-based gene expression studies showed that MLL-fusion target gene expression is much more dependent on DOT1L than is gene expression more generally (Bernt 2011). These studies highlight the importance of aberrant H3K79 methylation for the transforming activity of MLL fusion proteins including MLL-AF4, MLL-AF9, MLL-AF10, and MLL-ENL and show that DOT1L is required for continued HOXA cluster gene expression. These results potentially have profound clinical implications since these fusions are present in the vast majority of MLL-translocated leukemias.

The genetic and small molecule inhibitor data described above point to DOT1L as a potential therapeutic target in MLL-translocated, MLL-rearranged, and MLL-partial tandem duplication associated leukemias. A critical next step in the validation of DOT1L as a therapeutic target is to demonstrate that small molecule inhibitors exhibit similar responses as found in genetic loss-of-function models.

The small molecule DOT1L inhibitor EPZ004777 is an s-adenosyl methionine mimetic that has remarkable specificity for DOT1L as compared to other methyl transferases (FIG. 1). Daigle et al., *Cancer Cell* 20(1):53-65 (2011). EPZ004777 inhibits H3K79 methylation in MLL-translocated leukemia cell lines in the mid-nM range. EPZ004777 shows a dose-dependent inhibition of MLL fusion driven gene expression, including suppression of HOXA9 and MEIS1 (Bernt 2011). The growth of MV4-11 leukemia cells and the MLL-AF9 cell line Molm-13 is exquisitely sensitive to DOT1L inhibition, whereas the growth of MLL-germline Jurkat cells is unaffected by EPZ004777 (Daigle, 2011). In contrast, EPZ004777 has no anti-proliferative effect on MLL germline leukemia cell lines despite the inhibition of H3K79 methylation.

In total, these data provide strong support for the continued development of DOT1L as a potential therapeutic target in MLL-translocated, MLL-rearranged, and MLL-partial tandem duplication associated leukemias and have prompted the initiation of a phase 1 clinical trial (U.S. NIH, Clinical Trial No. NCT01684150), which is designed to assess the effect of DOT1L inhibitors in patients with relapsed/refractory hematologic malignancies.

The above mentioned data, however, do not support DOT1L as a potential target in other types of leukemia, namely leukemias that do not exhibit an MLL-translocation, an MLL-rearrangement, or an MLL-partial tandem duplication. Moreover, increased levels of HOX cluster HOX cluster-associated gene expression in leukemias other than those that exhibit an MLL-translocation,—rearrangement, or—partial tandem duplication has not been associated with the activity of DOT1L.

BRIEF SUMMARY OF THE DISCLOSURE

The present disclosure provides uses/methods for the identification of treatment susceptible patients and for the treatment of certain leukemias, including acute lymphoblastic leukemia (ALL) and acute myelogenous leukemia (AML), which do not exhibit MLL-translocations, MLL-rearrangements, and/or MLL-partial tandem duplications (PTDs), but which are nevertheless characterized by elevated expression of one or more HOX cluster gene(s) and/or one or more HOX cluster-associated gene(s) despite the absence of the foregoing MLL aberrations. The patients may possess one or more mutations that have been determined to be associated with elevated expression of one or more HOX cluster genes or HOX cluster-associated genes and the presence of such mutations may serve as a surrogate for assessing HOX cluster gene or HOX cluster-associated gene expression levels. As is described in detail herein, such leukemias may be effectively treated with one or more DOT1L inhibitor(s). Accordingly, the present disclosure also identifies the leukemia subtypes susceptible to treatment with DOT1L inhibitors.

Thus, the present disclosure greatly expands the range of patients that can be efficaciously treated by the administration of a DOT1L inhibitor beyond those exhibiting the MLL aberrations described above. The present disclosure provides a treatment for those patients having a disease or condition, including a leukemia, which is characterized by the elevated expression of one or more HOX cluster gene(s) and/or one or more HOX cluster-associated gene(s) regardless of whether those patients exhibit an MLL-translocation, an MLL-rearrangement, and/or an MLL-partial tandem duplication (PTD).

Within one embodiment, the present disclosure provides methods/uses for determining whether a leukemia patient is susceptible to treatment with a DOT1L inhibitor independently of whether it is known that the patient has a mutation other than an MLL-translocation, an MLL-rearrangement, and/or an MLL-PTDs. In other words susceptibility is inferred if the patient has a mutation associated with elevated expression of a HOX cluster gene or a HOX cluster-associated gene. By these methods, the level of expression of one or more HOX cluster gene(s) and/or one or more HOX cluster-associated gene(s) is determined in a leukemia patient tissue sample or cell and in a non-leukemia donor control tissue sample or cell (e.g., a tissue sample or cell from a healthy donor that is known not to exhibit elevated HOX cluster and/or HOX cluster-associated gene expression). By comparing the level of expression of one or more HOX cluster and/or one or more HOX cluster-associated gene(s) in the patient sample or cell (or to a predetermined standard) to the corresponding level of gene expression in the control sample or cell, an elevated level of HOX cluster and/or HOX cluster-associated gene expression is detected, which elevated HOX cluster and/or HOX cluster-associated gene expression is predictive of the therapeutic efficacy of a DOT1L inhibitor.

Within another embodiment, the present disclosure provides additional methods/uses for identifying in a leukemia patient, the susceptibility of the leukemia patient to treatment with a DOT1L inhibitor. By these methods, a leukemia patient tissue sample or cell is tested or has already been tested for the presence of genetic mutation, alteration, and/or abnormality, other than an MLL-translocation, an MLL-rearrangement, and/or an MLL-PTDs, which is known to be associated with an elevated expression of one or more HOX cluster gene(s) and/or one or more HOX cluster-associated gene(s), wherein the detection of such a genetic mutation, alteration, and/or abnormality is predictive of the therapeutic efficacy of a DOT1L inhibitor. If such a genetic mutation, alteration, and/or abnormality is detected in the leukemia patient, treatment with a DOT1L inhibitor can be initiated.

Within a further embodiment, the present disclosure provides additional methods/uses for identifying in a leukemia tissue sample or cell one or more genetic mutation, alteration, and/or abnormality, other than an MLL-translocation, an MLL-rearrangement, and/or an MLL-PTD, and determining the levels of expression of one or more HOX cluster gene(s) and/or one or more HOX cluster-associated gene(s) in the leukemia tissue sample or cell and in a non-leukemia control tissue sample or cell that is known not to exhibit elevated HOX cluster and/or HOX cluster-associated gene expression, wherein an elevated level of one or more HOX cluster gene and/or one or more HOX cluster-associated gene in the leukemia tissue sample or cell relative to the control tissue sample or cell is predictive of the therapeutic efficacy of a DOT1L inhibitor in a leukemia patient that exhibits one or more of the genetic mutation(s), alteration(s), and/or abnormality(ies) identified in the leukemia tissue sample or cell.

Within another embodiment, the present disclosure provides methods/uses for inhibiting the proliferation and/or inducing apoptosis of a leukemia cell, the methods comprising contacting a leukemia cell that has been known or determined to (i) exhibit one or more genetic mutation, alteration, and/or abnormality, other than an MLL-translocation, an MLL-rearrangement, and/or an MLL-PTD, which is known or determined to be associated with elevated expression of one or more HOX cluster gene and/or one or more HOX cluster-associated gene. The method comprises exposing such a leukemia cell to a DOT1L inhibitor.

Within yet other embodiments, the present disclosure provides methods/uses for the treatment of a leukemia patient who does not possess an MLL-translocation, or an MLL-rearrangement or an MLL-PTD, and yet exhibits a genetic mutation, alteration and/or abnormality which is known or determined to be associated with elevated expression of one or more HOX cluster gene and/or one or more HOX cluster-associated gene. By these methods, such a leukemia patient is treated by the administration of one or more DOT1L inhibitors, a composition or formulation comprising one or more DOT1L inhibitors, and/or a composition or formulation comprising one or more DOT1L inhibitor in combination with one or more other agent that is effective in the treatment of leukemia.

Within still further embodiments, the present disclosure provides methods/uses for treating a leukemia patient, comprising identifying in a tissue sample or cell from the leukemia patient one or more genetic mutation, alteration, and/or abnormality, other than an MLL-translocation, an MLL-rearrangement, and/or an MLL-PTD, which is known or determined to be associated with elevated expression of one or more HOX cluster gene and/or one or more HOX cluster-associated gene and treating the leukemia patient by administering one or more DOT1L inhibitor, one or more composition or formulation comprising one or more DOT1L inhibitor, and/or one or more composition or formulation comprising one or more DOT1L inhibitor in combination with one or more other agent that is effective in the treatment of leukemia.

Within yet other embodiments, the present disclosure provides methods/uses for treating a leukemia patient exhibiting elevated expression of one or more HOX cluster and/or one or more HOX cluster-associated gene by administering to the leukemia patient one or more DOT1L inhibitor, one or more composition or formulation comprising one or more DOT1L inhibitor, and/or one or more composition or formulation comprising one or more DOT1L inhibitor in combination with one or more other agent that is effective in the treatment of leukemia In a further embodiment the present disclosure provides a method/use of reducing the risk of therapy-related leukemia in a patient at high risk therefor said patient not having been treated previously with a DOT1L inhibitor, the method comprising administering to said patient a therapeutically effective amount of a DOT1L inhibitor, wherein the patient exhibits an actual or inferred elevated expression of a HOX cluster gene or a HOX cluster-associated gene and wherein the patient does not possess an MLL-translocation or an MLL-rearrangement or an MLL-partial tandem duplication.

In another embodiment the present disclosure provides a method/use for treating a leukemia patient exhibiting elevated expression of a HOX cluster gene and/or a HOX cluster-associated gene, said method comprising administering to said leukemia patient one or more DOT1L inhibitor, one or more composition or formulation comprising one or more DOT1L inhibitor, and/or one or more composition or formulation comprising one or more DOT1L inhibitor in combination with one or more other agent that is effective in the treatment of leukemia, wherein said leukemia patient does not exhibit an MLL-translocation, an MLL-rearrangement, and/or an MLL-PTD.

BRIEF DESCRIPTION OF THE DRAWINGS

FIG. 1A). The inhibition is specific for H3K79me as compared to methylation by other histone methyltransferases (right panel; FIG. 1B FIG. 2 is a graph presenting data that the DOT1L inhibitor EPZ004777 selectively inhibits the proliferation of MLL-translocated cell lines. The $IC_{50}$ for six MLL-translocated (MLL-AF4, MLL-AF9, MLL-ENL) and six non-rearranged MLL-germline leukemia cell lines is shown.

FIG. 5A is a graph of relative proliferation over time (up to 17 days), showing a decrease in proliferation upon treatment of NUP98-NSD1 cells with various concentrations (0.1, 1, and 10 μM) of EPZ004777 compared to the DMSO treated controls. FIG. 5B is a histogram showing mRNA expression of HOXA7, HOXA9, HOXA10, and MEIS1 relative to GAPDH (ddCT). A strong inhibitory effect of EPZ004777 on mRNA levels of HOXA7, HOXA9, HOXA10, and MEIS1 in NUP98-NSD1 transformed cells is observed.

FIG. 6A) and differentiation (top right panel; FIG. 6B). The conditional DOT1L allele (flox) is translocated upon cre induction and does not reappear by 12-days (bottom right panel; FIG. 6C).

FIGS. 7A-7D are plots of cell counts vs. time for human cell lines exhibiting leukemia associated mutations that are in contact with DMSO (negative control) or a DOT1L inhibitor (EPZ004777). An MLL-AF9 translocated human cell line (positive control, FIGS. 7A and 7B); an NPMJ mutant human cell line (FIG. 7C), and an AML1-ETO translocated human cell line (negative control, FIG. 7D) were treated with 10 μM EPZ004777 or DMSO (control) and cells were counted on the indicated days (days 3, 7, and 10). These data demonstrate that the DOT1L inhibitor dramatically inhibited the proliferation of the human cell line exhibiting an NPM1 mutation.

FIG. 8A is an autoradiograph showing decrease in histone methylation of H3K79 after treatment of cells with the DOT1L inhibitor EPZ004777 (10 μM). MLL-AF9 and NUP98-NSD1 transformed cells were treated with EPZ004777 (10 μM) for 10 days, and the protein levels of H3K79me2 were determined by Western blotting. FIG. 8B is a bar graph showing that the DOT1L inhibitor EPZ004777 induces apoptosis in both MLL-AF9 and NUP98-NSD1 transformed cells. Annexin V staining was assessed 10 days after treatment of MLL-AF9 or NUP98-NSD1 transformed cells with either DMSO control or with 10 μM EPZ004777. The percentage of Annexin V positive cells is shown.

FIG. 11A is a bar graph showing OCI-AML3 cells treated with 10 µM EPZ004777 or DMSO (control) for 4, 7, or 10 days. The percentage of apoptotic cells was assessed by Annexin V staining. FIG. 11B is a series of graphs showing flow cytometry analysis of surface marker Cb11 expression in OCI-AML3 cells treated with 10 µM EPZ04777 for indicated number of days (4, 7, and 10). Increase in Cb11 marker expression indicates differentiation.

FIG. 13A shows the Kaplan-Meier survival curves (% survival versus days elapsed) for the syngeneic C57/BL6 mice injected with $Npm1^{cA/+}Rosa^{SB/+}$ AML cells previously treated for 6 days with either DMSO or 10 µM of EPZ004777. FIG. 13A indicates prolonged survival of animals treated with the DOT1L inhibitor. FIG. 13B is an image of peripheral blood smears isolated from animals injected with $Npm1^{cA/+}Rosa^{SB/+}$ AML cells (previously treated for 6 days with either DMSO or 10 µM of EPZ004777) on day 19 and stained with Wright-Giemsa stain. FIG. 13B indicates differentiation in EPZ00477 treated cells (and not in cells exposed to only DMSO). FIG. 13C is a series of graphs showing complete blood counts of samples collected on day 19 from mice injected with $Npm1^{cA/+}Rosa^{SB/+}$ AML cells treated for 6 days with either control (DMSO) or 10 µM of EPZ004777. Numbers of white blood cells and platelets are expressed as number of cells per microliter (µL) of blood. Hemoglobin levels are expressed in grams per deciliter (g/dl).

FIGS. 14A and 14B show that HOXA9, HOXA10, MEIS1, HOX3A, HOXA4, and HOXA5 expression is decreased after treatment of both cell lines with 10 µM of EPZ004777.

DETAILED DESCRIPTION

Figure 1:
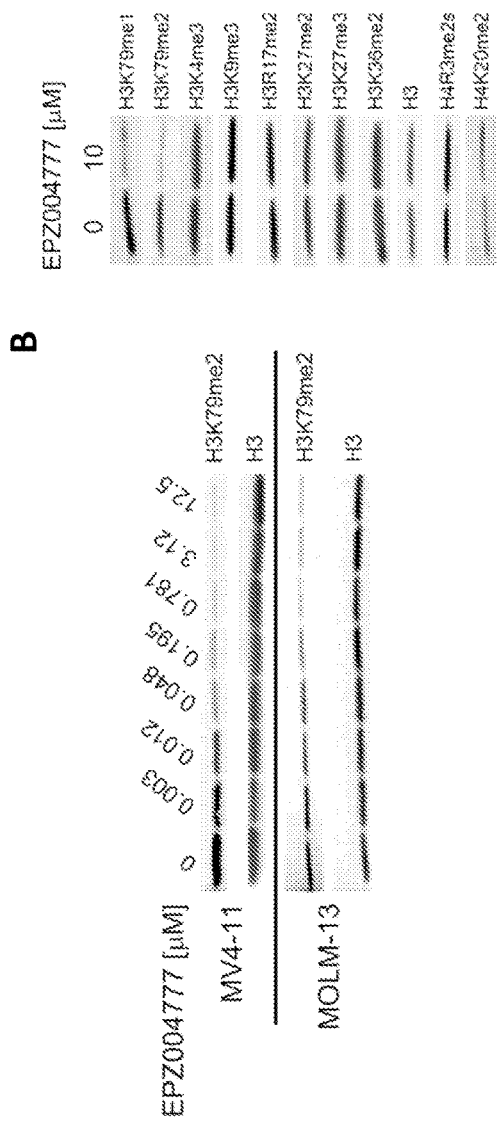
FIG. 1 is an autoradiograph showing histone methylation of H3K79me2 after treatment with the DOT1L inhibitor EPZ004777. H3K79me2 is inhibited by treatment with 0.048, 0.195, 0.781, 3.12, and 12.5 μM of the DOT1L inhibitor EPZ004777 in MLL-AF4 translocation cell line MV4-11 and MLL-AF9 translocated leukemia cells MOLM-13 (left panel.

The present disclosure is based upon the discovery that leukemias that exhibit one or more genetic mutation(s), alteration(s), and/or abnormality(ies)—other than MLL-translocations, MLL-rearrangements, and MLL-partial tandem duplications (PTDs)—that are associated with elevated expression of one or more HOX cluster gene(s) and/or one or more HOX cluster-associated gene(s), are sensitive to DOT1L inhibitor-mediated growth inhibition and/or apoptosis. Moreover, leukemias exhibiting: (1) elevated expression of one or more HOX cluster gene(s) and/or one or more HOX cluster-associated gene(s) and/or (2) one or more leukemia-associated genetic mutation, alteration, and/or abnormality other than an MLL-translocation, MLL-rearrangement, or MLL-partial tandem duplication, which is associated with elevated expression of one or more HOX cluster gene(s) and/or one or more HOX cluster-associated gene(s) can be effectively treated by the administration of one or more DOT1L inhibitor(s). On other words, while a mutation causing elevated HOX cluster or HOX-cluster-associated gene expression most likely will be present, and if it is, it can serve as a surrogate for predicting that expression of HOX cluster or HOX cluster-associated genes will be elevated there is no requirement that such a mutation be present. Even if elevated expression is the result of some other factor, treatment with a DOT1L inhibitor is expected to be effective because it will reduce the elevated HOX cluster or HOX cluster-associated gene expression.

The wild type MLL protein is a histone 3 lysine 4 (H3K4) methyltransferase that methylates H3K4 near gene promoters. This modification imparts the potential to be activated during hematopoietic development. DOT1L is a histone 3 lysine 79 (H3K79) methyltransferase that modifies H3K79 on the promoters and bodies of genes that are actively transcribed. Thus, H3K4 methylation "prepares" the genes for expression and H3K79 methylation allows or promotes gene expression.

Studies in yeast have shown that the two complexes are regulated similarly and simultaneously leading to the hypothesis that these two modifications work together in a highly regulated fashion during gene transcription. It has been hypothesized that translocations of MLL lead to an aberrant protein that disrupts this intimate relationship between H3K79 and H3K4 methylation making it irreversible and leading to aberrant gene expression.

Prior to the discoveries that form the basis for the present disclosure, it was believed that this deregulated relationship accounted for the selectivity of DOT1L inhibitors in MLL-translocated, MLL-rearranged, and MLL-PTD leukemias. As disclosed herein, however, it was discovered that DOT1L is independently required for HOX gene expression during normal blood development and for HOX gene expression in leukemias that have high level HOX gene expression but no MLL abnormality. Thus, according to the present disclosure, DOT1L inhibition is broadly applicable to leukemias, beyond just leukemias exhibiting an MLL-translocation, an MLL-rearrangement, or an MLL-partial tandem duplication, which are associated with elevated HOX gene expression.

Based upon these and other discoveries, which are described in further detail herein, the present disclosure provides:

(1) Uses/methods for predicting or determining whether a leukemia tissue sample or cell is susceptible to growth and/or survival inhibition when contacted with a DOT1L inhibitor;

(2) Uses/methods for predicting or determining whether a newly-identified genetic mutation, alteration, and/or abnormality in a tissue or cell, in particular a leukemia tissue or cell, renders that tissue or cell susceptible to growth and/or survival inhibition when contacted with a DOT1L inhibitor;

(3) Uses/methods for inhibiting the growth and/or survival of a leukemia tissue or cell that either (i) exhibits one or more leukemia-associated genetic mutation, alteration, and/or abnormality other than an MLL-translocation, MLL-rearrangement, or MLL-partial tandem duplication, which is associated with elevated expression of a HOX cluster gene or HOX cluster-associated gene; or (ii) otherwise exhibits elevated expression of a HOX cluster or a HOX cluster-associated gene, by contacting that tissue or cell with one or more DOT1L inhibitor(s); and (4) Uses/methods for the treatment of a leukemia patient who either (i) exhibits one or more genetic mutation, alteration, and/or abnormality other than an MLL-translocation, MLL-rearrangement, or MLL-partial tandem duplication which is associated with elevated expression of a HOX cluster gene or HOX cluster-associated gene; or (ii) otherwise exhibits elevated expression of a HOX cluster or a HOX cluster-associated gene, by administering to the leukemia patient a composition comprising one or more DOT1L inhibitor(s).

(5) Uses/methods for inhibiting growth or survival of tissue or a cell or treatment of a leukemia patient fulfilling the characteristics outlined in paragraphs (3) and (4) above comprising contacting the tissue or cell with or administering to the patient one or more DOT1L inhibitors in combination with a FLT3 inhibitor.

As described in greater detail herein, these uses/methods for identifying, predicting, determining, inhibiting, and treatment are all based upon the newly discovered, and presently disclosed, relationships between: (1) the elevated expression of one or more HOX cluster gene(s) and/or one or more HOX cluster-associated gene(s) in a tissue and/or cell; (2) certain leukemia-associated genetic mutations, alterations, and/or abnormalities, which are not MLL-translocations, MLL-rearrangements, or MLL-partial tandem duplications; and (3) the therapeutic efficacy of a treatment regimen for leukemia that includes the administration of one or more DOT1L inhibitor(s).

These and other aspects of the present disclosure are described in further detail herein, including: (1) methodology for determining elevated HOX cluster and/or HOX cluster-associated gene expression; (2) methodology for detecting in a human tissue sample and/or cell genetic mutations, alterations, and/or abnormalities, other than MLL-translocations, MLL-rearrangements, or MLL-partial tandem duplications, which are associated with elevated HOX cluster and/or HOX cluster-associated gene expression with or without concomitantly assessing HOX cluster gene expression levels or HOX cluster-associated gene expression levels; (3) exemplary DOT1L inhibitors that may be advantageously employed to inhibit the proliferation and/or survival of a leukemia tissue or cell and to treat a leukemia patient exhibiting one or more genetic mutation, alteration, and/or abnormality, other than MLL-translocations, MLL-rearrangements, or MLL-partial tandem duplications, which is associated with elevated HOX cluster and/or HOX cluster-associated gene expression; (4) compositions, including pharmaceutical compositions, and formulations that include one or more DOT1L inhibitor; and (5) methodology for the treatment of a leukemia patient by the administration of a composition containing one or more DOT1L inhibitor, including methodology for administering one or more DOT1L inhibitors and suitable treatment regimen that employ the administration of one or more DOT1L inhibitors. The DOT1L inhibitors may be administered as monotherapy or in combination with an additional therapeutic agent such as an FLT3 inhibitor, and ATR inhibitor, an IDH1/2 inhibitor or a CDK4/CDK6 inhibitor. Nonlimiting examples of suitable ATR inhibitors include the following commercially available compounds AZ20, BEZ235; nonlimiting examples of CDK4/CDK6 inhibitors include LEE011; Nonlimiting examples of IDH1/2 inhibitors include AGI-6780 and AGI-5198. All are available from Selleckchem, Boston, Mass.

Definitions

"HOX cluster gene" and "HOX cluster-associated gene" are defined as is customary in the field. The term "HOX cluster" refers to a group of homeobox genes (class of regulatory genes that contain a 180 base pair long DNA sequence called homeobox) that are found in gene clusters on the chromosomes. HOX cluster genes code for proteins that are transcription factors and play a critical role in embryonic development and hematopoiesis. Humans contain 4 clusters (A-D) with 39 HOX genes identified to date: (1). cluster A on chromosome 7, which includes HOXA1, HOXA2, HOXA3, HOXA4, HOXA5, HOXA6, HOXA7, HOXA9, HOXA10, HOXA11, HOXA12, and HOXA13; (2) cluster B on chromosome 17, which includes HOXB1, HOXB2, HOXB3, HOXB4, HOXB5, HOXB6, HOXB7, HOXB8, HOXB9, and HOXB13; (3) cluster C on chromosome 12, which includes HOXC4, HOXC5, HOXC6, HOXC8, HOXC9, HOXC10, HOXC11, HOXC12, and HOXC13; and (4) cluster D on chromosome 2 which includes HOXD1, HOXD3, HOXD4, HOXD8, HOXD9, HOXD10, HOXD11, HOXD12, and HOXD13. The DNA-binding specificity of HOX genes is due in part to their interactions with other proteins which act as HOX cofactors and are referred to as HOX cluster-associated genes. Example of well-defined HOX cluster-associated genes are three-amino acid loop extension (TALE) genes, PBX3 and MEIS genes.

As used herein, the term "internal control" refers to a nucleotide sequence, typically but not exclusively a sequence of a housekeeping gene, or a portion thereof, which codes for a protein that is stably and constitutively expressed at high levels in most tissues and cells. Housekeeping genes are selected from those remaining generally unaffected by pathological and experimental conditions. Suitable genes that can serve as "internal controls" include, for example and without limitation, $\beta$-actin, $\beta$-tubulin, GAPDH, and cyclophyllin. The levels of HOX cluster and/or HOX cluster-associated gene expression and internal control gene expression (i.e. non-HOX cluster and non-HOX cluster-associated gene expression) can be determined (e.g., by quantifying the number of HOX and non-HOX transcripts), a ratio of HOX and non-HOX gene expression can be derived, and the level of HOX cluster and/or HOX cluster-associated gene expression within a given leukemia tissue sample or cell can be expressed in terms of the ratio of HOX and non-HOX gene expression.

In contrast, as used herein, the term "external control" refers to a HOX cluster or a HOX cluster-associated gene or genetic sequence from a non-leukemia tissue or cell, which HOX cluster or HOX cluster-associated gene or genetic sequence does not exhibit elevated expression in the non-leukemia tissue or cell but is being tested for elevated expression in a corresponding leukemia tissue or cell. Thus, for example, an "external control" can be used as a "negative control" for assessing whether a given HOX cluster gene or a given HOX cluster-associated gene exhibits elevated expression levels in a leukemia tissue sample or cell by comparing the level of expression (e.g., the number of mRNA transcripts) in a leukemia tissue sample or cell to a corresponding non-leukemia tissue sample, such as a tissue sample from a normal donor, or non-leukemia cell, such as a $CD34^+$ non-leukemia cell.

As used herein, the term "elevated gene expression," in particular the terms "elevated HOX cluster gene expression" and "elevated HOX cluster-associated gene expression," refers to increased expression of a specific gene product, including the increased amount of transcribed mRNA of HOX cluster gene(s) and HOX cluster-associated gene(s) which is elevated by at least about three-fold, at least about five-fold, at least about 10-fold, at least about 15-fold, at least about 20-fold, at least about 25-fold, or greater in a leukemia tissue sample or cell as compared to a control, including an internal control or an external control.

By "solid support" is meant a material that is essentially insoluble in the solvent and temperature conditions of a method such as the method comprising joining free chemical groups to an oligonucleotide or nucleic acid. The solid support can be covalently coupled to an oligonucleotide designed to bind, either directly or indirectly, a target nucleic acid. When the target nucleic acid is an mRNA, the oligonucleotide attached to the solid support is preferably a poly-T sequence. A preferred solid support is a particle, such as a micron- or submicron-sized bead or sphere. A variety of solid support materials are contemplated, such as, for example, silica, polyacrylate, polyacrylamide, metal, polystyrene, latex, nitrocellulose, polypropylene, nylon or combinations thereof. The solid support can be capable of being attracted to a location by means of a magnetic field, such as a solid support having a magnetite core. Exemplary supports include monodisperse magnetic spheres.

As used herein, "tissue sample" as it pertains to leukemia patients, includes without limitation, a blood sample, a bone marrow sample or a lymph node sample, or a collection of cells isolated from the patient such as, such as leukemic cells.

As used herein, the phrase "nucleic acid amplification conditions" refers to reaction conditions, including salt concentration, temperature, the presence or absence of temperature cycling, the presence of a nucleic acid polymerase, nucleoside triphosphates, and cofactors, that are sufficient to permit the production of multiple copies of a target nucleic acid or its complementary strand using a nucleic acid amplification method.

A "target-binding sequence" of an amplification primer is the portion that determines target specificity because that portion is capable of annealing to the target nucleic acid strand or its complementary strand but does not detectably anneal to non-target nucleic acid strands under the same conditions. The complementary target sequence to which the target-binding sequence hybridizes is referred to as a primer-binding sequence.

Methodologies for Detecting Elevated Expression of HOX Cluster and HOX Cluster-Associated Genes Elevated HOX cluster and HOX cluster-associated gene expression can be determined by one or more methodology(ies) that are well known in the art including, for example, microarray, quantitative PCR, including real-time-PCR (RT-PCR), and direct RNA sequencing. Each of the methodologies described herein for the detection of elevated HOX cluster gene or HOX cluster-associated gene expression has in common the detection of a leukemia-specific polynucleotide via the amplification, hybridization, and/or sequencing of one or more mRNA encoded by a HOX cluster gene and/or a HOX cluster-associated gene.

Elevated HOX cluster and/or HOX cluster-associated gene expression can also be assessed on the basis of the percentage or fraction of blasts (i.e., leukemia cells) relative to the total number of cells in a given tissue or blood sample from a leukemia patient. By this methodology, for example, the number of HOX cluster and/or HOX cluster-associated transcripts in a leukemia tissue sample can be quantified and multiplied by the inverse percentage or fraction of blasts in the leukemia tissue sample. The resulting HOX cluster and/or HOX cluster-associated transcript number can then be assessed relative to a threshold transcript number for HOX cluster and/or HOX cluster-associated gene expression and, based upon that assessment, the responsiveness of a leukemia patient from whom the leukemia tissue sample is derived to a therapeutic regimen comprising the administration of a DOT1L inhibitor can be predicted. More specifically, by this methodology, a transcript number for HOX cluster and/or HOX cluster-associated gene expression that is greater than a threshold transcript number would be predictive of the therapeutic efficacy of such a DOT1L inhibitor treatment regimen.

Elevated HOX cluster gene or HOX cluster-associated gene expression can, for example, be assessed by (1) quantifying a HOX cluster or HOX cluster-associated RNA (and/or protein) in a tissue sample from a leukemia patient; (2) quantifying the level of the HOX cluster or HOX cluster-associated RNA (and/or protein) in a tissue sample from a non-leukemia control donor; and (3) comparing the level of the HOX cluster or HOX associated cluster RNA (and/or protein) in the tissue sample from the leukemia patient with the level of the HOX cluster or HOX cluster-associated RNA (and/or protein) in the tissue sample from the control donor. It will be understood that an elevated level of HOX cluster or HOX cluster-associated RNA (and/or protein) in the leukemia patient tissue sample as compared to HOX cluster or HOX cluster-associated RNA and/or in the control donor tissue sample indicates the susceptibility of the leukemia patient to treatment with a DOT1L inhibitor.

Alternatively, elevated HOX cluster or HOX cluster-associated gene expression can be assessed by (1) quantifying a HOX cluster or HOX cluster-associated RNA in a tissue sample from a leukemia patient; (2) quantifying the level of a non-HOX cluster/non-HOX cluster-associated RNA in the leukemia patient tissue sample, such as, for example, GAPDH or actin; and (3) comparing the level of the HOX cluster or HOX cluster-associated RNA in the tissue sample from the leukemia patient with the level of the non-HOX cluster/non-HOX cluster-associated RNA in the leukemia patient tissue sample. It will be understood that an elevated level of the HOX cluster or HOX cluster-associated RNA in the leukemia patient tissue sample as compared to the non-HOX cluster/non-HOX cluster-associated RNA in the leukemia patient tissue sample indicates the susceptibility of the leukemia patient to treatment with a DOT1L inhibitor.

Within certain aspects of these methods a HOX cluster or HOX cluster-associated RNA can be quantified by amplifying RNA in a tissue sample, whether a leukemia tissue sample or cell, a non-leukemia tissue sample or cell from a leukemia patient, or a tissue sample or cell from a non-leukemia control donor, with a primer pair that is specific for a HOX cluster or HOX cluster-associated RNA (see Table 1). Likewise, a non-HOX cluster or non-HOX cluster-associated RNA can be quantified by amplifying RNA in a tissue sample, whether a leukemia tissue sample or cell, a non-leukemia tissue sample or cell from a leukemia patient, or a tissue sample or cell from a non-leukemia control donor, with a primer pair that is specific for a non-HOX cluster or non-HOX cluster-associated RNA, such as one of the housekeeping genes (GAPDH, β-actin, β-tubulin, etc). A primer pair comprises a forward primer and a reverse primer, wherein the forward primer hybridizes toward the 5' end of an RNA and wherein said reverse primer hybridizes toward the 3' end of the RNA, whether the RNA is a HOX cluster or HOX cluster-associated RNA or a non-HOX cluster or non-HOX cluster-associated RNA.

HOX cluster genes that are assessed for elevated expression in leukemia tissues and cells include, for example, one or more HOXA cluster gene(s) including, one or more of HOXA1, HOXA2, HOXA3, HOXA4, HOX45, HOXA6, HOXA7, HOXA9, HOXA10, HOXA11, and HOXA13 such as, for example, one or more of HOXA5, HOXA6, HOXA7, HOXA9 and/or HOXA10. HOX cluster genes that are assessed for elevated expression in leukemia samples also include, for example, one or more HOXB cluster gene(s) including one or more of HOXB1, HOXB2, HOXB3, HOXB4, HOXB5, HOXB6, HOXB7, HOXB8, HOXB9, and HOXB13. HOX cluster-associated genes that are assessed for elevated expression in leukemia samples include, for example, one or more of MEIS1, PBX3, and MEIS2A.

Nucleotide sequences for mRNA encoded by each of those HOX cluster genes and HOX cluster-associated genes are presented in Table 1, as are the corresponding accession numbers, sequence identifiers, and citations to specific references within the scientific literature, each of which is incorporated by reference herein.

be determined, and an assessment of elevated gene expression can be made by comparing the mRNA levels determined for a leukemia tissue sample or cell and a non-leukemia control tissue sample or cell.

Alternatively, a leukemia tissue sample or cell that has elevated HOX cluster gene or HOX cluster-associated gene expression can be identified by isolating for example, mRNA from a leukemia tissue sample or cell and then (i) determining the ratio of a HOX cluster gene or HOX cluster-associated gene mRNA level to the mRNA level of a housekeeping control gene in a leukemia tissue or cell; (ii) determining the ratio of HOX cluster gene or HOX cluster-associated gene mRNA level to the mRNA level of a housekeeping control gene in a healthy tissue or cell, and (iii) comparing the ratio of (i) to the ratio of (ii) and concluding that elevated expression exists if the ratio of (i) is at least 3× higher than the ratio of (ii). As used in this context, a housekeeping gene mRNA refers to a mRNA from a gene that has stable expression in both leukemic tissue or cell and a healthy tissue or cell. Suitable mRNA housekeeping genes include, for example, β-actin, β-tubulin, GAPDH, and cyclophyllin. Another way of assessing HOX cluster gene and HOX cluster-associated gene expression elevation in a leukemia tissue or cell is by comparison to a predetermined standard curve. The standard can be generated for

TABLE 1

Examples of Homeobox (HOX) Cluster Genes and HOX Cluster-associated Genes

|  | Accession Number | Sequence Identifier | References |
| --- | --- | --- | --- |
| *H. sapiens* HOX Cluster Gene (mRNA) |  |  |  |
| HOXA1 (Var. 1) | NCBI: NM_005522.4 | SEQ ID NO: 1 | Zha, Tumour Biol. 33(6): 2125-2134 (2012) |
| HOXA2 | NCBI: NM_006735.3 | SEQ ID NO: 2 | Monks, Int. J. Pediatr. Otorhinolaryngol. 74(8): 878-882 (2010) |
| HOXA3 (Var. 2) | NCBI: NM_153631.2 | SEQ ID NO: 3 | Yerges, J. Bone Miner. Res. 24(12): 2039-2049 (2009) |
| HOXA4 | NCBI: NM_002141.4 | SEQ ID NO: 4 | Gray, JOP 12(3): 216-219 (2011) |
| HOXA5 | NCBI: NM_019102.3 | SEQ ID NO: 5 | Liang, J. Dermatol. Sci. 66(3): 197-206 (2012) |
| HOXA6 | NCBI: NM_024014.3 | SEQ ID NO: 6 | Yerges, J. Bone Miner. Res. 24(12): 2039-2049 (2009) |
| HOXA7 | NCBI: NM_006896.3 | SEQ ID NO: 7 | Li, Blood 119(10): 2314-2324 (2012) |
| HOXA9 | NCBI: NM_152739.3 | SEQ ID NO: 8 | Li, Blood 121(8): 1422-1431 (2013) |
| HOXA10 | GB: AF040714.1 | SEQ ID NO: 9 | Fleischman, Br. J. Haematol. 116(2): 367-375 (2002) |
| HOXA11 | NCBI: NM_005523.5 | SEQ ID NO: 10 | Li, Blood 119(10): 2314-2324 (2012) |
| HOXA13 | NCBI: NM_000522.4 | SEQ ID NO: 11 | Ekici, Gene 518(2): 267-272 (2013) |
| HOXB1 | NCBI: NM_002144.3 | SEQ ID NO: 12 | Webb, Am. J. Hum. Genet. 91(1): 171-179 (2012) |
| HOXB2 | NCBI: NM_002145.3 | SEQ ID NO: 13 | Boimel, Genomics 98(3): 164-172 (2011) |
| HOXB3 | NCBI: NM_002146.4 | SEQ ID NO: 14 | Chen, Cancer Lett. 330(2): 217-224 (2013) |
| HOXB4 | NCBI: NM_024015.4 | SEQ ID NO: 15 | Wen-jun, Cell Biochem. Biophys. 63(2): 133-141 (2012) |
| HOXB5 | NCBI: NM_002147.3 | SEQ ID NO: 16 | Stavnes, Gynecol. Oncol. 129(2): 358-363 (2013) |
| HOXB6 | NCBI: NM_018952.4 | SEQ ID NO: 17 | di Pietro, Proc. Natl. Acad. Sci. U.S.A. 109(23): 9077-9082 (2012) |
| HOXB7 | NCBI: NM_004502.3 | SEQ ID NO: 18 | Nguyen Kovochich, Cancer 119(3): 529-539 (2013) |
| HOXB8 | NCBI: NM_024016.3 | SEQ ID NO: 19 | Stavnes, Gynecol. Oncol. 129(2): 358-363 (2013) |
| HOXB9 | NCBI: NM_024017.4 | SEQ ID NO: 20 | Shrestha, FEBS J. 279(19): 3715-3726 (2012) |
| HOXB13 | NCBI: NM_006361.5 | SEQ ID NO: 21 | Stott-Miller, Prostate 73(6): 634-641 (2013) |
| *Homo sapiens* Hox Cluster-associated Gene (mRNA) |  |  |  |
| MEIS1 | NCBI: NM_002398.2 | SEQ ID NO: 22 | Nurnberg, Blood 120(24): 4859-4868 (2012) |
| PBX3 (Var. 1) | NCBI: NM_006195.5 | SEQ ID NO: 23 | Li, Blood 121(8): 1422-1431 (2013) |
| MEIS2A | GB: AF178948.1 | SEQ ID NO: 24 | Yang, J. Biol. Chem. 275(27): 20734-20741 (2000) |

In order to identify a leukemia tissue sample or cell that has elevated HOX cluster gene or HOX cluster-associated gene expression, mRNA can be isolated from a leukemia tissue sample or cell and from a non-leukemia control tissue sample or cell, the level of expression of a given mRNA can example by qPCR of a reference HOX RNA/DNA expression (i.e. normal not elevated expression). Furthermore, in addition to mRNA levels, HOX cluster gene and HOX cluster-associated gene elevation can be determined by measuring DNA and/or protein levels.

Suitable leukemia tissue samples include, for example, blood, lymph node, bone marrow, and/or tumor biopsy samples from a leukemia patient. Suitable non-leukemia control tissue samples include, for example, blood, lymph node, and/or bone marrow samples from a non-leukemia donor, such as a healthy, disease-free donor. Such blood, lymph node, and/or bone marrow samples from a non-leukemia donor typically contain $CD34^+$ cells. It will be understood that, regardless of the precise nature or source of the donor tissue sample or cell, it is essential that the donor tissue or cell is known not to exhibit elevated expression of a HOX cluster gene or a HOX cluster-associated gene.

Suitable leukemia cells include, for example, lymphocytes or myelocytes from a leukemia patient. Suitable non-leukemia control cells, in particular non-leukemia $CD34^+$ control cells, include, for example, lymphocytes or myelocytes from a non-leukemia donor, such as a healthy, disease-free donor or one or more cell line, such as a $CD34^+$ cell line including, for example, the Kasumi-1 cell line. Regardless of its source or identity, it will be understood that a suitable non-leukemia control tissue sample or cell will not display elevated levels of the particular HOX cluster gene(s) or HOX cluster-associated gene(s) that are being tested for elevated expression in the leukemia patient tissue sample or cell.

Methodologies for detecting elevated expression of HOX cluster and HOX cluster-associated gene expression have been described. For example, Armstrong et al., *Nat. Genet.* 30(1):41-47 (2002) and U.S. Patent Publication No. 2009/0324618 describe the detection and quantification of HOXA5, HOXA6, HOXA7, HOXA9, and HOXA10 as well as the HOX cluster gene associated co-factor MEIS1 by amplifying a cDNA from total RNA using primer pairs that are specific for each HOX cluster gene or HOX cluster-associated gene. Ferrando et al., *Blood* 102(1):262-268 (2003) and Ferrando et al., *Cancer Cell* 1:75-87 (2002) describe quantitative real-time reverse transcriptase polymerase chain reaction (RT-PCR) methodology to quantify the expression of the oncogenic transcription factors HOX11 and HOX11L2.

These and other methodologies for quantifying expression levels that can be readily adapted to detecting elevated expression of HOX cluster and HOX cluster-associated genes are now described in further detail.

Microarray Analysis

Elevated HOX cluster and HOX cluster-associated gene expression can be detected and quantified by microarray analysis of RNA isolated from a leukemia patient and/or control donor tissue sample—or cell. Microarray is an effective method for simultaneously evaluating the expression level of multiple HOX cluster and HOX cluster-associated genes. But, due to limitations on its sensitivity, microarray methodology may not accurately determine the absolute tissue distribution of low abundance genes or may underestimate the degree of elevated HOX cluster and HOX cluster-associated gene expression due to signal saturation. For those genes showing elevated expression by microarray expression profiling, further analysis can be performed using one or more quantitative PCR methodology such as, for example, RT-PCR based on Taqman™ probe detection (Invitrogen Life Sciences, Carlsbad, Calif.), or the fluorescent dye SYBR Green, both of which provide a greater dynamic range of sensitivity.

Briefly, microarray analysis includes that PCR amplification of RNA extracted from a leukemia patient or control donor tissue sample or cell with primer pairs that hybridize to coding sequences within each HOX cluster and HOX cluster-associated gene and/or coding sequences within each non-HOX cluster and non-HOX cluster-associated gene the expression of which is to be detected and/or quantified. PCR products are dotted onto slides in an array format, with each PCR product occupying a unique location in the array. The RNA is then reverse transcribed and fluorescent-labeled cDNA probes are generated. Microarrays probed with the fluorescent-labeled cDNA probes are scanned, and fluorescence intensity is measured. The level of fluorescence intensity correlates with hybridization intensity, which correlates with relative level of gene expression.

HOX cluster and HOX cluster-associated gene expression analysis can be performed using a commercially available microarray (e.g., the U133A chip; Affymetrix, Santa Clara, Calif.) or using a custom microarray. Alternatively, elevated HOX cluster and HOX cluster-associated gene expression can be detected using a Synteni microarray (Palo Alto, Calif.) according to the manufacturer's instructions and as described by Schena et al., *Proc. Natl. Acad. Sci. U.S.A.* 93:10614-10619 (1996) and Heller et al., *Proc. Natl. Acad. Sci. U.S.A.* 94:2150-2155 (1997). Microarray hybridization can be performed according to methodology described in Abraham et al., *Blood* 105:794-803 (2005).

Probe level data can be normalized using a commercial algorithm (e.g., the Affymetrix Microarray Suite 5.0 algorithm) or a custom algorithm. HOX cluster and HOX cluster-associated gene expression intensity values as well as non-HOX cluster and non-HOX cluster-associated gene expression intensity values can be log transformed, median centered, and/or analyzed using commercially available programs (e.g., GeneSpring 7.3.1 GX; Agilent Technologies, Santa Clara, Calif.) or a custom algorithm.

A number of factors can be used to assess the quality of the HOX cluster and HOX cluster-associated gene expression analysis such as, for example, the GAPDH 3':5' ratio and the actin 3':5' ratio. While an ideal 3':5' ratio is 1, the ratio for the housekeeping genes should not exceed 3.

Elevated HOX cluster and HOX cluster-associated gene expression can be determined using Welch's ANOVA (analysis of variance) using variance computed by applying the cross-gene error model based on deviation from 1 available within GeneSpring. This can overcome a lack of replicates and variance associated with the individual samples and can be considered to be similar in principle to variance filtering. Unsupervised clustering can be done using a hierarchical agglomerative algorithm. Pearson's correlation coefficient and centroid linkage can be used as similarity and linkage methods, respectively.

To detect possible differences between samples, genes can be extracted from the dataset that had 1.5-fold difference in expression between individual samples and/or were statistically significant at a corrected P value of 0.05 by Student's t test with Benjamini-Hochberg multiple testing corrections. Differentially expressed genes can be assessed for Gene Ontology (GO) enrichment (e.g., using GeneSpring).

Quantitative PCR

Depending upon such factors as the relative number of leukemia cells present in a leukemia tissue sample and/or the level of HOX cluster and HOX cluster-associated gene expression within each leukemia cell within a tissue sample, it may be preferred to perform a quantitative PCR analysis to detect and/or quantify the level of HOX cluster and HOX cluster-associated gene expression.

For example, at least two oligonucleotide primers can be employed in a PCR-based assay to amplify at least a portion of a HOX cluster or HOX cluster-associated gene mRNA and/or a non-HOX cluster/non-HOX cluster-associated gene mRNA, or a corresponding cDNA, which is derived from a leukemia tissue sample or cell and/or a non-leukemia control donor tissue sample or cell. At least one of the oligonucleotide primers is specific for, and hybridizes to a nucleic acid portion fragment specific for HOX cluster and HOX cluster-associated gene. The amplified cDNA may, optionally, be subjected to a fractionation step such as, for example, gel electrophoresis prior to detection.

RT-PCR is a quantitative PCR methodology in which PCR amplification is performed in conjunction with reverse transcription. RNA is extracted from a tissue sample or cell, such as a blood, lymph node, bone marrow, and/or tumor biopsy sample, and is reverse transcribed to produce cDNA molecules. PCR amplification using at least one specific primer amplifies the cDNA molecule, which may be separated and visualized using, for example, gel electrophoresis. Amplification may be performed on tissue samples or cells taken from a patient and from a heathy individual who serves as a negative control. The amplification reaction may be performed on several dilutions of cDNA spanning two orders of magnitude. An increase in expression of at least about three-fold, at least about five-fold, at least about 10-fold, at least about 15-fold, at least about 20-fold, at least about 25-fold, or greater in several dilutions of the test leukemia patient sample as compared to the same dilutions of the non-leukemia healthy control donor sample is typically considered positive.

HOX cluster and HOX cluster-associated gene expression may be further characterized or, alternatively, originally detected and/or quantified by employing the quantitative real-time PCR methodology. Gibson et al., *Genome Research* 6:995-1001 (1996) and Heid et al., *Genome Research* 6:986-994 (1996). Real-time PCR is a technique that evaluates the level of PCR product accumulation during the course of amplification. This technique permits quantitative evaluation of mRNA levels in multiple samples. By this methodology, a leukemia tissue sample or cell may be tested along-side a corresponding non-leukemia control donor sample or cell and/or a panel of unrelated normal non-leukemia tissue samples or cells.

Real-time PCR may, for example, be performed either on the ABI 7700 Prism or on a GeneAmp® 5700 sequence detection system (Applied Biosystems, Foster City, Calif.). The 7700 system uses a forward and a reverse primer in combination with a specific probe with a 5' fluorescent reporter dye at one end and a 3' quencher dye at the other end (Taqman™). When real-time PCR is performed using Taq DNA polymerase with 5'-3' nuclease activity, the probe is cleaved and begins to fluoresce allowing the reaction to be monitored by the increase in fluorescence (real-time). The 5700 system uses SYBR® green, a fluorescent dye, which only binds to double stranded DNA, and the same forward and reverse primers as the 7700 instrument. Matching primers and fluorescent probes may be designed according to the primer express program (Applied Biosystems, Foster City, Calif.). Optimal concentrations of primers and probes are initially determined by those of ordinary skill in the art. Control (e.g., β-actin-specific) primers and probes may be obtained commercially from, for example, Perkin Elmer/Applied Biosystems (Foster City, Calif.).

To quantify the amount of HOX cluster and HOX cluster-associated gene expression in a sample, a standard curve is generated using a plasmid containing the gene of interest. Standard curves are generated using the Ct values determined in the real-time PCR, which are related to the initial cDNA concentration used in the assay. Standard dilutions ranging from $10-10^6$ copies of the gene of interest are generally sufficient. In addition, a standard curve is generated for the control sample sequence. This permits standardization of initial RNA content of a leukemia tissue sample or cell to the amount of a control tissue sample or cell for comparison purposes.

Total RNA may be isolated and extracted from leukemia tissue samples or cells and non-leukemia control tissue samples or cells using Trizol reagent as described herein. First strand synthesis may be carried out using 1-2 μg of total RNA with SuperScript II reverse transcriptase (Life Technologies, Carlsbad, Calif.) at 42° C. for one hour to yield full length cDNA. cDNA may then be amplified by PCR using HOX cluster and HOX cluster-associated gene-specific primers that are designed based upon the HOX cluster and HOX cluster-associated mRNA sequences presented in Table 1, disclosed within the references cited in Table 1, or that are otherwise known and readily available to those skilled in the art.

To ensure the quantitative nature of the RT-PCR, a housekeeping gene, such as j-actin, can be used as an internal control for each of the leukemia patient and non-leukemia control donor tissue samples and/or cells examined. Serial dilutions of the first strand cDNAs are prepared and RT-PCR assays are performed using β-actin specific primers. A dilution is then chosen that enables the linear range amplification of the β-actin template and that is sensitive enough to reflect the differences in the initial copy numbers. Using these conditions, the β-actin levels are determined for each reverse transcription reaction from each tissue. DNA contamination is minimized by DNase treatment and by assuring a negative PCR result when using first strand cDNA that was prepared without adding reverse transcriptase.

In an exemplary RT-PCR reaction using the Dynabeads mRNA direct microkit (Invitrogen, Life Sciences Technologies, Carlsbad, Calif.), samples containing $10^5$ cells or less are tested in a total reaction volume of 30 μl with 14.25 μl $H_2O$; 1.5 μl BSA; 6 μl first strand buffer; 0.75 mL of 10 mM dNTP mix; 3 μl Rnasin; 3 μl 0.1 M dTT; and 1.5 μl Superscript II. The resulting solution is incubated for 1 hour at 42° C., diluted 1:5 in $H_2O$, heated at 80° C. for 2 min to detach cDNA from the beads, and immediately placed on MPS. The supernatant containing cDNA is transferred to a new tube and stored at −20° C.

RNA Sequencing

Elevated expression of one or more HOX cluster gene and/or one or more HOX cluster-associated gene can be determined by the direct sequencing of mRNA in a leukemia patient tissue sample or cell and/or a non-leukemia donor control tissue sample or cell. Alternatively, elevated expression of one or more HOX cluster gene and/or one or more HOX cluster-associated gene can be determined following conversion of mRNA into cDNA by reverse transcription.

True Single Molecule Sequencing (tSMS™) and/or Direct RNA Sequencing (DRS™) are useful techniques for quantifying gene expression that can be readily adapted for detecting and quantifying the expression one or more HOX cluster gene and/or one or more HOX cluster-associated gene. These sequencing-by-synthesis technologies can be performed on mRNAs derived from a tissue sample or cell without the need for prior reverse transcription or PCR amplification.

Direct RNA sequencing technology (Helicos BioSciences Corporation, Cambridge, Mass.) and transcriptome profiling using single-molecule direct RNA sequencing are described in Ozsoolak et al., *Nature* 461(7265):814-818 (2009) and Ozsolak and Milos, *Methods Mol Biol* 733:51-61 (2011). True Single Molecule and Direct RNA Sequencing technologies are further described in U.S. Patent Publication Nos. 2008/0081330, 2009/0163366, 2008/0213770, 2010/0184045, 2010/0173363, 2010/0227321, 2008/0213770, and 2008/0103058 as well as U.S. Pat. Nos. 7,666,593; 7,767,400; 7,501,245; and 7,593,109, each of which is hereby incorporated by reference in its entirety.

mRNAs encoded by HOX cluster and HOX cluster-associated genes as well as non-HOX cluster and non-HOX cluster-associated genes can be directly sequenced by True Single Molecule and Direct RNA Sequencing technologies by utilizing specific sequencing primers that are designed based upon the HOX cluster and HOX cluster-associated mRNA sequences and non-HOX cluster and non-HOX cluster-associated mRNA sequences (e.g., as presented in Table 1, disclosed within the references cited in Table 1, or which are otherwise known and readily available to those skilled in the art).

Methodologies for Detecting Leukemias Exhibiting Elevated HOX Cluster and/or HOX Cluster-Associated Gene Expression In general, a leukemia cell may be detected in a patient based on the presence of one or more genes that are known to be associated with leukemia, a subset of which are also known to be associated with elevated HOX cluster and HOX cluster-associated gene expression. According to the present disclosure, leukemia patients that exhibit one or more genetic mutation, alteration, and/or other abnormality, other than an MLL-translocation, MLL-rearrangement, or MLL-partial tandem duplication, which is known, or determined to be associated with elevated HOX cluster and HOX cluster-associated gene expression, are suitably treated by the administration of one or more DOT1L inhibitor as described herein.

This section describes representative methodologies that are well known and that can be easily adapted by those skilled in the art to the detection of one or more genetic mutation, alteration, and/or other abnormality in a tissue sample or cell. These methodologies include, for example, nucleic acid amplification and sequencing technologies; nucleic acid hybridization technologies, including fluorescent in situ hybridization (FISH).

Exemplary genes that, when mutated or otherwise altered, are known to be associated with leukemia in a patient are presented in Tables 2 and 3. Table 2 presents those leukemia-associated genes, including NPM1, DNMT3A, IDH1, IDH2, RUNX1, TET2, and ASXL1 mutations and NUP98-NSD1 and other NUP98 translocations, which, when exhibiting one or more mutation(s), rearrangement(s), and/or translocation(s) (other than MLL-translocation(s), an MLL-rearrangement(s), and/or an MLL-partial tandem duplication(s)), are known to be associated with elevated expression of one or more HOX cluster and/or HOX cluster-associated gene(s) in a cell, as compared to the level of expression of the respective HOX cluster and/or HOX cluster-associated gene(s) in a normal $CD34^+$ bone marrow cells.

The detection and/or presence of one or more mutation(s), rearrangement(s), translocation(s) and/or other genetic alteration(s) or abnormality(s) in one or more of the leukemia-associated genes from Table 2 in a leukemia patient tissue sample or cell is, according to the discoveries upon which the present disclosure is based, predictive of a leukemia tissue sample or cell the proliferation and/or survival of which can be inhibited, prevented, or terminated by contacting with one or more DOT1L inhibitor.

Thus, according to the present disclosure, a leukemia patient having a tissue or cell that exhibits (1) one or more of the mutation(s), rearrangement(s), translocation(s) and/or other genetic alteration(s) or abnormality(s) in one or more of the leukemia-associated genes presented in Table 2 and/or (2) one or more mutation(s), rearrangement(s), translocation(s) and/or other genetic alteration(s) or abnormality(s) in one or more leukemia-associated gene(s) that is determined (e.g., according to the methods provided herein) to be associated with elevated HOX cluster and/or HOX cluster-associated gene expression, may be advantageously treated by the administration of one or more DOT1L inhibitor, including a composition or formulation comprising one or more DOT1L inhibitor, either individually, as a combination of two or more DOT1L inhibitors, and/or in further combination with another suitable therapeutic agent. Suitable DOT1L inhibitors, compositions, formulations, and other suitable therapeutic agents for the treatment of leukemia are described in further detail herein, are well known to those of skill in the art, and are presented in the scientific and patent literature cited herein, each of which is incorporated by reference into the present disclosure.

TABLE 2

Leukemia Genes Associated with Elevated HOX Cluster and/or HOX Cluster-associated Gene Expression

| H. sapiens Leukemia Gene (mRNA) | Accession Number | Sequence Identifier | Level of HOXA9 Gene Expression Relative to Normal CD34+ Bone Marrow Cells | References |
|---|---|---|---|---|
| NUP98 | GenBank: AB040538.1 | SEQ ID NO: 27 | 25** (NUP98-NSD1) | Hollink, NUP98/NSD1 Characterizes a Novel Poor Prognostic Group in Acute Myeloid Leukemia with a Distinct HOX Gene Expression Pattern, Blood 118(13): 3645-56 (2011) Wang, NUP98-NSD1 Links H3K36 Methylation to Hox-A Gene Activation and Leukaemogenesis, Nat Cell Biol 9(7): 804-12 (2007) Arai, Heterogenous Fusion Transcripts Involving the NUP98 Gene and HOXD13 Gene Activation in a Case of Acute Myeloid Leukemia with the t(2; 11)(q31; p15) Translocation, Leukemia 14(9): 1621-9 (2000) |
| NSD1 | GenBank: AF322907.1 | SEQ ID NO: 28 | | Jaju, A Novel Gene, NSD1, is Fused to NUP98 in the t5; 11)q35; p15.5) in De novo Childhood Acute Myeloid Leukemia, Blood 98(4): 1264-1267 (2001) |
| NPM1 | GenBank: AY740639.1 | SEQ ID NO: 29 | 18* | Zangenberg, The Combined Expression of HOXA4 and MEIS1 is an Independent Prognostic Factor in Patients with AML, Eur J Haematol 83(5): 439-48 (2009) |

TABLE 2-continued

Leukemia Genes Associated with Elevated HOX Cluster and/or HOX Cluster-associated Gene Expression

| H. sapiens Leukemia Gene (mRNA) | Accession Number | Sequence Identifier | Level of HOXA9 Gene Expression Relative to Normal CD34+ Bone Marrow Cells | References |
|---|---|---|---|---|
| | | | | Haferlach, AML with Mutated NPM1 Carrying a Normal or Aberrant Karyotype Show Overlapping Biologic, Pathologic, Immunophenotypic, and Prognostic Features, Blood 114(14): 3024-32 (2009)<br>Mullighan, Pediatric Acute Myeloid Leukemia with NPM1 Mutations is Characterized by a Gene Expression Profile with Dysregulated HOX Gene Expression Distinct from MLL-rearranged Leukemias, Leukemia 21(9): 2000-9 (2007)<br>Falini, Cytoplasmic Nucleophosmin in Acute Myelogenous Leukemia with a Normal Karyotype, N. Engl. J. Med. 352(3): 254-266 (2005) |
| DNMT3A | GenBank: AF331856.1 | SEQ ID NO: 30 | 13* | Hajkova, Decreased DNA Methylation in Acute Myeloid Leukemia Patients with DNMT3A Mutations and Prognostic Implications of DNA Methylation, Leuk Res 36(9): 1128-33 (2012)<br>Kim, Co-operation and Communication between the Human Maintenance and De novo DNA (cytosine-5) Methyltransferases, EMBO J 21(15): 4183-95 (2002) |
| IDH1 | GenBank: CR533522.1 | SEQ ID NO: 31 | 13* | Schaap, Mutations in the Isocitrate Dehydrogenase Genes IDH1 and IDH2 in Tumors, Adv Anat Pathol 20(1): 32-8 (2013)<br>Feng, Prognostic Significance of IDH1 Mutations in Acute Myeloid Leukemia: A Meta-Analysis, Am J Blood Res 2(4): 254-64 (2012)<br>Westman, IDH1 and IDH2 Mutations in Therapy-related Myelodysplastic Syndrome and Acute Myeloid Leukemia are Associated with a Normal Karyotype and with Der(1; 7)(q10; p10), Leukemia 27(4): 957-9 (2013)<br>Ibáñez, Rapid screening of ASXL1, IDH1, IDH2, and c-CBL mutations in de novo acute myeloid leukemia by high-resolution melting, J Mol Diagn 14(6): 594-601 (2012)<br>Zhou, Potential Application of IDH1 and IDH2 Mutations as Prognostic Indicators in Non-promyelocytic Acute Myeloid Leukemia: A Meta-Analysis, Leuk Lymphoma 53(12): 2423-9 (2012)<br>Brecqueville, Mutation Analysis of ASXL1, CBL, DNMT3A, IDH1, IDH2, JAK2, MPL, NF1, SF3B1, SUZ12, and TET2 in Myeloproliferative Neoplasms, Genes Chromosomes Cancer 51(8): 743-55 (2012)<br>Chotirat, Molecular Alterations of Isocitrate Dehydrogenase 1 and 2 (IDH1 and IDH2) Metabolic Genes and Additional Genetic Mutations in Newly Diagnosed Acute Myeloid Leukemia Patients, J Hematol Oncol 5:5 (2012)<br>Byers, Detection of IDH1 R132H Mutation in Acute Myeloid Leukemia by Mutation-specific Immunohistochemistry, Appl Immunohistochem Mol Morphol 20(1): 37-40 (2012) |
| IDH2 | NCBI: NM_002168.2 | SEQ ID NO: 32 | 8* | See, IDH1 |
| RUNX1 | GenBank: AY509915.1 | SEQ ID NO: 33 | 10* | Grossmann, The molecular profile of adult T-cell acute lymphoblastic leukemia: mutations in RUNX1 and DNMT3A are associated with poor prognosis in T-ALL, Genes Chromosomes Cancer 52(4): 410-22 (2013)<br>Mendler, RUNX1 Mutations are Associated with Poor Outcome in Younger and Older Patients with Cytogenetically Normal Acute Myeloid Leukemia and with Distinct Gene and MicroRNA Expression Signatures, J Clin Oncol 30(25): 3109-18 (2012)<br>Greif, RUNX1 Mutations in Cytogenetically Normal Acute Myeloid Leukemia are Associated with a Poor Prognosis and Up-regulation of Lymphoid Genes, Haematologica 97(12): 1909-15 (2012)<br>Camós, Gene Expression Profiling of Acute Myeloid Leukemia with Translocation t(8; 16)(p11; p13) and MYST3-CREBBP Rearrangement Reveals a Distinctive Signature with a Specific Pattern of HOX Gene Expression, Cancer Res 66(14): 6947-54 (2006) |
| TET2 | NCBI: NM_001127208.2<br>NCBI: NM_017628.4 | SEQ ID NO: 34<br>SEQ ID NO: 35 | 7* | Liang, Cooperating Gene Mutations in Childhood Acute Myeloid Leukemia with Special Reference on Mutations of ASXL1, TET2, IDH1, IDH2, and DNMT3A, Blood 121(15): 2988-2995 (2013)<br>Tefferi, Detection of Mutant TET2 in Myeloid Malignancies other than Myeloproliferative Neoplasms: CMML, MDS, MDS/MPN and AML, Leukemia 23(7): 1343-1345 (2009)<br>Jankowska, Loss of Heterozygosity 4q24 and TET2 Mutations Associated with Myelodysplastic/Myeloproliferative Neoplasms, Blood 113 (25), 6403-6410 (2009) |
| ASXL1 | NCBI: NM_015338.5<br>NCBI: | SEQ ID NO: 36<br>SEQ ID NO: 37 | 3* | Schnittger, ASXL1 Exon 12 Mutations are Frequent in AML with Intermediate Risk Karyotype and are Independently Associated with an Adverse Outcome, Leukemia 27(1): 82-91 (2013) |

TABLE 2-continued

Leukemia Genes Associated with Elevated HOX Cluster and/or HOX Cluster-associated Gene Expression

| H. sapiens Leukemia Gene (mRNA) | Accession Number | Sequence Identifier | Level of HOXA9 Gene Expression Relative to Normal CD34+ Bone Marrow Cells | References |
|---|---|---|---|---|
| | NM_001164603.1 | | | Ibanez, Rapid screening of ASXL1, IDH1, IDH2, and c-CBL mutations in de novo acute myeloid leukemia by high-resolution melting, J Mol Diagn 14(6): 594-601 (2012)<br>Abdel-Wahab, Role of TET2 and ASXL1 mutations in the pathogenesis of myeloproliferative neoplasms, Hematol. Oncol. Clin. North Am. 26(5): 1053-1064 (2012) |

*Compared to CD34+ Bone Marrow Cells
**Compared to NUP98-NSD1 Negative Patients

Table 3 presents those leukemia-associated genes that, when exhibiting one or more mutation(s), rearrangement(s), and/or translocation(s), are known not to be associated with elevated expression of a HOX cluster and/or HOX cluster-associated gene in a cell, as compared to the level of expression of the respective HOX cluster and/or HOX cluster-associated gene(s) in a normal CD34$^+$ bone marrow cells.

The detection and/or presence of one or more mutation(s), rearrangement(s), translocation(s) and/or other genetic alteration(s) or abnormality(s) in one or more of the leukemia-associated genes from Table 3 in a leukemia patient tissue sample or cell is, according to the discoveries upon which the present disclosure is based, predictive of a leukemia tissue sample or cell the proliferation and/or survival of which cannot be inhibited, prevented, or terminated by contacting with one or more DOT1L inhibitor.

Thus, according to the present disclosure, a leukemia patient having a tissue or cell that exhibits one or more of the mutation(s), rearrangement(s), translocation(s) and/or other genetic alteration(s) or abnormality(s) in one or more of the leukemia-associated genes in Table 3, but does not also exhibit (1) one or more of the mutation(s), rearrangement(s), translocation(s) and/or other genetic alteration(s) or abnormality(s) in one or more of the leukemia-associated genes in Table 2; (2) one or more MLL-translocation(s), MLL-rearrangement(s), and/or an MLL-partial tandem duplication(s); and/or (3) one or more mutation(s), rearrangement(s), translocation(s) and/or other genetic alteration(s) or abnormality(s) in one or more leukemia-associated gene(s) that is determined (e.g., according to the methods provided herein) to be associated with elevated HOX cluster and/or HOX cluster-associated gene expression, is likely not advantageously treated by the administration of one or more DOT1L inhibitor.

TABLE 3

Leukemia Genes that are Not Associated with Elevated HOX Cluster and/or HOX Cluster-associated Gene Expression

| H. sapiens Leukemia Gene (mRNA) | Accession Number | Sequence Identifier | References |
|---|---|---|---|
| EZH2 | NCBI: NM_004456.4 | SEQ ID NO: 38 | Larsson, The Changing Mutational Landscape of Acute Myeloid Leukemia and Myelodysplastic Syndrome, Mol Cancer Res. [Epub ahead of print] (2013)<br>Wang, EZH2 Mutations are Related to Low Blast Percentage in bone Marrow, PLoS One 8(4): e61341 (2013) |
| CEBPA | NCBI: NM_004364.3 | SEQ ID NO: 39 | Zhang, Molecular Genetic Tests for FLT3, NPM1, and CEBPA in Acute Myeloid Leukemia, Methods Mol Biol. 999: 105-21 (2013)<br>van Vliet, Detection of CEBPA Double Mutants in Acute Myeloid Leukemia using a Custom Gene Expression Array, Genet Test Mol Biomarkers 17(5): 395-400 (2013)<br>Greif, GATA2 Zinc Finger 1 Mutations Associated with Biallelic CEBPA Mutations Define a Unique Genetic Entity of Acute Myeloid Leukemia, Blood 120(2): 395-403 (2012)<br>Hendricks-Taylor, The CCAAT/enhancer binding protein (C/EBP alpha) gene (CEBPA) maps to human chromosome 19q13.1 and the related nuclear factor NF-IL6 (C/EBP beta) gene (CEBPB) maps to human chromosome 20q13.1, Genomics 14(1): 12-17 (1992) |
| NRAS | NCBI: NM_002524.4 | SEQ ID NO: 40 | Aly, Prognostic Significance of NRAS Gene Mutations in Children with Acute Myelogenous Leukemia, Mediterr. J. Hematol. Infect. Dis. 3(1): e2011055 (2011)<br>Paulsson, Mutations of FLT3, NRAS, KRAS, and PTPN11 are Frequent and Possibly Mutually Exclusive in High Hyperdiploid Childhood Acute Lymphoblastic Leukemia, Genes Chromosomes Cancer 47(1): 26-33 (2008)<br>Hirai, Transforming Genes in Human Leukemia Cells, Blood 66(6): 1371-1378 (1985)<br>Hall, Human N-ras: cDNA Cloning and Gene Structure, Nucleic Acids Res. 13(14): 5255-5268 (1985) |
| KRAS | NCBI: NM_033360.2 | SEQ ID NO: 41 | Mansour, Oncogenic Kras and Notch-1 Cooperate in T-cell Acute Lymphoblastic Leukemia/Lymphoma, Expert Rev Hematol 2(2): 133-6 (2009)<br>Sabnis, Oncogenic Kras Initiates leukemia in Hematopoietic Stem Cells, PLoS Biol 7(3): e59 (2009)<br>Bollag, Biochemical Characterization of a Novel KRAS Insertion Mutation from a Human Leukemia, J Biol Chem 271(51): 32491-4 (1996) |

TABLE 3-continued

Leukemia Genes that are Not Associated with Elevated HOX Cluster and/or HOX Cluster-associated Gene Expression

| H. sapiens Leukemia Gene (mRNA) | Accession Number | Sequence Identifier | References |
|---|---|---|---|
| SMC1A | NCBI: NM_006306.3 | SEQ ID NO: 42 | Homme, Low SMCIA Protein Expression Predicts Poor Survival in Acute Myeloid Leukemia, Oncol Rep 24(1): 47-56 (2010)<br>Laugsch, Imbalance of SMC1 and SMC3 Cohesins Causes Specific and Distinct Effects, PLoS One 8(6): e65149 (2013)<br>Sun, The SMC1-SMC3 Cohesion Heterodimer Structures DNA through Supercoiling-dependent Loop Formation, Nucleic Acids Res 41(12): 6149-60 (2013)<br>Stursberg, Cloning and Characterization of Mammalian SMC1 and SMC3 Genes and Proteins, Components of the DNA Recombinant Complexs RC-1, Gene 228(1-2): 1-12 (1999) |
| SMC3 | NCBI: NM_005445.3 | SEQ ID NO: 43 | See, SMC1 |
| STAG2 | NCBI: NM_001042749.1 | SEQ ID NO: 44 | Chung, Somatic Mutation of STAG2, an Aneuploidy-related Gene, is Rare in Acute Leukemias, Leuk Lymphoma 53(6): 1234-5 (2012)<br>Chen, Novel Non-TCR Chromosome Translocations t(3; 11)(q25; p13) and t(X; 11)(q25; p13) Activating LMO2 by Juxtaposition with MBNL1 and STAG2, Leukemia 25(10): 1632-5 (2011) |
| RAD21 | NCBI: NM_006265.2 | SEQ ID NO: 45 | Deardorff, RAD21 Mutations Cause a Human Cohesinopathy, Am J Hum Genet 90(6): 1014-27 (2012) |
| PRAM1 | NCBI: NM_032152.4 | SEQ ID NO: 46 | Choi, Spectra of Chromosomal Aberations in 325 Leukemia Patients and Implications for the Development of New Molecular Detection Systems, J Korean Med Sci 26(7): 886-92 (2011)<br>Moog-Lutz, PRAM-1 is a Novel Adaptor Protein Regulated by Retinoic Acid (RA) and Promyelocytic Leukemia (PML)-RA Receptor Alpha in Acute Promyelocytic Leukemia Cells, J Biol Chem 276(25): 22375-81 (2001) |
| AML1-ETO | GenBank: S78158.1 | SEQ ID NO: 47 | Licht, AML1 and the AML1-ETO Fusion Protein in the Pathogenesis of t(8; 21) AML, Oncogene 20(40): 5660-79 (2001) |
| CBFA2T3 | NCBI: NM_005187.5 | SEQ ID NO: 48 | Masetti, CBFA2T3-GLIS2 Fusion Transcript is a novel Common Feature in Pediatric, Cytogenetically Normal AML, not Restricted to FAB M7 Subtype, Blood 121(17): 3469-72 (2013)<br>Gruber, An Inv(16)(p13.3q24.3)-encoded CBFA2T3-GLIS2 Fusion Protein Defines an Aggressive Subtype of Pediatric Acue Megakaryoblastic Leukemia, Cancer Cell 22(5): 683-97 (2012)<br>Kawashima, Childhood Acute Myeloid Leukemia with Bone Marrow Eosinophilia Caused by t(16; 21)(q24; q22), Int J Hematol 95(5): 577-80 (2012) |
| GLIS2 | NCBI: NM_032575.2 | SEQ ID NO: 26 | See, GLIS2 |

Mutations in one or more of the NPM1, DNMT3A, IDH1, IDH2, RUNX1, TET2, and ASXL genes and NUP98-NSD1 and other NUP98 translocations presented in Table 2 can be detected by one or more of the gene-detection methodologies that are well known in the art and that can be readily adapted, as appropriate, by skilled artisan.

Nucleic Acid Amplification

Genomic DNA from a leukemia or control tissue sample or cell can be PCR amplified by utilizing specific primer pairs that are designed based upon the NUP98, NSD1, NPM1, DNMT3A, IDH1, IDH2, RUNX1, TET2, and ASXL1 sequences that are presented in Table 2, disclosed within the references cited in Table 2, or that are otherwise known and readily available to those skilled in the art. The resulting PCR amplicon can then be isolated and subjected to a sequencing and/or hybridization reaction to determine whether any of the known mutations in the NPM1, DNMT3A, IDH1, IDH2, RUNX1, TET2, and ASXL1 genes and NUP98-NSD1 and other NUP98 translocations, which are associated with leukemia, as well as elevated HOX cluster and/or HOX cluster-associated gene expression are present in the respective leukemia patient's genomic DNA.

As used herein, the term "amplification" refers to the production of multiple copies of a target nucleic acid that contains at least a portion of the intended specific target nucleic acid sequence. The multiple copies are referred to, interchangeably, as amplicons or amplification products. In certain aspects of the present disclosure, the amplified target contains less than the complete target mRNA sequence (i.e., spliced transcript of exons and flanking untranslated sequences) and/or target genomic sequence (including introns and/or exons). For example, specific amplicons may be produced by amplifying a portion of the target polynucleotide by using amplification primers that hybridize to, and initiate polymerization from, internal positions of the target polynucleotide. The amplified portion contains a detectable target sequence that may be detected using any of a variety of well-known methods.

Many well-known methods of nucleic acid amplification require thermocycling to alternately denature double-stranded nucleic acids and hybridize primers; however, other well-known methods of nucleic acid amplification are isothermal. The polymerase chain reaction (PCR; described in U.S. Pat. Nos. 4,683,195; 4,683,202; 4,800,159; 4,965,188) uses multiple cycles of denaturation, annealing of primer pairs to opposite strands, and primer extension to exponentially increase copy numbers of the target sequence. In a variation called RT-PCR, reverse transcriptase (RT) is used to make a complementary DNA (cDNA) from mRNA, and the cDNA is then amplified by PCR to produce multiple copies of DNA.

The ligase chain reaction (LCR; Weiss, Science 254:1292 (1991) uses two sets of complementary DNA oligonucleotides that hybridize to adjacent regions of a target nucleic acid. The DNA oligonucleotides are covalently linked by a DNA ligase in repeated cycles of thermal denaturation, hybridization, and ligation to produce a detectable double-stranded ligated oligonucleotide product.

Strand displacement amplification (SDA; Walker et al., *Proc. Natl. Acad. Sci. USA* 89:392-396 (1992); U.S. Pat. Nos. 5,270,184 and 5,455,166) uses cycles of annealing pairs of primer sequences to opposite strands of a target sequence, primer extension in the presence of a dNTPαS to produce a duplex hemi-phosphorothioated primer extension product, endonuclease-mediated nicking of a hemimodified restriction endonuclease recognition site, and polymerase-mediated primer extension from the 3' end of the nick to displace an existing strand and produce a strand for the next round of primer annealing, nicking and strand displacement, resulting in geometric amplification of product. Thermophilic SDA (tSDA) uses thermophilic endonucleases and polymerases at higher temperatures in essentially the same method (EP Patent No. 0 684 315).

Other amplification methods include: nucleic acid sequence based amplification (U.S. Pat. No. 5,130,238), commonly referred to as NASBA; one that uses an RNA Replicase to amplify the probe molecule itself (Lizardi et al., *BioTechnol* 6:1197-1202 (1988)), commonly referred to as QP Replicase; a transcription based amplification method (Kwoh et al., *Proc. Natl. Acad. Sci. U.S.A.* 86:1173-1177 (1989)); self-sustained sequence replication (Guatelli et al., *Proc. Natl. Acad. Sci. U.S.A.* 87:1874-1878 (1990)); and, transcription mediated amplification (U.S. Pat. Nos. 5,480,784 and 5,399,491), commonly referred to as TMA. For further discussion of known amplification methods see Persing, "In Vitro Nucleic Acid Amplification Techniques" in Diagnostic Medical Microbiology: Principles and Applications pp. 51-87 (Persing et al., Eds.; American Society for Microbiology, Washington, D.C., 1993).

TMA employs an RNA polymerase to produce multiple RNA transcripts of a target region and a "promoter-primer" that hybridizes to a target nucleic acid in the presence of a reverse transcriptase and an RNA polymerase to form a double-stranded promoter from which the RNA polymerase produces RNA transcripts. These transcripts can become templates for further rounds of TMA in the presence of a second primer capable of hybridizing to the RNA transcripts. Unlike PCR, LCR or other methods that require heat denaturation, TMA is an isothermal method that uses an RNase H activity to digest the RNA strand of an RNA:DNA hybrid, thereby making the DNA strand available for hybridization with a primer or promoter-primer. Generally, the RNase H activity associated with the reverse transcriptase provided for amplification is used.

In an illustrative TMA method, one amplification primer is an oligonucleotide promoter-primer that comprises a promoter sequence which becomes functional when double-stranded, located 5' of a target-binding sequence, which is capable of hybridizing to a binding site of a target RNA at a location 3' to the sequence to be amplified. A promoter-primer may be referred to as a "T7-primer" when it is specific for T7 RNA polymerase recognition. Under certain circumstances, the 3' end of a promoter-primer, or a subpopulation of such promoter-primers, may be modified to block or reduce primer extension. From an unmodified promoter-primer, reverse transcriptase creates a cDNA copy of the target RNA, while RNase H activity degrades the target RNA. A second amplification primer then binds to the cDNA. This primer may be referred to as a "non-T7 primer" to distinguish it from a "T7-primer". From this second amplification primer, reverse transcriptase creates another DNA strand, resulting in a double-stranded DNA with a functional promoter at one end.

When double-stranded, the promoter sequence is capable of binding an RNA polymerase to begin transcription of the target sequence to which the promoter-primer is hybridized. An RNA polymerase uses this promoter sequence to produce multiple RNA transcripts (i.e., amplicons), generally about 100 to 1,000 copies. Each newly-synthesized amplicon can anneal with the second amplification primer. Reverse transcriptase can then create a DNA copy, while the RNase H activity degrades the RNA of this RNA:DNA duplex. The promoter-primer can then bind to the newly synthesized DNA, allowing the reverse transcriptase to create a double-stranded DNA, from which the RNA polymerase produces multiple amplicons. Thus, a billion-fold isothermic amplification can be achieved using two amplification primers.

For primers or amplification methods that do not require additional functional sequences in the primer (e.g., PCR amplification), the primer sequence includes a target-binding sequence, whereas other methods (e.g., TMA or SDA) include additional specialized sequences adjacent to the target-binding sequence (e.g., an RNA polymerase promoter sequence adjacent to a target-binding sequence in a promoter-primer or a restriction endonuclease recognition sequence for an SDA primer).

It will be appreciated by those skilled in the art that all of the primer and probe sequences of the present disclosure may be either commercially available or synthesized using standard in vitro synthetic methods. Also, it will be appreciated that those skilled in the art could modify primer sequences disclosed herein using routine methods to add additional specialized sequences (e.g., promoter or restriction endonuclease recognition sequences) to make primers susceptible to use in a variety of amplification methods. Similarly, promoter-primer sequences described herein can be modified by removing the promoter sequences to produce amplification primers that are essentially target-binding sequences susceptible to amplification procedures that do not use these additional functional sequences.

By "target sequence" is meant the nucleotide base sequence of a nucleic acid strand, at least a portion of which is capable of being detected using primers and/or probes in the methods as described herein, such as a labeled oligonucleotide probe. Primers and probes bind to a portion of a target sequence, which includes either complementary strand when the target sequence is a double-stranded nucleic acid.

By "equivalent RNA" is meant a ribonucleic acid (RNA) having the same nucleotide base sequence as a deoxyribonucleic acid (DNA) with the appropriate U for T substitution(s). Similarly, an "equivalent DNA" is a DNA having the same nucleotide base sequence as an RNA with the appropriate T for U substitution(s). It will be appreciated by those skilled in the art that the terms "nucleic acid" and "oligonucleotide" refer to molecular structures having either a DNA or RNA base sequence or a synthetic combination of DNA and RNA base sequences, including analogs thereof, which include "abasic" residues.

By "detecting" an amplification product or an amplicon is meant any of a variety of methods for determining the presence of an amplified nucleic acid, such as, for example, hybridizing a labeled probe to a portion of the amplified product. A labeled probe is an oligonucleotide that specifically binds to another sequence and contains a detectable group that may be, for example, a fluorescent moiety, chemiluminescent moiety, radioisotope, biotin, avidin, enzyme, enzyme substrate, or other reactive group. A labeled probe can include an acridinium ester (AE) moiety that can be detected chemiluminescently under appropriate conditions (as described, e.g., in U.S. Pat. No. 5,283,174).

Other well-known detection techniques include, for example, gel filtration, gel electrophoresis and visualization of the amplicons, and High Performance Liquid Chromatography (HPLC). The detecting step may either be qualitative or quantitative.

Assays for purifying and detecting a target polynucleotide often involve capturing a target polynucleotide on a solid support. The solid support retains the target polynucleotide during one or more washing steps of a target polynucleotide purification procedure. One technique involves capture of the target polynucleotide by a polynucleotide fixed to a solid support and hybridization of a detection probe to the captured target polynucleotide (e.g., U.S. Pat. No. 4,486,539). Detection probes not hybridized to the target polynucleotide are readily washed away from the solid support. Thus, remaining label is associated with the target polynucleotide initially present in the sample.

Another technique uses a mediator polynucleotide that hybridizes to both a target polynucleotide and a polynucleotide fixed to a solid support such that the mediator polynucleotide joins the target polynucleotide to the solid support to produce a bound target (e.g., U.S. Pat. No. 4,751,177). A labeled probe can be hybridized to the bound target and unbound labeled probe can be washed away from the solid support.

The primers and probes of the present disclosure may be used in amplification and detection methods that use nucleic acid substrates isolated by any of a variety of well-known and established methodologies (e.g., Sambrook et al., Molecular Cloning, A laboratory Manual, $2^{nd}$ ed., pp. 7.37-7.57 (Cold Spring Harbor Laboratory Press, Cold Spring Harbor, N.Y., 1989); Lin et al., "Simple and Rapid Sample Preparation Methods for Whole Blood and Blood Plasma" in Diagnostic Molecular Microbiology, Principles and Applications, pp. 605-616 (Persing et al., Eds., American Society for Microbiology, Washington, D.C., 1993).

In one illustrative example, the target mRNA may be prepared by the following procedure to yield mRNA susceptible to use in amplification. Briefly, a tissue sample or cell (e.g., peripheral blood or bone marrow cells) are lysed by contacting the cell suspension with a lysing solution containing at least about 150 mM of a soluble salt, such as lithium halide, a chelating agent and a non-ionic detergent in an effective amount to lyse the cellular cytoplasmic membrane without causing substantial release of nuclear DNA or RNA.

The cell suspension and lysing solution are mixed at a ratio of about 1:1 to 1:3. The detergent concentration in the lysing solution is between about 0.5-1.5% (v/v). Any of a variety of known non-ionic detergents are effective in the lysing solution (e.g., TRITON®-type, TWEEN®-type, and NP-type); typically, the lysing solution contains an octylphenoxy polyethoxyethanol detergent, preferably 1% TRITON® X-102.

This procedure may be used advantageously with leukemia tissue sample that contain cell suspensions (e.g., blood and bone marrow), but it works equally well on other tissues if the cells are separated using standard mincing, screening and/or proteolysis methods to separate cells individually or into small clumps.

After cell lysis, the released total RNA is stable and may be stored at room temperature for at least 2 hours without significant RNA degradation without additional RNase inhibitors. Total RNA may be used in amplification without further purification or mRNA may be isolated using standard methods generally dependent on affinity binding to the poly-A portion of mRNA.

In certain aspects of the present disclosure, mRNA isolation employs capture particles that include poly-dT oligonucleotides attached to insoluble particles. The capture particles are added to the above-described lysis mixture, the poly-dT moieties annealed to the poly-A mRNA, and the particles separated physically from the mixture. Generally, superparamagnetic particles may be used and separated by applying a magnetic field to the outside of the container. For example, a suspension of about 300 μg of particles (in a standard phosphate buffered saline (PBS), pH 7.4, of 140 mM NaCl) having either $dT_{14}$ or $dT_{30}$ linked at a density of about 1 to 100 pmoles/mg, or 10 to 100 pmols/mg, or from 10 to 50 pmols/mg are added to about 1 ml of lysis mixture.

Any superparamagnetic particles may be used, although typically the particles are a magnetite core coated with latex or silica (e.g., commercially available from Serodyn or Dynal) to which poly-dT oligonucleotides are attached using standard procedures (Lund et al., Nuc. Acids Res. 16:10861-10880 (1988)). The lysis mixture containing the particles is gently mixed and incubated at about 22-42° C. for about 30 minutes, when a magnetic field is applied to the outside of the tube to separate the particles with attached mRNA from the mixture and the supernatant is removed. The particles are washed one or more times, generally three, using standard resuspension methods and magnetic separation as described above. Then, the particles are suspended in a buffer solution and can be used immediately in amplification or stored frozen.

A number of parameters may be varied without substantially affecting the sample preparation. For example, the number of particle washing steps may be varied or the particles may be separated from the supernatant by other means (e.g., filtration, precipitation, centrifugation). The solid support may have nucleic acid capture probes affixed thereto that are complementary to the specific target sequence or any particle or solid support that non-specifically binds the target nucleic acid may be used (e.g., polycationic supports as described, for example, in U.S. Pat. No. 5,599,667).

For amplification, the isolated RNA is released from the capture particles using a standard low salt elution process or amplified while retained on the particles by using primers that bind to regions of the RNA not involved in base pairing with the poly-dT or in other interactions with the solid-phase matrix. The exact volumes and proportions described above are not critical and may be varied so long as significant release of nuclear material does not occur. Vortex mixing is preferred for small-scale preparations but other mixing procedures may be substituted. It is important, however, that samples derived from a leukemia patient tissue or a non-leukemia control donor tissue be treated to prevent coagulation and that the ionic strength of the lysing solution be at least about 150 mM, preferably 150 mM to 1 M, because lower ionic strengths lead to nuclear material contamination (e.g., DNA) that increases viscosity and may interfere with amplification and/or detection steps to produce false positives. Lithium salts are preferred in the lysing solution to prevent RNA degradation, although other soluble salts (e.g., NaCl) combined with one or more known RNase inhibitors would be equally effective.

Alternatively, amplification techniques, such as those described above, can be useful for obtaining at least a portion of one or more NPM1, DNMT3A, IDH1, IDH2, RUNX1, TET2, and/or ASXL1 gene and/or a NUP98-NSD1 or other NUP98 translocation. One such amplification technique is inverse PCR (see Triglia et al., Nucl. Acids Res. 16:8186 (1988)), which uses restriction enzymes to generate a fragment in the known region of the gene. The fragment is then circularized by intramolecular ligation and used as a template for PCR with divergent primers derived from the known region.

Within an alternative approach, sequences adjacent to a partial sequence may be retrieved by amplification with a primer to a linker sequence and a primer specific to a known region. The amplified sequences are typically subjected to a second round of amplification with the same linker primer and a second primer specific to the known region. A variation on this procedure, which employs two primers that initiate extension in opposite directions from the known sequence, is described in PCT Patent Publication No. WO 1996/038591.

Another such technique is "rapid amplification of cDNA ends" or RACE, which uses an internal primer and an external primer, which hybridizes to a sequence that is 5' or 3' of a known sequence. Additional techniques include capture PCR (Lagerstrom et al., *PCR Methods Applic.* 1:111-119 (1991)) and walking PCR (Parker et al., *Nucl. Acids. Res.* 19:3055-3060 (1991)). Other methods employing amplification may also be employed to obtain a full length cDNA sequence.

A wide variety of labels and conjugation techniques are known by those skilled in the art and may be used in various nucleic acid assays. Means for producing labeled hybridization or PCR probes for detecting sequences related to polynucleotides include oligolabeling, nick translation, end-labeling or PCR amplification using a labeled nucleotide. Alternatively, the sequences, or any portions thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits. Suitable reporter molecules or labels, which may be used include radionuclides, enzymes, fluorescent, chemiluminescent, or chromogenic agents as well as substrates, cofactors, inhibitors, magnetic particles, and the like.

Nucleic Acid Sequencing

Chain termination methods were first developed by Frederick Sanger, and can be referred to as Sanger sequencing methods. In chain termination methods, four PCR reactions are performed wherein each reaction is spiked with a single dideoxynucleotide (ddNTP), which is a nucleotide lacking a 3' hydroxyl group (e.g., ddATP, ddTTP, ddCTP, ddGTP). When a ddNTP is incorporated into a nascent chain of DNA, synthesis of the nascent chain is halted; this generates a mixture of variable length oligonucleotides that can be resolved by size using, for example, DNA electrophoresis in a slab gel or capillary. Any number of detection methods can be used to read the DNA sequence as determined by the relative lengths of oligonucleotides in each of the four reactions, for example, autoradiography, UV light detection, or fluorescent dye detection. Dye termination methods are a variation of chain termination methods whereby each type of ddNTP (e.g., ddATP, ddTTP, ddCTP, ddGTP) is labeled with a different color fluorescent dye. This enables DNA to be sequenced in a single PCR reaction.

Massively Parallel Signature Sequencing (MPSS) is a high-throughput sequencing method that can be used in the methods disclosed herein. It is a bead-based method that utilized adapter ligation followed by adapter decoding to generated hundreds of thousands of short DNA sequences. Further information on this technology can be found in Brenner et al., Nat Biotechnol. 18(6):630-634 (2000); Reinartz et al., *BriefFunct Genomic Proteomic.* 1(1):95-104 (2002); and U.S. Pat. No. 6,013,445.

Polony sequencing is another high throughput sequencing technology that can be used according to the methods disclosed herein. Polony sequencing combines emulsion PCR, an automated microscope, and ligation-based sequencing chemistry. Further information on this technology can be found in U.S. Patent Publication Nos. 2009/0318298, 2011/0172127, 2010/0047876, and 2009/0099041 and U.S. Pat. No. 7,425,431.

454 pyrosequencing is a high-throughput sequencing method that can be used in the methods disclosed herein. In 454 pyrosequencing, DNA is amplified inside water droplets in an oil solution (emulsion PCR), with each droplet containing a single DNA template attached to a single primer-coated bead, forming a clonal colony. The sequencing machine contains many picoliter-volume wells, each containing a single bead and sequencing enzymes. Luciferase generated light is used to detect individual nucleotides added to the nascent DNA, and the combined data are used to generate sequence read-outs. Further information on this technology can be found in U.S. Pat. Nos. 6,210,891 and 7,648,824.

A high-throughput sequencing method that can be useful in the methods disclosed herein is the sequencing by synthesis (SBS) technology (Illumina®, San Diego, Calif.), which utilizes reversible dye-terminators. Single stranded polynucleotides are first attached to primers on a slide and amplified so that local clonal colonies are formed. Four differentially labeled ddNTPs are added, extending the nascent polynucleotides by one base-pair, after which the non-incorporated nucleotides are washed away. An image of the slide is recorded and the terminal nucleotide for each nascent DNA molecule is determined based upon the color of the fluorescent signal. Then, the dye and the terminal 3' blocker are chemically removed from the DNA, allowing the next cycle. More information on this technology can be found in U.S. Pat. Nos. 7,985,565; 7,115,400; 7,972,820; and 7,790,418 and U.S. Patent Publication Nos. 2008/0286795, 2002/0055100, and 2007/0015200.

SOLiD (Sequencing by Oligonucleotide Ligation and Detection) sequencing is another high-throughput sequencing method that can be used in the methods disclosed herein. (Applied Biosystems). This method involves multiple rounds of sequencing by ligation, wherein each ligation probe is eight-bases long and each base is effectively probed in two ligation reactions. Base calls are made based upon fluorescence data captured by a camera. More information on this technology can be found in U.S. Patent Publication No. 2009/0181860 and U.S. Pat. No. 7,851,158.

Ion semiconductor sequencing can be a useful high-throughput sequencing technology according to the methods disclosed herein. In ion semiconductor sequencing, the hydrogen ions that are released during polymerization of DNA are detected. A microwell containing a single template DNA strand is flooded with a single polynucleotide, which is incorporated into a nascent strand of DNA if it is complementary to the leading nucleotide of the template strand. The level of hydrogen detected can be used to detect insertion of more than one nucleotide, for example in regions of polynucleotide repeat. Further information on this technology can be found in U.S. Pat. Nos. 7,242,241; 7,888,015; 7,649,358; 7,686,929; and 8,114,591 and U.S. Patent Publication No. 2010/0159461.

DNA nanoball sequencing is another useful high-throughput sequencing technique that can be utilized in the methods disclosed herein. In this technology, rolling circle replication is used to generate DNA nanoballs from DNA fragments. Then, the DNA nanoballs can be anchored into a microarray flow cell, where a process termed unchained sequencing by ligation is used to generate reads about 10 by in length (Complete Genomics). Further information can be found in U.S. Patent Publication Nos. 2009/0011943, 2009/0270273, 2011/0268347, and 2009/0264299.

According to the methods disclosed herein, paired-end tag libraries can be constructed from polynucleotides (e.g., DNA, RNA, mRNA, cDNA, etc.) derived from a tissue sample and used in the high-throughput sequencing technology to increase the speed and/or accuracy sequence assembly. Nucleotides can be sequenced utilizing capture-based technology; alternatively, nucleotides can be sequenced after amplification by PCR. Nucleotides can be treated with bisulfites prior to sequencing in order to identify methylated sequences. Methylation specific PCR can be utilized prior to sequencing in order to determine whether specific loci are methylated. Polynucleotides derived from a leukemia sample can be sequence using paired-end whole exome sequencing (WES), shallow mate-pair whole genome sequencing (sMP-WGS), and/or paired-end RNA sequencing (RNAseq). Polynucleotides derived from a leukemia sample can be sequenced using Illumina® sequencing.

Fluorescent In Situ Hybridization

Mutations in one or more of a NPM1, DNMT3A, IDH1, IDH2, RUNX1, TET2, and/or ASXL1 genomic sequence and/or a NUP98-NSD1 or other NUP98 translocation within a leukemia tissue sample or cell can be detected by fluorescent in situ hybridization (FISH).

FISH is a cytogenetic technique that can be used to detect and localize the presence or absence of specific DNA sequences on chromosomes. FISH uses fluorescently-tagged nucleic acid probes that bind to only those parts of the chromosome with which they show a high degree of sequence complementarity. Thus, FISH can be employed to localize specific nucleotide sequences within a tissue or cell (e.g., on a particular chromosome or within a particular cell). Thus, FISH can be utilized to permit karyotype analysis and the detection of translocations, rearrangements, duplications, and copy number variations through the gain or loss of chromosomal material that include one or more of a NPM1, DNMT3A, IDH1, IDH2, RUNX1, TET2, and/or ASXL1 genomic sequence and/or a NUP98-NSD1 or other NUP98 translocation. FISH can also be used to detect and localize specific RNA targets, including mRNA, in leukemia tissues and cells and can be used to define spatial-temporal patterns of gene expression within leukemia tissues and cells.

FISH can also be utilized to localize mRNAs within a tissue or cell, thereby detecting expression of a gene, such as a gene carrying a mutation associated with leukemia including a mutation in one or more of a NPM1, DNMT3A, IDH1, IDH2, RUNX1, TET2, and/or ASXL1 genomic sequence and/or a NUP98-NSD1 or other NUP98 translocation.

Probes that are susceptible to use with FISH technology can be designed for detecting one or more mutations in one or more of a NPM1, DNMT3A, IDH1, IDH2, RUNX1, TET2, and/or ASXL1 genomic sequence and/or a NUP98-NSD1 or other NUP98 translocation and/or for visualization of an mRNA that is encoded by one or more of a NPM1, DNMT3A, IDH1, IDH2, RUNX1, TET2, and/or ASXL1 genomic sequence and/or a NUP98-NSD1 or other NUP98 translocation in a leukemia tissue sample or cell.

Suitable probes contain duplexes of at least about 20 consecutive nucleotides of one or more of a NPM1, DNMT3A, IDH1, IDH2, RUNX1, TET2, and/or ASXL1 genomic sequence and/or a NUP98-NSD1 or other NUP98 translocation and can be derived from PCR amplicons generated by amplification of a region within one or more of those genomic sequences. Probes must be large enough to hybridize specifically with its target sequences but not so large as to impede hybridization process or to bind non-specifically to non-target sequences. A mixture of probe sequences that hybridize along an entire chromosome can be used to detect gene translocations or to identify extra-chromosomal fragments of chromatin. Fluorescent tagging of probes can be achieved by nick translation of by PCR using tagged nucleotides.

Formalin-fixed paraffin-embedded (FFPE) or frozen tissue sections are fixed, then permeabilized to allow target accessibility. Interphase or metaphase chromosomes are prepared and attached to a solid substrate, such as a glass slide. A probe is then applied to the chromosome DNA and incubated for approximately 12 hours to permit hybridization of the target-specific probe to the target mRNA(s) and/or genomic DNA(s). Several wash steps remove unhybridized or partially hybridized probes. Target-specific hybridization is then visualized and/or quantified via fluorescent microscopy, which employs technologies to exciting the fluorescent dye and record images.

A mixture of smaller probes that are specific to a particular region (locus) of DNA can be used to detect deletion mutations. When combined with a specific color, a locus-specific probe mixture is used to detect very specific translocations.

QuantiGene ViewRNA FISH is a technique for detecting and quantifying RNA molecules in tissue samples and cells that are formalin-fixed paraffin-embedded (FFPE). ViewRNA FISH probes allow single molecule RNA sensitivity with virtually no background. Each oligonucleotide pair forms a platform for assembly of a signal amplification structure (tree) through a series of sequential hybridization steps using branched DNA (bDNA) signal amplification technology. Each fully-assembled structure, covers a space of 40-50 bit/s of the target nucleic acid, and has the capacity for 400-fold signal amplification.

Stellaris FISH, (a/k/a Single Molecule RNA FISH) is a method of detecting and quantifying mRNA and other long RNA molecules in a thin tissue sample. Targets can be reliably imaged through the application of multiple short singly labeled oligonucleotide probes. The binding of up to 48 fluorescently-labeled oligonucleotides to a single molecule of mRNA provides sufficient fluorescence to accurately detect and localize each target mRNA in a wide-field fluorescent microscopy image. Probes that do not bind to an intended nucleotide sequence do not achieve sufficient localized fluorescence to be distinguished from background. Single-molecule RNA FISH assays can be performed in simplex or multiplex and can be used as a follow-up experiment to quantitative PCR or imaged simultaneously with a fluorescent antibody assay.

Fiber FISH is a technique in which interphase chromosomes are attached to a slide in such a way that they are stretched out in a straight line, rather than being tightly coiled, as in conventional FISH, or adopting a random conformation, as in interphase FISH. This is accomplished by applying mechanical shear along the length of the slide (e.g., by chromosome combing), either to cells that have been fixed to the slide and then lysed, or to a solution of purified DNA. The extended conformation of the chromosomes allows dramatically higher resolution, even down to a few kilobases.

Following are exemplary applications of the techniques described herein as well as other techniques known and available in the art for the detection of mutations within genomic sequences. In particular, the following describes the detection of MLL-translocations and MLL-partial tandem duplications as well as a variety of mutations within one or more of the NPM1, DNMT3A, IDH1, IDH2, RUNX1, TET2, and/or ASXL1 genomic sequences and/or a NUP98-NSD1 or other NUP98 translocations disclosed herein. One skilled in the art will recognize that the various techniques described herein can be broadly applied to other genes and other mutations by adapting the techniques described and exemplified herein.

MLL-Translocations and MLL-Partial Tandem Duplications (PTDs)

Gene expression profiles of lymphoblastic leukemias that possess an MLL-translocation and MLL-partial tandem duplications (PTDs) are remarkably consistent, differ significantly from those of other leukemias, and are considered a distinct disease that is referred to as MLL for "Mixed Lineage Leukemia." Methodology for detecting MLL-translocations are described in U.S. Patent Publication No. 2006/0057630. Evaluation of expression profiles using principal component analysis distinguishes MLL from conventional ALL and also AML. A subset of human acute leukemias with a decidedly unfavorable prognosis possess a chromosomal translocation involving the Mixed Lineage Leukemia (MLL, HRX, A U-1) gene on chromosome segment 11q23. A DNA segment spanning the human MLL-gene translocation breaking point is provided as SEQ ID NO: 25.

Methodology for detecting MLL-primary tandem duplications (PTDs) is described in US Patent Publication No. 20070212687; Whitman et al., *Blood* 106:345-352 (2005); and Caligiuri et al., *Cancer Res.* 58:55-59 (1998). Such PTDs have been described, e.g., in Strout, M. P., et al. *PNAS (USA)* 95:2390-2395, (1998), incorporated by reference. Methodology for screening for MLL-PTD include nested RT-PCR and Southern blotting. Conventional nested reverse transcription-polymerase chain reaction (RT-PCR) can be performed as previously described by Caligiuri et al., *Cancer Res.* 56(6):1418-1425 (1996). Cloned PCR products can then be sequenced.

MLL-PDT can also be detected by quantitative real-time RT-PCR (QRT-PCR). Primer pairs and dual-labeled probe sets are designed to amplify sites that are unique to the MLL-PTD or common to both MLL PTD and MLL WT transcripts. Primer and probe sets can be designed to amplify the "unique amplicons" exon 11 to exon 5 or exon 12 to exon 5 fusions specific for the 2 most common forms of the MLL PTD, and to amplify the "common amplicons" exon 11 to exon 12, exon 13 to exon 14, and exon 26 to exon 27 junctions that can be found in both the MLL-PTD and the MLL WT transcripts. Standard curves can be constructed to allow for measurement of target amplicon copy numbers. QRT-PCR data can then be collected using the ABI Prism 7700 Sequence Detection System (PE Applied Biosystems, Foster City, Calif.).

Immunoblotting analysis for detection of the p300-kDa MLL WT and p420-kDa MLL PTD N-terminal fragments can be carried out as described by Nakamura et al., *Mol. Cell.* 10:1119-1128 (2002). Briefly, nuclear extracts are size fractionated in a 4.9% sodium dodecyl sulfate-polyacrylamide gel electrophoresis (SDS-PAGE). After transfer, membranes are probed with anti-MLL 170 antibody, an affinity-purified anti-MLL antibody directed against the N-terminal p300 MLL WT posttranslational cleavage product. Proteins can be visualized using enhanced chemiluminescence Plus (Amersham-Pharmacia, Piscataway, N.J.).

MLL 5'-CpG islands can be identified using the algorithm described in http://www.ebi.ac.uk/emboss/cpgplot/ and MLL genomic sequence (NCBI GenBank Accession No. NT033899.6). Methylation status can be assessed by bisulfite PCR sequencing (BS-PCR) of genomic DNA as previously described. Frommer et al., *Proc. Natl. Acad. Sci. USA*. (1992). PCRs can be optimized to minimize the potential for bias toward amplification of nonmethylated sequences. Single PCR products can then be purified from the agarose gel, cloned into the pCR2.1 cloning vector (Invitrogen, Carlsbad, Calif.), and sequenced. In the present example, a minimum of 10 clones per PCR would be evaluated.

An MLL-specific primer pair is designed to amplify a region upstream of the transcriptional initiation site in MLL (nucleotides −168 to −2). For normalization, ChIP analysis of the housekeeping gene such as GAPDH, can be performed using GAPDH promoter-specific primers previously described in Barlev et al., *Mol Cell.* 8:1243-1254 (2001). PCR conditions can be optimized such that products are detected during the exponential phase of amplification. Relative quantification can be carried out using SybrGreen-dye and real-time PCR. The comparative real-time PCR ($2^{-\Delta\Delta C_T}$) method can be used, normalizing first to input DNA followed by depsipeptide-treated levels relative to control levels.

NPM1 Mutations

Mutations in nucleophosmin NPM1 are the most frequent acquired molecular abnormalities in acute myeloid leukemia (AML). Mutations in exon 12 of the gene encoding NPM1 in approximately 35% of cases of de novo AML and typically include a four nucleotide insertion that results in a frame shift and consequent replacement of the 7 C-terminal amino acids of the NPM1 protein by 11 different residues. It has been suggested that the disruption of 1 of the 2 C-terminal tryptophan residues and the last 5 residues (i.e., VSLRK) the final 9 amino acids (i.e., AVEEVSPLRK) are important for NPM1 mutant function. Falini et al., *N. Engl. J. Med.* 352:254-266 (2005) and Verhaak et al., *Blood* 106(12):3747-3754 (2005).

Mutations in NPM1 can be detected by a variety of methodologies that are well known in the art as exemplified by those methodologies described in Verhaak et al., *Blood* 106(12):3747-3754 (2005). RNA can be isolated from leukemia cells and cDNA synthesis performed as previously described. Valk el al., *N. Engl. J. Med.* 350:1617-1628 (2004) and Van der Reijden and van der Poel et al., *Hematol. J.* 2:206-209 (2001).

NPM1 mutations in exon 12 can, for example, be determined by polymerase chain reaction (PCR) amplification using the primers NPM1-FOR 5'-CTTCCGGATGACT-GACCAAGAG-3' and primer NPM1-REV 5'-CCTGGA-CAACATTTATCAAACACG-3' in a reaction containing 25 mM deoxyribonucleoside triphosphate [dNTP], 15 pmol primers, 2 mM MgCl$_2$, Taq polymerase, and 10× buffer [Invitrogen Life Technologies, Breda, The Netherlands]). Cycling conditions for NPM1 mutation detection can include 1 cycle, 5 minutes at 94° C.; 30 cycles, 1 minute at 94° C., 1 minute at 58'C, and 1 minute at 72° C.; and 1 cycle, 7 minutes at 72'C.

PCR products can be subjected to dHPLC using a Transgenomics (Omaha, Nebr.) WAVE dHPLC system (Choy et al., *Ann. Hum. Genet.* 63(pt 5):383-391 (1999)) and samples run at 56'C and 58° C. The exact NPM1 mutant sequence can be confirmed for samples showing an abnormal high-performance liquid chromatography (dHPLC) profile and PCR. products can be purified using the Multiscreen-PCR 96-well system (Millipore, Bedford, Mass.) followed by direct sequencing with NPM1-REV using an ABI-PRISM3100 genetic analyzer (Applied Biosystems. Foster City, Calif.). Each NPM1 mutation variant reveals a specific dHPLC WAVE profile. Thus, each type of NPM1 mutation could be predicted on the basis of a specific dHPLC WAVE profile.

Gene expression profiling is a powerful way to comprehensively classify individuals with AML and to further resolve the heterogeneous nature of AML. Valk et al., *Curr. Opin. Hematol.* 12:76-81 (2005). The effect of mutant NPM1 has been studied using gene expression profiling and revealed a distinctive signature for NPM1 mutations. Alcalay et al., *Blood* 106:899-902 (2005). AML cases with an NPM1 mutation cluster in specific subtypes of AML with previously established gene expression signatures, are highly associated with a homeobox gene-specific expression signature, and can be predicted with high accuracy. Among players in this signature were several homeodomain-containing family members of homeobox (HOX) transcription factors.

Leukemia cells can also be analyzed by gene expression profiling and unsupervised cluster analyses using Affymetrix HGU133A GeneChips (Affymnetrix, Santa Clara, Calif.). Valk et al., *N Engl J Med.* 350:1617-1628 (2004). Unsupervised cluster analysis on the basis of the gene expression profiles can be performed using the correlation view tool (version 3.6) of OmniViz (Maynard, Mass.). The Pearson correlation values calculated in OmniViz can be imported into the MicroArray Data Explorer (MADEx) and used to visualize the relations between the OmniViz unsupervised clustering results and other parameters, such as clinical and molecular characteristics of the cells from leukemia patients. MADEx is a database system that stores, mines, and visualizes microarray data in a secure and scalable manner.

A dominant homeobox (HOX) gene-specific signature is strongly associated with AML carrying an NPM1 mutation. Moreover, the expression of members of the HOXA and HOXB gene families, but also the HOX gene-related three-amino acid loop extension (TALE) genes, PBX3 and MEIS1, is increased.

NPM1 mutation prediction analyses can be performed using a PAM algorithm. Tibshirani et al., *Proc Natl Acad Sci USA.* 99:6567-6572 (2002). AML samples are randomly assigned to a training set, consisting of samples without NPM1 mutations and samples with NPM1 mutations, and a validation series, consisting of samples lacking the NPM1 mutation and samples with mutations in NPM1. Cross-validation can be used to predict the mutation status of NPM1 on the training set NPM1 mutant AML cases have a distinct signature and are, therefore, predicted with high accuracy. AML cases with mutant NPM1 exhibit a strong HOX gene-specific SAM and PAM signatures. Previous studies have demonstrated for a number of HOX genes that sustained overexpression and coexpression with the protein binding partner MEIS1, results in leukemia. Daser and Rabbitts, *Semin. Cancer Biol.* 15:175-188 (2005).

NUP98-NSD1 Translocations

In AML, the recurring t(5;11)(q35;p15.5) translocation fuses nuclear receptor-binding SET domain-containing protein 1 (NSD1) to nucleoporin 98 (NUP98). Cerveira et al., *Leukemia* 17:2244-2247 (2003). NUP98-NSD1 was shown to induce AML in vivo and sustain self-renewal of myeloid stem cells in vitro. Wang et al., *Nat Cell Biol* 9:804-812 (2007).

Mechanistically, the NUP98-NSD1 complex binds genomic elements adjacent to HOXA7 and HOXA9, and maintains EZH2-mediated transcriptional repression of the HOXA locus during differentiation through regulation of histone H3 Lys 36 (H3K36) methylation and histone acetylation. Wang et al., *Nat Cell Biol* 9:804-812 (2007). Either deletion of the NUP98 FG-repeat domain or mutations in NSD1 that lead to inactivation of the methyltransferase activity, preclude both HOXA gene activation and myeloid progenitor immortalization, indicating that the methyltransferase activity of NSD1 is likely to play a critical role in tumorigenesis.

In a NUP98-NSD1 translocation, the NUP98 and NSC1 mRNA are fused in-frame joining nucleotides 1552 of NUP98 to nucleotide 3506 of NSD1. The reciprocal transcript fuses NSD1 and NUP98 mRNA in-frame joining nucleotide 3505 of NSD1 to nucleotide 1553 of NUP98.

NUP98-NSD1 translocation can be detected by polymerase chain reaction (PCR) amplification using the sense NUP98-5 (5'-TCTTGGTACAGGAGCCTTTG-3'), and antisense NSD1-1 (57'CCAAAAGCCACTTTGCTTGGC-3') primers in a reaction containing 25 mM deoxyribonucleoside triphosphate [dNTP], 15 pmol primers, 2 mM $MgCl_2$, Taq polymerase, and 10× buffer [Invitrogen Life Technologies, Breda, The Netherlands]). Cycling conditions for NPM1 mutation detection can include 1 cycle, 5 minutes at 94° C.; 30 cycles, 1 minute at 94° C., 1 minute at 58° C., and 1 minute at 72° C.; and 1 cycle, 7 minutes at 72° C.

DOT1L Inhibitors

DOT1L inhibitors that may be suitably employed in the presently disclosed methods for treating leukemia patients with a DOT1L inhibitor are generally disclosed in US Patent Publication No. 2012/0142625 and PCT Patent Publication Nos. WO 2012/075381; WO 2012/075492; WO 2012/075500; and WO 2012/082436; Yu et al., *Nat. Commun.* 3:1288 (2013); Yu et al., *Nat. Commun.* 4:1893 (2013); Yu et al., *Bioorg. Med. Chem.* 21(7):1787-1794 (2013); Yao et al., *J. Am. Chem. Soc.* 133(42):16746-16749 (2011); Basavapathruni et al., *Chem. Biol. Drug Des.* 80(6):971-980 (2012); and Daigle et al., *Cancer Cell* 20(1):53-65 (2011). Each of these references, as well as all other references disclosed herein, is incorporated herein by reference in its entirety. Several DOT1L inhibitors are commercially available including EPZ005676; EPZ004777; SGC-0946; SYC-522; SYC-534; SYC-687 and others commercially available, e.g., from Selleckchem, Boston, Mass. or from Otava Chemicals, Inc. Vaughan, Ontario.

DOT1L inhibitors susceptible to use in the methods disclosed herein inhibit DOT1L with an IC50 of from about 100 nM to about 10 µM or from about 250 nM to about 5 µM or from about 500 nM to about 1 µM and include the purine, 7-deazapurine, and carbocycle-substituted purine compounds described herein, which are exemplified by EPZ004777 (1-(3-(((((2R,3S,4R,5R)-5-(4-Amino-7H-pyrrolo[2,3-d]pyrimidin-7-yl)-3,4-dihydroxytetrahydrofuran-2-yl)methyl)(isopropyl)amino) propyl)-3-(4-(tert-butyl)phenyl)urea) and EPZ005676 (9H-Purin-6-amine, 9-[5-deoxy-5-[[cis-3-[2-[6-(1,1-dimethylethyl)-1H-benzimidazol-2-yl] ethyl]cyclobutyl](1-methylethyl)amino]-β-D-ribofuranosyl]-).

DOT1L inhibitors that may be suitably employed in the presently disclosed methods for inhibiting the proliferation and/or survival of cell and for treatment of leukemia patients include the 7-deazapurine compounds as described in WO 2012/075500 and WO/2012/082436 as represented by Formula I:

Formula I

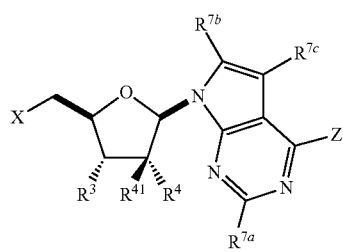

DOT1L inhibitors that may be suitably employed in the presently disclosed methods for inhibiting the proliferation and/or survival of cell and for treatment of leukemia patients include carbocycle-substituted purine and 7-deazapurine compounds as described in WO 2012/075492 as represented by Formula II:

Formula II

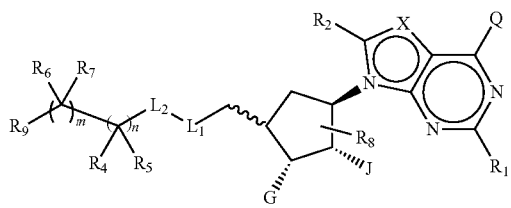

DOT1L inhibitors that may be suitably employed in the presently disclosed methods for inhibiting the proliferation and/or survival of cell and for treatment of leukemia patients include purine and 7-deazapurine compounds as described in US 2012/0142625 and WO 2012/075381 as represented by Formula III:

Formula III

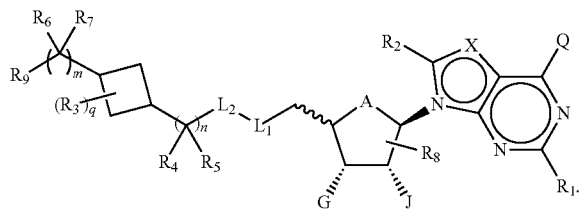

Compounds that are encompassed within the range of compounds defined by Formulas I, II, and III, and methodologies for the synthesis of those compounds, are presented in U.S. Patent Publication No. 2012/0142625 and PCT Patent Publication Nos. WO 2012/075381; WO 2012/075492; WO 2012/075500; and WO 2012/082436. Two exemplary such compounds are EPZ004777 and EPZ005676, which are presented in the following section along with a description of methodologies for synthesizing those compounds from readily available starting materials (e.g., Sigma-Aldrich, St. Louis, Mo.).

EPZ004777

The small molecule DOT1L inhibitor EPZ004777 is an s-adenosyl methionine mimetic is highly specific for DOT1L as compared to other methyl transferases. Daigle et al., *Cancer Cell* 20(1):53-65 (2011) and Yu et al., *Nat. Commun.* 3:1288 (2013). EPZ004777 binds within the S-(5'-adenosyl)-1-methionine (SAM) binding site in the catalytic domain of human DOT1L.

EPZ004777 binds to DOT1L with a $K_i$ value of 0.3 nM and exhibits >1,000-fold selectivity for DOT1L as compared to other methyltransferases tested, as measured biochemically in vitro and in cells. Daigle further confirmed highly selective antiproliferative, differentiating, and apoptotic activities of EPZ004777 toward leukemia cells harboring MLL fusions that correlate with transcriptional repression of the key leukemogenic MLL fusion target genes HOXA9 and MEIS1. Leukemic cells lacking MLL fusions are less sensitive to EPZ004777 by a factor of approximately 100. This in vitro selectivity translates to the targeting of leukemic cells in mouse models of mixed-lineage leukemia, which results in prolonged survival.

The chemical structure of EPZ004777 (1-(3-(((2R,3S,4R,5R)-5-(4-Amino-7H-pyrrolo[2,3-d]pyrimidin-7-yl)-3,4-dihydroxytetrahydrofuran-2-yl)methyl)(isopropyl)amino)propyl)-3-(4-(tert-butyl)phenyl)urea) is presented as Formula XIV:

Formula IV

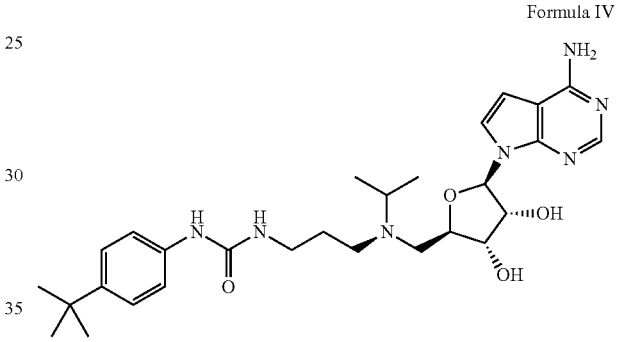

The synthesis of EPZ004777 (1-(3-((((2R,3S,4R,5R)-5-(4-Amino-7H-pyrrolo[2,3-d]pyrimidin-7-yl)-3,4-dihydroxytetrahydrofuran-2-yl)methyl)(isopropyl)amino)propyl)-3-(4-(tert-butyl)phenyl)urea) is described in PCT Patent Publication No. WO 2012/075500.

Step 1: Synthesis of (2R,3R,4S,SR)-2-(4-((2,4-dimethoxybenzyl)amino)-7H-py pyrrolo[2,3-d]pyrimidin-7-yl)-S-(hydroxymethyl)tetrahydrofuran-3,4-diol A suspension of 7-chloro tubercidin (1.67 g, 5.84 mmol) in 1-butanol (16.0 ml) is treated with N,N-diisopropylethylamine (1.22 ml, 7.01 mmol) and 1-(2,4-dimethoxyphenyl)methanamine (1.05 ml, 7.01 mmol) and heated at 100-110° C. overnight. After 20 h, LCMS indicated a new product forms and the starting material is consumed. The mixture is cooled to room temperature and the solvent removed under high vacuum. The material is purified by flash chromatography (200 g silica gel; 5-10% MeOH/CH$_2$Cl$_2$) to yield the title compound (2.19 g, 90%) as a foam: MS (ESI+) for C20H24N4O6 m/z 417.1 (M+H)+; (ESI−) for C20H24N4O6 m/z 415.2 (M−H)⁻; HPLC purity 97% (ret. time, 2.41 min).

Step 2: ((3aR,4R,6R,6aR)-6-(4-((2,4-dimethoxybenzyl)amino)-7H-pyrrolo[2,3-d]pyrimidin-7-yl)-2,2-dimethyltetrahydrofuro[3,4-d][1,3]dioxol-4-yl)methanol A solution of (2R,3R,4S,5R)-2-(4-((2,4-dimethoxybenzyl)amino)-7H-pyrrolo[2,3-d]pyrimidin-7-yl)-5-(hydroxymethyl)tetrahydrofuran-3,4-diol (3.30 g, 7.45 mmol) in acetone (76.5 ml) and 2,2-dimethoxypropane (16.5 ml, 134 mmol) is treated with 10-camphorsulfonic acid (1.73 g, 7.44 mmol) in one portion and the reaction is allowed to stir at room temperature. After 1 h, all SM is consumed by HPLC. The reaction is quenched by the addition of sodium bicarbonate (1.88 g, 22.3 mmol) and the reaction mixture is stirred for 30 minutes during which time a precipitate formed. The reaction mixture is partitioned between 200 ml CHCl3 and 75 ml H2O. The mixture is diluted with 15 ml brine, extracted and the phases separated. The aqueous phase is washed twice with 50 ml portions of CHCl3 and the combined organic phase is dried over Na2SO4. The solution is filtered and concentrated to yield a foam. The crude product is taken up in methanol (130 ml, 3200 mmol) and treated with p-toluenesulfonic acid monohydrate (1.27 g, 6.70 mmol) in one portion. The mixture is stirred at room temperature for 2 h upon which time the reaction mixture is quenched with sodium bicarbonate (1.88 g, 22.3 mmol) and the mixture is stirred for 30 minutes. The solvent is removed in vacuuo and the residue partitioned between 50 ml H2O and 150 ml CH2Cl2 and extracted. The organic phase is washed with 50 ml sat NaHCO3, dried over Na2SO4, filtered and concentrated to yield a foam. The product is isolated by flash chromatography (120 g silical gel, 60-80% EA/hept) to yield the title compound (2.83 g, 83%) as a light yellow stiff foam: MS (ES1+) for C23H28N4O6 m/z 457.4 (M+H)+; (ES1-) for C23H28N4O6 m/z 455.2 (M-H); HPLC purity 99% (ret. time, 3.08 min).

Step 3: 7-((3aR,4R,6R,6aR)-6-(azidomethyl)-2,2-dimethyltetrahydrofuro[3,4-d][1,3]dioxol-4-yl)-N-(2,4-dimethoxybenzyl)-7H-pyrrolo[2,3-d]pyrimidin-4-amine A solution of ((3aR,4R,6R,6aR)-6-(4-((2,4-dimethoxybenzyl)amino)-7H-pyrrolo[2,3-d]pyrimidin-7-yl)-2,2-dimethyltetrahydrofuro[3,4-d][1,3]dioxol-4-yl)methanol (2.83 g, 6.20 mmol) and triphenylphosphine (2.28 g, 8.68 mmol) in dry tetrahydrofuran (32 ml) is cooled at 0° C. in an ice/water bath. Diisopropyl azodicarboxylate (1.71 ml, 8.68 mmol) is added dropwise, followed by a solution of diphenylphosphonic azide (1.87 ml, 8.68 mmol) in tetrahydrofuran (5.3 ml, 66 mmol). Upon addition of the DPPA solution, a white milky precipitate forms. After about 30 minutes, the reaction mixture is allowed to warm to room temperature and stir overnight. After 24 h, HPLC indicates that all the starting material has been consumed. The reaction mixture is concentrated to about ½ the original volume and purified by flash chromatography (175 g silica gel, 10-55% EA/hept) to yield the title compound (2.49 g, 83%) as a slightly yellow stiff foam: MS (ES1+) for C23H27N7O5 m/z 482.2 (M+H)+; (ESI-) for C23H27N7O5 m/z 480.1 (M+H)-, m/z 526.1 (M+CO2H)-; HPLC purity 97% (ret. time, 3.64 min).

Step 4: 7-((3aR,4R,6R,6aR)-6-(aminomethyl)-2,2-dimethyltetrahydrofuro[3,4-d][1,3]dioxol-4-yl)-N-(2,4-dimethoxybenzyl)-7H-pyrrolo[2,3-d]pyrimidin-4-amine A solution of ((3aR,4R,6R,6aR)-6-(azidomethyl)-2,2-dimethyltetrahydrofuro[3,4-d][1,3]dioxol-4-yl)-N-(2,4-dimethoxybenzyl)-7H-pyrrolo[2,3-d]pyrimidin-4-amine (2.49 g, 5.17 mmol) in tetrahydrofuran (50 mL, 600 mmol) is treated dropwise with a solution of 1.0 M of trimethylphosphine in tetrahydrofuran (7.24 mL, 7.24 mmol) and the mixture is stirred at room temperature overnight. After 20 h all starting material is consumed by HPLC. The reaction mixture is treated with water (1.80 mL, 99.9 mmol) and stirred at rt for 2 h. The reaction mixture is concentrated, the crude product is taken up in 90 mL CH2Clz and washed with four 30 mL portions of H2O and 15 ml brine. The solution is dried over Na2SO4, filtered and concentrated to yield an oil that under the application of a high vacuum becomes a foam. The crude material is purified by flash chromatography (120 g silica gel, 3-10% 7N NH3 in CH3OH/CH2Clz) to yield the title compound (1.76 g, 75%) as a foam: MS (ES1+) for C23H29NO5 m/z 456.2 (M+Ht; (ES1-) for C26H3SNsOs m/z 454.1 (M-HY; HPLC purity 92% ret. time, 2.65 min).

Step 5: N-(2,4-dimethoxybenzyl)-7-((3aR,4R,6R,6aR)-6-((isopropylamino)methyl)-2,2-dimethyltetrahydrofuro[3,4-d][1,3]dioxol-4-yl)-7H-pyrrolo[2,3-d]pyrimidin-4-amine A solution of ((3aR,4R,6R,6aR)-6-(aminomethyl)-2,2-dimethyltetrahydrofuro[3,4-d][1,3]dioxol-4-yl)-N-(2,4-dimethoxybenzyl)-7H-pyrrolo[2,3-d]pyrimidin-4-amine (1.76 g, 3.86 mmol) in 1,2-dichloroethane (34 ml) is treated with acetone (0.31 ml, 4.2 mmol) and acetic acid (0.22 ml, 3.9 mmol) dropwise followed by sodium triacetoxyborohydride (0.98 g, 4.6 mmol) and the mixture is stirred at room temperature until complete. After 1 h, HPLC indicated the starting material had been consumed and the reaction is complete. The reaction mixture is diluted with 60 mL CH₂Cb and washed with 50 mL sat NaHCO₃. The aqueous phase is washed with 30 mL CH₂Cb and the combined organic phase is washed with 40 mL brine and dried over Na₂SO₄. The solution is filtered and concentrated to yield the title compound (1.76 g, 92%) as a glass that is used directly in the next step: MS (ES1+) for C26H3SNsOs m/z 498.3 (M+Ht; HPLC purity 90% (ret. time, 2.74 min).

Step 6: 2-(3-((((3aR,4R,6R,6aR)-6-(4-((2,4-dimethoxybenzyl)amino)-7H-pyrrolo[2,3-d]pyrimidin-7-yl)-2,2-dimethyltetrahydrofuro[3,4-d][1,3]dioxol-4-yl)methyl)(isopropyl)amino)propyl)isoindoline-1,3-dione A mixture of y-bromopropylphthalimide (2.37 g, 8.85 mmol), tetra-n-butylammonium iodide (0.234 g, 0.632 mmol), N,N-diisopropylethylamine (1.40 ml, 8.04 mmol) and N-(2,4-dimethoxybenzyl)-7-((3aR,4R,6R,6aR)-6-((isopropylamino)methyl)-2,2-dimethyl tetrahydrofuro[3,4-d][1,3]dioxol-4-yl)-7H-pyrrolo[2,3-d]pyrimidin-4-amine (3.42 g, 6.32 mmol) is taken up in propanenitrile (25 ml) and is heated at 95° C. After 48 hours at 95° C., HPLC indicates that the reaction is nearly complete. The reaction mixture is cooled to room temperature, the mixture is diluted with 200 ml ethyl acetate and washed with two 100 ml portions of H₂O and 100 ml brine. The organic phase is dried over Na₂SO₄, filtered and concentrated to yield a glass. The crude material is purified by flash chromatography (250 g silica gel, 2-4% 7N NH3 in CH3OH/CH2Cb) to yield the title compound (3.12 g, 72%) as a foam: MS (ES1+) for C37H44N6O7 m/z 685.2 (M+Ht, (ESI-) for C37H44N6O7 m/z 729 (M+HC02Y; HPLC purity 99% (ret. time, 3.17 min).

Step 7: N1-(((3aR,4R,6R,6aR)-6-(4-((2,4-dimethoxybenzyl)amino)-7H-pyrrolo[2,3-d]pyrimidin-7-yl)-2,2-dimethyltetrahydrofuro[3,4-d][1,3]dioxol-4-yl)methyl)-N1-isopropylpropane-1,3-diamine 2-(3-((((3 aR,4R,6R,6aR)-6-(4-((2,4-dimethoxybenzyl)amino)-7H-pyrrolo[2,3-d]pyrimidin-7-yl)-2,2-dimethyltetrahydrofuro[3,4-d][1,3]dioxol-4-yl)methyl)(isopropyl)amino)propyl)isoindoline-1,3-dione (1.37 g, 2.00 mmol) is dissolved in 2M methylamine in methanol (30 mL, 60 mmol). The solution is stirred at room temperature for 5 minutes then heated at 55-60° C. After 1 h, the SM is consumed by HPLC. The reaction mixture is cooled to room temperature and concentrated in vacuo. The resultant tan oil is taken up in 20 mL MeOH and concentrated. The procedure is repeated to an oil. The material is placed on high vacuum to yield a solid which contained the title compound along with N-methylphthalimide and is used as is in the next step: MS (ES1+) for C29H42N6OS m/z 555.4 (M+Ht; HPLC ret. time 2.57 min.

Step 8: 1-(4-(tert-butyl)phenyl)-3-(3-(((((3aR,4R,6R,6aR)-6-(4-((2,4-dimethoxybenzyl)amino)-7H-pyrrolo[2,3-d]pyrimidin-7-yl)-2,2-dimethyltetrahydrofuro[3,4-d][1,3]dioxol-4-yl)methyl)(isopropyl)amino) propyl)urea A suspension of N1-(((3aR,4R,6R,6aR)-6-(4-((2,4-dimethoxybenzyl)amino)-7H-pyrrolo[2,3-d]pyrimidin-7-yl)-2,2-dimethyltetrahydrofuro[3,4-d][1,3]dioxol-4-yl)methyl)-N1_isopropylpropane-1,3-diamine (1.11 g, 2.00 mmol, crude from step 6) in methylene chloride (40 ml) is treated dropwise with a solution of I-tert-butyl-4-isocyanatobenzene (0.36 ml, 2.0 mmol) in methylene chloride (3.5 ml) and allowed to stir at room temperature. After 1 h, reaction is complete by HPLC. The reaction mixture is concentrated to yield a glass. The crude material is purified by flash chromatography (100 g silica gel, 2-4% 7N NH3 in CH3OH/CH2Cb to yield the title compound (1.07 g, 73%) as a foam: MS (ES1+) for C4oHssN7O6 m/z 730.4 (M+Ht; (ESI-) for C4oHssN7O6 m/z 728.5 (M-HY; HPLC purity, 89% (ret. time, 3.78 min).

Step 9: 1-(3-((((2R,3S,4R,SR)—S-(4-amino-7H-pyrrolo[2,3-d]pyrimidin-7-yl)-3,4-dihydroxytetrahydrofuran-2-yl)methyl)(isopropyl)amino)propyl)-3-(4-(tertbutyl)phenyl)urea 1-(4-(tert-butyl)phenyl)-3-(3-(((((3aR,4R,6R,6aR)-6-(4-((2,4-dimethoxybenzyl)amino)-7H-pyrrolo[2,3-d]pyrimidin-7-yl)-2,2-dimethyltetrahydrofuro[3,4-d][1,3]dioxol-4-yl)methyl)(isopropyl)amino)propyl)urea (1.07 g, 1.39 mmol) is dissolved in a mixture of trifluoroacetic acid (25 ml) and water (2.5 ml) which has been cooled at 0° C. and the resulting solution is stirred at 0° C. for 30 minutes, then warmed to room temperature. After 4 h, the reaction is confirmed to be complete by HPLC. The reaction mixture is concentrated in vacuuo and the residue is taken up in 25 mL MeOH (white slurry) and concentrated. This process is repeated three times and the resultant residue is placed under high vacuum. The material is taken up in 100 mL 10% MeOH/CH2Cb and washed with two 75 mL portions of sat NaHCO3 and 50 mL 1% aq Na2CO3. The organic phase is dried over Na2SO4, filtered and concentrated to yield a glass/solid. The crude material is purified by flash chromatography (100 g silica gel, 5-10% 7N NH3 in CH3OH/CH2Clz) to yield the title compound (0.35 g, 46%) as a colorless glass: MS (ES1+) for C28H41N7O4 m/z 540.3 (M+Ht; (ESI-) for C28H41N7O4 m/z 538.3 (M-Hr, m/z 584.4 (M+HCO2Y; HPLC purity 98% (ret. time 2.86 min); IH NMR (400 MHz, d4-MeOH) ppm 8.05 (s, 1H), 7.27 (d, 1=3.73 Hz, 1H), 7.24 (m, 2H), 7.18 (m, 2H), 6.63 (d, 1=3.73 Hz, 1H), 6.15 (d, 1=4.77 Hz, 1H), 4.46 (t, 1=5.08 Hz, 1H), 4.18 (t, 1=5.39 Hz, 1H), 4.11 (m, 1H), 3.22 (m, 2H), 3.07 (m, 1H), 2.85 (m, 1H), 2.72 (m, 1H), 2.60 (t, 1=6.43 Hz, 2H), 1.68 (m, 2H), 1.28 (s, 9H), 1.05 (d, 1=6.63 Hz, 3H), 1.01 (d, 1=6.43 Hz, 3H).

Step 10: 1-(3-((((2R,3S,4R,5R)-5-(4-Amino-7H-pyrrolo[2,3-d]pyrimidin-7-yl)-3,4-dihydroxytetrahydrofuran-2-yl)methyl)(isopropyl)amino)propyl)-3-(4-(tert-butyl)phenyl)urea hydrochloride A solution of 1-(3-(((((2R,3S,4R,5R)-5-(4-amino-7H-pyrrolo[2,3-d]pyrimidin-7-yl)-3,4-dihydroxytetrahydrofuran-2-yl)methyl)(isopropyl)amino)propyl)-3-(4-(tert-butyl)phenyl)urea (1.64 g, 3.04 mmol) in 50 ml 50% aq methanol is treated with 1.0N of hydrogen chloride in water (3.87 mL, 3.04 mmol). The solution is concentrated to remove most of the methanol and lyophilized overnight. The cloudy mixture is filtered through a fine frit and the filtrate is concentrated in vacuuo to remove the MeOH. The resultant solution is lyophilized overnight to yield the title compound (1.70 g, 97%) as a solid: MS (ES1+) for C28H41N7O4 m/z 540.4 (M+Ht; MS (ES1+) for C28H41N7O4 m/z 538.4 (M+Ht, m/z 574.4 (M+C1Y; HPLC purity 97% (ret. time, 2.88 min); IH NMR (400 MHz, d4-MeOH) ppm 8.12 (s, 1H), 7.29 (m, 2H), 7.23 (m, 3), 6.68 (m, 1H), 6.09 (br. s., 1H), 4.57 (m, 1H), 4.35 (m, 2H), 3.79 (br. s., 1H), 3.55 (m, 2H), 3.26 (br. s., 4H), 1.94 (m, 2H), 1.35 (m, 6H), 1.29 (s, 9H). ICso<10 nM.

In vivo administration of EPZ004777 leads to extension of survival in a mouse MLL xenograft model and support the efficacy of EPZ004777 for the treatment of MLL-translocated leukemias.

EPZ005676

EPZ005676 is a small molecule S-adenosyl methionine (SAM) competitive inhibitor of DOT1L methyltransferase activity that displays a Ki value of 80 pM and a drug-target residence time of >24 hours. Daigle et al., *Blood Epub Ahead of Print* (2013). The compound is highly selective for DOT1L, demonstrating >37,000-fold selectivity against all other methyltransferases tested.

The chemical structure of EPZ005676 (2R,3R,4S,5R)-2-(6-amino-9H-purin-9-yl)-5-(((((1r,3S)-3-(2-(5-(tert-butyl)-1H-benzo[d]imidazol-2-yl)ethyl)cyclobutyl)(isopropyl)amino)methyl)tetrahydrofuran-3,4-diol is presented as Formula V:

Formula V

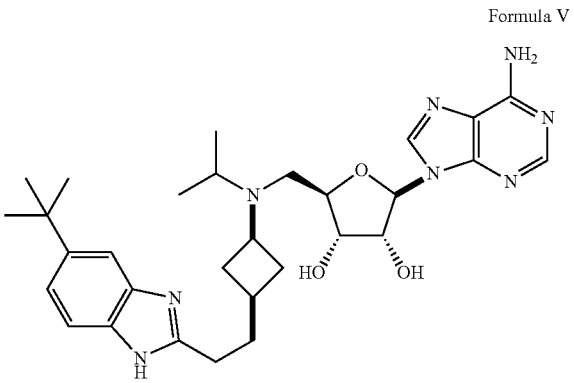

The synthesis of EPZ005676 (2R,3R,4S,5R)-2-(6-amino-9H-purin-9-yl)-5-(((((1r,3S)-3-(2-(5-(tert-butyl)-1H-benzo[d]imidazol-2-yl)ethyl)cyclobutyl)(isopropyl)amino)methyl)tetra-hydrofuran-3,4-diol is described in U.S. Patent Publication No 2002/0142625.

Step 1: Synthesis of cis and trans methyl 3-((((3aR, 4R,6R,6aR)-6-(6-amino-9H-purin-9-yl)-2,2-dimethyltetrahydrofuro-[3,4-d][1,3]dioxol-4-yl)methyl) amino)cyclobutanecarboxylate A solution of methyl 3-oxocyclobutanecarboxylate (4.60 g, 35.94 mmol), 9-((3aR,4R,6R,6aR)-6-(aminomethyl)-2,2-dimethyltetrahydrofuro[3,4-d][1,3]dioxol-4-yl)-9H-purin-6-amine (11.0 g, 35.94 mmol) and Ti(iPrO)$_4$ (4.0 g, 14.08 mmol) in MeOH (80 ml) is stirred at 45° C. for 2 h, then NaCNBH$_3$ (4.5 g, 71.87 mmol) is added. The reaction is stirred at RT overnight. The reaction is quenched with aq. sat. NaHCO$_3$ (40 ml) and filtered, extracted with DCM (80 ml×3), dried over Na$_2$SO$_4$ and concentrated. The residue is purified by preparative-HPLC to obtain the title compound (6.2 g, Yield 41%). NMR (500 MHz, CDCl3): On 8.38-8.34 (m, 1H), 7.90 (s, 1H), 5.98 (d, J=3.0 Hz, 1H), 5.75 (br s, 2H), 5.48-5.46 (m, 1H), 5.03-5.01 (m, 1H), 4.35-4.33 (m, 1H), 3.69-3.66 (m, 3H), 3.50-3.17 (m, 1H), 3.05-2.73 (m, 3H), 2.48-2.44 (m, 2H), 1.95-1.91 (m, 2H), 1.62 (s, 3H), 1.39 (s, 3H) ppm; ESI-MS (m/z): 419.2 [M+1]+. The cis/trans mixture of methyl 3-((((3aR,4R,6R,6aR)-6-(6-amino-9H-purin-9-yl)-2,2-dimethyltetrahydrofuro-[3,4-d][1,3]dioxol-4-yl)methyl)amino)cyclobutanecarboxylate (6.2 g) is separated via chiral HPLC(CHIRALCEL AD-H 20*250 mm, 5 um (Daicel), Column temperature: 35° C., mobile phase: CO$_2$/Methanol (0.1% DEA)=70/30, Flow rate: 50 g/min) to give the pure cis product (3.5 g) and pure trans product (1.7 g).

Step 2: Synthesis of (1S,3s)-methyl 3-((((3aR,4R, 6R,6aR)-6-(6-amino-9H-purin-9-yl)-2,2-dimethyltetrahydrofuro-[3,4-d][1,3]dioxol-4-yl)methyl)(isopropyl)amino)cyclobutanecarboxylate To a solution of cis methyl 3-((((3aR,4R,6R,6aR)-6-(6-amino-9H-purin-9-yl)-2,2-dimethyltetrahydrofuro-[3,4-d][1,3]dioxol-4-yl)methyl)amino)cyclobutanecarboxylate (2.0 g, 4.78 mmol) in CH$_3$CN (15 ml) is added 2-iodopropane (4.0 g, 23.92 mmol) and K$_2$CO$_3$ (1.0 g, 7.18 mmol). The reaction is heated to 95° C. overnight in a sealed tube. The mixture is filtered, the filtrate is concentrated and purified by SGC (DCM:MeOH=12:1) to obtain the title compound (1.9 g, Yield 86%). 1H NMR (500 MHz, CDCl3): ΔH 8.37 (s, 1H), 7.89 (s, 1H), 6.03 (d, J=1.5 Hz, 1H), 5.53-5.48 (m, 3H), 5.00 (br s, 1H), 4.25 (brs, 1H), 3.66 (s, 3H), 3.19-3.18 (m, 1H), 2.96 (brs, 1H), 2.80-2.78 (m, 1H), 2.67-2.58 (m, 2H), 2.20-2.12 (m, 4H), 1.62 (s, 3H), 1.39 (s, 3H), 1.00 (d, J=6.0 Hz, 3H), 0.84 (d, J=6.0 Hz, 3H) ppm; ESI-MS (m/z): 461.4 [M+1]+.

Step 3: Synthesis of (1S,3s)-3-((((3aR,4R,6R,6aR)-6-(6-amino-9H-purin-9-yl)-2,2-dimethyltetrahydrofuro[3,4-d][1,3]dioxol-4-yl)methyl)(isopropyl)amino)cyclobutanecarbaldehyde To a solution of (1S,3s)-methyl 3-((((3aR,4R,6R,6aR)-6-(6-amino-9H-purin-9-yl)-2,2-dimethyltetrahydrofuro-[3,4-d][1,3]dioxol-4-yl)methyl)(isopropyl)amino)cyclobutanecarboxylate (1.2 g, 2.60 mmol) in DCM (50 ml) is added DIBAL-H dropwise at −78° C. until all the starting material is consumed as determined by TLC. MeOH (2 ml) is added and the mixture is stirred at RT for 30 min upon which water (50 ml) is added and the mixture is extracted with DCM (50 ml×2). The organic layer is dried over Na$_2$SO$_4$ and concentrated to obtain crude title compound (1.0 g which is used) directly in the next step. 1H NMR (500 MHz, CDCl3): ΔH 9.56 (d, J=2.5 Hz, 1H), 8.36 (s, 1H), 7.88 (s, 1H), 6.03 (d, J=2.5 Hz, 1H), 5.66 (br s, 2H), 5.50 (dd, J=2.0, 6.5 Hz, 1H), 5.01 (dd, J=3.5, 6.5 Hz, 1H), 3.331-3.337 (m, 1H), 2.96-2.97 (m, 1H), 2.77-2.59 (m, 3H), 2.14-2.05 (m, 4H), 1.60 (s, 3H), 1.39 (s, 3H), 1.01 (d, J=6.5 Hz, 3H), 0.85 (d, J=6.0 Hz, 3H) ppm.

Step 4. Synthesis of (E)-ethyl 3-((1S,3s)-3-((((3aR, 4R,6R,6aR)-6-(6-amino-9H-purin-9-yl)-2,2-dimethylt-rahydrofuro[3,4-d][1,3]dioxol-4-yl)methyl) (isopropyl)amino)cyclobutyl)acry-late To a solution of (1S,3s)-3-((((3aR,4R,6R,6aR)-6-(6-amino-9H-purin-9-yl)-2,2-dimethyltetrah-ydrofuro[3,4-d][1,3]dioxol-4-yl)methyl)(isopropyl)amino)cyclobutane carbaldehyde (930 mg, 2.16 mmol) in CH$_3$CN:DCM=5:1 (50 ml) is added ethyl 2-(diethoxyphosphoryl)acetate (484 mg, 2.16 mmol), DBU (328 mg, 2.16 mmol) and LiCl (91 mg, 2.16=01). The mixture is stirred at RT for 1 h and then concentrated. Water (20 ml) is added and the mixture extracted with DCM (25 ml×3). The combined organic layers are dried over Na2SO4, concentrated and the residue is purified by SGC (DCM:MeOH=30:1) to obtain title compound (900 mg, Yield 83%). 1H NMR (500 MHz, CDCl3): ΔH 8.36 (s, 1H), 7.89 (s, 1H), 6.94-6.90 (m, 1H), 6.03 (s, 1H), 5.72-5.89 (m, 1H), 5.57 (s, 2H), 5.52 (d, J=4.5 Hz, 1H), 5.00 (dd, J=3.5, 6.0 Hz, 1H), 4.25 (d, J=3.0 Hz, 1H), 4.21-4.17 (m, 2H), 3.14 (brs, 1H), 2.961-2.936 (m, 1H), 2.74-2.52 (m, 3H), 2.22-2.14 (m, 2H), 1.79-1.76 (m, 2H), 1.60 (s, 3H), 1.40 (s, 3H), 1.30-1.27 (m, 3H), 1.00 (d, J=7.0 Hz, 3H), 0.82 (d, J=6.5 Hz, 3H) ppm; ESI-MS (m/z): 501.4 [M+1]+.

Step 5: Synthesis of ethyl 3-((1S,3r)-3-((((3aR,4R, 6R,6aR)-6-(6-amino-9H-purin-9-yl)-2,2-dimethyltetrahydrofuro[3,4-d][1,3]dioxol-4-yl)methyl)(isopropyl)amino)cyclobutyl)propanoate To a solution of (E)-ethyl 3-((1S,3s)-3-((((3aR,4R,6R, 6aR)-6-(6-amino-9H-purin-9-yl)-2,2-dimethyltet-rahydrofuro[3,4-d][1,3]dioxol-4-yl)methyl)(isopropyl)amino)cyclobutyl)acry-late (900 mg, 1.8 mmol) in MeOH (50 ml) is added Pd/C (20 mg). The mixture is stirred at RT overnight under an atmosphere of hydrogen. The mixture is filtered and the filtrate is concentrated to obtain title compound (700 mg, Yield 78%). 1H NMR (500 MHz, CDCl3): ΔH 8.36 (s, 1H), 7.89 (s, 1H), 6.03 (d, J=2.5 Hz, 1H), 5.69 (s, 2H), 5.51 (dd, J=2.5, 8.0 Hz, 1H), 4.99 (dd, J=4.0, 7.5 Hz, 1H), 4.26 (brs, 1H), 4.13-4.08 (m, 2H), 2.99-2.92 (m, 2H), 2.706-2.655 (m, 1H), 2.539-2.486 (m, 1H), 2.18-2.02 (m, 4H), 1.76 (brs, 1H), 1.65-1.60 (m, 5H), 1.43-1.37 (m, 5H), 1.26-1.23 (m, 2H), 0.97 (d, J=9.0 Hz, 3H), 0.79 (d, J=8.5 Hz, 3H) ppm; ESI-MS (m/z): 503.4 [M+1]+.

Step 6: Synthesis of 3-((1S,3r)-3-((((3aR,4R,6R, 6aR)-6-(6-amino-9H-purin-9-yl)-2,2-dimethyltetrahydro furo[3,4-d][1,3]dioxol-4-yl)methyl)(isopropyl) amino)cyclobutyl)propanoic acid To a solution of ethyl 3-((1S,3r)-3-((((3aR,4R,6R,6aR)-6-(6-amino-9H-purin-9-yl)-2,2-dimethyltet-rahydrofuro[3,4-d][1,3]dioxol-4-yl)methyl) (isopropyl)amino)cyclobutyl) propanoate (650 mg, 1.29 mmol) in THF:MeOH=5:1 (30 ml) is added LiOH.H2O (543 mg, 1.29 mmol). The mixture is stirred at RT overnight, concentrated and then taken up in MeOH (10 ml). 1M HCl solution is added dropwise at 0° C. until pH=7. The mixture is concentrated and purified with preparative-HPLC to give title compound (170 mg).

Step 7: Synthesis of N-(2-amino-4-(tert-butyl)phenyl)-3-((1 S,3r)-3-((((3aR,4R,6R,6aR)-6-(6-amino-9H-purin-9-yl)-2,2-dimethyltetrahydrofuro[3,4-d][1,3]dioxol-4-yl)methyl-)(isopropyl)amino)cyclobutyl)propanamide To a solution of 3-((1S,3r)-3-((((3aR,4R,6R,6aR)-6-(6-amino-9H-purin-9-yl)-2,2-dimethyltet-rahydrofuro[3,4-d][1,3]dioxol-4-yl)methyl)(isopropyl)amino)cyclobutyl)propanoic acid (170 mg, 0.36 mmol) in DCM (15 ml) is added 4-tert-butylbenzene-1,2-diamine (117 mg, 0.72 mmol), EDCI (137 mg, 0.72 mmol), HOBT (97 mg, 0.72 mmol) and TEA (217 mg, 2.15 mmol). The mixture is stirred at RT overnight and concentrated. Saturated NaHCO3 solution (20 ml) is added and the mixture extracted with DCM (20 ml×3). The organic layers are dried over Na2SO4 and concentrated. The crude is purified with preparative-TLC (DCM:MeOH=12:1) to afford the title compound (110 mg crude).

Step 8: Synthesis of 9-((3aR,4R,6R,6aR)-6-((((1r,3S)-3-(2-(5-(tert-butyl)-1H-benzo[d]imidazol-2-yl)ethyl)cyclobutyl)(isopropyl)amino)methyl)-2,2-dimethyltetrahydrofuro[-3,4-d][1,3]dioxol-4-yl)-9H-purin-6-amine A solution of N-(2-amino-4-(tert-butyl)phenyl)-3-((1S,3r)-3-((((3aR,4R,6R,6aR)-6-(6-ami-no-9H-purin-9-yl)-2,2-dimethyltetrahydrofuro[3,4-d][1,3]dioxol-4-yl)methyl-)(isopropyl)amino)cyclobutyl)propanamide (110 mg) in AcOH (10 ml) is heated to 65° C. Overnight. The mixture is concentrated, saturated NaHCO3 solution (20 ml) is added and the mixture extracted with DCM (20 ml×3). The combined organic layers are dried over Na2SO4 and concentrated to give the title compound (105 mg crude). 1H NMR (500 MHz, CDCl3): ΔH 8.36 (s, 1H), 7.89 (s, 1H), 7.48-7.24 (m, 3H), 6.01 (d, f=1.5 Hz, 1H), 5.60-5.53 (m, 3H), 4.98 (dd, J=3.0, 6.5 Hz, 1H), 4.22 (brs, 1H), 2.97 (brs, 1H), 2.874-2.847 (m, 1H), 2.56-2.50 (m, 3H), 1.87-1.78 (m, 2H), 1.70-1.54 (m, 7H), 1.35-1.17 (m, 14H), 0.90 (d, J=6.5 Hz, 3H), 0.80 (d, J=6.5 Hz, 3H) ppm; ESI-MS (m/z): 603.5 [M+1]+.

Step 9: Synthesis of (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)(isopropyl)amino)methyl)tetra-hydrofuran-3,4-diol A solution of 9-((3aR,4R,6R,6aR)-6-((((1r,3S)-3-(2-(5-(tert-butyl)-1H-benzo[d]imidazol-2-yl)ethyl)cyclobutyl)(isopropyl)amino)methyl)-2,2-dimethyltetrahydrofuro[-3,4-d][1,3]dioxol-4-yl)-9H-purin-6-amine (105 mg) in HCl/MeOH (2.5 mol/L) (10 mL) is stirred at RT for 2 h, then concentrated to dryness. K2CO3 (96 mg) in water (0.5 mL) and MeOH (5 mL) are added and the resulting mixture is stirred for another 10 min at RT and then filtered. The filtrate is concentrated and the residue is purified by preparative-HPLC (xbridge 30 mm*150 mm, Mobile phase: A: water (10 mM NH4HCO3) B: CAN, Gradient: 35-45% B in 10 min, 45-45% B in 6 min, stop at 20 min, Flow rate: 50 ml/min) to give Compound 2 (50 mg, yield: 51%) as a white solid. 1H NMR (500 MHz, MeOD): AH 8.29 (s, 1H), 8.20 (s, 1H), 7.47-7.39 (m, 3H), 5.96 (d, J=4.0 Hz, 1H), 4.70-4.75 (m, 1H), 4.26-4.27 (m, 1H), 4.05-4.06 (m, 1H), 3.140-3.155 (m, 1H), 3.00-2.76 (m, 5H), 2.18-2.16 (m, 2H), 1.87-1.85 (m, 2H), 1.57-1.55 (m, 2H), 1.36 (s, 9H), 1.01 (d, J=6.5 Hz, 3H), 0.94 (d, J=6.5 Hz, 3H) ppm; ESI-MS (m/z): 563.4 [M+1]+.

EPZ005676 is soluble in aqueous solution and can be formulated for intravenous administration. The effective pharmacokinetic half-life of EPZ005676 in systemic circulation is 0.25 in rats and 1.5 h in dogs.

Continuous intravenous infusion of EPZ005676 for 21 days in a nude rat subcutaneous xenograft model of MLL-rearranged leukemia provides dose-dependent anti-tumor activity. At the highest dose, complete tumor regressions are achieved with no regrowth for up to 32 days after the cessation of treatment. No significant weight loss or obvious toxicity is observed in rats treated with EPZ005676. EPZ005676 is thus a potent, selective inhibitor of DOT1L that demonstrates strong efficacy in a rat xenograft model of MLL-rearranged leukemia.

EPZ005676 is currently being evaluated in a phase I study in human patients having relapsed/refractory leukemia involving translocations of the MLL gene at 11q23 or other advanced hematologic cancers. EPZ005676 is being administered via continuous intravenous infusion over 21 days.

Compositions and Formulations Comprising DOT1L Inhibitors

The present disclosure provides compositions, including therapeutic compositions comprising one or more DOT1L inhibitor(s) and/or one or more EZH2 inhibitor(s), for the treatment of a leukemia, such as ALL or AML. One or more DOT1L inhibitor(s) and/or one or more EZH2 inhibitor(s) can be administered to a human patient by themselves or in pharmaceutical compositions where they are mixed with suitable carriers or excipient(s) at doses to treat or ameliorate a disease or condition as described herein. Mixtures of these inhibitors can also be administered to the patient as a simple mixture or in suitably formulated pharmaceutical compositions.

Compositions within the scope of this disclosure include compositions wherein the therapeutic agent is a DOT1L inhibitor and/or an EZH2 inhibitor in an amount effective to inhibit the proliferation of a leukemia cell in a patient. Determination of optimal ranges of effective amounts of each component is within the skill of the art. The effective dose is a function of a number of factors, including the specific inhibitor, the presence of a prodrug, the patient and the clinical status of the latter.

Compositions comprising a DOT1L inhibitor and/or an EZH2 inhibitor may be administered parenterally. As used herein, the term "parenteral administration" refers to modes of administration other than enteral and topical administration, usually by injection, and include, without limitation, intravenous, intramuscular, intraarterial, intrathecal, intracapsular, intraorbital, intracardiac, intradermal, intraperitoneal, transtracheal, subcutaneous, subcuticular, intra-articular, subcapsular, subarachnoid, intraspinal, and intrasternal injection and infusion. Alternatively, or concurrently, administration may be orally.

The dosage administered will be dependent upon the age, health, and weight of the recipient, kind of concurrent treatment, if any, frequency of treatment, and the nature of the effect desired.

Compositions comprising a DOT1L inhibitor and/or an EZH2 inhibitor may, for example, be administered parenterally, such as intravenously via an intravenous push or bolus. Alternatively, compositions comprising a DOT1L inhibitor and/or an EZH2 inhibitor may be administered via an intravenous infusion. As used herein, the term "parenteral administration" refers to modes of administration other than enteral and topical administration, usually by injection, and include, without limitation, intravenous, intramuscular, intraarterial, intrathecal, intracapsular, intraorbital, intracardiac, intradermal, intraperitoneal, transtracheal, subcutaneous, subcuticular, intra-articular, subcapsular, subarachnoid, intraspinal, and intrasternal injection and infusion.

Suitable dosages for intravenous infusion of a composition comprising a DOT1L inhibitor and/or an EZH2 inhibitor include a dosage of at least about 2 mg inhibitor/m2/day or at least about 10 mg inhibitor/m2/day or at least about 20 mg inhibitor/m2/day or at least bout 50 mg inhibitor/m2/day or at least about 100 mg inhibitor/m2/day or at least about 200 mg inhibitor/m2/day or at least about 500 mg inhibitor/m2/day.

Compositions comprising a DOT1L inhibitor and/or a EZH2 inhibitor generally include a therapeutically effective amount of a compound, and a pharmaceutically acceptable carrier. As used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skimmed milk, glycerol, propylene, glycol, water, ethanol and the like. The composition, if desired, can also contain minor amounts of wetting or emulsifying agents, or pH buffering agents.

These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, and the like. Such compositions will contain a therapeutically effective amount of the inhibitor, preferably in purified form, together with a suitable amount of carrier so as to provide the form for proper administration to the patient. The formulation should suit the mode of administration.

Compositions can be formulated in accordance with routine procedures as a pharmaceutical composition adapted for intravenous administration to a human. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The inhibitors disclosed herein can be formulated as neutral or salt forms. Pharmaceutically acceptable salts include those formed with anions such as those derived from hydrochloric, phosphoric, acetic, oxalic, tartaric acids, and the like, and those formed with cations such as those derived from sodium, potassium, ammonium, calcium, ferric hydroxides, isopropylamine, triethylamine, 2-ethylamino ethanol, histidine, procaine, and the like.

Many of the inhibitors of the present disclosure may be provided as salts with pharmaceutically compatible counterions (i.e., pharmaceutically acceptable salts). A "pharmaceutically acceptable salt" means any non-toxic salt that, upon administration to a recipient, is capable of providing, either directly or indirectly, a compound or a prodrug of a compound of this invention. A "pharmaceutically acceptable counterion" is an ionic portion of a salt that is not toxic when released from the salt upon administration to a subject. Pharmaceutically compatible salts may be formed with many acids, including but not limited to hydrochloric, sulfuric, acetic, lactic, tartaric, malic, and succinic acids. Salts tend to be more soluble in water or other protic solvents than their corresponding free base forms. The present invention includes such salts.

Methods for Inhibiting the Growth and/or Survival of a Cell, and for Treating a Leukemia Patient Exhibiting a Genetic Mutation, Alteration, and/or Abnormality that is Associated with Elevated Expression of a HOX Cluster Gene and/or a HOX Cluster-Associated Gene The present disclosure further provides therapies that involve administering a composition comprising one or more DOT1L inhibitor and one or more EZH2 inhibitor to a human patient for treating a leukemia wherein the leukemia exhibits high level expression of one or more HOXA cluster genes but does not possess an MLL-translocation.

The amount of the DOT1L inhibitor and/or EZH2 inhibitor that will be effective in the treatment, inhibition, and/or prevention of a leukemia characterized by a high level expression of one or more HOX cluster genes, but not possessing an MLL-translocation can be determined by standard clinical techniques. In vitro assays may optionally be employed to help identify optimal dosage ranges. The precise dose to be employed in the formulation will also depend on the route of administration, and the seriousness of the disease or disorder. Effective doses may be extrapolated from dose-response curves derived from in vitro or animal model test systems.

The compounds or pharmaceutical compositions of the invention can be tested in vitro, and then in vivo for the desired therapeutic or prophylactic activity, prior to use in humans. For example, in vitro assays to demonstrate the therapeutic or prophylactic utility of a compound or pharmaceutical composition include the effect of a compound on a cell line or a patient tissue sample. The effect of the compound or composition on the cell line and/or tissue sample can be determined utilizing techniques known to those of skill in the art including, but not limited to proliferation and apoptosis assays. In accordance with the present disclosure, in vitro assays that can be used to determine whether administration of a specific compound is indicated, include in vitro cell culture assays in which a patient tissue sample is grown in culture, and exposed to or otherwise administered a compound, and the effect of such compound upon the tissue sample is observed.

The present disclosure provides methods of treatment and inhibition by administration to a subject of an effective amount of a DOT1L and/or EZH2 inhibitor compound or pharmaceutical composition as described herein. In one aspect, the compound is substantially purified such that the compound is substantially free from substances that limit its effect or produce undesired side-effects.

Various delivery systems are known and can be used to administer a composition of the present disclosure, for example, encapsulation in liposomes, microparticles, microcapsules, receptor-mediated endocytosis (see, e.g., Wu and Wu, J. Biol. Chem. 262:4429-4432 (1987)), and the like as will be known by one of skill in the art.

Methods of administration include, but are not limited to, intradermal, intramuscular, intraperitoneal, intravenous, subcutaneous, intranasal, epidural, and oral routes. The inhibitors or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the inhibitors or compositions into the central nervous system by any suitable route, including intraventricular and intrathecal injection. Intraventricular injection may be facilitated by an intraventricular catheter, for example, attached to a reservoir, such as an Ommaya reservoir. Pulmonary administration can also be employed, for example, by use of an inhaler or nebulizer, and formulation with an aerosolizing agent.

It may be desirable to administer the inhibitors or compositions of locally to the area in need of treatment; this may be achieved by, for example, local infusion during surgery, topical application, by injection, by means of a catheter, by means of a suppository, or by means of an implant, said implant being of a porous, non-porous, or gelatinous material, including membranes, such as sialastic membranes, or fibers.

The inhibitor can be delivered in a vesicle, such as a liposome (Langer, Science 249:1527-1533 (1990)) or in a controlled release system. A controlled release system can be placed in proximity of the therapeutic target, thus requiring only a fraction of the systemic dose (see, e.g., Goodson, in Medical Applications of Controlled Release, Vol. 2, pp. 115-138 (1984)).

Intravenous infusion of a compositions comprising a DOT1L inhibitor and/or a EZH2 inhibitor may be continuous for a duration of at least about one day, or at least about three days, or at least about seven days, or at least about 14 days, or at least about 21 days, or at least about 28 days, or at least about 42 days, or at least about 56 days, or at least about 84 days, or at least about 112 days.

Continuous intravenous infusion of a composition comprising a DOT1L inhibitor and/or a EZH2 inhibitor may be for a specified duration, followed by a rest period of another duration. For example, a continuous infusion duration may be from about 1 day, to about 7 days, to about 14 days, to about 21 days, to about 28 days, to about 42 days, to about 56 days, to about 84 days, or to about 112 days. The continuous infusion may then be followed by a rest period of from about 1 day, to about 2 days to about 3 days, to about 7 days, to about 14 days, or to about 28 days. Continuous infusion may then be repeated, as above, and followed by another rest period.

Regardless of the precise continuous infusion protocol adopted, it will be understood that continuous infusion of a composition comprising a DOT1L inhibitor and/or a EZH2 inhibitor will continue until either desired efficacy is achieved or an unacceptable level of toxicity becomes evident.

KITS for Detecting HOXA Cluster Gene Expression

The present disclosure also provides kits for use in testing patient samples for the elevated expression of a HOX cluster gene or a HOX cluster-associated gene and/or the presence of genetic mutation, such as a mutation in one or more of the NPM1, DNMT3A, IDH1, IDH2, RUNX1, TET2, and ASXL1 genes and/or an NUP98-NSD1 or other NUP98 translocation and/or a mutation, alteration, and/or abnormality in any of the genes presented in Table 2, which is associated with elevated HOX cluster gene and/or a HOX cluster-associated gene expression.

The diagnostic kits include a primer pair for amplifying a HOX cluster gene and/or a HOX cluster-associated gene and/or any of the genes presented in Table 2 and a probe for detecting and/or sequencing the amplicon generated from an amplification reaction that employs the primer pair.

FLT3 Inhibitors

Within certain embodiments, the present disclosure provides methods that employ one or more DOT1L inhibitors in combination or in conjunction with one or more FLT3 inhibitors thereby providing a desired therapeutic benefit by further inhibiting the proliferation and/or survival of a cell exhibiting and for the treatment of leukemia patients whose leukemia is associated with elevated expression of a HOX cluster gene and/or a HOX cluster-associated gene.

The FMS-like tyrosine kinase 3 (FLT3) gene encodes a membrane bound receptor tyrosine kinase that affects hematopoiesis leading to hematological disorders and malignancies. See, e.g., Drexler et al., Leukemia 10:588-599 (1996); Gilliland and Griffin, Blood 100:1532-1542 (2002); and Stirewalt and Radich, Nat. Rev. Cancer 3:650-665 (2003). Activation of FLT3 receptor tyrosine kinases is initiated through the binding of the FLT3 ligand (FLT3L) to the FLT3 receptor, which is expressed on hematopoietic progenitor and stem cells.

FLT3 is a frequently mutated gene in hematological malignancies, present in approximately 30% of adult acute myeloid leukemia (AML). Nakao et al., Leukemia 10:1911-1918 (1996); Kiyoi et al., Leukemia 12:1333-1337 (1998); Kottaridis et al., Blood 98:1742-1759 (2001); Yamamoto et al., Blood 97:2434-2439 (2001); and Thiede et al., Blood 99:4326-4335 (2002).

The most common FLT3 mutations are internal tandem duplications (ITDs) that lead to in-frame insertions within the juxtamembrane domain of the FLT3 receptor. FLT3-ITD mutations have been reported in 15-35% of adult AML patients. Nakao et al., Leukemia 10:1911-1918 (1996); Kiyoi et al., Leukemia 12:1333-1337 (1998); Kiyoi et al., Leukemia 11:1447-1452 (1997); and Schnittger et al., Blood 100:59-66 (2002). A FLT3-ITD mutation is an independent predictor of poor patient prognosis and is associated with increased relapse risk after standard chemotherapy, and decreased disease free and overall survival. AbuDuhier et al., British J. Hematol. 11:190-195 (2000); Kiyoi et al., Blood 93:3074-3080 (1999). Less frequent are FLT3 point mutations that arise in the activation loop of the FLT3 receptor. The most commonly affected codon is aspartate 835 (D835). Nucleotide substitutions of the D835 residue occur in approximately 5-10% of adult acute myeloid leukemia patients. Stirewalt and Radich, Nature Rev. Cancer 3:650-665 (2003); Yamamoto et al., Blood 97:2434-2439

(2001); Thiede et al., *Blood* 99:4326-4335 (2002); and Bacher et al., *Blood* 111:2527-2537 (2008).

The high frequency of constitutively activated mutant FLT3 in adult AML has made the FLT3 gene a highly attractive drug target in this leukemia. Several FLT3 inhibitors with varying degrees of potency and selectivity for the target have been or are currently being investigated and examined in AML patients. Kindler et al., *Blood* 116:5089-102 (2010).

FLT3 inhibitors are classified as Type I or Type II inhibitors. These two distinct classifications are based on relative affinities and mechanism of binding to phosphorylated and non-phosphorylated receptor sites. Type I inhibitors recognize the active conformation of kinases. This conformation is conducive to phosphotransfer. Type I inhibitors are generally composed of a heterocyclic ring system. Liu and Gray, *Nat. Chem. Biol.* 2:358-354 (2006). Examples of Type I FLT3 inhibitors include Crenolanib besylate and Midostaurin. Muralidhara et al., *Cancer Res.* 72 8 Supp.:3683 (2012); and Cools et al., *Cancer Res.* 64:6385-6389 (2004). Mutations rendering the FLT3 receptor tyrosine kinase constitutively phosphorylated may also be sensitive to type I inhibitors.

Type II inhibitors bind to an inactive FLT3 conformation that is typically referred to as 'DFG-out,' which refers to the motif rearrangement. Zhang et al., *Nature Rev. Cancer* 9:28-39 (2009). Inhibitors such as Imatinib, Sorafenib, and Nilotinib (a/k/a/AMN107 or Tasigna®) bind in the type II conformation. Manley et al., *Biochim. Biophys. Acta.* 1754: 3-13 (2005); Wan et al., *Cell* 116:855-867 (2004). Mutations that confer resistance to Type II inhibitors render the kinase domain of the FLT3 receptor tyrosine kinase constitutively phosphorylated. Type I inhibitors that target the phosphorylated kinase can overcome the resistance resulting from the treatment with Type II inhibitors, and therefore have potential use in treating diseases that harbor these resistance mutations.

FLT3 inhibitors that may be suitably employed in combination with one or more DOT1L inhibitors for use in the presently disclosed methods, including methods for treating leukemia patients, are reviewed, generally, in Leung et al., *Leukemia* 27:260-268 (2013); Grunwald and Levis, *Int. J. Hematol.* 97:683-694 (2013); Wiernik, *Clin. Adv. Hem. & Onc.* 8(6):429 (2010) and are disclosed in further detail in U.S. Pat. Nos. 8,557,847 and 7,977,338 (phenylacetamides); US Patent Publication No. 2003/0219827; PCT Patent Publication Nos. WO 2014/027199; WO 2013/142382; WO 2008/067280; WO 2006/020145; and within the scientific literature in Sato et al., *Blood* 117(12):3286-3293 (2011); Levis, *Hematology*, pp. 220-226 (Am. Soc. Hematol. Educ. Prog., Washington D.C., 2013); Fischer et al., *J. Clin. Oncol.* 28(28):4339-4345 (2010); Fischer, *Blood* 117(12):3247-3248 (2011); Kindler et al., *Blood* 116(24):5089-5102 (2010); and Fathi and Chabner, *Oncologist* 16:1162-1174 (2011).

Additional FLT3 inhibitors are disclosed in PCT Patent Publication Nos. WO 2002/032861, WO 2002/092599, WO 2003/035009, WO 2003/024931, WO 2003/037347, WO 2003/057690, WO 2003/099771, WO 2004/005281, WO 2004/016597, WO 2004/018419, WO 2004/039782, WO 2004/043389, WO 2004/046120, WO 2004/058749, WO 2004/058749, WO 2003/024969; U.S. Patent Publication No. 2004/0049032; and Levis et al., *Blood* 98(3):885-887 (2001); Tse et al., *Leukemia* 15(7):1001-1010 (2001); Smith et al., *Blood* 103:3669-3676 (2004); Griswold et al., *Blood* 104(9):2912-2918 (2004); Yee et al., *Blood* 100(8):2941-2949 (2002); O'Farrell et al., *Blood* 101(9):3597-3605 (2003); Stone et al., *Ann. Hematol.* 83 Supp 1:S89-90 (2004); Murata et al., *J. Biol. Chem.* 278(35):32892-32898 (2003); and Levis et al., *Curr. Pharm. Design* 10:1183-1193 (2004). The selection of candidate kinase inhibitors for pharmacological validation of drug targets is described in Uitdehaag et al., *Br. J. Pharmacol.* 166(3):858-76 (2012). Each of these references, as well as all other references disclosed herein, is incorporated herein by reference in its entirety.

FLT3 inhibitors that may be used in these methods include small-molecule tyrosine kinase inhibitor compounds including 2-phenyl amino pyrimidine compounds; imidazolothiazole compounds; 2,4,5-substituted pyrimidine and pyridopyrimidine compounds; pyrrole substituted 2-indolinone compounds; and substituted indolocarbazole compounds, which are well known in the art and are exemplified by specific compounds that have been shown to exhibit FLT3 inhibitory activity and which are being or have been investigated for the treatment of a variety of disease, in particular the hematological malignancies ALL and AML.

A number of small molecule FLT3 tyrosine kinase inhibitors (TKIs) are used routinely in the management of ALLs and are in development for the treatment of FLT3-mutated AML, including, for example, Tandutinib (a/k/a MLN-518 or CT53518, COR Therapeutics Inc. and Millennium Pharmaceuticals Inc.), CHIR-258 (Chiron Corp.); EBIO and IMC-EBlO (ImClone Systems Inc.); XL 999 (Exelixis USA and Symphony Evolution, Inc.); GTP 14564 (Merck Biosciences UK); AG1295 and AG1296; CEP-5214 and CEP-7055 (Cephalon); Nilotinib (a/k/a/l AMN107 or Tasigna®), Sorafenib, Sunitinib (a/k/a SU1 1248, Pfizer USA), Midostaurin (a/k/a PKC412, Novartis AG), Lestaurtinib (a/k/a CEP 701 or KT-555, Cephalon), KW-2449, Quizartinib (a/k/a AC220, Ambit Biosciences), and Crenolanib. Of these FLT3 inhibitors, Lestaurtinib, Midostaurin, Sorafenib, KW-2449, and AC220 have been or are being evaluated in clinical trials. In addition, the small molecule compounds PLX3397 and AC220 have been developed for the specific purpose of treating patients with AML that is associated with FLT3 internal tandem duplications (ITDs).

FLT3 inhibitors that may be suitably employed in combination with one or more DOT1L inhibitors for use in the presently disclosed methods, including methods for treating leukemia patients, include the 2-phenyl amino pyrimidine compounds, which are described in U.S. Pat. No. 5,521,184; exemplified by the small molecule FLT3 tyrosine kinase inhibitor imatinib [N-(4-methyl-3-(4-(pyridin-3-yl)pyrimidin-2-ylamino)phenyl)-4-((4-methylpiperazin-1-yl)methyl) benzamide methanesulfonic acid]; and represented by Formula VI:

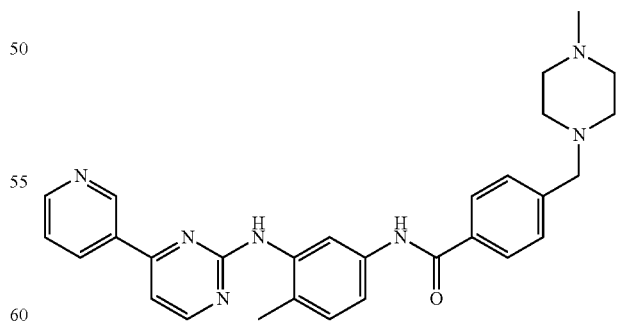

Formula VI

Imatinib (a/k/a STI-571) is available commercially from Novartis under the names Gleevec® in Canada, South Africa, and the United States or Glivec® in Australia, Europe and Latin America). The synthesis of a wide variety of 2-phenyl amino pyrimidine compounds, in addition to Imatinib, is disclosed in U.S. Pat. No. 5,521,184.

FLT3 inhibitors that may be suitably employed in combination with one or more DOT1L inhibitors for use in the presently disclosed methods, including methods for treating leukemia patients, include the imidazolothiazole compounds, which are described in U.S. 2007/0232604 and represented by Formula VII:

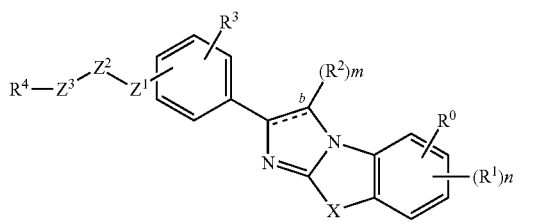

Formula VII

Imidazolothiazole compounds of Formula VII are exemplified herein by Quizartinib (a/k/a AC220), which is being developed by Ambit Biosciences (San Diego, Calif.) for the treatment of acute myeloid leukemia. Quizartinib has the chemical structure 1-(5-(tert-Butyl)isoxazol-3-yl)-3-(4-(7-(2-morpholinoethoxy)benzo[d]imidazo[2,1-b]thiazol-2-yl)phenyl)urea, which is presented as Formula VIIa:

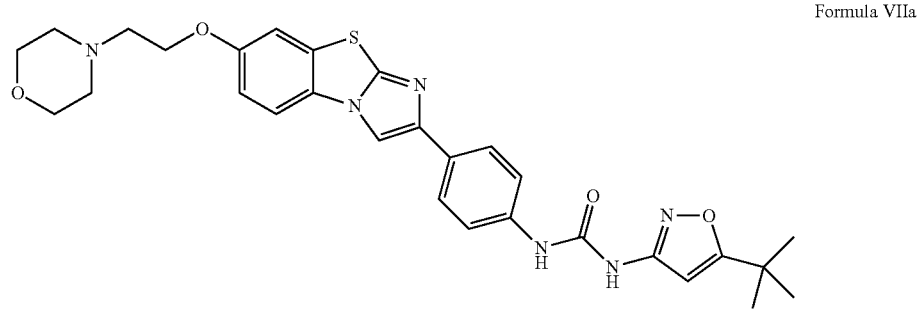 [SMILES: CC(C)(C)c1cc(NC(=O)Nc2ccc(-c3cn4c(n3)sc3cc(OCCN5CCOCC5)ccc34)cc2)no1]

Formula VIIa

Quizartinib is a second-generation FLT3 inhibitor of Flt3(ITD/WT) having high affinity for FLT3, with a $K_d$ value of 1.6 nM, and an IC50 of 1.1 nM for Flt3-ITD and 4.2 nM for WT FLT3, which is about 10-fold greater than its IC50 for the related tyrosine kinase receptors KIT, PDGFRα, PDGFRβ, RET, and CSF-1R. The synthesis of Quizartinib is described in U.S. Pat. No. 7,820,657 and PCT Patent Publication Nos. WO 2007/109120, WO 2011/056939, and WO 2009/038757.

FLT3 inhibitors that may be suitably employed in combination with one or more DOT1L inhibitors for use in the presently disclosed methods, including methods for treating leukemia patients, include the 2,4,5-substituted pyrimidine compounds as disclosed in PCT Patent Publication No. WO 2014/027199 and represented by Formula VIII:

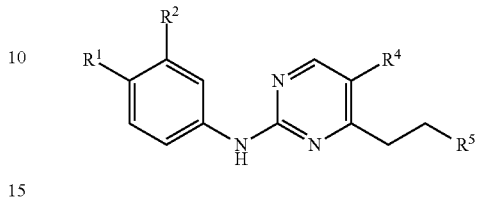

Formula VIII

FLT3 inhibitors that may be suitably employed in combination with one or more DOT1L inhibitors for use in the presently disclosed methods, including methods for treating leukemia patients, include the pyridopyrimidine compounds as disclosed in PCT Patent Publication No. WO 2013/142382 and represented by Formula IX:

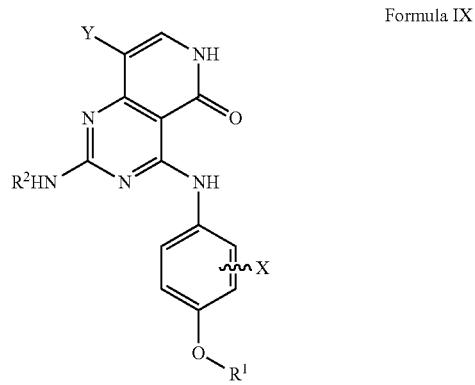

Formula IX

FLT3 inhibitors that may be suitably employed in the presently disclosed methods for inhibiting the proliferation and/or survival of cell and for treatment of leukemia patients include PLX3397 (Plexxikon Inc., Berkeley, Calif.). Synthesis of PLX3397 and related compounds is described in Zhang et al., *Proc. Natl. Acad. Sci. U.S.A.* 110(14):5689-94 (2013)

FLT3 inhibitors that may be suitably employed in the presently disclosed methods for inhibiting the proliferation and/or survival of cell and for treatment of leukemia patients include Tandutinib (MLN518; N-(4-isopropoxyphenyl)-4-(6-methoxy-7-(3-(piperidin-1-yl) propoxy) quinazolin-4-yl) piperazine-1-carboxamide) and is represented by Formula X:

Formula X

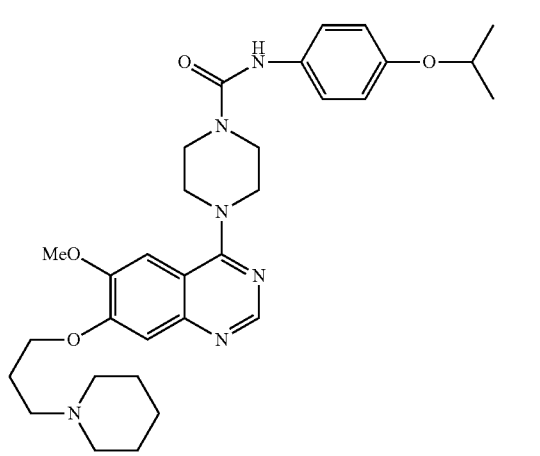

Tandutinib (MLN518, CT53518) is a potent FLT3 antagonist with IC50 of 0.22 μM, also inhibits PDGFR and c-Kit, 15 to 20-fold higher potency for FLT3 versus CSF-1R and >100-fold selectivity for the same target versus FGFR, EGFR and KDR. Tandutinib has been described for the treatment of AML. DeAngelo et al., *Blood* 108:3674-81 (2006).

Sorafenib (2-pyridinecarboxamide, 4-[4-[[[[4-chloro-3-trifluoromethyl) phenyl]amino]carbonyl]amino]phenoxy]-N-methyl-4-(4-(3-(4-chloro-3 trifluoro methylphenyl) ureido)phenoxy) pyridine-2-carboxyllic acid methyamide-4-methylbenzenesulfonate tosylate (a/k/a 4-(4-{3-[4-Chloro-3-(trifluoromethyl) phenyl]ureido}phenoxy) N2methylpyridine-2-carboxamide 4-methylbenzenesulfonate) and is represented by the following Formula XI:

Formula Xi

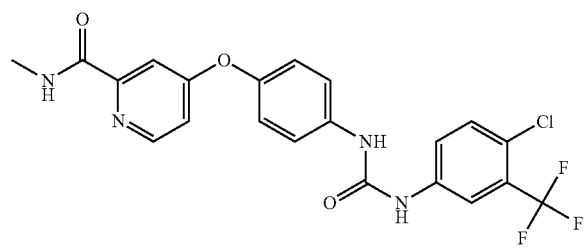

Sorafenib is co-developed and co-marketed by Bayer and Onyx Pharmaceuticals as Nexavar). The synthesis of sofafenib is disclosed in US Patent Publication No. 2008/0262236.

Pyrrole substituted 2-indolionone protein kinase inhibitors are disclosed in U.S. Pat. Nos. 7,119,090; 6,395,734; 6,575,293; and 7,125,905 and are represented by the following Formula XII:

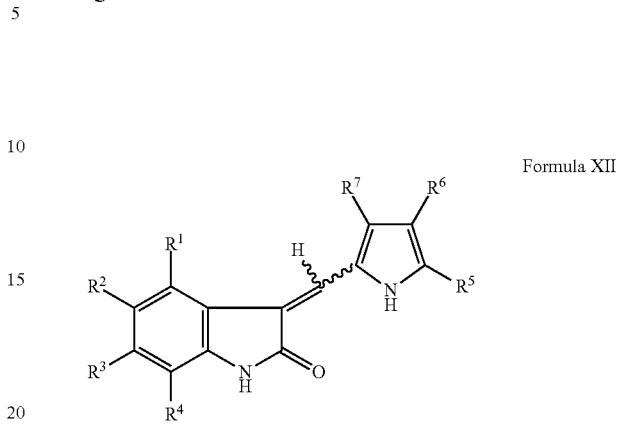

Formula XII

Sunitinib (N-(2-diethylaminoethyl)-5-[(Z)-(5-fluoro-2-oxo-1H-indol-3-ylidene)methyl]-2,4-dimethyl-1H-pyrrole-3-carboxamide); previously known as SU11248) is available commercially under the name Sutent® from Pfizer (New York, N.Y.). The synthesis of Sunitinib is disclosed in U.S. Pat. No. 6,573,293 (compound 80) and is represented by the following Formula XIII:

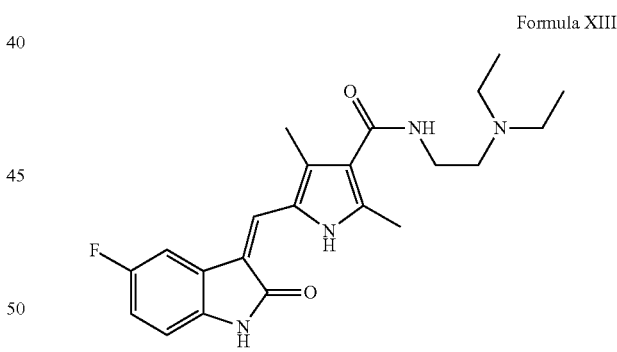

Formula XIII

Substituted indolocarbazole compounds are exemplified by Midostaurin (PKC412; (9S,10R,11R,13R)-2,3,10,11,12,13-Hexahydro-10-methoxy-9-methyl-11-(methylamino)-9,13-epoxy-1H,9H-diindolo[1,2,3-gh:3',2',1'-lm]pyrrolo[3,4-j][1,7]benzodiamzonine-1-one), which is a multi-target protein kinase inhibitor being investigated for the treatment of AML (Levis, *Best Pract Res Clin Haematol* 23(4):489-494 (2010) and is represented by the following Formula XIV:

Formula XIV

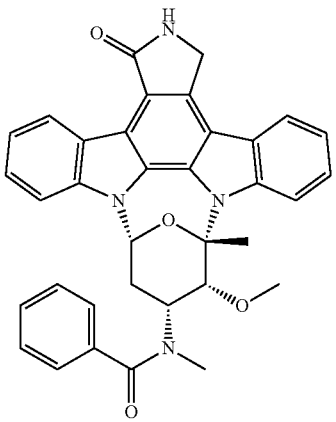

KW-2449 is a multiple-targeted inhibitor, mostly for Flt3 with IC50 of 6.6 nM (Shiotsu et al., *Blood* 114(8):(2009), which is represented by the following Formula XV:

Formula XV

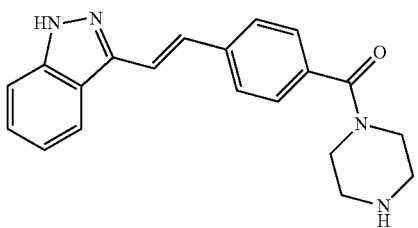

Combination Therapies Employing DOT1L Inhibitors and FLT3 Inhibitors

Within certain embodiments, the present disclosure provides methods, including therapeutic methods, which employ a combination of a DOT1L inhibitor that is administered prior to, coincident with, or after the administration of a FLT3 inhibitor as disclosed herein. These methods for inhibiting the growth and/or survival of a cell and for treating a patient, in particular a leukemia patient, exhibiting an elevated level of HOX cluster gene and/or HOX cluster-associated gene expression, employ a combination of compounds, including therapeutic compounds, including one or more DOT1L inhibitor(s) in combination with one or more Flt3 inhibitors, for the treatment of a leukemia, such as ALL or AML.

By these methods, one or more FLT3 inhibitors and one or more DOT1L inhibitor(s) can be administered to a human patient by themselves or in pharmaceutical compositions where they are mixed with suitable carriers or excipient(s) at doses to treat or ameliorate a disease or condition as described herein. Mixtures of these inhibitors can also be administered to the patient as a simple mixture or as pharmaceutical compositions.

Compositions within the scope of this disclosure include compositions wherein a first therapeutic agent is a DOT1L inhibitor and a second therapeutic agent is a FLT3 inhibitor, wherein the first therapeutic agent and the second therapeutic agent are administered at least substantially simultaneously or sequentially in an amount at a time that is effective to inhibit the proliferation of a leukemia cell in a patient. Determination of optimal ranges of effective amounts of each first and second therapeutic agent is within the skill of the art. The effective dose is a function of a number of factors, including the specific inhibitors and the patient's clinical status.

Compositions comprising a FLT3 inhibitor in combination with a DOT1L inhibitor may be administered parenterally. As used herein, the term "parenteral administration" refers to modes of administration other than enteral and topical administration, usually by injection, and include, without limitation, intravenous, intramuscular, intraarterial, intrathecal, intracapsular, intraorbital, intracardiac, intradermal, intraperitoneal, transtracheal, subcutaneous, subcuticular, intra-articular, subcapsular, subarachnoid, intraspinal, and intrasternal injection and infusion.

Alternatively, a composition comprising a FLT3 inhibitor may be administered prior to, concurrently with, or following the administration of a DOT1L inhibitor. For example, the administration of a DOT1L inhibitor may occur following the completion of a first therapeutic regimen comprising the administration of a FLT3 inhibitor. Conversely the administration of a FLT3 inhibitor may occur following the completion of a first therapeutic regiment comprising the administration of a DOT1L inhibitor.

The dosage of each inhibitor that is administered will be dependent upon the age, health, and weight of the recipient, the nature of the concurrent treatment, the frequency of treatment, and the nature of the effect desired.

Suitable dosages for intravenous infusion of a composition comprising a FLT3 inhibitor and a DOT1L inhibitor will depend upon the therapeutic efficacy of each inhibitor administered and may, for example, include a dosage of at least about 2 mg of a first inhibitor/m2/day or at least about 10 mg of a first inhibitor/m2/day or at least about 20 mg of a first inhibitor/m2/day or at least about 50 mg of a first inhibitor/m2/day or at least about 100 mg first inhibitor/m2/day or at least about 200 mg of a first inhibitor/m2/day or at least about 500 mg of a first inhibitor/m2/day, where a first inhibitor may be a FLT3 inhibitor or a DOT1L inhibitor. Likewise, a second inhibitor may be administered at a dosage of at least about 2 mg of a second inhibitor/m2/day or at least about 10 mg of a second inhibitor/m2/day or at least about 20 mg of a second inhibitor/m2/day or at least about 50 mg of a second inhibitor/m2/day or at least about 100 mg of a second inhibitor/m2/day or at least about 200 mg of a second inhibitor/m2/day or at least about 500 mg of a second inhibitor/m2/day. It will be understood that if a first inhibitor is a FLT3 inhibitor then a second inhibitor is a DOT1L inhibitor. Conversely, if a first inhibitor is a DOT1L inhibitor then a second inhibitor is a FLT3 inhibitor.

Compositions comprising a FLT3 inhibitor, compositions comprising a DOT1L inhibitor, and compositions comprising a combination of a FLT3 inhibitor and a DOT1L inhibitor generally include a therapeutically effective amount of the compound(s), and a pharmaceutically acceptable carrier. Because the two inhibitors are used in combination, one or the other may be administered at a subthreshold level and that is still considered a therapeutically effective amount. As used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skimmed milk, glycerol, propylene, glycol, water, ethanol and the like. The composition, if desired, can also contain minor amounts of wetting or emulsifying agents, or pH buffering agents.

These FLT3 inhibitor and/or DOT1L inhibitor compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, and the like. Such compositions will contain a therapeutically effective amount of the inhibitor, preferably in purified form, together with a suitable amount of carrier so as to provide the form for proper administration to the patient. The formulation should suit the mode of administration.

Compositions can be formulated in accordance with routine procedures as a pharmaceutical composition adapted for intravenous administration to a human. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The inhibitors disclosed herein can be formulated as neutral or salt forms. Pharmaceutically acceptable salts include those formed with anions such as those derived from hydrochloric, phosphoric, acetic, oxalic, tartaric acids, and the like, and those formed with cations such as those derived from sodium, potassium, ammonium, calcium, ferric hydroxides, isopropylamine, triethylamine, 2-ethylamino ethanol, histidine, procaine, and the like.

Many of the inhibitors of the present disclosure may be provided as salts with pharmaceutically compatible counterions (i.e., pharmaceutically acceptable salts). A "pharmaceutically acceptable salt" means any non-toxic salt that, upon administration to a recipient, is capable of providing, either directly or indirectly, a compound or a prodrug of a compound of this disclosure. A "pharmaceutically acceptable counterion" is an ionic portion of a salt that is not toxic when released from the salt upon administration to a subject. Pharmaceutically compatible salts may be formed with many acids, including but not limited to hydrochloric, sulfuric, acetic, lactic, tartaric, malic, and succinic acids. Salts tend to be more soluble in water or other protic solvents than their corresponding free base forms. The present disclosure includes such salts.

The amount of the FLT3 inhibitor, DOT1L inhibitor and combination of the two that will be effective in the treatment, inhibition, and/or prevention of a leukemia characterized by a high level expression of one or more HOX cluster genes or HOX cluster associated genes, but not possessing an MLL-translocation can be determined by standard clinical techniques. In vitro assays may optionally be employed to help identify optimal dosage ranges. The precise dose to be employed in the formulation will also depend on the route of administration, and the seriousness of the disease or disorder. Effective doses may be extrapolated from dose-response curves derived from in vitro or animal model test systems.

The FLT3 and DOT1L inhibitor compounds or compositions comprising FLT3 and/or DOT1L compounds can be tested in vitro, and then in vivo for the desired therapeutic or prophylactic activity, prior to use in humans. For example, in vitro assays to demonstrate the therapeutic or prophylactic utility of a compound or pharmaceutical composition include the effect of a compound on a cell line or a patient tissue sample. The effect of the compound or composition on the cell line and/or tissue sample can be determined utilizing techniques known to those of skill in the art including, but not limited to proliferation and apoptosis assays. In accordance with the present disclosure, in vitro assays that can be used to determine whether administration of a specific compound is indicated, include in vitro cell culture assays in which a patient tissue sample is grown in culture, and exposed to or otherwise administered a compound, and the effect of such compound upon the tissue sample is observed.

The present disclosure provides methods of treatment and inhibition by administration to a subject of an effective amount of a first inhibitor or composition thereof prior to, concomitantly or in combination with, or following administration of a second inhibitor or composition thereof, wherein a first inhibitor or composition thereof may include a FLT3 inhibitor and a second inhibitor or composition thereof or may include a DOT1L inhibitor. Alternatively, a first inhibitor or composition thereof may include a DOT1L inhibitor and a second inhibitor or composition thereof may include a FLT3 inhibitor. In one aspect, the compound is substantially purified such that the compound is substantially free from substances that limit its effect or produce undesired side-effects.

Various delivery systems are known and can be used to administer a composition of the present disclosure, for example, encapsulation in liposomes, microparticles, microcapsules, receptor-mediated endocytosis (see, e.g., Wu and Wu, J. Biol. Chem. 262:4429-4432 (1987)), and the like as will be known by one of skill in the art.

Methods of administration include, but are not limited to, intradermal, intramuscular, intraperitoneal, intravenous, subcutaneous, intranasal, epidural, and oral routes. The inhibitors or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the inhibitors or compositions into the central nervous system by any suitable route, including intraventricular and intrathecal injection. Intraventricular injection may be facilitated by an intraventricular catheter, for example, attached to a reservoir, such as an Ommaya reservoir. Pulmonary administration can also be employed, for example, by use of an inhaler or nebulizer, and formulation with an aerosolizing agent.

The FLT3 and DOT1L inhibitors, individually or together, can be delivered in a vesicle, such as a liposome (Langer, *Science* 249:1527-1533 (1990)) or in a controlled release system. A controlled release system can be placed in proximity of the therapeutic target, thus requiring only a fraction of the systemic dose (see, e.g., Goodson, in Medical Applications of Controlled Release, Vol. 2, pp. 115-138 (1984)).

Intravenous infusion of a compositions comprising a FLT3 inhibitor, a DOT1L inhibitor or both may be continuous for a duration of at least about one day, or at least about three days, or at least about seven days, or at least about 14 days, or at least about 21 days, or at least about 28 days, or at least about 42 days, or at least about 56 days, or at least about 84 days, or at least about 112 days.

Continuous intravenous infusion of a composition comprising a FLT3 inhibitor, a DOT1L inhibitor may be for a specified duration, followed by a rest period of another duration. For example, a continuous infusion duration may be from about 1 day, to about 7 days, to about 14 days, to about 21 days, to about 28 days, to about 42 days, to about 56 days, to about 84 days, or to about 112 days. The continuous infusion may then be followed by a rest period of from about 1 day, to about 2 days to about 3 days, to about 7 days, to about 14 days, or to about 28 days. Continuous infusion may then be repeated, as above, and followed by another rest period.

Regardless of the precise continuous infusion protocol adopted, it will be understood that continuous infusion of a composition comprising a FLT3 inhibitor, a DOT1L inhibitor will continue until either desired efficacy is achieved or an unacceptable level of toxicity becomes evident.

Use of DOT1L Inhibitors in Patients at High Risk of Developing Therapy-Related Leukemia and Exhibiting Mutations Associated with HOX Gene Cluster Overexpression or HOX Cluster-Associated Gene Overexpression Therapy-related AML (t-AML) and therapy-related ALL (t-ALL) are well-recognized clinical syndromes believed to occur as a direct consequence of mutations induced by cytotoxic chemotherapy and/or radiation used to treat a pre-existing condition, such as hematopoietic and solid malignancies. Approximately, 8-10% of all patients treated for cancer will develop t-AML an average 5 years following the treatment. Development of t-AML has been reported after treatment of various primary cancers, including Hodgkin's lymphoma, non-Hodgin's lymphoma, ovarian, breast, and lung cancers. Larson R A, *Haematologica,* 2009 April; 94(4):454-9. Specifically, it has been shown that alkylating chemotherapy agents, which bind DNA and prevent its replication, increase the risk of therapy-related leukemia. Furthermore, use of topoisomerase II inhibitors to treat certain types of cancers, such as lung cancer, has too been linked to increased risk of developing therapy-related AML. Bhatia S. *Semin Oncol.* 2013; December; 40(6):666-75.

Cytogenetic abnormalities observed in t-AML and t-ALL resemble those found in de novo AML and ALL. For example, similar to de novo AML, MLL rearrangement is a common feature of therapy-related AML (Schoch, *Blood.* 2003 October 1; 102 (7):2395-402.) Additionally, several of the known NUP90 translocations have been identified in patients with t-AML (Lam D H, *Leukemia,* 15(11):1689-95 (2001)). Similarly, it has been shown that IDH1 and IDH1 mutations are of the same type and occur at the same prevalence in t-AML and de novo AML (Westman, M K, Leukemia (2013)27, 957-959). Overall, the cited evidence strongly suggests that de novo AML and t-AML share common biological characteristics including the presence of mutations associated with elevated HOX cluster gene expression. Accordingly, DOT1L inhibitors would be useful in treating the foregoing type of high-risk individuals when the individuals exhibit overexpression of one or more HOX cluster gene(s) and/or one or more HOX cluster-associated gene(s). Instead of measuring such overexpression, such individuals can be identified if they are shown to possess a genetic mutation, alteration, and/or abnormality, other than an MLL-translocation, an MLL-rearrangement, and/or an MLL-PTD, which is known or determined to be associated with elevated expression of one or more HOX cluster genes and/or one or more HOX cluster-associated genes. The aim of the therapy would be to decrease such overexpression and thus reduce the risk of these individuals developing t-ALL and t-AML.

It will be understood that, unless indicated to the contrary, terms intended to be "open" (e.g., the term "including" should be interpreted as "including but not limited to," the term "having" should be interpreted as "having at least," the term "includes" should be interpreted as "includes but is not limited to," etc.). Phrases such as "at least one," and "one or more," and terms such as "a" or "an" include both the singular and the plural.

It will be further understood that where features or aspects of the disclosure are described in terms of Markush groups, the disclosure is also intended to be described in terms of any individual member or subgroup of members of the Markush group. Similarly, all ranges disclosed herein also encompass all possible sub-ranges and combinations of sub-ranges and that language such as "between," "up to," "at least," "greater than," "less than," and the like include the number recited in the range and includes each individual member.

Moreover, all of the foregoing sections pertaining to methods, kits, compositions comprising DOT1L inhibitors are deemed to apply to DOT11 inhibitors and FLT3 inhibitors in combination or conjunction All references cited herein, whether supra or infra, including, but not limited to, patents, patent applications, and patent publications, whether U.S., PCT, or non-U.S. foreign, and all technical and/or scientific publications are hereby incorporated by reference in their entirety.

While various embodiments have been disclosed herein, other embodiments will be apparent to those skilled in the art. The various embodiments disclosed herein are for purposes of illustration and are not intended to be limiting, with the true scope and spirit being indicated by the claims.

The present disclosure will be further described with reference to the following non-limiting examples. The teaching of all patents, patent applications and all other publications cited herein are incorporated by reference in their entirety.

EXAMPLES

Example 1

Inhibition of DOT1L Inhibits Growth of Leukemia Cells that Exhibit an MLL-Translocation, MLL-Rearrangement, or MLL-Partial Tandem Duplication (Prior Art)

This Example confirms, as is generally understood in the art, that leukemias exhibiting an MLL-translocation, MLL-rearrangement, or MLL-partial tandem duplication and an elevated expression of one or more HOX cluster gene or one or more HOX cluster-associated gene are sensitive to DOT1L inhibition.

DOT1L is a histone methyltransferase that is central to the mechanism by which multiple leukemogenic fusion oncoproteins induce inappropriate gene expression in developing white blood cells, thus reprograming them and blocking their differentiation. Inhibition of DOT1L suppresses the leukemia-associated gene expression signature and induces differentiation of MLL-fusion driven leukemias.

It has been demonstrated that HOX cluster genes are important for continued proliferation and survival of leukemia cells (Faber et al., HOXA9 is required for Survival in Human MLL-rearranged Acute Leukemias, *Blood* 113(11): 2375-85 (2009)) and it has been suggested that elevated HOX cluster gene expression in AML may be associated with adverse outcome. It has also been shown that, in MLL-translocated leukemias, inhibition of the DOT1L histone methyltransferase causes a decrease in HOX cluster gene expression and a corresponding decrease in cellular proliferation.

Based upon these findings, DOT1L was postulated as a potential therapeutic target for MLL-translocated leukemias, which depend upon DOT1L for continued proliferation and survival and exhibit elevated HOX cluster gene expression.

Figure 2:
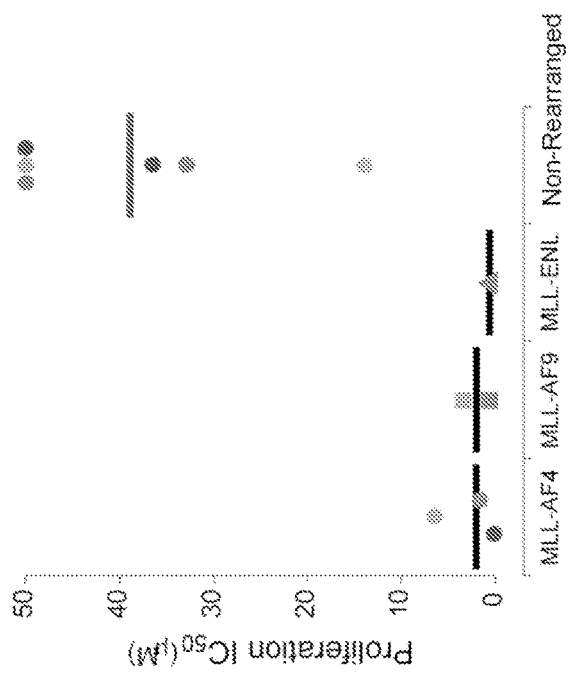
Figure 3:
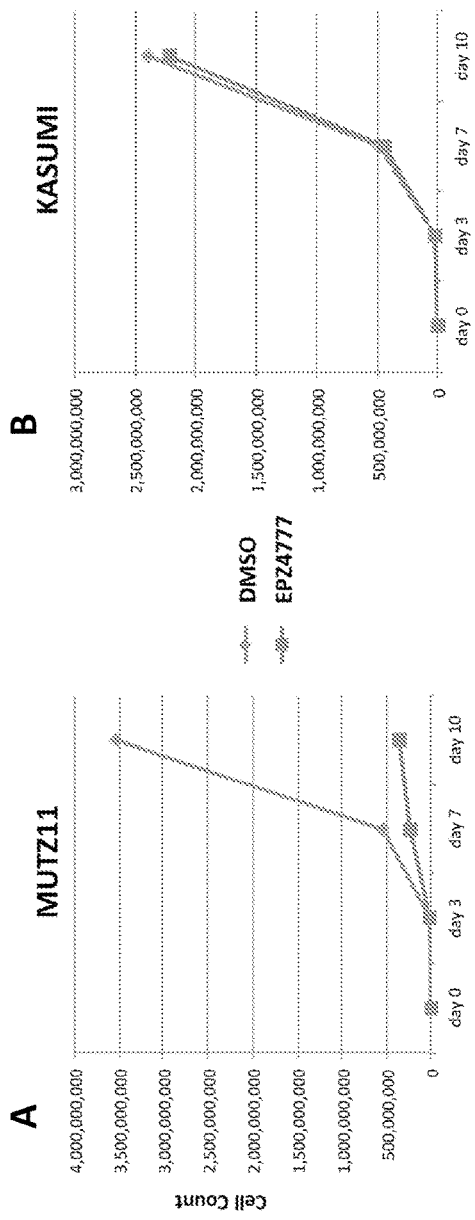
FIGS. 3A and 3B are growth curves showing number of cells (y axis) over 10 day period (x axis). The proliferation of the human MLL-PTD AML cell line (MUTZ11) is inhibited by DOT1L (FIG. 3A) whereas the proliferation of AML1-ETO (Kasumi) cells is insensitive to DOT1L (FIG. 3B). The indicated cell lines were treated with 10 μM EPZ004777 or DSMO (control) and cell counts were assessed on the days indicated.

Studies were performed to determine the IC50 for cell proliferation in six leukemia cell lines with MLL-translocations and six cell lines without MLL-translocations. The IC50s for MLL-translocated lines are: MV4-11 (ATCC®, CRL-9591, Manassas, Va.), 170 nM; SEMK2 (S, Armstrong, MSKCC), 1.7 mM; KOPN-8 (Creative Bioarray, Shirley, N.Y.), 620 nM; Molm-13 (Creative Bioarray, Shirley, N.Y.), 720 nM; and THP-1 (ATCC® TIB-202), 3 mM. In contrast, the IC50s for non-MLL-translocated cell lines are: Jurkat (ATCC® CRL-2898), >50 mM; Kasumi-1 (ATCC® CRL-2724), 33 mM; 697 (Creative Bioarray, Shirley, N.Y.), 35 mM; REH (ATCC® CRL-8286), 14 mM; and HL-60 (ATCC® CCL-240), >50 mM (FIG. 2).

Dependencies on DOT1L and H3K79 methylation were identical in murine MLL-AF9 transformed cell lines whether DOT1L was genetically inactivated using a conditional knockout model or inhibited with the small molecule EPZ004777. Specifically, HOXA9/MEIS1 transformed cells were insensitive to DOT1L inhibition whereas MLL-AF9 transformed cells undergo cell cycle arrest and apoptosis as a result of DOT1L inhibition.

Two human leukemia cell lines, MUTZ-11 (H. Drexler, DSMZ, Braunschweig, Del.) and EOL-1 (Sigma-Aldrich, St. Louis, Mo.), which exhibit elevated HOX cluster gene expression and possess an MLL-partial tandem duplication (MLL-PTD) were tested for proliferation in the presence of the selective small molecule aminonucleoside DOT1L inhibitor EPZ004777 (Daigle et al., *Cancer Cell* 20(1):53-65, 2011). The MUTZ11 and EOL1 cell lines were treated with 10 μM EPZ004777, a concentration that does not influence the proliferation of cell lines that do not show elevated HOXA gene expression (FIG. 2). EPZ004777 significantly inhibited proliferation of both of the MLL-PTD cell lines tested over a 10-day period (FIG. 2).

Figure 4:
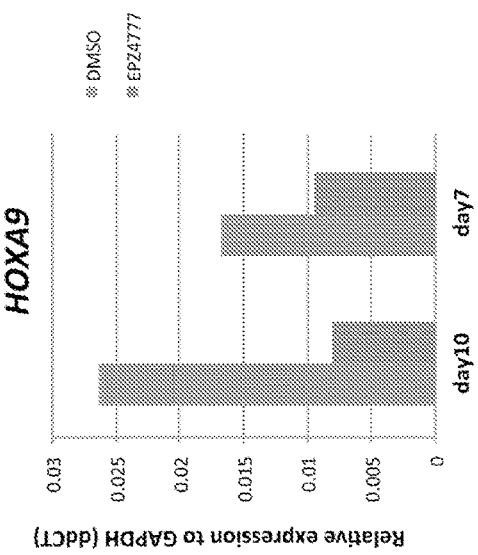
FIG. 4 is a bar graph showing relative expression of HOXA9 relative to GAPDH (ddCT) and showing that HOXA9 expression is decreased after treatment of MLL-PTD AML cell line MUTZ11 cells with the DOT1L inhibitor EPZ004777. MUTZ11 cells were treated with DMSO (control) or EPZ004777 and HOXA9 expression was assessed at days 7 and 10.

HOXA gene expression was assessed at seven and 10 days after treatment of the MLL-PTD cell line MUTZ11. HOXA cluster gene expression decreased significantly (FIG. 4), suggesting that DOT1L is required for continued proliferation and elevated HOXA cluster gene expression in MLL-PTD leukemia cells.

Example 2

Inhibition of DOT1L Inhibits Growth of Leukemia Cells that Exhibit a Genetic Mutation that is not an MLL-Translocation, MLL-Rearrangement, or MLL-Partial Tandem Duplication but is Associated with Elevated HOX Cluster Gene Expression This Example demonstrates that certain leukemia tissues and cells that exhibit: (1) one or more leukemia-associated mutation in a gene other than an MLL-translocation, MLL-rearrangement, or MLL-partial tandem duplication (MLL-PTD) and (2) elevated expression of one or more HOX cluster gene and/or one or more HOX cluster-associated gene, are sensitive to DOT1L inhibition and, therefore, may be advantageously treated by the administration of a DOT1L inhibitor.

In addition to leukemias associated with MLL-translocations, MLL-rearrangements, and MLL-PTDs, other leukemias, for example leukemias with one or more mutation(s) in any of the NPM1, DNMT3A, IDH1, IDH2, RUNX1, TET2, and/or ASXL1 genes and/or an NUP98-NSD1 and/or other NUP98 translocation also display elevated HOX cluster gene and/or HOX cluster-associated gene expression. (See Tables 2 and 3, which discloses leukemia associated genes that are associated with (Table 2) and that are not associated with (Table 3) elevated HOX cluster gene and/or HOX cluster-associated gene expression).

The role of DOT1L in regulating HOX cluster gene expression and HOX cluster-associated gene expression and maintenance of cell proliferation and survival was assessed as part of the present disclosure in representative leukemias exhibiting mutations in the NPM1, DNMT3A, IDH1, IDH2, RUNX1, TET2, and ASXL1 genes and NUP98-NSD1 and other NUP98 translocation, which leukemias do not also exhibit an MLL-translocation, an MLL-rearrangement, or an MLL-PTD.

Leukemia cells driven by the NUP98-NSD1 fusion protein also exhibit elevated HOX cluster gene expression, presumably as a result of aberrant H3K36 methylation as NSD1 is an H3K36 methyl-transferase. Wang et al., NUP98-NSD1 Links H3K36 Methylation to HOX-A Gene Activation and Leukaemogenesis, *Nature Cell Biology* 9(7):804-12 (2007).

Figure 5:
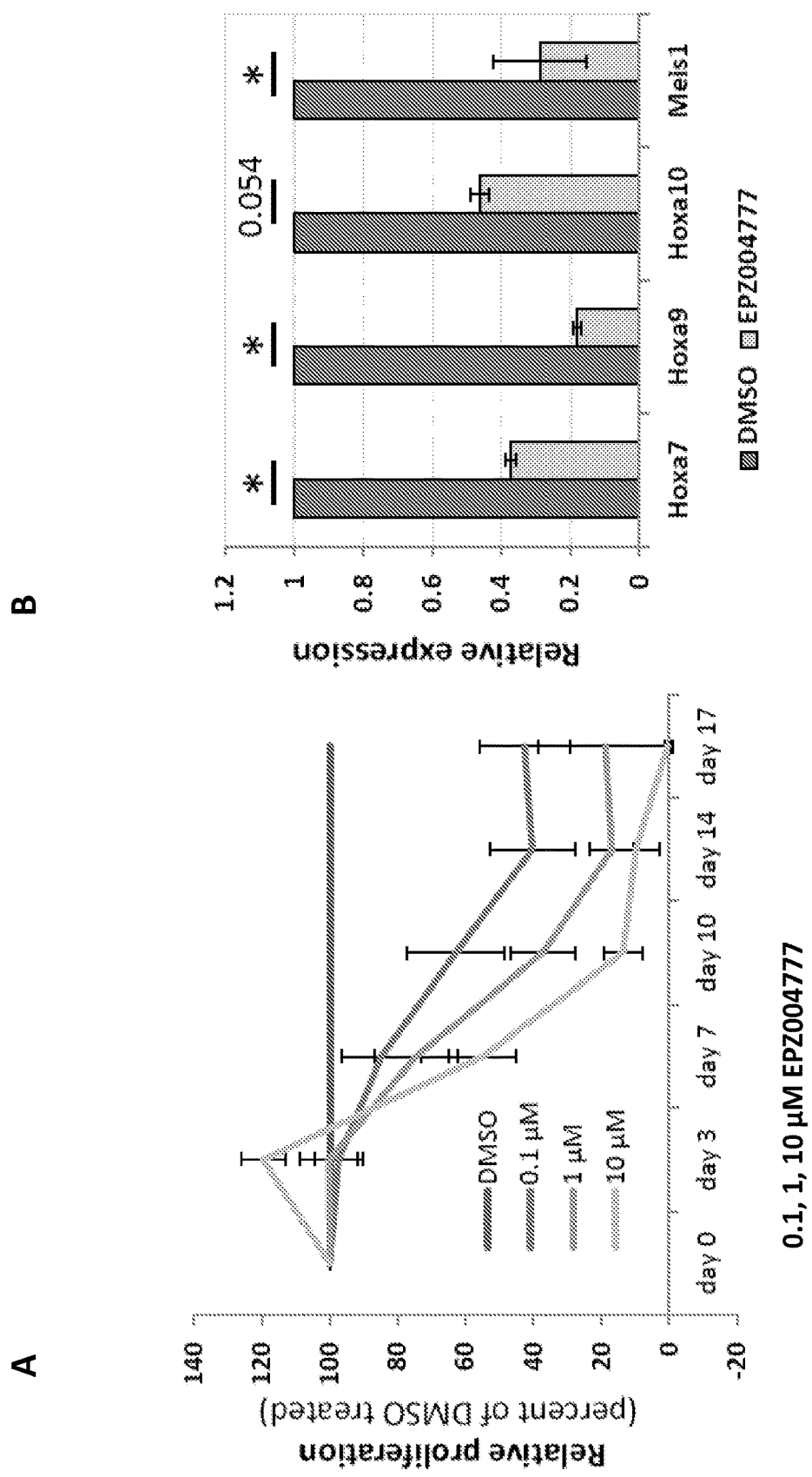
FIGS. 5A and 5B show effects of EPZ004777 in NUP98-NSD1 transformed mouse cells, where

As disclosed herein, proliferation of leukemia cells expressing a NUP98-NSD1 gene fusion is inhibited by EPZ004777 DOT1L. Because NSD1 drives aberrant H3K36 methylation, these data further implicate an important, and previously unrecognized, connection between histone K36 methylation by NSD1 and K79 methylation by DOT1L (FIG. 5).

An NPM1 mutant human AML cell line, OCI-AML3 (DSMZ, ACC-582; Braunschweig, Del.), was also treated with the DOT1L inhibitor EPZ004777 and proliferation of those EPZ004777-treated OCI-AML3 cells was compared to the proliferation of an EPZ004777-sensitive MLL-translocated line and an EPZ004777-insensitive AML1-ETO-translocated cell line in the presence of EPZ004777. The OCI-AML3 cells were as sensitive to growth inhibition by EPZ004777 as were the MLL-translocated lines while the AML1-ETO-translocated cell line was not sensitive to EPZ004777-mediated growth inhibition (FIG. 7A-D).

The data presented in this Example demonstrate that leukemias that exhibit elevated HOX cluster gene or HOX cluster-associated gene expression, but do not possess an MLL-translocation, an MLL-rearrangement, or an MLL-PTD, are responsive to DOT1L inhibition and that proliferation of such elevated HOX cluster gene expressing leukemia cells is reduced when such cells are contacted with a DOT1L inhibitor, such as EPZ004777.

Moreover, and without intending to be limited by theory, the data presented herein suggest that H3K79 methylation by DOT1L is important for the maintenance of HOX gene expression in normal hematopoietic cells and support the clinical efficacy of DOT1L inhibitors for the treatment of leukemias in patients exhibiting elevated HOX cluster gene expression, regardless of whether those leukemias possess an MLL-translocation, MLL-rearrangement, or MLL-PTD.

Example 3

A Mouse Model System for Defining Roles for Epigenetic Regulators in Leukemias

In order to develop a mouse model system of NUP98-NSD1 driven leukemia, a cDNA that encodes the NUP98-NSD1 fusion protein was introduced it into Lin−, Sca1+, c-Kit+ (LSK) mouse bone marrow cells enriched for hematopoietic stem cells (HSCs). These cells proliferate indefinitely in culture and induce leukemia in mice. Therefore, NUP98-NSD1 transformed HSC-enriched LSK cells can be assessed for DOT1L inhibition.

NUP98-NSD1 transformed HSC-enriched LSK cells were treated with the DOT1L inhibitor EPZ004777 and found to be remarkably sensitive to EPZ004777 as evident by proliferation defect upon the exposure of cells to various concentration of DOT1L inhibitor (FIG. 5A). Moreover, 7 day treatment of NUP98-NSD1 transformed mouse cells with 10 μM of DOT1L inhibitor significantly reduced HOX promoter associated H3K79 methylation, which was accompanied by a substantial decrease in HOXa7, HOXa9, HOXa10, and Meis1 cluster gene expression (FIG. 5B).

In order to begin to address the role of DOT1L in normal hematopoietic stem cells (HSC), a conditional DOT1L knockout mouse was crossed with a Mx1-CRE mouse to generate a mouse in which HSC DOT1L expression could be conditionally inactivated upon treatment with polyinosinic-polycytidylic acid (pIpC).

Inactivation of DOT1L led to a gradual decrease in the number and function HSCs. Prior to this decrease in number and function, global gene expression was assessed to determine which gene expression programs are DOT1L dependent in HSC. Inactivation of DOT1L led to a decrease in the expression of a number of genes important for HSC biology as well as in HOXA cluster and MEIS1 gene expression. Indeed, a number of the MLL-fusion target genes decreased in expression upon DOT1L inactivation in normal HSC. The fact that DOT1L and, thus, H3K79 methylation controls HOXA cluster gene expression in normal HSC further demonstrates that other leukemias (beyond those with MLL-translocations, MLL-rearrangements, or MLL-PTDs) that exhibit elevated HOXA cluster gene expression are also sensitive to DOT1L inhibition.

Example 4

Efficacy of DOT1L Inhibitors in Leukemias Associated with NPM1, DNMT3A, IDH1, IDH2, RUNX1, TET2, ASXL1, NUP98-NSD1 and Other NUP98 Translocations Experiments with DOT1L inhibitors are performed to further define the role for DOT1L in leukemias associated with mutations in the NPM1, DNMT3A, IDH1, IDH2, RUNX1, TET2, and ASXL1 genes and NUP98-NSD1 and other NUP98 translocations.

Figure 8:
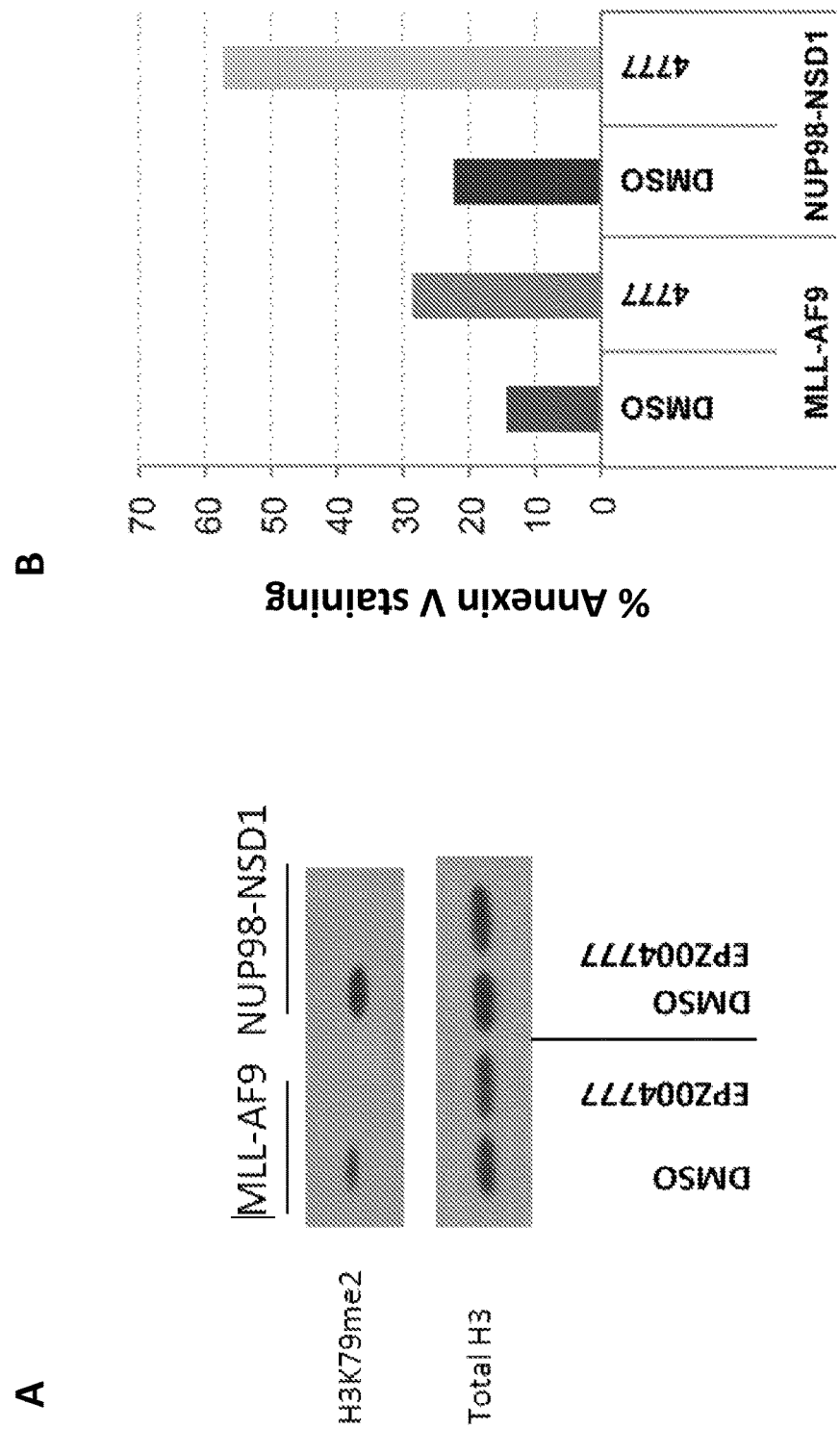
FIGS. 8A and 8B show the effects of EPZ004777 on H3K79me2 and apoptosis in MLL-AF9 and NUP98-NSD1 transformed cells, respectively.

In order to determine if NUP98-NSD1 mouse transformed cells exhibit similar level of sensitivity to DOT1L inhibition as do previously described MLL-AF9 cells, the ability of DOT1L inhibitor EPZ004777 to reduce H3K79 methylation was monitored. Following 10-day treatment with 10 μM of EPZ004777, global H3K79 levels were determined in both NUP98-NSD1 and MLL-AF9 cells by Western blotting. While NUP98-NSD1 cells exhibit higher levels of endogenous H3K79me2, EPZ004777 treatment completely abrogated H3K79me2 in both cell types (FIG. 8A). Furthermore, in order to test if DOT1L inhibitor induced apoptosis in NUP98-NSD1 transformed cells, cells were treated with 10 μM of the DOT1L inhibitor EPZ004777 or vehicle control. Apoptosis was assessed by staining cells with Annexin V 10 days after treatment. The extent of apoptosis was compared to that found in MLL-AF9 transformed cells treated in a similar fashion. It was found that the DOT1L inhibitor induced more apoptosis in the NUP98-NSD1 transformed cells than in the MLL-AF9 transformed cells (FIG. 8B). To further test the hypothesis that cell lines expressing high levels of the HOXA9 and MEIS1 genes would be sensitive to treatment with DOT1L inhibitors independent of the presence of MLL mutations, two cell lines, OCI-AML2 and OCI-AML3, which exhibit DNTM3A and NPM1 mutations, respectively, and which exhibit high level of HOXA9 expression, but do not possess an MLL mutation, were treated with either 10 μM of the DOT1L inhibitor EPZ004777 or vehicle control. Simultaneously, HL60 cells (negative control), which do not express HOXA9, and Molm-13 cells (positive control), which exhibit high level expression of HOXA9 and possess an MLL-translocation, were also treated with either 10 μM of the DOT1L inhibitor EPZ004777 or vehicle control.

Figure 9:
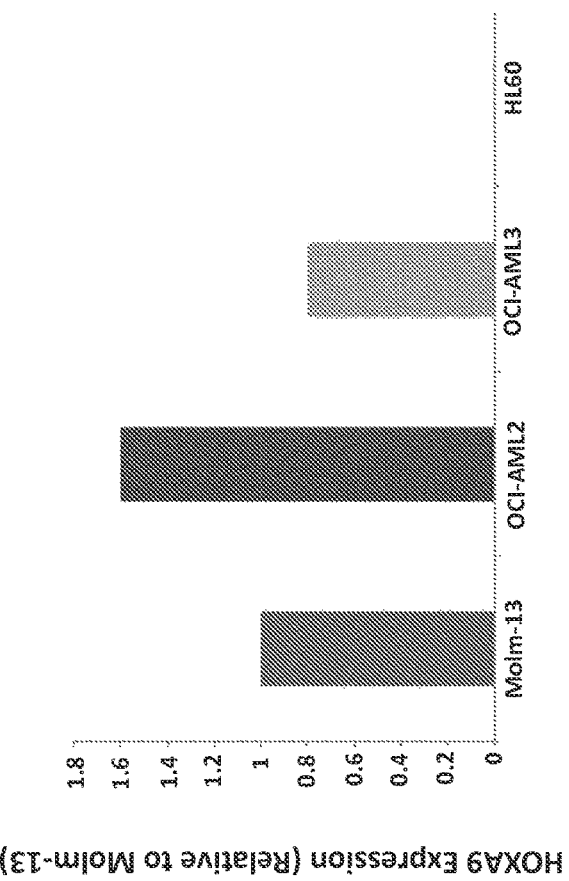
FIG. 9 is a bar graph showing HOXA9 gene expression assessed by quantitative PCR in various cell lines, including the AML cell lines OCI-AML2 and OCI-AML3, which exhibit DNTM3A and NPM1 mutations, respectively, as compared to the negative control cell line HL60 and the positive control cell line Molm-13, which exhibits an MLL-AF9 translocation.
Figure 10:
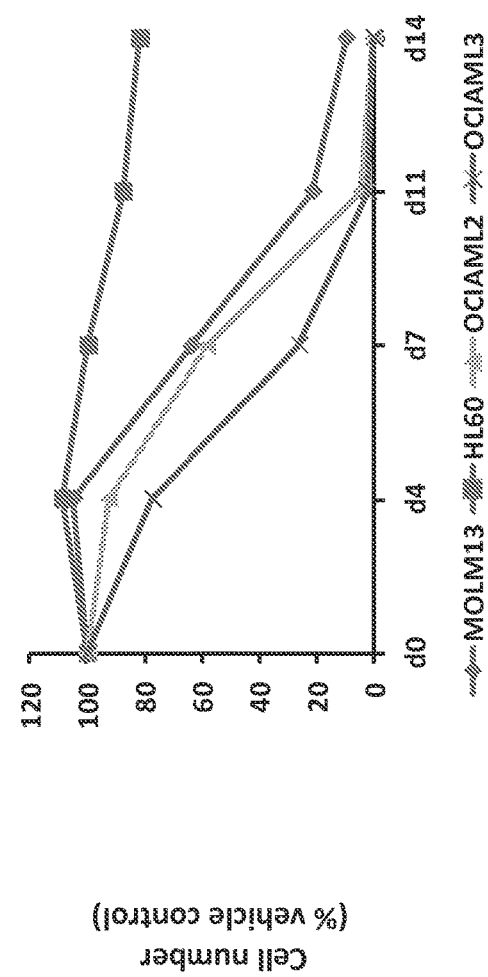
FIG. 10 is a graph of cell number plotted against the number of treatment days demonstrating that cell lines with DNTM3A or NPM1 mutations are sensitive to DOT1L inhibition. Cell lines OCI-AML2, OCI-AML3, Molm-13, and HL-60 were treated with either DMSO (control) or 10 μM DOT1L inhibitor EPZ004777. The number of cells was assessed at indicated time points and the percentage of cells present in the EPZ004777 treated vs. DMSO (control) treated conditions was graphed at each time point. OCI- AML2, OCI-AML3, and Molm-13 cell lines express high levels of HOXA9 and MEIS1, whereas HL60 does not express high levels of either HOXA9 or MEIS1.
Figure 11:
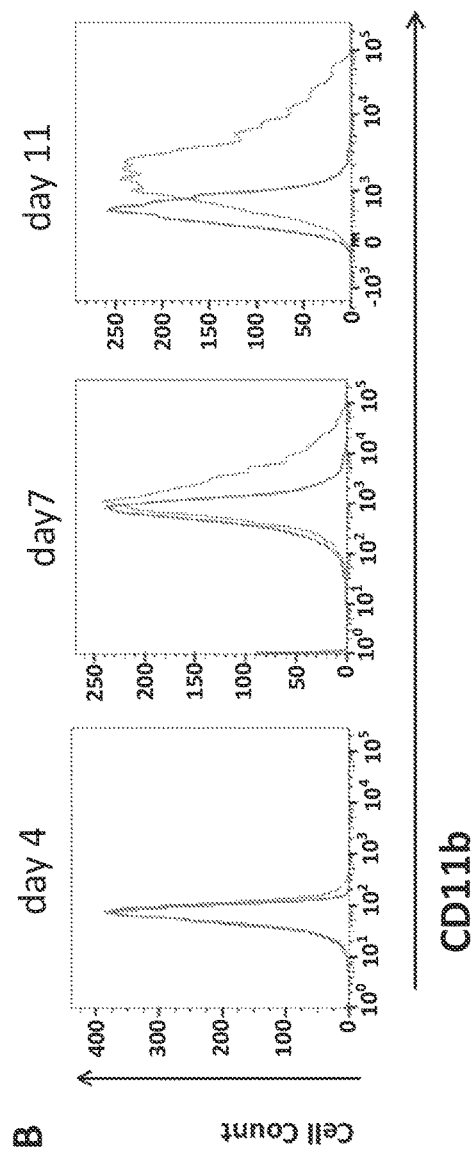
FIGS. 11A and 11B demonstrate that OCI-AML3 cells undergo apoptosis and differentiation in response to DOT1L inhibition.
Figure 11:
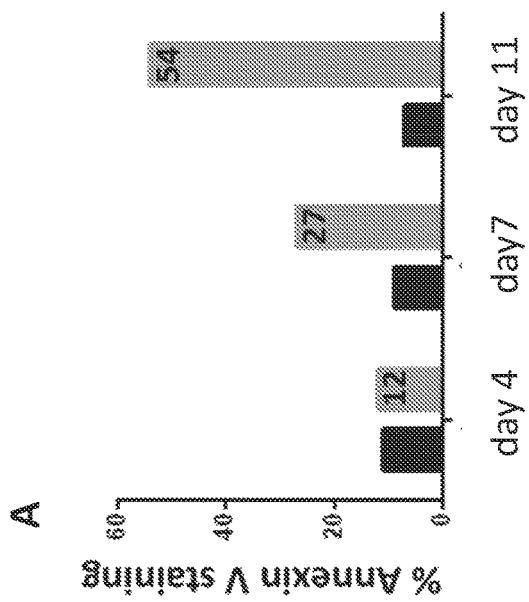

Cell numbers were assessed at multiple time points after treatment was initiated. The OCI-AML2 and OCI-AML3 cells were equally, if not more sensitive, to the DOT1L inhibitor then were the MLL-rearranged cell line Molm-13 (FIGS. 9 and 10). Next, we assessed whether the DOT1L inhibitor induced apoptosis in the OCI-AML3 cells and found that it indeed induced a tremendous increase in apoptotic cells in the culture (FIG. 11A). Cell cycle status determined by flow cytometry showed that cells in contact with DOT1L inhibitor exhibited Sub G1 accumulation, which is suggestive of apoptosis. Evidence of differentiation was assessed after DOT1L inhibition via characterization of cell surface marker expression—such as CD11b and CD15 expression, both of which are induced upon differentiation of myelomonocytic leukemia cells. Treatment of OCI-AML3 cells with EPZ004777 was marked with increased differentiation as measured by the expression of cell surface differentiation marker CD11b (FIG. 11B).

OCI-AML2 and OCI-AML3 human cells, which exhibit DNTM3A and NPM1 mutations, respectively, were treated with increasing concentrations of DOT1L inhibitor EPZ00477 for up to 10 μM. MTT assays were performed on day 11. The IC50 was determined to be 0.15 μM for both OCI-AML2 and OCI-AML3 cell lines, which is lower than the historical IC50 values for MLL-fusion cell lines.

The influence of DOT1L inhibition is assessed on the colony growth from hematopoietic stem cells (Lin− c-kit+ Sca-1+ CD150+ CD48−) isolated from mice and CD34+/CD38− cells from human cord blood to determine the effects of the DOT1L inhibitors on normal stem and progenitor cells. Preclinical studies with the DOT1L inhibitor EPZ005676, which is being tested in a phase 1 clinical trial, did not show hematopoietic toxicity in mice or rats at a dose that was efficacious against human and murine MLL-translocated leukemia cells.

Example 5

Mouse Studies

Figure 12:
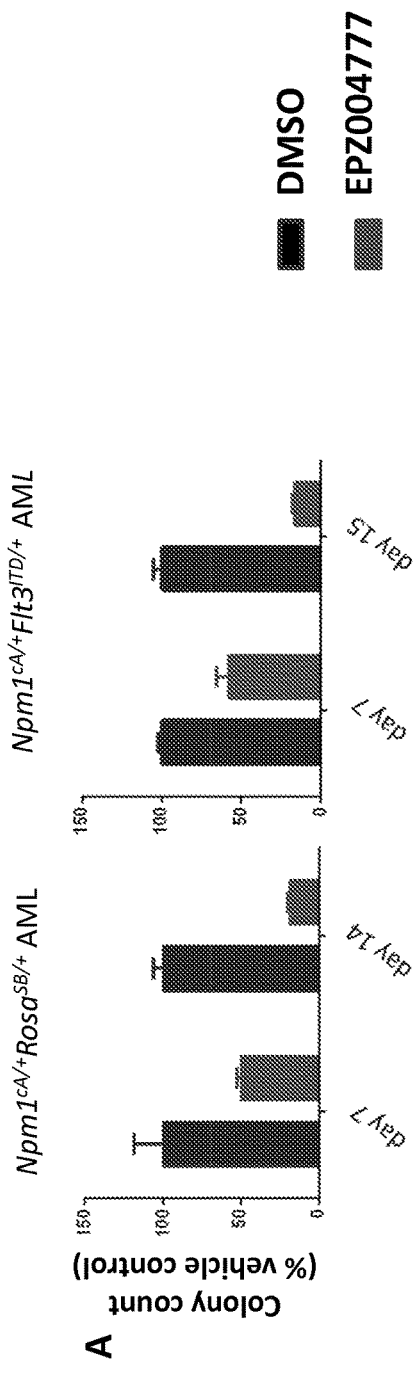
FIGS. 12A and 12B are graphs of AML cells isolated from $Npm1^{cA/+}Rosa^{SB/+}$ or $Npm1^{cA/+}Flt3^{ITD/+}$ mice, which were tested for their clonogenic potential following primary (FIG. 12A) and secondary (FIG. 12B) transplantation of cells into the recipients. AML cells isolated from $Npm1^{cA/+} Rosa^{SB/+}$ or $Npm1^{cA/+}Flt3^{ITD/+}$ mice were cultured for 6 days in the presence of 10 µM of DOT1L inhibitor prior to transplantation of cells into the recipients. Following the primary (FIG. 12A) and secondary (FIG. 12B) transplantations, $Npm1^{cA/+}Rosa^{SB/+}$ and $Npm1^{cA/+}Flt3^{ITD/+}$ AML cells were treated with vehicle control (DMSO) or 10 µM of EPZ00477 for indicated number of days (7, 14, and 15 for primary; 1, 14, and 22 for secondary transplantation) after which colony formation assay was performed. Treatment of AML mouse cell lines with 10 µM of DOT1L inhibitor resulted in significant reduction of the colony formation potential following both the primary and secondary transplantation.
Figure 12:
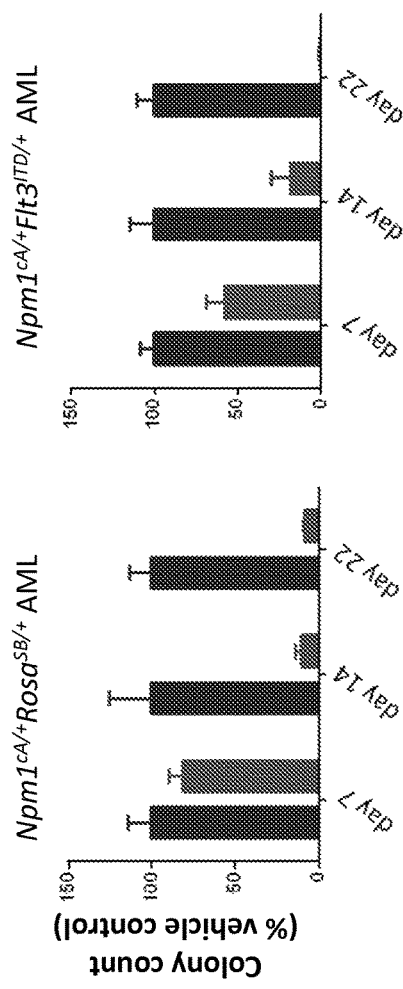

Experiments using mouse models were performed to understand the consequences of DOT1L inhibition in vivo. Mouse models of AML were used to test the in vivo efficacy of DOT1L inhibitor EPZ004777. Animals engineered to contain NPM1c mutation in combination with an additional mutation such as Npm1$^{cA/+}$Rosa$^{SB/+}$ (Vassiliou G, Nature Genetics, 2011) or Npm1$^{cA/+}$Flt3$^{ITD/+}$ (Mupo A, Leukemia, 2013) develop AML within 1 year and 68 days, respectively. AML cells isolated from Npm1$^{cA/+}$Rosa$^{SB/+}$ or Npm1$^{cA/+}$Flt3$^{ITD/+}$ mice and cultured for 6 days in the presence of 10 μM of DOT1L inhibitor were tested for their clonogenic potential following transplantation of cells into the recipients. Following the primary and secondary transplantations, Npm1$^{cA/+}$Rosa$^{SB/+}$ and Npm1$^{cA/+}$Flt3$^{ITD/+}$ AML cells were treated with vehicle control (DMSO) or 10 μM of EPZ00477 for indicated number of days (7, 14, 15 or 22 as written) (FIGS. 12A and B) after which colony formation assay was performed. Culture of AML mouse cell lines in the presence of DOT1L inhibitor resulted in significant reduction of the colony formation potential following both the primary and secondary transplantation (FIGS. 12A and B). The effects of DOT1L inhibition on colony formation were more prominent at later time points (day 14, 15 and 22).

In order to assess the effects of DOT1L inhibition on leukemia initiating potential, syngeneic C57/BL6 mice were injected with Npm1$^{cA/+}$Rosa$^{SB/+}$ cells previously treated for 6 days with DMSO or 10 μM of EPZ004777. The Kaplan-Meier survival curves for the two groups (DMSO and EPZ004777) are illustrated in FIG. 13A and show extended survival time of animals injected with cells that received DOT1L inhibitor. Furthermore, peripheral blood smears stained with Wright-Giemsa stain indicate differentiation in EPZ00477 treated cells (and not in cells exposed to only DMSO) (FIG. 13B). Finally, complete blood counts were analyzed, showing a significant reduction in the number of white blood cells, which was accompanied by a parallel slight increase in the levels of hemoglobin and platelet counts (FIG. 13C). Collectively, these results demonstrate that DOT1L inhibitor abates leukemogenesis in vivo in a mouse model of AML driven by NPM1 and not by MLL mutation, translocation, or duplications.

Figure 14:
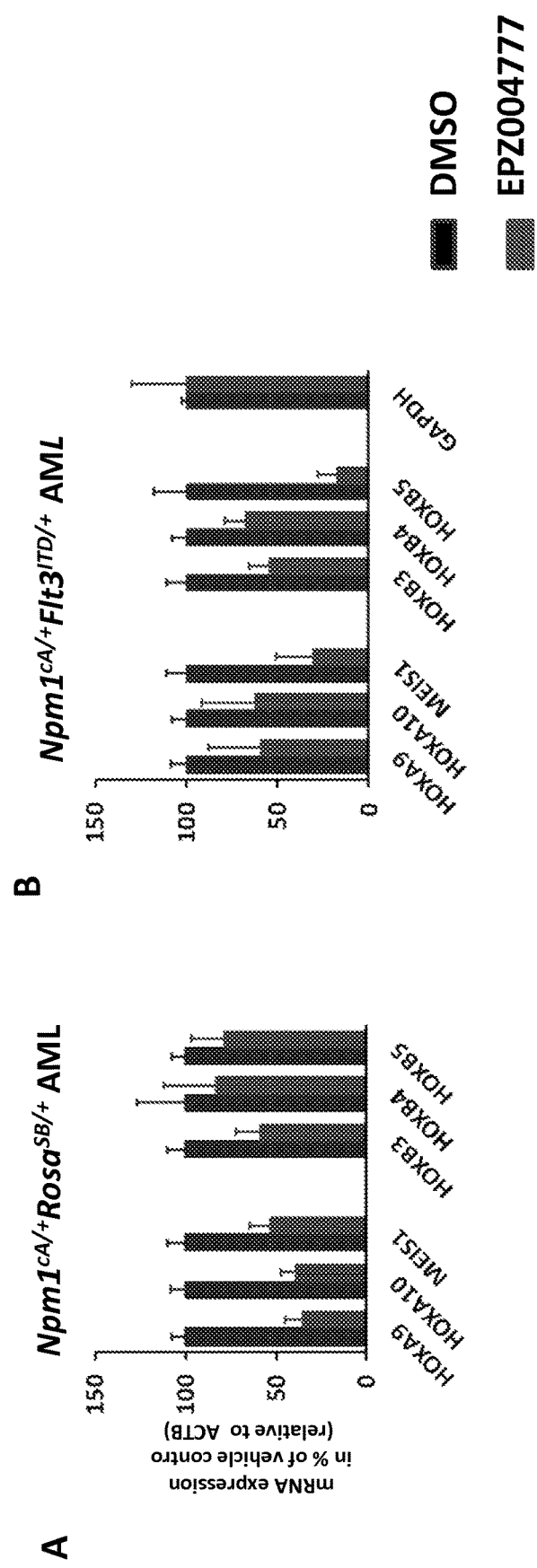
FIGS. 14A and 14B show bar graphs of relative expression of HOXA9, HOXA10, MEIS1, HOX3A, HOXA4, and HOXA5 relative to GAPDH (ddCT) in $Npm1^{cA/+}Rosa^{SB/+}$ (FIG. 14A) and $Npm1^{cA/+}Flt3^{ITD/+}$ (FIG. 14B) AML cells following the treatment of cells with DMSO or 10 µM EPZ004777.

The effect of DOT1L inhibition on the levels of various HOX genes and HOX-associated genes was evaluated using qPCR. Treatment of Npm1$^{cA/+}$Rosa$^{SB/+}$ and Npm1$^{cA/+}$Flt3$^{ITD/+}$ murine AML cells with EPZ00477 led to a significant decrease of HOXA9, HOXA10, MEIS1, HOXB3, HOXB4 and HOXB5 mRNA levels (FIGS. 14A and B, wherein RNA level for each HOXA9, HOXA10, MEIS1, HOXB3, HOXB4 and HOXB5 are shown) further indicating HOX gene and HOX-associated gene expression is largely dependent on DOT1L activity.

Example 6

Mouse Studies (Prophetic)

This Example describes the generation of mice xenografted with leukemias, including leukemias associated with one or more mutation(s) in one or more of the NPM1, DNMT3A, IDH1, IDH2, RUNX1, TET2, and ASXL1 genes and/or an NUP98-NSD1 or other NUP98 translocation(s) and the testing of the resulting mouse models for the in vivo efficacy of DOT1L inhibitors.

Leukemia samples (pediatric and adult) are characterized for NPM1, DNMT3A, IDH1, IDH2, RUNX1, TET2, and ASXL1 mutations and NUP98-NSD1 and other NUP98 translocations. It is known that infusion, including continuous infusion, of EPZ005676 suppresses the growth of MLL-translocated leukemia cells in mice. Similar experiments are performed with NPM1, DNMT3A, IDH1, IDH2, RUNX1, TET2, and ASXL1 cell lines and cell lines exhibiting NUP98-NSD1 or other NUP98 translocations (and MLL-translocated and/or MLL-PTD cell lines as controls) to determine the activity of the small-molecule inhibitor in vivo.

Initial experiments are with cell lines where the growth kinetics and drug response characteristics are already known. Armstrong et al., Inhibition of FLT3 in MLL: Validation of a Therapeutic Target Identified by Gene Expression based Classification, *Cancer Cell* 3(2):173-83 (2003). Biomarker assessment, such as inhibition of H3K79me2, is defined in vitro in the same cell line studies as described above, and similar analysis is performed on the cells treated in vivo.

The in vivo efficacy of DOT1L inhibitors can be tested in immunodeficient rats xenografted with NPMJ, DNMT3A, IDH1, IDH2, RUNX1, TET2, and/or ASXL1 cell lines and/or cell lines exhibiting NUP98-NSD1 or other NUP98 translocation(s) according to the methodology described in Daigle et al., *Blood* (2013, June 25) [Epub ahead of print], which describes the in vivo efficacy of the DOT1L inhibitor EPZ005676 in immunodeficient rats xenografted with the MLL-translocation cell line MV4-11.

The in vivo efficacy of DOT1L inhibitors can be tested in immunodeficient mice xenografted with NPMJ, DNMT3A, IDH1, IDH2, RUNX1, TET2, and/or ASXL1 cell lines and/or cell lines exhibiting NUP98-NSD1 or other NUP98 translocation(s) according to the methodology described in Wang et al., NUP98-NSD1 Links H3K36 Methylation to HOX-A Gene Activation and Leukaemogenesis, *Nature Cell Biology* 9(7):804-12 (2007)), which describes the generation of immunodeficient NSG mice engrafted with an NUP98-NSD1 murine leukemia. DOT1L inhibitors are then assessed against NPM1, DNMT3A, IDH1, IDH2, RUNX1, TET2, and/or ASXL1 leukemias and/or leukemias exhibiting NUP98-NSD1 or other NUP98 translocation(s) in those leukemia engrafted immunodeficient mice.

Biomarker assessment strategies are combined to assess the extent of inhibition of H3K79ME2. These biomarker assessment studies correlate enzyme inhibition and response that is relevant to clinical trial assessment of small molecule DOT1L inhibitors in patients. Group sizes of n=9 is sufficient to detect a 30% difference in tumor burden with a two-sided test at α=0.05, with a power ≥80%. Group sizes of n=9-10 animals are, therefore, used for the in vivo efficacy studies.

These experiments will provide further support for the therapeutic efficacy of DOT1L inhibitors against NPM1, DNMT3A, IDH1, IDH2, RUNX1, TET2, and/or ASXL1 mediated leukemias and/or leukemias mediated by NUP98-NSD1 or other NUP98 translocation(s).

Example 7

Identification of Genes that Modulate Sensitivity to DOT1L Suppression in NPM1, DNMT3A, IDH1, IDH2, RUNX1, TET2, and/or ASXL1 Mediated Leukemias and/or Leukemias Mediated by NUP98-NSD1 or Other NUP98 Translocation(s) (Prophetic)

Given that DOT1L appears to be critical for NPM1, DNMT3A, IDH1, IDH2, RUNX1, TET2, ASXL1, and NUP98-NSD1 cell proliferation, other genes that are either enhancers or suppressors of this pathway are also identified. Modulators of the DOT1L complex are all potential therapeutic targets. Also, identification of genes that either suppress or enhance the DOT1L inhibitor mediated growth inhibition clarify the mechanism of action of both the inhibitor and the NPM1, DNMT3A, IDH1, IDH2, RUNX1, TET2, ASXL1, and NUP98-NSD1 genes.

Previous studies demonstrated that NUP98-NSD1 influences H3K36 methylation as part of its mechanism to induce HOX gene expression and transformation, but it is unclear how H3K79 methylation plays a role in this leukemia. ChIP-seq studies further define the changes in histone modifications that take place after DOT1L inhibition. The screens defined herein clarify the role that DOT1L plays in these leukemias.

High throughput, genome-scale shRNA screening (HT-shRNA) leads to the identification of new targets of drug sensitivity/resistance. Experiments are performed akin to genetic enhancer/suppressor screens using either small molecules or genetic loss of function models in mammalian systems.

Figure 6:
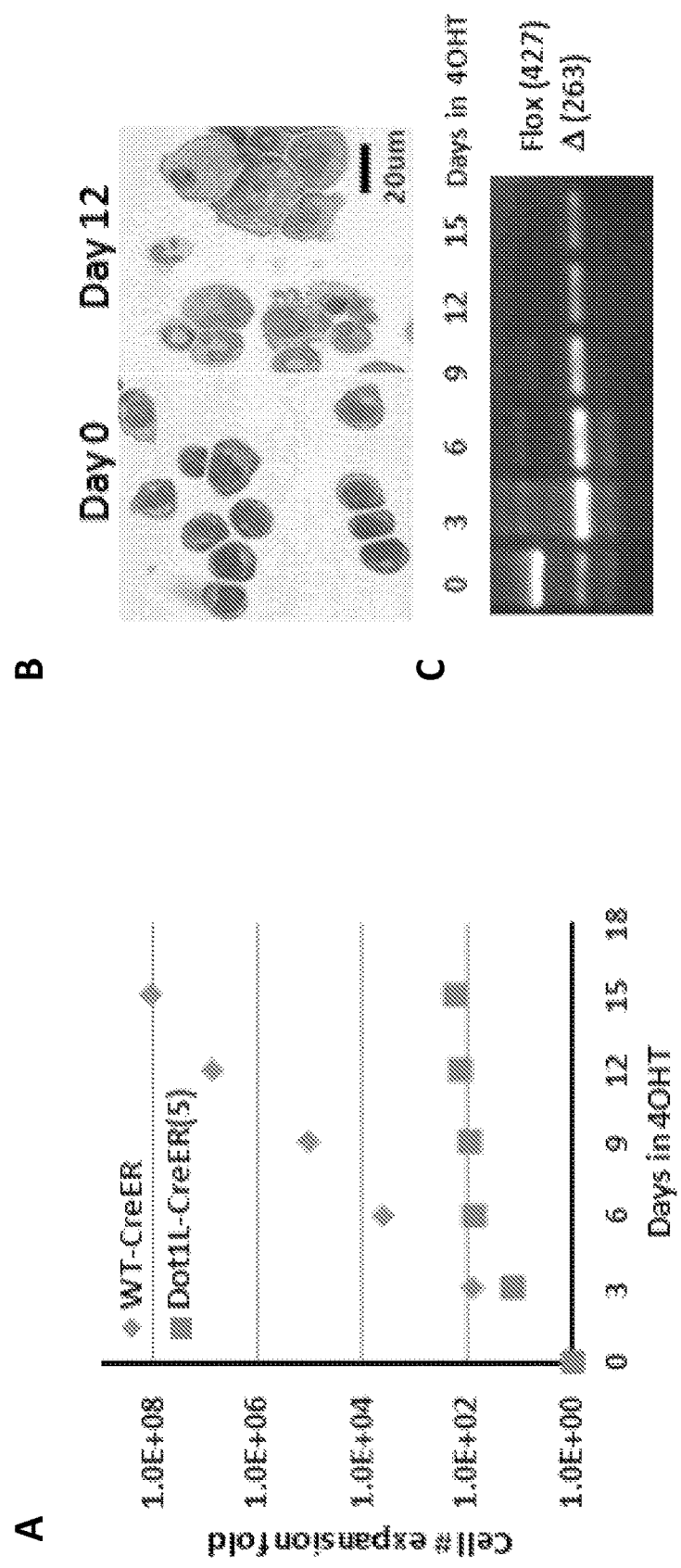
FIGS. 6A, 6B, and 6C are, respectively, a plot of cell count versus days of exposure to tamoxifen (4-hydroxytamoxifen; 4-OHT), a photo micrograph of cells at day 0 and day 12, and a photograph of an agarose gel. These data show, collectively, the development of an inducible DOT1L loss-of-function cell line. Tamoxifen (4-OHT) induction of the Cre recombinase leads to growth arrest (left panel.
Figure 7:
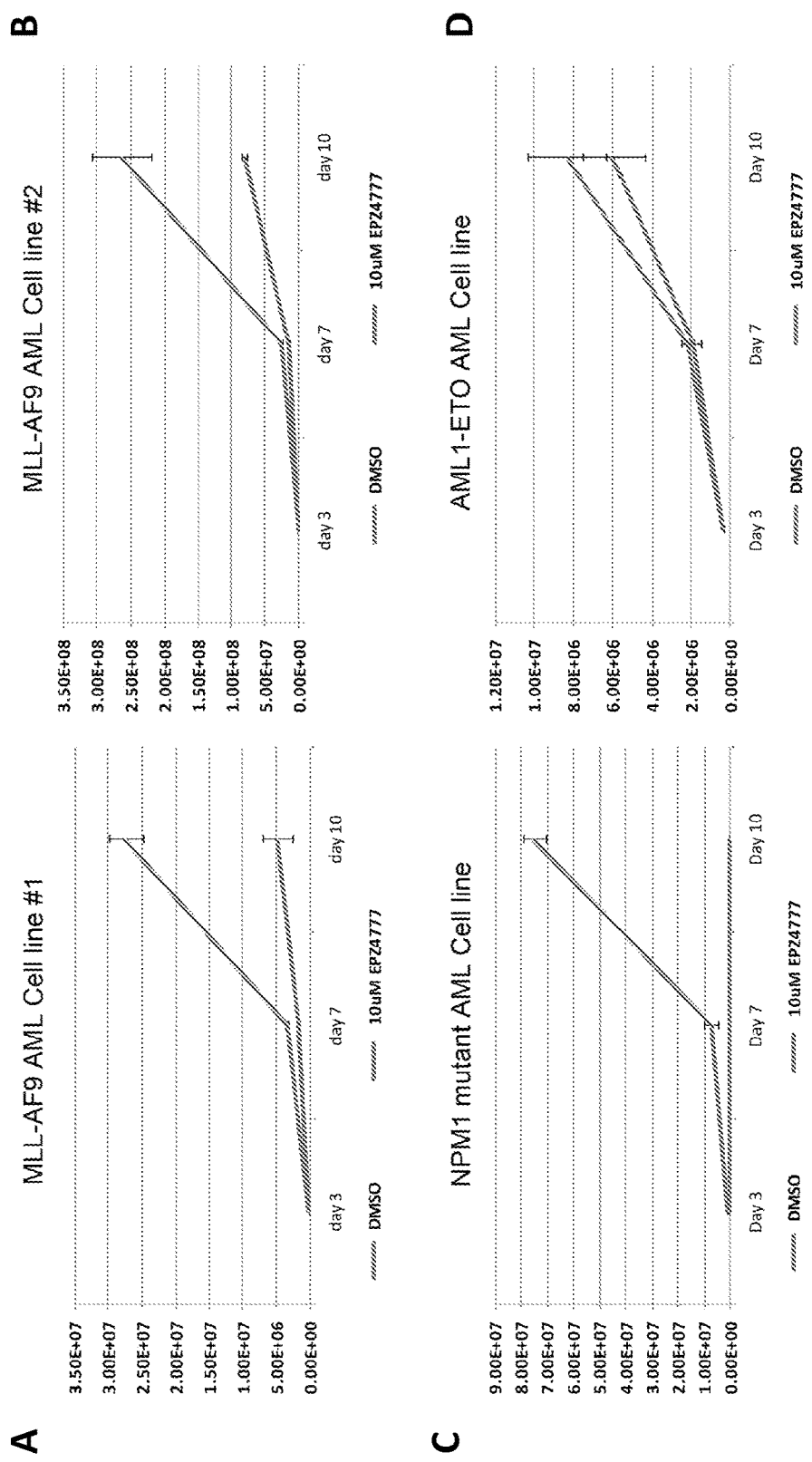
FIGS. 7A-7D show the effects of DOT1L inhibitor EPZ004777 versus vehicle control DMSO on proliferation of different leukemia cell lines.

Genome-wide pooled RNAi screens are performed in the presence or absence of a DOT1L inhibitor. MLL-AF9 transformed murine leukemia lines have been generated where DOT1L can be conditionally repressed via treatment of cells with tamoxifen and activation of Cre recombinase. The cell lines differentiate, stop proliferating, and start to undergo apoptosis approximately 6 days after Cre induction (FIG. 6). Furthermore, the recombination efficiency is such that outgrowth of cells is rarely seen where the DOT1L gene is not excised. Growth of the cells can be rescued by reintroduction of DOT1L or by expression of MLL-AF9 target genes, HOXA9 and MEIS1.

Similar cell lines are developed for NPM1, DNMT3A, IDH1, IDH2, RUNX1, TET2, ASXL1, and NUP98-NSD1 transformed cells. These cell lines are ideally suited for shRNA screens to identify shRNAs that select for or against growth in the absence of DOT1L.

NPMJ, DNMT3A, IDH1, IDH2, RUNX1, TET2, ASXL1, and NUP98-NSD1 transformed cells are treated with 10 μM EP00Z4777 or DMSO. For each cell line, experiments are performed with 5 biologic replicates of untreated cells and replicates of tamoxifen treated cells. Cells are harvested 0, 3, 6, 9, and 12 days after induction of cre recombinase for isolation of genomic DNA. shRNA is amplified, barcoded, and sequenced using Illumina sequencing.

shRNAs that are depleted or enriched in the presence, but not the absence of a DOT1L inhibitor are identified, indicating that knockdown of these genes sensitizes or confers resistance to DOT1L inhibition. Genes for which two different shRNAs scored significantly, are designated as candidate genes. For candidate genes, the knockdown of shRNAs is validated by quantitative PCR and Western blot and additional cell lines are analyzed. Genes identified in the shRNA screen are validated by rescue of the phenotype through expression of non-targetable versions of the gene. These genes are investigated in additional cell lines not included in the primary screen, and particularly in MLL-translocated lines to confirm a similar effect. For candidate proteins with available small molecule inhibitors, phenotypic consequences are determined for DOT1L inhibitors in each cell line on viability, cell cycle, and apoptosis.

Example 8

Molecular Effects of DOT1L and Preclinical Activities of DOT1L and EZH2 Inhibitors (Prophetic)

Recent studies have demonstrated remarkable activity of DOT1L inhibitors against MLL-translocated human leukemia cell lines and murine models, and preliminary evidence suggests that other AML subtypes depend on DOT1L enzymatic activity.

Changes in histone methylation that occur after DOT1L inhibitor treatment of NPM1, DNMT3A, IDH1, IDH2, RUNX1, TET2, ASXL1, and NUP98-NSD1 leukemia cells are assessed. NUP98-NSD1 induces H3K36me3 at HOX genes because NSD1 is an H3K36 methyltransferase. Wang et al., *Nature Cell Biology* 9(7):804-12 (2007). To this date, it is not clear why dimethylation of H3K79 is important in this subtype of leukemia. Therefore, it is of great interest to examine how specific H3K79 modifications change following DOT1L inhibition.

MLL-fusion target genes have been defined. Target gene expression is more dependent on DOT1L than is gene expression more broadly. In order to use the same approach for the NPM1, DNMT3A, IDH1, IDH2, RUNX1, TET2, ASXL1, and NUP98-NSD1 leukemias, the NPM1, DNMT3A, IDH1, IDH2, RUNX1, TET2, ASXL1, and NUP98-NSD1 target genes are determined as described with MLL-AF9. NPM1, DNMT3A, IDH1, IDH2, RUNX1, TET2, ASXL1, and NUP98-NSD1 proteins are generated that have a biotinylation sequence on the $NH_3$-terminus and expressed in mouse HSC. Upon cellular transformation, the cells are co-transfected with bacterial BirA, which biotinylates the $NH_3$-terminal sequence.

ChIPseq is performed using streptavidin beads and sites to which NPM1, DNMT3A, IDH1, IDH2, RUNX1, TET2, ASXL1, and NUP98-NSD1 is bound are determined. MLL-PTD, MLL-AF9, NPM1, DNMT3A, IDH1, IDH2, RUNX1, TET2, ASXL1, and NUP98-NSD1 mouse or human leukemia cell lines are treated with inhibitors and gene expression changes are assessed at 24, 48, and 72 hours after treatment. Expression changes with DOT1L inhibitor in the MLL-PTD and MLL-AF9 cells are compared to changes in other cell lines.

Standard gene expression algorithms such as gene set enrichment analysis are used to determine the extent of overlap in gene expression changes in MLL-fusion target genes and NPM1, DNMT3A, IDH1, IDH2, RUNX1, TET2, ASXL1, and NUP98-NSD1 target genes. This confirms whether the NPM1, DNMT3A, IDH1, IDH2, RUNX1, TET2, ASXL1, and NUP98-NSD1 driven gene expression program is reversed upon DOT1L inhibitor treatment.

Histone methylation is assessed by performing ChIP-seq for H3K79me2 as previously described [12]. H3K36me3 in the NPM1, DNMT3A, IDH1, IDH2, RUNX1, TET2, ASXL1, and NUP98-NSD1 transformed cells is assessed in order to determine if H3K36me3 profiles are aberrant in these cells. Changes in H3K79me2 and H3K36me3 are determined after DOT1L inhibitor treatment in order to determine how these modifications change in relation to one another. These experiments confirm that DOT1L inhibition reverses a leukemogeneic program as in MLL-fusion dependent leukemias.

Example 9

Anti-Leukemic Effects of DOT1L Inhibitors Combined with EZH2 Inhibitors In Vitro and In Vivo (Prophetic)

As disclosed herein, DOT1L inhibitors exhibit significant activity in NUP98-NSD1 and NPM1 leukemias. Combination approaches are assessed to effectively treat leukemias with targeted therapies in mouse model systems.

A number of different chromatin modifying enzymes and complexes have been shown to be important for MLL-translocated AML and other subtypes of AML. In particular, the histone H3K27 methyltransferase EZH2 is required for self-renewal of MLL-AF9 leukemia cells. Neff et al., Polycomb Repressive Complex 2 is Required for MLL-AF9 Leukemia, *Proc. Natl. Acad. Sci. U.S.A.* 109(13):5028-33 (2012). EZH2 works via a mechanism that is important for multiple subtypes of AML, namely suppression of p16/p19 and maintenance of a Myc-driven gene expression program. Wang et al., *Nature Cell Biology* 9(7):804-12 (2007).

The histone demethylase LSD1 has recently been shown to be important for continued AML cell proliferation and is tested as LSD1 inhibitors become available. Harris et al., The Histone Demethylase KDM1A Sustains the Oncogenic Potential of MLL-AF9 Leukemia Stem Cells, *Cancer Cell* 21(4):473-87 (2012). Combinations of DOT1L inhibitors and EZH2 inhibitors are tested in leukemia models, including NPM1, DNMT3A, IDH1, IDH2, RUNX1, TET2, ASXL1, and NUP98-NSD1 leukemia models. Other inhibitors are assessed in combination with DOT1L inhibition.

The combination of DOT1L and EZH2 inhibitors are assessed in vitro. Synergy in vitro in MLL-translocated and MLL-germline cells is assessed. Similar experiments are performed in NPM1, DNMT3A, IDH1, IDH2, RUNX1, TET2, ASXL1, and NUP98-NSD1 leukemia cells. A robotic pinning system has been established that allows titration of two different compounds at multiple concentrations. This provides detailed assessment of in vitro synergy that is used to assess DOT1L and EZH2 inhibitors.

Robotic liquid handling and an efficient library plate design allows the rapid, automated transfer of two compounds in combination to a 384-well plate of cultured cells. A 5×5 dose array of two compounds, in eight replicates, flanked by four replicates of each agent in dose-response format is generated. Following 7-10 day incubations, ATP content is determined as a surrogate for cell viability on a multi-label plate reader. These experiments are performed such that the cell lines are exposed to the DOT1L and EZH2 inhibitor compounds for 7-10 days prior to assessment of cell number. The prolonged period of incubation is necessary because both EZH2 and DOT1L inhibitors require up to one week to inhibit proliferation.

Results are plotted in the CompuSyn package according to the method of Chou and Talalay. The resulting dose-effect curves and isobolograms indicate whether there is an additive or synergistic effect. The combination index is obtained and compared to determine whether there is a significant synergy. Since the compounds induce differentiation, the effects of single agent and combinations of molecules are determined using microarray analyses to determine the extent of differentiation and whether a combination of expected gene expression changes is detected as expected based on previous studies with DOT1L and EZH2 loss of function models.

Combinations of inhibitors are tested in vivo. DOT1L inhibitors are assessed in mouse model systems from which appropriate dose and schedule for each of the compounds is determined. The dose and schedule of the EZH2 inhibitor has been published. McCabe et al., EZH2 Inhibition as a Therapeutic Strategy for Lymphoma with EZH2-activating Mutations, *Nature* 492(7427):108-12 (2012). Combination studies are performed to assess anti-leukemia activity by monitoring in vivo bioluminescence of luciferase expressing human and mouse MLL-fusion driven and MLL-PTD leukemias as well as NPM1, DNMT3A, IDH1, IDH2, RUNX1, TET2, ASXL1, and NUP98-NSD1 leukemia cells. Bernt et al., MLL-rearranged Leukemia is Dependent on Aberrant H3K79 Methylation by DOT1L, *Cancer Cell* 20(1):66-78 (2011) and Stubbs et al., MLL-AF9 and FLT3 Cooperation in Acute Myelogenous Leukemia: Development of a Model for Rapid Therapeutic Assessment, *Leukemia* 22(1):66-77 (2008).

Mice are treated daily with vehicle, individual inhibitors, or combinations of inhibitors until control animals reach institutional limits (i.e., onset of distress or tumor volume limits). Primary endpoints include tumor burden (as assessed by peripheral blood GFP positivity, % human CD45 in peripheral blood, and/or luminescent imaging). Time-to-sacrifice and secondary endpoints include full histopathological examination.

Efficacy is assessed against primary human MLL-translocated AMLs, of which samples are engrafted along with NPM1, DNMT3A, IDH1, IDH2, RUNX1, TET2, ASXL1, and NUP98-NSD1 leukemias. These studies provide important preclinical assessment of these compounds that support clinical translation of this combination.

Example 10

Dual Inhibition of NPM1 and FLT3 in a Mouse Model of ALM (Prophetic)

In leukemogenesis, more than one gene mutation is often required for the full development of the disease. Combinations of genetic alterations present in AML are major determinants of patient prognosis and response to therapy. Mutations in FLT3 and NPM1 genes represent the most frequent genetic aberrations in AML and serve as important prognostic indicators. While FLT3 is found in one third of AML cases (Thiede C, *Blood*. 2002 June 15; 99 (12):4326-35) and is associated with poor prognosis and outcome, NPM1 mutation is present in 50-60% of patients with AML and generally confers increased response to chemotherapy and favorable prognosis (Schlenk R F, *N Engl J Med* 2008; 358: 1909-1918). However, approximately 40% of patients positive for NPM1 mutation also carry FLT3 mutation where the presence of FLT3 mutation negates the beneficial outcome of patients carrying only NPM1 mutation, (Gale, R E. *Blood. Mar.* 1 2008; 111(5): 2776-84). Additionally, FLT3 receptor kinase has been shown to collaborate with NUP98-HOX fusions, inducing highly aggressive AML. Finally, elevated FLT3 levels have been observed in the subtype of AML characterized by high HOX gene expression (Palmqvist, L. *Blood.* August 1; 2006; 108 (3)). Interestingly, current studies suggest that FLT3 mutations are most likely not causally connected to high HOX cluster gene expression, further validating the importance of dual inhibition of two separate pathways that contribute to leukemogenesis (Andreeff M, *Leukemia* 2008, 22, 2041-2047). Collectively, these observations suggest that use of FLT3 inhibitors in HOX-induced AML and ALL accompanied with high FLT3 expression and/or mutation can provide additional benefit to patients treated with DOT1L inhibitors.

To test the efficacy of DOT1L inhibition in combination with FLT3 inhibition in vivo, a mouse model of AML is administered the DOT1L inhibitor EPZ004777 together with the FLT3 inhibitor Quizartinib (AC220). Animals engineered to contain NPM1c mutation in combination with a FLT3 mutation, Npm1$^{cA/+}$Flt3$^{ITD/+}$ (Mupo A, *Leukemia* September 2013; 27(9): 1917-1920.) develop AML and die within 68 days. In order to assess whether dual combination therapy (inhibition of both DOT1L and FLT3) abates the leukemogenic potential of cells treated with the combination and provides additional survival benefit to the mice transplanted with pre-treated cells compared to the inhibition using either protein alone, the efficacy of both EPZ004777 and AC220 is evaluated in parallel. Because of technical difficulties of subjecting mice to continuous infusion, AML cells isolated from Npm1$^{cA/+}$Flt3$^{ITD/+}$ mice are cultured for 6 days in the presence of DOT1L inhibitor EPZ004777, or FLT3 inhibitor AC220, or both, in a dose dependent manner and tested for their clonogenic potential following transplantation of the cells into recipient mice in a manner paralleling that of Example 5. Both primary and secondary transplantations are performed. After each transplantation, Npm1$^{cA/+}$Flt3$^{ITD/+}$ AML cells are harvested and treated with vehicle control (DMSO), or EPZ00477, or AC220, or both EPZ004777 and C220 for 7, 14, and 22 of days after which a colony formation assay is performed. Culturing of AML mouse cells (Npm1$^{cA/+}$Flt3$^{ITD/+}$) in the presence of DOT1L inhibitor has already been shown to reduce the colony formation potential following both the primary and secondary transplantation (FIGS. 12A and B and Example 5). Thus, the ability of dual inhibition (DOT1L inhibition with FLT3 inhibition) to inhibit colony formation potential is compared to that of each of DOT1L inhibition alone and FLT3 inhibition alone. It is anticipated that the clonogenic potential of cells treated with the combination will be significantly lower than that of cells treated with either agent alone.

Figure 13:
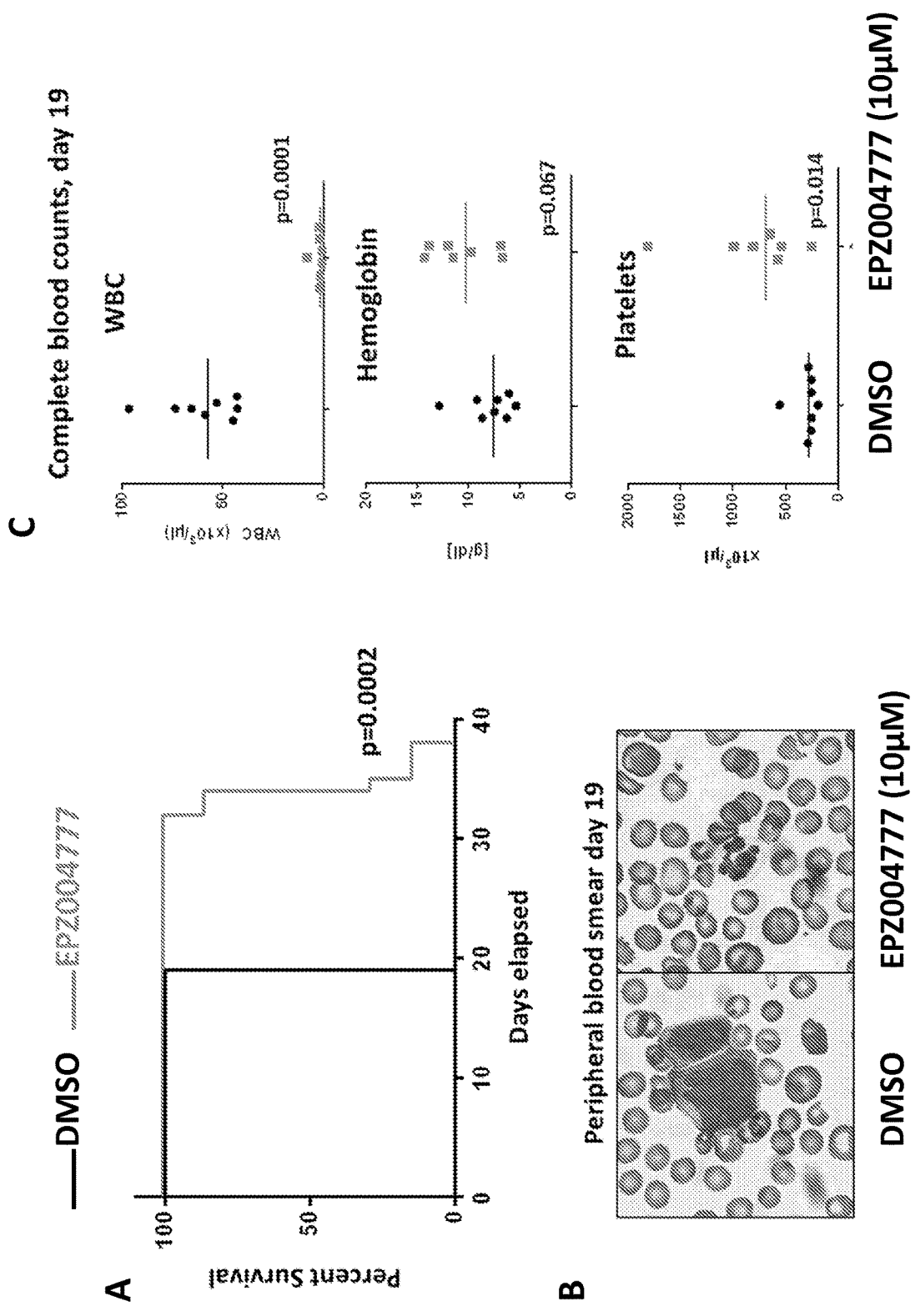
FIGS. 13A-13C show the effects of DOT1L inhibition on leukemia initiating potential in vivo.

In order to further assess the effects of dual DOT1L and FLT3 inhibition on leukemia initiating potential, syngeneic C57/BL6 mice are injected with Npm1$^{cA/+}$Flt3$^{ITD/+}$ cells previously treated for 6 days with DMSO, or DOT1L inhibitor EPZ004777, or FLT3 inhibitor AC220, or both, in a dose dependent manner using 01, 1, and 10 µM of each compound. It has been demonstrated that the treatment of Npm1$^{cA/+}$Flt3$^{ITD/+}$ AML cells with the DOT1L inhibitor leads to prolonged survival time. While mice injected with cells treated with DMSO die at day 19, animals injected with cells treated with EP004777 (10 µM) start dying on day 31 (FIG. 13 A). Thus, treatment comprising both DOT1L and FLT3 inhibitors is assessed for the ability to delay the onset of dying (more than 31 days post-injection). Additionally, dose response curves are informative of minimum required dosage in dual inhibition experiments (EPZ004777 and AC220) versus either inhibitor alone. It is anticipated that these results will show increased efficacy of the combination using both DOT1L and FLT3 inhibitors in prolonging survival of a mouse model of AML driven by NPM1 and FLT3 mutations, which has implications for human therapy. FLT3 inhibitors are being used or currently developed as a first line treatment for AML. Availability of a drug combination as a second line treatment will substantially increase the available arsenal against leukemia.

What is claimed is:

1. A method for identifying leukemia patients that are susceptible to treatment with a DOT1L inhibitor comprising:
   (a) detecting levels of a HOX cluster gene RNA and/or a HOX cluster-associated gene RNA in tissue samples or cell samples obtained from leukemia patients by amplifying RNA in the tissue samples or cell samples with a primer pair that is specific for the HOX cluster gene RNA or the HOX cluster-associated gene RNA, wherein the HOX cluster-associated gene is PBX3, MEIS1 or MEIS2;
   (b) identifying leukemia patients that express HOX cluster gene RNA and/or HOX cluster-associated gene RNA levels that are elevated compared to a predetermined threshold; and
   (c) administering a DOT1L inhibitor to the leukemia patients of step (b), wherein the tissue samples or cell samples from the leukemia patients comprise a NPM1 mutation and do not comprise an MLL-translocation, an MLL-rearrangement or an MLL-partial tandem duplication.

2. The method of claim 1, wherein the primer pair comprises a forward primer and a reverse primer, wherein the forward primer hybridizes toward the 5' end of the HOX cluster gene RNA and/or HOX cluster-associated gene RNA and wherein the reverse primer hybridizes toward the 3' end of the HOX cluster gene RNA and/or HOX cluster-associated gene RNA.

3. The method of claim 2, wherein the HOX cluster gene RNA is selected from the group consisting of HOXA1, HOXA2, HOXA3, HOXA4, HOXA5, HOXA6, HOXA7, HOXA9, HOXA10, HOXA11, HOXA13, HOXB1, HOXB2, HOXB3, HOXB4, HOXB5, HOXB6, HOXB7, HOXB8, HOXB9, and HOXB13.

4. A method for determining susceptibility of leukemia patients to treatment with a DOT1L inhibitor comprising:
   (a) detecting levels of a HOX cluster gene RNA and/or a HOX cluster-associated gene RNA in tissue samples or cell samples obtained from leukemia patients, wherein the HOX cluster-associated gene is PBX3, MEIS1 or MEIS2, and wherein the tissue samples or cell samples from the leukemia patients comprise a NPM1 mutation;
   (b) identifying leukemia patients that express HOX cluster gene RNA and/or HOX cluster-associated gene RNA levels that are at least about 3-fold greater than the HOX cluster gene RNA and/or HOX cluster-associated gene RNA levels observed in a control tissue sample or control cell obtained from a non-leukemia donor;
   (c) administering a DOT1L inhibitor to the leukemia patients of step (b)
   wherein the tissue samples or cell samples from the leukemia patients comprise a NPM1 mutation and do not comprise an MLL-translocation, an MLL-rearrangement, or an MLL-partial tandem duplication.

\* \* \* \* \*

```
                        SEQUENCE LISTING

<160> NUMBER OF SEQ ID NOS: 48

<210> SEQ ID NO 1
<211> LENGTH: 2561
<212> TYPE: DNA
<213> ORGANISM: Homo sapiens

<400> SEQUENCE: 1
attcatatca tttttcttct ccggccccat ggaggaagtg agaaagttgg cacagtcacg      60
ccgggcttcg caggaccagg tcactcagtg acagatggac aatgcaagaa tgaactcctt     120
cctggaatac cccatactta gcagtggcga ctcggggacc tgctcagccc gagcctaccc     180
ctcggaccat aggattacaa cttccagtc gtgcgcggtc agcgccaaca gttgcggcgg      240
cgacgaccgc ttcctagtgg gcaggggggt gcagatcggt tcgccccacc accaccacca     300
ccaccaccat caccaccccc agccggctac ctaccagact tccgggaacc tgggggtgtc     360
ctactcccac tcaagttgtg gtccaagcta tggctcacag aacttcagtg cgccttacag     420
cccctacgcg ttaaatcagg aagcagacgt aagtggtggg taccccagt gcgctcccgc      480 tgtttactct ggaaatctct catctcccat ggtccagcat caccaccacc accagggtta     540
tgctgggggc gcggtgggct cgcctcaata cattcaccac tcatatggac aggagcacca     600
gagcctggcc ctggctacgt ataataactc cttgtcccct ctccacgcca gccaccaaga     660
agcctgtcgc tcccccgcat cggagacatc ttctccagcg cagacttttg actggatgaa     720
agtcaaaaga aaccctccca aaacagggaa agttggagag tacggctacc tgggtcaacc     780
caacgcggtg cgcaccaact tcactaccaa gcagctcacg gaactggaga aggagttcca     840
```

```
cttcaacaag tacctgacgc gcgcccgcag ggtggagatc gctgcatccc tgcagctcaa    900
cgagacccaa gtgaagatct ggttccagaa ccgccgaatg aagcaaaaga acgtgagaa     960 ggagggtctc ttgcccatct ctccggccac cccgccagga aacgacgaga aggccgagga   1020
atcctcagag aagtccagct cttcgccctg cgttccttcc ccggggtctt ctacctcaga   1080
cactctgact acctcccact gaggcggctc cagccccaga caacagccca ggcatctcct   1140
tgggctggga cttcttaccc aaagcacatg cttagcttat ctttctttcc atttacagtc   1200 tcttcttcc tttctaatcc tatctgggga gctcctggcc aggataatat atttgcagat    1260
aattctggac cagagacttg gtgcgggggtt aacaccttca tccagattgg gtgccagcat  1320
acattttctg gtgggcctta acatccctcc tgcttttagg agaattcaca gaacctactg   1380
ttcctttcag atgacctttt ggaaaatagt tcccttttgcc aacagaaaca tgccagaagg  1440
aatcttctca tcttttatct aactatatgt acagctctcc cctcccttgt ccttgaaagt   1500
aggatatagc gaaaggcgag tccaggagct caggaagaag agatgcacta tatgtttaca   1560
caattaattc atcccttaat ttaagtcatt ttcatgtgtg tgagtttgct ggttgtaaat    1620
actttgtcct aagagattta tctttataca gattttctag aaatgtttag gttactaaaa   1680
cagggtgggc aaactctcta aactggtaca attttatagg tgaaagaaaa aattccctca   1740
tttaaaccca atcagatgcc tcagagggta gccttgattt gttcttacag ttaagaagcc   1800
ctgcagagca caaacttcag aaacccggct tcctgtgcta agtctttccc aatctctacc   1860
cctttcttct cgggccaccc tctgtttaaa atttgtgctg ggttattcag aacctaaaag   1920
tattattcaa accaatttct tccttccaca gttatcttag ctggatataa tgtattttca   1980
gctcaattgt taatgtgatg gatggcacaa tgaatgtata ttttgtgtta ttcgtgaata   2040
gtcttttgca tgtcgcacaa tgtttgatgt ccccaaagta ccacactgag ttctatcagt   2100
tatcctttgt gagcctatga tattccccat ttcctgtaca atcatgaaca gctctgagat   2160
cctggagtga tatgatccag agcagagttt acgggtctta ggatgtctgt aataaataaa   2220
tatactcaag tttcaggtat gcttaagcat ccgtgtattt ggctgggcta caatttgtta   2280
attcctatga agttggcaca tttcatgagg ggaaagggag aagggtggta aatattttca   2340
aagagatggg cctttttcttg aataaaagtt aataacagct cctttattat aatcaaagct   2400
cataatggaa aaaagactg atgaagaaat ttatgaagca gatttatttt tgaaacaaac    2460
atggatactt cctgggtcaa gtgctaacct tttcacctcc aactggatgt tgacgtatat   2520
ataaacagaa ctcccttcaa aagccaaaaa aaaaaaaaa a                        2561
```

<210> SEQ ID NO 2
<211> LENGTH: 1791
<212> TYPE: DNA
<213> ORGANISM: Homo sapiens

<400> SEQUENCE: 2

```
tcttttgatt aaagcccaaa ttgtcattgg gcagaagcaa tcatgtgaca gccaattcgg     60
tccaatttca accttgtctc catgaattca atagtttaat agtagcgcgg tccccatacg    120
gctgtaatca gtgaattaga aaaaaaacac cctagcagcg atattctatg atagatttt    180 tttcctctgc gctcgccttt ttcctaggcc ttgcccccc aaagcccctc caaaagaggg     240 aacttttct ctgaggggc tccaaggaga aggccatgaa ttcgaattt gagcgagaga       300 ttggttttat caatagccag ccgtcgctcg ctgagtgcct gacatctttt ccccctgtcg    360
```

-continued

| | |
|---|---|
| ctgatacatt tcaaagttca tcaatcaaga cctcgacgct ttcacactcg acactgattc | 420 |
| ctcctccttt tgagcagacc attcccagcc tgaaccccgg cagtcaccct cgccacggcg | 480 |
| ctggcggccg ccccaagccg agcccgcgg gcagccgcgg cagcccggtg cccgccggcg | 540 |
| ccctgcagcc gcccgagtac ccctggatga aggagaagaa ggcggccaag aaaaccgcac | 600 |
| ttctgccggc cgccgccgcc gccgccaccg ccgcagccac cggccctgct tgcctcagcc | 660 |
| acaaagaatc cctggaaatc gccgatggca cggcggggg atcgcggcgc ctgagaactg | 720 |
| cttacaccaa cacacagctt ctagagctgg aaaaagaatt tcatttcaac aagtaccttt | 780 |
| gcagaccccg aagggtggag attgcagcgc tgctggattt gactgagaga caagtgaaag | 840 |
| tgtggtttca gaaccggagg atgaagcaca agaggcagac ccagtgcaag gaaaaccaaa | 900 |
| acagcgaagg gaaatgtaaa agccttgagg actccgagaa agtagaggag gacgaggaag | 960 |
| agaagacgct ctttgagcaa gcccttagcg tctctggggc ccttctggag agggaaggct | 1020 |
| acacttttca gcaaaatgcc ctctctcagc agcaggctcc caatggacac aatggcgact | 1080 |
| cccaaagttt cccagtctcg cctttaacca gcaatgagaa aaatctgaaa cattttcagc | 1140 |
| accagtcacc cactgttccc aactgcttgt caacaatggg ccagaactgt ggagctggcc | 1200 |
| taaacaatga cagtcctgag gcccttgagg tcccctcttt gcaggacttt agcgttttct | 1260 |
| ccacagattc ctgcctgcag ctttcagatg cagtttcacc cagtttgcca ggttccctcg | 1320 |
| acagtcccgt agatatttca gctgacagct tagacttttt tacagacaca ctcaccacaa | 1380 |
| tcgacttgca gcatctgaat tactaaaaac attaaagcaa acaaagcat caccaaacaa | 1440 |
| aaactccttt gaccaggtgg ttttgccttc ttttatttgg gagtttattt tttattttct | 1500 |
| tcttgaccta cccccttccct cctttaagtg ttgaggattt tctgtttagt gattccctga | 1560 |
| cccagtttca aacagagcca tcttttacag attattttgg agttttagtt gttttaaacc | 1620 |
| taactcaaca acccctttatg tgattcctga gagcagtatg aggcctgcaa gaaagtgatc | 1680 |
| atataattgt atcttcactt tcttttattt tttgtattac attgggatgc attgtcatgc | 1740 |
| atattttttg tagaataaat tctcctttgc tataagtaaa aaaaaaaaa a | 1791 |

<210> SEQ ID NO 3
<211> LENGTH: 3396
<212> TYPE: DNA
<213> ORGANISM: Homo sapiens

<400> SEQUENCE: 3

| | |
|---|---|
| ttcttgcaaa taatgtggtc tcaggcaagg acacagcatc ttggctgtct gctaaaaaaa | 60 |
| aaaaatgcct agactctcag tggaaattga gtgtcaagct gcaaatctc aaatggcaga | 120 |
| ctatcatcat ttaagagcgc ctggacaccg gaaaaggcga ttccctgagc gcctggagtt | 180 |
| ggagacaatt cctggttcag aatttaaaca tctttctagg tctgcgcggg gcggccattg | 240 |
| gcggcggagt gtcacgtgac cgcggggggcg tgccaatgtg cgccctcacg ggtgtcaaac | 300 |
| ccctgtcaga gtgtgcgatc aagatcgtga acaacgcga tgcaaaaagc gacctactac | 360 |
| gacagctcgg cgatctacgg tggctacccc taccaggcag ccaacgggtt cgcttataat | 420 |
| gccaatcagc agccgtaccc ggcgtccgcc gctttgggcg ccgacggcga gtaccaccga | 480 |
| cccgcctgct ccctccagtc tccctccagc gccgggggcc accccaaggc cacgaactg | 540 |
| agtgaggcgt gctgcgcac cctgagcgcc ccactagcc agcctccaag cctgggagag | 600 |
| ccgcccctgc accgcgcc gccccaggcc gcgcccctg cccacagcc gcctcagccc | 660 |
| gcacctcagc cccctgcacc taccccctgcc gcgccccgc ctccctcttc tgcctcccct | 720 |

```
cctcagaatg ccagcaacaa ccctaccct gccaacgcgg ccaagagccc cctgctcaac    780
tcacccacag tggccaaaca aatcttcccc tggatgaaag agtctcgaca aaacacaaag    840
cagaaaacca gcagctccag ctcaggcgaa agctgcgctg gcgacaagag cccgccgggg    900
caggcttcgt ccaagcgcgc gcgcacggcc tacacgagcg cgcagctggt ggagctggag    960
aaagagttcc acttcaaccg ctacctgtgc cggccgcgcc gggtggagat ggccaatctg   1020
ctgaacctca ctgagcgcca gatcaagatc tggttccaga atcgccgcat gaagtacaaa   1080
aaggatcaga agggcaaggg catgctaacg tcatcggggg gccagtctcc aagtcgcagc   1140
cccgtgcccc ccggagccgg tggctatctg aactctatgc attcgctggt caacagcgtc   1200
ccgtatgagc cccagtcgcc cccgcccttc tccaagcccc ccagggtac ctacgggctg    1260 ccccccgcct cctaccctgc gtccctgccc agctgcgcac ccccgccacc cccacagaag   1320
cgctacacgg cggcaggggc gggcgcaggg ggcaccccg actatgaccc gcacgctcat    1380
ggcctgcagg gcaacggcag ctatgggacc ccacacatac agggaagccc cgtcttcgtg   1440
gggggcagct atgtggagcc catgagcaac tccgggccag ccctctttgg tctaactcac   1500
ctcccccacg ctgcctcggg cgccatggac tatgggggtg ccgggccgct gggcagcggc   1560
caccaccacg ggccggggcc tggggagccg caccccacct acacggacct taccggccac   1620
catccttctc agggaagaat tcaggaagca cccaagctca cccacctgtg atagtgggct   1680
tggggctacg cgccaggaga gtctccccc acccaccttt tttctttggt tgcttttttt    1740
tttttttttt tttaggttct tcctgcccctt tccttcctttc cttttctctc ttctccgccc   1800
cgcactccgt ttcccggttt cccccctcgt tggtaaggcg tttttatagt ttatgtgacg   1860
tagcaatctt ggttgctgga atggctgtat catagcgata tttatctctt cctgctcctc   1920
gataggccac tggccctgca ccctttacct tctccactct ttgatcagaa acagggtata   1980
tgaacaaatt ttctagtcga gttttcaatg tgaatttgtt cttacattat ggctcccgag   2040
gggaagcgat tactttttt aattttaaat tttttttta attgcacttc ttgtaaagag    2100
tgagaaaaaa aatcaaaggc gctttgaaac aggggctctc tgtgcaagga tgactaagtg   2160
tacgtctttc cgtgtgtgta tgctggtgaa cagtcagatt tatttatatt tttttgcaag   2220
cattgaataa tctaagtttt aaatattatt tatccccatc cgttcgtatt tatattaaag   2280
aattctgtac cctgatggtt cagaagggtt cttgggcctt tgttcaatt gtgtattggc    2340 gtacttagaa tttttttat ttgaaagaga aatataattc ctttaaacgg taacgataca    2400
ataaaaccag agaagatcca gcttttgaaa acagtgattt aggtttgtaa catccggcaa   2460
aactgaaaaa aaaatctgt aaacgcgaaa aatactagat ttgttttgag agttcttcat    2520
tccttgctgc tcacattctg agaaacaaaa agaaataaag tttttattct gaataatatc   2580
cgtgttaaga aggggttctt tggccgaaga cgtgggtctg cgtggaattc aggccgaggc   2640
gagccggcag agcaggccgg acgcagcagc cctctggctc cagcatgggg cctggccagg   2700
ctattcgcct ggaagctcgg cgaattctca ggatggcggc tggggctcca ggcggctgcg   2760
gcagctctgg taacgccgtg cggcgggcca gctgggctgc ccggttccca gctgctgcgg   2820
aggcaggctg agggcgcagg ggctgccgag tgctgtgcac ggaagaaaca aagacatccc   2880
ggcccaaggc gcagcgggag cgcacaggtg ccccgcggcc cagccggggg ataacgcagg   2940
gcggtcttct gctccatgct cttcctcggg tcaaagcgga ccaactaacg cctaaacctc   3000
ggtattagcc agccgcgcag aggatgccga gcactttccg ggagcaatcg gactcctggt   3060
```

```
ctcctccggg gatgcttcgc ggtctgttat cgcgtcagga ggaaagaatt gctccaaaaa    3120
tctgcacgcg gagcgaaaca gtttgaaagg gactgaggct cacccaggtc tccagcaaac    3180
ggaggactga actggggaga gtcaccctga gccagccctt ccctggactg ccggaatccc    3240
agcattagct tcctgctgaa tgtagtattt ggcattctct gaatttattt cctctccttc    3300
ccccacccag ctttcttttt atggccccag ggggagggg agagagcaag gagatcggta    3360
tctttgtaat aaaactgcaa ttttataaat ttttca                              3396

<210> SEQ ID NO 4
<211> LENGTH: 1728
<212> TYPE: DNA
<213> ORGANISM: Homo sapiens

<400> SEQUENCE: 4
aaaacgacaa cgcgagaaaa attagtattt ttgcacttca caaattaatg accatgagct      60 cgttttgat aaactccaac tacatcgagc ccaagttccc tcccttcgag gagtacgcgc     120
agcacagcgg ctcgggcggc gcagacggcg gcccgggcgg gggccccggc taccagcagc     180
ccccagcgcc cccgacccag cacctgccgc tgcagcagcc ccagctccct cacgcgggcg     240
gcggccgaga gcccactgcc tcctactacg cgccgcggac cgcccgcgag cccgcctacc     300
ctgctgccgc gctgtacccc gcgcatgggg ccgcggacac cgcctacccc tatggctacc     360
gcggcggcgc cagccccggg cggccgcccc agcccgagca gccccggcg caagccaagg     420 gcccagcgca cggcctgcat gcgagccacg tcctgcagcc ccagctgccg ccgccctgc     480 agcctcgcgc cgtgccccca gcggcccgc ggcgctgcga ggcggccccc gccaccccag     540
gcgtcccggc aggggcagc gccccgcgt gccgctgct cttggccgac aagagcccgc     600
tgggcctgaa gggcaaggag cccgtggtgt accctggat gaagaagatc catgtcagcg     660
ccgttaaccc cagttataac ggagggggagc ctaagcgctc tcgaaccgcc tacacccggc     720
agcaggtctt ggagctggag aaggagttcc acttcaatcg atacctgacc cggcggcgcc     780
gcatcgagat cgcccacacg ctctgttttgt ctgagcgcca ggtcaagatc tggtttcaga    840 accgaggat gaagtggaag aaagaccaca aactgcccaa caccaagatg cgatcctcca     900
attcggcctc ggcctctgcc ggcccaccag ggaaagcaca aactcagagc ccacacctcc     960
atccccaccc ccaccgagc acctccacac ccgttccctc ctccatataa tcttctagag    1020
atcttaacca gtttctatcc cttacctgct tttctcttct cttctcctgc tccgttcctc    1080
atccacccct cccatctgg accataatag acaccaaaac aaaaccaaat tggtgaaaag    1140
aataatcaaa aagaagacat tatccggtta agagtctgtg ctggttgcca cccaagagag    1200
aacagttgtc caggatgctg gctggtggaa caacctgctg gccgaaaca aggctgccag    1260 gtgtggatac ctgagaagga ctacttggta tcaaatactt ttgagatggc tacagtcagc    1320
tagctggaca gcccatgctg agtggggaca tacacttgca tctttgttga aagcagaaga    1380
agacagaccc tttccccacc ttccttacct cctcttcccc cattaaggca gctcatccaa    1440
gcttgtattt aactgaataa atgagtagac attgtggacc tcacaagatt atttaattct    1500
taagatgtgt agaccttgat ggtaggtgtg acatgttagt ttttcttact tgcatttatt    1560
taagacactg ttacagagat actgttgtcc ccttctgggg cacggtcttt ggggagaggg    1620
gagtgcattt agacttatgt ggaactgtac aaattgtgat gtggctacat agaaagccat    1680
gtgctaagaa taaactccat ttaaaaaaca ttaaaaatct aagattca                  1728
```

<210> SEQ ID NO 5
<211> LENGTH: 1657
<212> TYPE: DNA
<213> ORGANISM: Homo sapiens

<400> SEQUENCE: 5

```
gggtgctata gacgcacaaa cgaccgcgag ccacaaatca agcacacata tcaaaaaaca      60
aatgagctct tattttgtaa actcattttg cggtcgctat ccaaatggcc cggactacca     120
gttgcataat tatggagatc atagttccgt gagcgagcaa ttcagggact cggcgagcat     180
gcactccggc aggtacggct acggctacaa tggcatggat ctcagcgtcg gccgctcggg     240
ctccggccac tttggctccg gagagcgcgc ccgcagctac gctgccagcg ccagcgcggc     300
gcccgccgag cccaggtaca gccagccggc cacgtccacg cactctcctc agcccgatcc     360
gctgccctgc tccgccgtgg cccctcgcc cggcagcgac agccaccacg gcgggaaaaa     420
ctccctaagc aactccagcg gcgcctcggc cgacgccggc agcacccaca tcagcagcag     480
agaggggggtt ggcacggcgt ccggagccga ggaggacgcc cctgccagca gcgagcaggc     540
gagtgcgcag agcgagccga gccggcgcc gcccgcccaa ccccagatct acccctggat     600
gcgcaagctg cacataagtc atgacaacat aggcggcccg gaaggcaaaa gggcccggac     660
ggcctacacg cgctaccaga ccctggagct ggagaaggag ttccacttca accgttacct     720
gacccgcaga aggaggattg aaatagcaca tgctctttgc ctctccgaga gacaaattaa     780
aatctggttc caaaaccgga gaatgaagtg aaaaaagat aataagctga aaagcatgag     840
catggccgcg gcaggagggg ccttccgtcc ctgagtatct gagcgtttaa agtactgagc     900
agtattagcg gatcccgcgt agtgtcagta ctaaggtgac tttctgaaac tcccttgtgt     960
tccttctgtg aagaagccct gttctcgttg ccctaattca tcttttaatc atgagcctgt    1020
ttattgccat tatagcgcct gtataagtag atctgctttc tgttcatctc tttgtcctga    1080
atggctttgt cttgaaaaaa aatagatgtt ttaacttatt tatatgaagc aagctgtgtt    1140
acttgaagta actataacaa aaaagaaaa gagaaaaaaa aacacacaaa aagtccccct    1200
tcaatctcgt ttagtgccaa tgttgtgtgt tgcactcaag ttgtttaact gtgcatgtgc    1260
gtggaagtgt tcctgtctca atagctccaa gctgttaaag atattttat tcaaactacc    1320
tatattcctt gtgtaattaa tgctgttgta gaggtgactt gatgagacac aacttgttcg    1380
acgtgtagtg actagtgact ctgtgatgaa aactgtgact ccaagcggtg tgtccctgcg    1440
tgcctttata ggacccttg cacgaactct ggaagtggct cttataagcg cagcttcagt    1500
gatgtatgtt tttgtgaaca aagttacaaa tattgtccaa gtctggctgt tttaagcaaa    1560
ctgtgatcag ctttttttttt tttttttttt ttttttgtatt tgttttttaag gaaaaaatac    1620
tgactggaac aaaaaataaa ctttctattg taagttc                              1657
```

<210> SEQ ID NO 6
<211> LENGTH: 802
<212> TYPE: DNA
<213> ORGANISM: Homo sapiens

<400> SEQUENCE: 6

```
cacagtcctg cagaggggcg cgcaaatgag ttcctatttt gtgaatccca ctttccccgg      60
gagccttccc agcggccagg actccttctt gggccagctg cccctctacc aggctggcta     120
tgacgcgctg aggcccttcc cggcctcgta cggggcgtcg agtctcccgg acaagacgta     180
caccctcacct tgtttctacc aacagtccaa ctcggtcctg gcctgcaacc gggcgtccta     240
```

| | |
|---|---|
| cgagtacggg gcctcgtgtt tctattctga taaggacctc agtggcgcct cgccctcggg | 300 |
| cagtggcaag cagaggggcc ccggggacta cctgcacttt tctcccgagc agcagtacaa | 360 |
| acccgacagc agcagcgggc agggcaaagc actccatgac gaaggcgccg accggaagta | 420 |
| cacgagcccg gtttacccctt ggatgcagcg gatgaactcc tgcgcgggtg ctgtgtatgg | 480 |
| gagccatggg cgccgaggcc gccagaccta cacgcgctac cagacactgg agctggagaa | 540 |
| ggagttccac ttcaaccgct acctgacacg gcgccgccgc atcgagatcg ccaacgcgct | 600 |
| ctgcctcacc gagcgccaga tcaagatctg gttccagaac cgccgcatga agtggaaaaa | 660 |
| ggaaaacaag ctcatcaatt ccacgcagcc cagcggggag gactcagagg caaaggcggg | 720 |
| cgagtagatg cctgggcagg gaccaggcca gcgctgcaac ctccttcggc tttgcccccct | 780 |
| tgccctcgcc tgttccccaa ct | 802 |

<210> SEQ ID NO 7
<211> LENGTH: 2018
<212> TYPE: DNA
<213> ORGANISM: Homo sapiens

<400> SEQUENCE: 7

| | |
|---|---|
| gtgctgcggc gagctccgtc caaaagaaaa tggggtttgg tgtaaatctg ggggtgtaat | 60 |
| gttatcatat atcactctac ctcgtaaaac cgacactgaa agctgccgga caacaaatca | 120 |
| caggtcaaaa ttatgagttc ttcgtattat gtgaacgcgc tttttagcaa atatacggcg | 180 |
| ggggcttctc tgttccaaaa tgccgagccg acttcttgct cctttgctcc caactcacag | 240 |
| agaagcggct acggggcggg cgccggcgcc ttcgcctcga ccgttccggg cttatacaat | 300 |
| gtcaacagcc cccttttatca gagccccttt gcgtccggct acggcctggg cgccgacgcc | 360 |
| tacggcaacc tgcccctgcgc ctcctacgac caaaacatcc ccgggctctg cagtgacctc | 420 |
| gccaaaggcg cctgcgacaa gacggacgag ggcgcgctgc atggcgcggc tgaggccaat | 480 |
| ttccgcatct acccctggat gcggtcttca ggacctgaca ggaagcgggg ccgccagacc | 540 |
| tacacgcgct accagacgct ggagctggag aaggagttcc acttcaaccg ctacctgacg | 600 |
| cggcgccgcc gcattgaaat cgcccacgcg ctctgcctca ccgagcgcca gattaagatc | 660 |
| tggttccaga accgccgcat gaagtggaag aaagagcata aggacgaagg tccgactgcc | 720 |
| gccgcagctc ccgagggcgc cgtgccctct gccgccgcca ctgctgccgc ggacaaggcc | 780 |
| gacgaggagg acgatgatga agaagaggaa gacgaggagg aatgaggggc cgatccgggg | 840 |
| ccctctctgc accggacagt cggaaaagcg tctttaagag actcactggt tttacttaca | 900 |
| aaaatgggaa aaataaaaga aaatgtaaaa aacaaaaaca aaacaaaaa agcaacccag | 960 |
| tccccaacct gcactctacc caccccccatc acctactcca gctcccaact tttgtggact | 1020 |
| gagcggccgc agagactggg tcgccttgga ttccctctgc ctccgaggac cccaaaagac | 1080 |
| accccccaacc ccaggccagc cggccctgct ctggcgcgtc caaatactaa cctagcacag | 1140 |
| gcctctgctc gaggcacccc caaactacct atgtatccag ccccagaggg cctccattcc | 1200 |
| caggaagtcc ctatgtatcc caacactggc agacacccag caccaccctc ccagacccgc | 1260 |
| aagaaagtga atctcactac tacctactcc cctaaaacta cctattttgt gctggctggc | 1320 |
| ttgcctgcta cctagtgccg actgctccca ggcaagtccc ctgctgctta cagcccgcag | 1380 |
| cttttggggt ccctgaggct gccctgagaa tgtgctgagg tccaggatca gggtattggc | 1440 |
| atctatttaa atcgaaaaat aatatatttta ttccaaaaag catcctaagt gcttgcaccc | 1500 |
| tagaatcaat ccctccttct ctggcttggc acccacagct caggcccatc aaccccccact | 1560 |

```
tctggagggg aatgttcctg agctggctgc agatctgtgg gttagcttct gcttagcagg    1620
actgtggaga tgcttccagc ttcgctgtcc tttcctctgg ctcctgtatc ttactgttca    1680
gctgtgttaa atatgtacgc cctgatgttt cctataatag cagatactgt atatttgaac    1740 aagattttt tttatcattt ctatagtctt ggagttcatt tgtaaggcag tgtcttgact     1800
tggaaaggat gtgttaatgg ggtgactttg tagcatggta tgttgtcttg agttaactgt    1860
agtgggtggg gaggtccaat gccctccgca atgcccttca tctcctgtgt tgtcctgtac    1920
cctgctcagc tccatcctgg ggttcaggga aggcacactt cccagcccag ctgtgtttta    1980
tgtaaccgaa aataaagatg cgtggtgaca agaaaaa                             2018

<210> SEQ ID NO 8
<211> LENGTH: 2076
<212> TYPE: DNA
<213> ORGANISM: Homo sapiens

<400> SEQUENCE: 8
agttgttaca tgaaatctgc agtttcataa tttccgtggg tcggccgggc cgggccaggc      60
gctgggcacg gtgatggcca ccactggggc cctgggcaac tactacgtgg actcgttcct     120
gctgggcgcc gacgccgcgg atgagctgag cgttggccgc tatgcgccgg ggaccctggg     180
ccagcctccc cggcaggcgg cgacgctggc cgagcacccc gacttcagcc cgtgcagctt     240
ccagtccaag gcgacggtgt ttggcgcctc gtggaaccca gtgcacgcgg cgggcgccaa     300
cgctgtaccc gctgcggtgt accaccacca tcaccaccac ccctacgtgc accccccaggc   360 gcccgtggcg gcggcggcgc cggacggcag gtacatgcgc tcctggctgg agcccacgcc     420
cggtgcgctc tccttcgcgg gcttgccctc cagccggcct tatggcatta aacctgaacc     480
gctgtcggcc agaaggggtg actgtcccac gcttgacact cacactttgt ccctgactga     540
ctatgcttgt ggttctcctc cagttgatag agaaaaacaa cccagcgaag gcgccttctc     600
tgaaaacaat gctgagaatg agagcggcgg agacaagccc cccatcgatc ccaataaccc     660
agcagccaac tggcttcatg cgcgctccac tcggaaaaag cggtgcccct atacaaaaca     720
ccagaccctg gaactggaga aagagtttct gttcaacatg tacctcacca gggaccgcag     780
gtacgaggtg gctcgactgc tcaacctcac cgagaggcag gtcaagatct ggttccagaa     840
ccgcaggatg aaaatgaaga aaatcaacaa agaccgagca aaagacgagt gatgccattt     900
gggcttattt agaaaaaagg gtaagctaga gagaaaaaga aagaactgtc cgtccccctt     960
ccgccttctc ccttctctca cccccacccct agcctccacc atccccgcac aaagcggctc    1020
taaacctcag gccacatctt ttccaaggca aaccctgttc aggctggctc gtaggcctgc    1080
cgctttgatg gaggaggtat tgtaagcttt ccatttcta taagaaaaag gaaagttga      1140 gggggggggca ttagtgctga tagctgtgtg tgttagcttg tatatatatt tttaaaaatc    1200
tacctgttcc tgacttaaaa caaaggaaa gaaactacct ttttataatg cacaactgtt     1260
gatggtaggc tgtatagttt ttagtctgtg tagttaattt aatttgcagt ttgtgcggca    1320
gattgctctg ccaagatact tgaacactgt gttttattgt ggtaattatg ttttgtgatt    1380
caaacttctg tgtactgggt gatgcaccca ttgtgattgt ggaagataga attcaatttg    1440
aactcaggtt gtttatgagg ggaaaaaac agttgcatag agtatagctc tgtagtggaa     1500
tatgtcttct gtataactag gctgttaacc tatgattgta aagtagctgt aagaatttcc    1560
cagtgaaata aaaaaaaatt ttaagtgttc tcggggatgc atagattcat cattttctcc    1620
```

| | | | |
|---|---|---|---|
| accttaaaaa | tgcgggcatt | taagtctgtc | cattatctat | atagtcctgt | cttgtctatt | 1680 |
| gtatatataa | tctatatgat | taaagaaaat | atgcataatc | agacaagctt | gaatattgtt | 1740 |
| tttgcaccag | acgaacagtg | aggaaattcg | gagctataca | tatgtgcaga | aggttactac | 1800 |
| ctagggttta | tgcttaattt | taattggagg | aaatgaatgc | tgattgtaac | ggagttaatt | 1860 |
| ttattgataa | taaattatac | actatgaaac | cgccattggg | ctactgtaga | tttgtatcct | 1920 |
| tgatgaatct | ggggttttcca | tcagactgaa | cttacactgt | atattttgca | atagttacct | 1980 |
| caaggcctac | tgaccaaatt | gttgtgttga | gatgatattt | aacttttgc | caaataaaat | 2040 |
| atattgattc | ttttctaaaa | aaaaaaaaaa | aaaaaa | | | 2076 |

<210> SEQ ID NO 9
<211> LENGTH: 2691
<212> TYPE: DNA
<213> ORGANISM: Homo sapiens

<400> SEQUENCE: 9

| | | | | | | |
|---|---|---|---|---|---|---|
| atgccaggcc | ccccaccagc | cacgttgggg | cagcccccac | agctcccggc | cttcgggcca | 60 |
| aggtgtcggg | gtgcgtctcc | tggcccatca | atacagatta | catatttata | tcaatcgcgg | 120 |
| gctctgaggg | cgccctcgga | gagcggcccc | gcgcctacga | aaccaaactg | ggagtggtcg | 180 |
| cgcggaaact | ctggctcggg | attggctgcg | ggcgcccgcc | gcggtgcggg | gggattgcta | 240 |
| atcgtattca | gcatgttttg | cacaagaaat | gtcagccaga | aagggctatc | tgctcccttc | 300 |
| gccaaattat | cccacaacaa | tgtcatgctc | ggagagcccc | gccgcgaact | cttttttggt | 360 |
| cgactcgctc | atcagctcgg | gcagaggcga | ggcaggcggc | ggtggtggtg | gcgcgggggg | 420 |
| cggcggcggt | ggcggttact | acgcccacgg | cggggtctac | ctgccgcccg | ccgccgacct | 480 |
| gccatacggg | ctgcagagct | gcgggctctt | ccccacgctg | gcggcaagc | gcaatgaggc | 540 |
| agcgtcgccg | ggcagcggtg | gcggtggcgg | gggtctaggt | cccggggcgc | acggctacgg | 600 |
| gccctcgccc | atagacctgt | ggctagacgc | gcccgtgtct | tgccggatgg | agccgcctga | 660 |
| cgggccgccg | ccgccgcccc | agcagcagcc | gccgcccccg | ccgcaaccac | cccagccagc | 720 |
| gccgcaggcc | acctcgtgct | cttcgcgca | gaacatcaaa | gaagagagct | cctactgcct | 780 |
| ctacgactcg | gcggacaaat | gccccaaagt | ctcggccacc | gccgccgaac | tggctccctt | 840 |
| cccgcggggc | ccgccgcccg | acggctgcgc | cctgggcacc | tccagcgggg | tgccagtgcc | 900 |
| tggctacttc | cgccttttctc | aggcctacgg | caccgccaag | ggctatggca | gcggcggcgg | 960 |
| cggcgcgcag | caactcgggg | ctggcccgtt | cccgcgcag | ccccgggc | gcggtttcga | 1020 |
| tctcccgccc | gcgctagcct | ccggctcggc | cgatgcggcc | cggaaggagc | gagccctcga | 1080 |
| ttcgccgccg | cccccacgc | tggccttgcg | cagcggcggg | ggctcgcagg | gcgacgagga | 1140 |
| ggcgcacgcg | tcgtcctcgg | ccgcggagga | gctctccccg | gccccttccg | agagcagcaa | 1200 |
| agcctcgccg | gagaaggatt | ccctgggtaa | gcagggctgc | agagggctgc | agtcaggcgg | 1260 |
| gcagacaggc | agacacaagg | aggagaagga | tcagaaaact | aggagcccgc | gcagcagccg | 1320 |
| gccggccttg | gcccaagctg | caggcaggct | gaccttgtga | acttgctttt | taatatttgg | 1380 |
| gcgtgggggc | gcagtaaaat | tcatgtccgg | cttagcgccc | cacagcaaga | cgtcctcggc | 1440 |
| gctggcctca | gctccccctg | actagggacg | aggacaccag | cgagcaggcc | ccctcctgtg | 1500 |
| cgctctttcc | tgtggccggg | aggacccaga | gccctggtcc | ctgcccagcc | tgcgcggcgc | 1560 |
| gggccacgcg | gggggagggg | gagggaggga | aagtagctcg | cccgcagata | gcgcggatgt | 1620 |
| ttgtaaggca | tccaaaataa | gcagccgcca | gcgccaataa | ataagcccat | taaccggcga | 1680 |

```
agttcgagtg tacgatcccc catgctttt tcaaagttgc tgaggggcgg gaatcttcgt    1740
ggcgggaaga agaaaaggca aatccggcct ggaagcgggg ggccctgagc tgagagccag    1800
agaagggcca tttccccttcc cctggacctc ggaatcgccc agctatgtat cctggctcct    1860
ggagaaactt gagggagggc ccttgacccc cgaatcggtt tttcctgcct tccccattgg    1920
accaatgatg cccttctttc tccccttatc gagtcttggg caatcagggc cctggggtga    1980
gacagccaag ctgcctggcc catcttccaa gtaagcaccc cgcgctccta gcctgggggc    2040
tacaggaaat gcttgtctgc catatggcaa gaggcaaaga aaagcgttaa gttcaagatg    2100
tacagcctgc cctcccaggc ctttccttct gcaagcatct acggcttagc gctaaaacag    2160
gtgtttggaa aagtggggga aatgtaaatt ggaagggtca tgtagattga aggcccactc    2220 aattttgtc atgacttatg gaggaactgc ttgctctcag caagccaaaa acggggcac    2280 gactctcttc tctgtgactt gggacatctc tcttatggga gaaacggagg caattcaccc    2340
ccgcgggcag cccgtgtggc ctcgacttaa tcatcccctc tttattctct tacatgccag    2400
gcaattccaa aggtgaaaac gcagccaact ggctcacggc aaagagtggt cggaagaagc    2460
gctgccccta cacgaagcac cagacactgg agctggagaa ggagtttctg ttcaatatgt    2520
accttactcg agagcggcgc ctagagatta gccgcagcgt ccacctcacg gacagacaag    2580
tgaaaatctg gtttcagaac cgcaggatga aactgaagaa aatgaatcga gaaaaccgga    2640
tccgggagct cacagccaac tttaattttt cctgatgaat ctccaggcga c             2691

<210> SEQ ID NO 10
<211> LENGTH: 2653
<212> TYPE: DNA
<213> ORGANISM: Homo sapiens

<400> SEQUENCE: 10
cttcaaagag gcagctgcag tggagaatca tgttaagctc ggctactgcg gagagcccaa     60
ggtagcccaa taatggattt tgatgagcgt ggtccctgct cctctaacat gtatttgcca    120
agttgtactt actacgtctc gggtccagat ttctcccagcc tcccttcttt tctgccccag    180
accccgtctt cgcgcccaat gacatactcc tactcctcca acctgcccca ggtccaaccc    240
gtgcgcgaag tgaccttcag agagtacgcc attgagcccg ccactaaatg gcaccccgc    300 ggcaatctgg cccactgcta ctccgcggag gagctcgtgc acagagactg cctgcaggcg    360
cccagcgcgg ccggcgtgcc tggcgacgtg ctggccaaga gctcggccaa cgtctaccac    420
caccccaccc ccgcagtctc gtccaatttc tatagcaccg tgggcaggaa cggcgtcctg    480
ccacaggctt tcgaccagtt tttcgagaca gcctacggca cccccggaaaa cctcgcctcc    540 tccgactacc ccggggacaa gagcgccgag aaggggcccc cggcggccac ggcgacctcc    600
gcggcggcgg cggcggctgc aacgggcgcg ccggcaactt caagttcgga cagcggcggc    660
ggcggcggct gccgggagac ggcggcggca gcagaggaga aagagcggcg gcggcgcccc    720
gagagcagca gcagccccga gtcgtcttcc ggccacactg aggacaaggc cggcggctcc    780
agtggccaac gcacccgcaa aaagcgctgc ccctatacca gtaccagat ccgagagctg    840 gaacgggagt tcttcttcag cgtctacatt aacaaagaga agcgcctgca actgtcccgc    900
atgctcaacc tcactgatcg tcaagtcaaa atctggttc agaacaggag aatgaaggaa    960
aaaaaaatta acagagaccg tttacagtac tactcagcaa atccactcct ctaagactcc    1020
agcggctgga attgggtggg gggcttcata cacatgagat aatatgcaga ttttgcccctt    1080
```

```
gacaaagtca agccacatgg tgactttga aaagaggtgt gcaagagagg gatgcatgga      1140
gatagcccca caggaggtgg tctgggactc tcttgattaa gatctcagtg gttaagattc      1200
ctaataatca ttggattctg agagctgtgc atcagctaga atgacaggtt tgggacccct      1260
ggtggttcac tcttggagcc tgcagagctg cgggctgggt gtggtctcca ctggggattg      1320 ggccctgcc agacccctg gagactaacc ccaccacacc ctccctctac tgggagccta       1380 cccacccca ggaccctga gtaaaaaagc tgtgtgctct ccaagcccag ttcagcttgg        1440 ggacagggc aggaggaagg ggtaggatta ctaggtgccc agaatgaggc tgctttccaa      1500
agccaatgtg aacagcggct ggacttggag gtagctttga ggtggaagag ggctgcaaat      1560
ccttgtggga aaagaaatct atgattccag gtggcatcag tgtctttcca ctcctcctag      1620
ccacccacca cactgatcca gccctgagtt cctagccacc gcctcctaca gcccacctgg      1680
cttttctttc taccaaatga gggtcttggt tccagcctgc cactcaggcc caaagcctcg      1740
acacagagtg gactgttccc tgaggtggga gatgtggaaa agccaagagg ctgcagccag      1800
gccactggcc cctgagatct ctgcaggaaa tggctgtgga gtgtggcagt ttggcaaact      1860
ctccaccaca cgtaatgaaa cttggatttg ctcagtgtct ggctgcagag cagtgggcct      1920
ggccagcagg tccccagctt tggctatgag ggccttgagt cccccaaaac accgggttcc      1980
agcaccacac tcagccctca ttggctcttg aactgagctt ggaagcttct ggtgaccttc      2040
caagagcctg agagtgaggt ggaattattt taaaagataa atattatatt atatatatat      2100
atatttccct gaaggaacca aagcgaattt taaagatgc aatgtagagg ggaaaagaga      2160
tgatgaaaat atttaaaggc cctatctgtt tacagtgttc cgtggttaaa ctcgctcact      2220
gctaagaata tttgaatgta tgcttcatac agggatggtg ttcaaaaaac ttgtaaataa      2280
aggaaccata atcaattttc ttttctttct ttctcttttt cttttttctt ttgccattag      2340
ttgatttcct ttagggtgtt ggaggggtg gaaaaggtat tgagaatggt cttttaatc       2400 tcttgcaaca tttggaaaga gttagggaaa tgctcagagg cagtcggcct ggccggcctg      2460
gggatctcat ctgggaaagc caggcaccct cccattgaat ctcctttgcc tccctgtgtt      2520
aagaaatgtc tgttggctcc atttgtactg ggagtgttgg cctgtcctca attctggttc      2580
ttacccaccg tgtgtgttgc agcacttata caggcaactg ggcacaagga aaataaagac      2640
ggtggaaatt tga                                                         2653
```

<210> SEQ ID NO 11
<211> LENGTH: 2514
<212> TYPE: DNA
<213> ORGANISM: Homo sapiens

<400> SEQUENCE: 11

```
actgggtct tctccatgcg gctcgggcta tgacagcctc cgtgctcctc cacccccgct        60
ggatcgagcc caccgtcatg tttctctacg acaacggcgg cggcctggtg gccgacgagc      120
tcaacaagaa catggaaggg gcggcggcgg ctgcagcagc ggctgcagcg gcggcggctg      180
ccggggccgg gggcggggc ttcccccacc cggcggctgc ggcggcaggg gcaacttct       240 cggtggcggc ggcggccgcg gctgcggcgg cggccgcgc caaccagtgc cgcaacctga      300
tggcgcaccc ggcgcccttg gcgccaggag ccgcgtccgc ctacagcagc gccccggggg      360
aggcgccccc gtcggctgcc gccgctgctg ccgcggctgc gctgcagcc gccgccgccg      420 ccgccgcgtc gtcctcggga ggtcccgcc cggcgggccc ggcgggcgca gaggccgcca      480
agcaatgcag cccctgctcg gcagcggcgc agagctcgtc ggggcccgcg gcgctgccct      540
```

```
atggctactt cggcagcggc tactacccgt gcgcccgcat gggcccgcac cccaacgcca      600
tcaagtcgtg cgcgcagccc gcctcggccg ccgccgccgc cgccttcgcg acaagtaca      660 tggataccgc cggcccagct gccgaggagt tcagctcccg cgctaaggag ttcgccttct      720
accaccaggg ctacgcagcc gggccttacc accaccatca gcccatgcct ggctacctgg      780
atatgccagt ggtgccgggc ctcggggggcc ccggcgagtc gcgccacgaa cccttgggtc     840
ttcccatgga aagctaccag ccctgggcgc tgcccaacgg ctggaacggc caaatgtact      900
gccccaaaga gcaggcgcag cctccccacc tctggaagtc cactctgccc gacgtggtct      960
cccatccctc ggatgccagc tcctatagga gggggagaaa gaagcgcgtg ccttatacca     1020
aggtgcaatt aaaagaactt gaacgggaat cgccacgaa taaattcatt actaaggaca     1080
aacggaggcg gatatcagcc acgacgaatc tctctgagcg gcaggtcaca atctggttcc     1140
agaacaggag ggttaaagag aaaaaagtca tcaacaaact gaaaaccact agttaatgga     1200
ttaaaaatag agcaagaagg caacttgaag aaacgcttca gaactcgttg ctttgcccag     1260
ataatgataa taatgcttaa taataattga agaatgggaa agagaaagag acagagactg     1320
gcattttcct ctcccgaagg agatctcttt ctctttaatg gaatctacaa ctgttttaaa     1380
actttaagaa aggtaaagac tgccagttct tccgccaacc ccatcagccc agcccgttaa     1440
atgtcaaacg tcaaccccca aaatacgcaa tttcagataa gttacgcagt tactgaaatc     1500
ttgtaagtat ttaagtgatc gttacatttt aggacactgc gttagatggt aataatctgg     1560
aagttggtta caaacgcaag aggccattgt aaacatctgc ttgtccttct taggtcgcca     1620 ttcccttttgc atgttaagcg tctgctcagg taaatcttag tgaaattcct accgttgttg     1680
tacgttctgc aaaacatttt atgtatagat ttagagggga aacgagaagg tactgaaata     1740
atgatcttgg aatatttgct gtgaagggag aaagggagag aaaactcttc tgaggatcat     1800
ttgtcttggt agtatagtaa aaccaaccag ctgaaccttt caggctacaa gagaaccccgg    1860 gtcggtaatg tcttttttaag aataatttttt aattgcttat aacaagcata ttttgtggca    1920
tttgaactat atttactgct ccaatatccg ttatttttcca aaggattttg tatcttttg    1980 aaaatgttta catcatcaga tgatccacag aattcacttt atgtgagatc tcccgagagt     2040
ttccatccca acatgatgga ctttggtttg aacacaattc gttttttcat ttgaattggc     2100
atttcccaat atttgctaaa catttgctgg agaaatcatt tttctttttt ctttttttaga    2160 aaactcagaa tgaaaattca ttcccctgaa atatttaggt gtctatattc tatattttga     2220
tctattaagg gattagtatt tttccatgtt tattgtgtta tcagagtgca ttagaaagat     2280
tagtgattca tcttcacagc acatttttaa tcaagcagtt atttcaacca gcacattcgt     2340
tttgttcata ttcactatag aatgatatct tgtaaataaa gacattcagc acactgtgaa     2400
aatgtatttg tgcacctgct tttttaaatat ttctactaaa aatgaaaaaa aaaaacccttt    2460 agacctgtag atagtgatat cgtaatatta attgttaata aaatagtcac tgcc           2514
```

<210> SEQ ID NO 12
<211> LENGTH: 1014
<212> TYPE: DNA
<213> ORGANISM: Homo sapiens

<400> SEQUENCE: 12

```
tgacgcatgg actataatag gatgaactcc ttcttagagt acccactctg taaccgggga      60
cccagcgcct acagcgccca cagcgcccca acctcctttc ccccaagctc ggctcaggcg     120
```

```
gttgacagct atgcaagcga gggccgctac ggtggggggc tgtccagccc tgcgtttcag      180
cagaactccg gctatcccgc ccagcagccg ccttcgaccc tggggggtgcc cttccccagc     240 tccgcgccct cggggtatgc tcctgccgcc tgcagcccca gctacgggcc ttctcagtac      300
taccctctgg gtcaatcaga aggagacgga ggctattttc atccctcgag ctacggggcc     360
cagctagggg gcttgtccga tggctacgga gcaggtggag ccggtccggg gccatatcct     420
ccgcagcatc cccttatgg gaacgagcag accgcgagct ttgcaccggc ctatgctgat      480
ctcctctccg aggacaagga aacaccctgc ccttcagaac ctaacacccc cacggcccgg     540
accttcgact ggatgaaggt taagagaaac ccacccaaga cagcgaaggt gtcagagcca     600
ggcctgggct cgcccagtgg cctccgcacc aacttcacca caaggcagct gacagaactg     660
gaaaaggagt tccatttcaa caagtacctg agccgggccc ggagggtgga gattgccgcc     720
accctggagc tcaatgaaac acaggtcaag atttggttcc agaaccgacg aatgaagcag     780
aagaagcgcg agcgagagga aggtcgggtc cccccagccc caccaggctg ccccaaggag     840
gcagctggag atgcctcaga ccagtcgaca tgcacctccc cggaagcctc acccagctct     900
gtcacctcct gaactgaacc tagccaccaa tggggcttcc aggcactgga gcgccccagt     960
ccagccctat cccaggctct ccccaacccc aggcctgggc ttcactggcc tggg           1014

<210> SEQ ID NO 13
<211> LENGTH: 1614
<212> TYPE: DNA
<213> ORGANISM: Homo sapiens

<400> SEQUENCE: 13
aatctccccc tcccaaaatc gctccattac ataaatcggg gggggtgcag gaggggggtc      60
ccttccgatc ctccctcctg acgccccccc cagcagcccc ctcccccacc attgaaagcc     120
atgaattttg aatttgagag ggagattggg tttataaaca gccagccgtc gctcgccgag     180
tgtctgactt cctccccgc tgtcttggag acatttcaaa cttcatcaat caaggagtcg     240
acattaattc ctcctcctcc tcctttcgag caaaccttcc ccagcctcca gcccggcgcc     300
tccacccttc agagacccag gagccaaaag cgagccgaag atgggcctgc tctgccgccg     360
ccaccgccgc cgccactccc cgctgccccc ccggccccg agttcccttg gatgaaagag     420
aagaaatccg ccaagaaacc cagccaatcc gccacgtctc cttctccggc cgcctccgcc     480
gttccggcct ccggggtcgg atcgcctgca gatggcctgg gactgccgga ggctggtggc     540
ggcggggcgc gcaggctgcg cacggcttac accaacacgc agctgctgga actggagaag     600
gaattccact ttaataagta cctgtgccgg ccacgccgcg tcgagatcgc ggccttgctg     660
gacctcaccg aaaggcaggt caaagtctgg tttcagaacc ggcgcatgaa gcacaagcgg     720
cagacgcagc accgagagcc gccggatggg gagcctgcct gccgggagc cctggaggac     780 atctgcgacc ctgccgagga accgcgggcc agcccgggcg gccctccgc ctcgcgggcg     840 gcgtgggaag cctgctgtca cccgccggag gtggtgccgg gggccttaag gcgggacccc     900 cggccttag ccgttcgctt agagggcgca ggcgcgtcga gtcccggctg cgcgctgcgc     960
ggggccggcg ggctggagcc cgggccattg ccagaagacg tcttctcggg gcgccaggat    1020
tcacctttcc ttcccgacct caacttcttc gcggccgact cctgtctcca gctatccgga   1080
ggcctctccc ctagcctaca gggttctctc gacagcccgg tccttttttc cgaggaagag   1140
ctggattttt tcaccagtac gctctgtgcc atcgacctgc agtttcccta acctgtttcc   1200
tcctcccggt cctttcgacc cccgcgctcc ttggccgtct actggaaaaa tcgagcctct   1260
```

```
cccaccctca gtcgcataga cttatgtgtt ttgctaaaat tcaggtatta ctgaattagc      1320
gtttaatcca ctcccttctt tcttcttcta aaatattggg cactcggtta tcttttaaaa      1380
ttcacacaga aaaattccgt ttggtagact ccttccaatg aaatctcagg aataattaaa      1440
ctctaggggg actttcttaa aaataactag agggacctat tttcctcttt tttatgtttt      1500
agactgtaga ttatttatta aaattcttta ataataggaa aaggggaaag tatttattgt      1560
acattatttt catagattaa ataaatgtct ttataatacc aaaaaaaaaa aaaa            1614

<210> SEQ ID NO 14
<211> LENGTH: 3627
<212> TYPE: DNA
<213> ORGANISM: Homo sapiens

<400> SEQUENCE: 14
ctgggtaggg caggggggaac cgacaggccg gtgtccccag ccgcaaaaga gctgctgaac       60
tgtccgttta aatgctgctg ggagactcgt aaaaaaatca tcgtggacct ggaggatgag      120
aggggcgagc tttatttcgg tcggattgcg gtgtggtggt ttagctgcaa ggggatgccg      180
cagccccagt tgagggggaa aatagttctt aaaaagcata tgccccccta aggaatgtct      240
ctaaagaacc aaatcaaagc tgctctttgg aaggtatgaa tagaatttaa aaaaaaaga      300 tttctatgga gcttaaagtt cacagccatt ctgtgtagac aagagctaag aaaaatgtga      360
gaattataca gaaaaccatt aatcacttct tttctttaaa tacgtatcct ctctcctttg      420
ttattattca acagcaaatc tccttggacc ggctgttggg ggaaaaaagt gttagccgtc      480
tctcccggat ctgcaagggg gaaaaaattt ggaaccataa agttgaaaac tttttttctct      540 cagtttggaa gaagcccttc gtcatgaatg ggatctgcag agttcgggcg agaggaggcg      600
agaggcgcaa aggaggggag atttgtcgcc tgccgctcgc tctgggcttc gatgtgaata      660
tatattatgt ctgcctgttc tcccctcgtc ggtggctaag gtcagccgct tggaacagac      720
cccggaggag gggggcagag aggggaggtg gggggggggg gtccggcgtg tcacgtgacc      780
cccaggggtt gccaatgtcc ggtcctgaggg tatcaggcct ttccaagttg ccacccactg      840
cccaggcctc acccagcgat gcagaaagcc acctactacg acaacgccgc ggctgctctc      900
ttcggaggct attcctcgta ccctggcagc aatggcttcg gcttcgatgt ccccccccaa      960
cccccatttc aggccgccac gcacctggag ggcgactacc agcgctcagc ttgctcgctg     1020
cagtccctgg gcaacgctgc cccacatgcc aagagcaagg agctcaacgg cagctgcatg     1080
aggccgggtc tggcccccga gccctgtcg ggcccgcctg gctcaccccc gcccagtgcc     1140
gcacctacca gtgccactag caacagcagt aatggggcg ggcccagcaa agtggtccc     1200 ccaaagtgcg gtcccggcac caactccacc ctcaccaaac agatattccc ctggatgaaa     1260
gagtcgaggc aaacgtccaa gctgaaaaac aactcccccg gcacagcaga gggctgtggt     1320
ggcggcggcg gtggcggcgg cggcggaggc agtggtggca gcggggggcgg tggcggcggc     1380 ggcgggggag gggacaagag ccccccgggg tcggcggcgt ccaagcgggc gcggacggcg     1440
tacacgagcg cgcagctggt ggagctggag aaggagttcc atttcaaccg ctacctgtgc     1500
cggcctcgcc gtgtagagat ggccaacctg ctgaacctca gcgagcggca gatcaagatc     1560
tggttccaga accggcgcat gaagtacaag aaggaccaga aggccaaggg attggcctcg     1620 tcgtcgggggg gccatctcc agccggcagc ccccgcagc ccatgcagtc cacggccggc     1680
ttcatgaacg ccttacactc catgacccccc agctacgaga gcccgtcccc accgccttc     1740
```

-continued

| | |
|---|---|
| ggtaaagccc accagaatgc ctacgcgctg ccctccaact accagccccc tctcaaaggc | 1800 |
| tgcggcgccc cgcagaagta ccctccgacc ccggcgcccg agtatgagcc gcacgtcctc | 1860 |
| caagccaacg ggggcgccta cgggacgccc accatgcagg gcagtccggt gtacgtgggc | 1920 |
| gggggcggct acgcggatcc gctgccgccc cctgccggcc cctccctcta tggcctcaac | 1980 |
| cacctttccc atcacccttc cgggaacctg gactacaacg gggcgccccc tatggcgccc | 2040 |
| agccagcacc acggaccctg cgaaccccac cccacctaca cagacctctc ctctcaccac | 2100 |
| gcgcctcctc ctcagggtag aatccaagaa gcgcccaaat taacacacct gtgatgggaa | 2160 |
| agggcgaacg aggattaggg gatggggagg aagagagaga ctgtggagct ctgggggggca | 2220 |
| acctggaggt ctgaaaagag gagccagaga aggtggtacc caggcttcct ggtcagaacc | 2280 |
| ggcctggagc tccttccctt cccctggcc tgagaggttg cttttaagtc ttccacccct | 2340 |
| tgttccatct gcctgccaac ccatcggaaa ggaatccaca tcatattgga gatgacccca | 2400 |
| tcaaccccag ggctccagca ctaccaagtt ggaattccac gcccgggagt ggggtagagg | 2460 |
| aagacgagac aggacgaggc agaaaagcac attttaaaaa ccagacaaga tggctaggcc | 2520 |
| atcaccaacc aacggactta ccttacatct ttgtaggtaa ttcccccaa atcttgattt | 2580 |
| tttttttcc tcaattatcc tttaaaaaat aagaaaacac atttcaaacc caaaaggcac | 2640 |
| aaaacacgtt cccttccaac tttcccaaaa cctcaaattt gttcccattt gaggtttatt | 2700 |
| gaggtacact tctagccccc ggttttctg ctctagaaca ttcatatcta tacatcccac | 2760 |
| ccccatcaat tacagttttt agagggctca gggatggtga gagatcctga aagagctgcc | 2820 |
| tatattataa attatataca ttttttttta aggaaaagtg tggaggctag ggcaggcagg | 2880 |
| ttgttaggac tgaaggtttg cccattctgc tgcctccatc tcagctccag ctccatcccc | 2940 |
| ctctccacag aaagcagttg gtgacacgag gttctatact tttcttctgt tgctctcttg | 3000 |
| acttaacgtg aaaacagggt atatttgaac aaactgtccc aggcaggggc tgggcagggc | 3060 |
| ctgtgtgcct tgctcagcct cctgacagga cacttttgtt gcacttagaa tttacatttt | 3120 |
| aatggatgta aaacaactg tgagagatgt ctgggcctgc agaagtccag cattgctcaa | 3180 |
| aaaagcgtgt gttctagtga acattttcat atatatttat tggttatagc ctgttaaaat | 3240 |
| attttctttt ttgtattatt tatcccccta cattatgtat ttatatgagg gaaaaaagg | 3300 |
| aaaaaattgt acttttttag tatttacctg ttacaaagga cattgtgttt cctgtcatgt | 3360 |
| aaaaccagct attttagtta ctattgtact ctagaaaaga gctgtagatt tatgttaaac | 3420 |
| tcgtacttac gaacaattgt aattagttct aaaaggcatg aactcagctc ctaatcgtca | 3480 |
| ctgtatagtc ctgaatttgt agaactagag ttaattccct cttggaactt tcttttgttct | 3540 |
| tcagtagtta cttttttcct tacctaaaag ggttgtctgt caaacaattc ttgaataaac | 3600 |
| tttctgttat caattttaaa aaaaaa | 3627 |

<210> SEQ ID NO 15
<211> LENGTH: 2042
<212> TYPE: DNA
<213> ORGANISM: Homo sapiens

<400> SEQUENCE: 15

| | |
|---|---|
| ggaaaacgag tcaggggtcg gaataaattt tagtatattt tgtgggcaat tcccagaaat | 60 |
| taatggctat gagttctttt ttgatcaact caaactatgt cgaccccaag ttccctccat | 120 |
| gcgaggaata ttcacagagc gattacctac ccagcgacca ctcgcccggg tactacgccg | 180 |
| gcggccagag gcgagagagc agcttccagc cggaggcggg cttcgggcgg cgcgcggcgt | 240 |

```
gcaccgtgca gcgctacgcg gcctgccggg accctgggcc cccgccgcct ccgccaccac    300
ccccgccgcc cccgccaccg cccggtctgt ccctcgggc tcctgcgccg cacccgccg     360 gggccctcct cccggagccc ggccagcgct gcgaggcggt cagcagcagc ccccgccgc    420 ctccctgcgc ccagaacccc ctgcaccca gcccgtccca ctccgcgtgc aaagagcccg    480
tcgtctaccc ctggatgcgc aaagttcacg tgagcacggt aaaccccaat tacgccggcg   540
gggagcccaa gcgctctcgg accgcctaca cgcgccagca ggtcttggag ctggagaagg   600
aatttcacta caaccgctac ctgacacggc gccggagggt ggagatcgcc cacgcgctct   660
gcctctccga gcgccagatc aagatctggt tccagaaccg gcgcatgaag tggaaaaaag   720
accacaagtt gcccaacacc aagatccgct cgggtggtgc ggcaggctca gccggagggc   780
cccctggccg gcccaatgga ggccccgcg cgctctagtg cccccgcacg cgggagccac    840
gaacctcggg gtggggtgg gcagtgagtg caggggatgg ggtgggggga caggagggg    900 ccctggggcc tgggccccgg aaaaatctat ctgccctccc ccacacttta tatacgaata   960
aacgcagaag aggggggggg gaagctttat ttatagaaat gacaatagag ggccacgggg   1020
aggccccccc agaagcaaga ttcaaatctc ttgctttctt tcttaaaaaa aagaaaaaga   1080
aaaagcaaga agaaggaaga aagaaaaaga cagaaagaga aataggagga ggctgcagct   1140
cctcgttttc agctttggcg aagatggatc cacgttcat ctttaatcac gccaggtcca   1200
ggcccatctg tcttgtttcc tctgccgagg agaagacggg cctcggtggc gaccattacc   1260
tcgacacccg ctaacaaatg aggcccggct cggccgcctc cgcctctgct actgccgctg   1320
ctggaagaca gcctggattt cctttctttg tcccccactc ccgatacccca gcgaaagcac   1380 cctctgactg ccagatagtg cagtgttttg gtcacggtaa cacacacaca ctctccctca   1440
tctttcgtgc ccattcactg agggccagaa tgactgctca cccacttcca ccgtgggtt    1500 gggggtgggc aacagaggag gggagcaagt agggaagggg gtggccttga caactcagga   1560
gtgagcagga aaattgagtc caaggaaaaa gagagactca gagacccggg agggccttcc   1620
tctgaaaggc caagccaagc catgcttggc agggtgaggg gccagttgag ttctgggagc   1680
tgggcactac tctgccagtc cagagttgta cagcagaagc ctctctccta gactgaaaat   1740
gaatgtgaaa ctaggaaata aaatgtgccc ctcccagtct gggaggagga tgttgcagag   1800
ccctctccca tagtttatta tgttgcatcg tttattatta ttattgataa tattattatt   1860
actatttttt tgtgtcatgt gagtcctctc tccttttctc tttctgacat tccaaaacca   1920
ggccccttcc tacctctggg gctgcttgag tctagaaccc ttcgtatgtg tgaatatctg   1980
tgtgctgtac agagtgacaa tagaaataaa tgtttggttt cttgtgacca gcaaaaaaaa   2040
aa                                                                   2042
```

<210> SEQ ID NO 16
<211> LENGTH: 1830
<212> TYPE: DNA
<213> ORGANISM: Homo sapiens

<400> SEQUENCE: 16

```
gtgaagcaca gggttataac gaccacgatc cacaaatcaa gccctccaaa atcacccaaa    60
tgagctcgta ctttgtaaac tccttctcgg ggcgttatcc aaatggcccg gactatcagt   120
tgctaaatta tggcagtggc agctctctga gcggctctta cagggatccc gctgccatgc   180
acaccggctc ttacggctac aattacaatg ggatggacct cagcgtcaac cgctcctcgg   240
```

| | |
|---|---|
| cctcctccag ccactttggg gcggtgggcg agagctcgcg cgccttcccc gcgcccgccc | 300 |
| aggagcccg cttcaggcaa gcggcttcga gctgctccct gtcctcgccc gagtccctgc | 360 |
| cctgcaccaa cggcgacagc cacggcgcca agccctctgc ttcgtccccc tccgaccagg | 420 |
| cgacctcagc cagctccagc gccaatttca ccgaaataga cgaggccagc gcgtcctcgg | 480 |
| agcctgagga agcggcaagc cagctaagca gccccagcct agctcgggcg cagccagagc | 540 |
| ccatggccac ctccacagcc gcgcccgagg ggcagactcc gcaaatattc ccctggatga | 600 |
| ggaagcttca catcagccat gatatgaccg ggccggacgg gaaaagggcc cggaccgcgt | 660 |
| atacccgcta ccagaccctg gagctggaaa aggagttcca cttcaaccgc tacctgaccc | 720 |
| ggcgacggcg catcgagatc gcccacgcac tctgcctgtc cgagcgccag atcaagatct | 780 |
| ggttccagaa ccggcgcatg aagtggaaga aggacaacaa attgaaaagt atgagcctgg | 840 |
| ctacagctgg cagcgccttc cagccctgag cccgcccaga ggagcccagc ggcccaagag | 900 |
| cccgtgccac ccccagccct gcccctcca atcctcccg ctctgccgcc gccgctggg | 960 |
| gaccggttcc cacaagcctg cctcgccttg tgttacgata tttcgtttgg tcttaggtct | 1020 |
| tcctgtggct ccctctctcc tggactggtt atcttgttat tattgttaat aataattatt | 1080 |
| attattattt tccttccatg ctcccaactc ccttctgctt gtcccaaatc cgccagtgtt | 1140 |
| tctgaatgtt tgtgtctgtg gttgcagtct ttccccagg aaaaaaaaaa aaagaaattc | 1200 |
| gcatgtttaa tgtgaactct ccctccccca tctgtgttct aacttattta taaaagatg | 1260 |
| atcgctgtat tttgagtttc agctggaaac ttctgtaagg ggcagcagtt gaggtggggt | 1320 |
| agtgccgcag tggggtcaag ctgagctggc ttcggagatg gagtcccttt tcattctcct | 1380 |
| cctcctccct cctcactccc taggcccaag tctcctaggg gcttggtcct agggtgggaa | 1440 |
| ggggctaggg aggaccaaag ggatggtatt gagaagagag aaagaagata gtgagattta | 1500 |
| agttcctgct gcctgggtag gccccacaag gcctggtctg ggagtatacg gaaacaaaaa | 1560 |
| tgatcctcag tgcaaaatgt cttgtgtatt tctctgtgaa tccatgggtc tggctagagg | 1620 |
| gcccaaagct tgtaaatatg gggatagtct gggtcagacc catctctccc ttacccatct | 1680 |
| tgcttccaag accatttgta gtgagcgagt ggatgctgtg ctacgtgtga aatctgtctt | 1740 |
| tgcggggcct gtctcagtga ttcgcttttg gtatttgttt gtagctttcc tggaagtcaa | 1800 |
| ataaatgttt cccccactcc aaaaaaaaaa | 1830 |

<210> SEQ ID NO 17
<211> LENGTH: 1686
<212> TYPE: DNA
<213> ORGANISM: Homo sapiens

<400> SEQUENCE: 17

| | |
|---|---|
| caccacacct aggtcggagc actgtcgtcc ttcagggctc cagcctcttg atattttgt | 60 |
| acttcagtat cagctcgata gagcaaaaga gagagaggac gagagagggg gtcagagaag | 120 |
| gggaagcaac ggctctcacg ttgggacaat attatctgga agctgaagaa gaaactgaat | 180 |
| actccttcct tcctccccac ccattccttt aaatccggag ggggaaaaaa tcccaaggtc | 240 |
| tgcaaaggcg cggcgctcgg actataaaac acaacaaatc ataaacccgg cggagcagca | 300 |
| gcggccgcgc gcgcctcccc tcccaatgag ttcctatttc gtgaactcca ccttccccgt | 360 |
| cactctggcc agcgggcagg agtccttcct gggccagcta ccgctctatt cgtcgggcta | 420 |
| tgcggacccg ctgagacatt accccgcgcc ctacgggcca gggccgggcc aggacaaggg | 480 |
| cttttgccact tcctcctatt acccgccggc gggcggtggc tacggccgag cggcgccctg | 540 |

```
cgactacggg ccggcgccgg ccttctaccg cgagaaagag tcggcctgcg cactctccgg      600
cgccgacgag cagcccccgt tccacccgga gccgcggaag tcggactgcg cgcaggacaa      660
gagcgtgttc ggcgagacag aagagcagaa gtgctccact ccggtctacc cgtggatgca      720
gcggatgaat tcgtgcaaca gttcctcctt tgggcccagc ggccggcgag gccgccagac      780
atacacacgt taccagacgc tggagctgga gaaggagttt cactacaatc gctacctgac      840
gcggcggcgg cgcatcgaga tcgcgcacgc cctgtgcctg acggagaggc agatcaagat      900
atggttccag aaccgacgca tgaagtggaa aaaggagagc aaactgctca gcgcgtctca      960
gctcagtgcc gaggaggagg aagaaaaaca ggccgagtga aggtgctgga aaggaggga      1020 ggacgcgagg ggaaaggcct gtggggagcc gagggcgtca gagagacccg ggaaggaagg     1080
ctctcgggtg ggggagccag agacctgctc tccggcgca gacaggcggg gcccagcgct      1140
ctcctggacg ccccgcccg cacagctccc ggcgggtgct ctgaggcctc actactcgag       1200
cccacccagc atcccgcgcg cccttccttc ccgaggaact cgcctcagcc tgatcaggct      1260
tcctggtgag aactgaggag cggactcact tgatgtttcc tggaagcaga gcaaaatgct      1320
cttgtccctg tcgcgtctca ttttgtccat gtccccgtg cacggttcaa tggtagattc       1380
gctgtcccct cagcggggc cttgaagact ccctgatccc agacctgtcg tctctcccac       1440
cccctcccca aagccactgg aaggagcaca tactacctag aagtaagaag aggagcctca     1500
gaagaaaaca aagttctatt ttattaattt tctatgtgtt gtgtttgtag tcttgtctta       1560
gctctggacg tgaaatactt cgatgatgat gatgatgatg atgatgataa taataataat      1620
aataacaaca acaacaacaa taataaagat gtgaaaactc gacgctcggt cacctcaaaa      1680
aaaaaa                                                                 1686
```

<210> SEQ ID NO 18
<211> LENGTH: 1377
<212> TYPE: DNA
<213> ORGANISM: Homo sapiens

<400> SEQUENCE: 18

```
ggtccttttt ggtgtaaatc tggactctaa ttctgtaata tatcaaggaa tctcgtaaaa       60
ccgacactaa aacgtccctg cctacaaatc atccggccaa attatgagtt cattgtatta      120
tgcgaatact ttatttttcta aatatccagc ctcaagttcg gttttcgcta ccggagcctt    180
cccagaacaa acttcttgtg cgtttgcttc caaccccag cgcccgggct atggagcggg      240 ttcggcgct tccttcgccg cctcgatgca gggcttgtac cccggcgggg ggggcatggc     300
gggccagagc gcggccggcg tctacgcggc cggctatggg ctcgagccga gttccttcaa    360
catgcactgc gcgcccttg agcagaacct tcccggggtg tgtcccggcg actccgccaa      420
ggcggcgggc gccaaggagc agagggactc ggacttggcg gccgagagta acttccggat    480
ctacccctgg atgcgaagct caggaactga ccgcaaacga ggccgccaga cctacacccg    540
ctaccagacc ctggagctgg agaaagaatt tcactacaat cgctacctga cgcggcggcg    600
gcgcatcgag atcgcgcaca cgctctgcct cacggaaaga cagatcaaga tttggttttca    660 gaaccggcgc atgaagtgga aaaggagaa caagaccgcg ggcccgggga ccaccggcca    720
agacagggct gaagcagagg aggaagagga agagtgaggg atggagaaag ggcagaggaa    780
gagacatgag aaagggagag gaagagaagc ccagctctgg gaactgaatc aggaaactca    840
aatcgaatag ggaagtaaaa aaacaaaaca aaaacaaaaa aaaacaaaaa aaaaccccta    900
```

|                                                        |      |
|--------------------------------------------------------|------|
| tttaaatgaa aggagtttaa aaacattttt taaggaggga gaaaggagaa attttggttt | 960  |
| ttcaacactg aaaaaatact acctatagga aagtctgtca ggtttggttt ttttgtacaa | 1020 |
| tatgaaaagg atattatcta cctgttctgt agctttctgg aatttacctc cccttttcta | 1080 |
| tgttgctatt gtaaggtctt tgtaaaatct tgcagttttg taagccctct ttaatgctgt | 1140 |
| ctttgtggac tgtgggtctg gactaaccct gtggttgcct gccctcctga gcctccgcct | 1200 |
| tcccagcagc ggcaccaagg ggccttaggg agccccaaaa cctaccactc gcgtgttccc | 1260 |
| caagcgcctg gctgctgctt cttgcttccc gtccccagc cccatgctcc cttttacatt  | 1320 |
| ctgtgtgtat ctaaaggatg gaaaaataaa acgcaattaa aaataaaaaa aaaaaaa    | 1377 |

<210> SEQ ID NO 19
<211> LENGTH: 1834
<212> TYPE: DNA
<213> ORGANISM: Homo sapiens

<400> SEQUENCE: 19

|                                                        |      |
|--------------------------------------------------------|------|
| cctttctat tcctggaaac cacaaaaagt gtgtcggctt cgagatcttc ttcgcctttt  | 60   |
| ctttctttc ttttttccc tcctctcttt ccctctcctt tcctggcgag ggtgactagg   | 120  |
| agccggcgaa tccgcgtttt tttctctctc tccctcccctt tcccctccc cacccctcc  | 180  |
| ccaacagccc ccaactatag cctccgccgc cgccgccgcc tcaaaattca ataaaatgag | 240  |
| ctcttatttc gtcaactcac tgttctccaa atacaaaacc ggggagtccc tgcgccccaa | 300  |
| ttattatgac tgcggcttcg cccaggacct gggcggccga ccaccgtgg tgtacggtcc  | 360  |
| cagcagcggc ggcagcttcc agcacccgtc gcaaatccag gagttctacc acgggccgtc | 420  |
| gtcgctgtcc acggctccct accagcagaa cccgtgcgcc gtggcgtgcc acggggaccc | 480  |
| cggcaatttc tacggctacg acccgctgca acgccagagc ctattcggtg cgcaggatcc | 540  |
| agacctggtg cagtacgcag actgcaagct gccgccgcc agcggcctgg gcgaggaggc  | 600  |
| cgagggctcc gagcagagcc cgtcgcccac acagctcttc cctggatgc gcccgcaagc  | 660  |
| agccgccgga cgcaggcgag gccgacagac ctacagccgc taccagaccc tggagctgga | 720  |
| gaaggagttc ctatttaatc cctatctgac tcgtaagcgg cgaatcgagg tatcgcacgc | 780  |
| cctgggactg acagagagac aggtcaaaat ctggttccag aaccggagga tgaagtggaa | 840  |
| aaaagagaac aacaaagaca agttccccag cagcaaatgc gagcaggagg agctggagaa | 900  |
| acagaagctg gagcgggccc cagaggcggc ggacgagggc gacgcgcaga agggcgacaa | 960  |
| gaagtaggct tcagctggga ctgccagggc gcggccgcc cgcacgtccg cgggtcccgg  | 1020 |
| ccgcgccgcc gccgcgcgcc cctgcccgag agagctctgg ccccgctagc ggggccagga | 1080 |
| gccgggcctc ccaccgcagc gtcccccgcc gcgccagtcc ccgctagtgg tagtatctcg | 1140 |
| taatagcttc tgtgtgtgag ctaccgtgga tctccttccc ttctcttggg ggccgggggg | 1200 |
| aaagaaaagg atttaagcaa aggctccctc gccctgtgag ggcgagcggc aaaggcccgg | 1260 |
| ctgagccccc catgccctc ccctcccgt gtaaaaagcc tccttgtgca attgtctttt   | 1320 |
| ttttcctttg aacgtgcttc tttgtaatga ccaaggtacc gatttctgct aagttctccc | 1380 |
| aacaacatga aactgcctat tcacgcctga attcttctg tctcccttct ctctctctct  | 1440 |
| ctcgctcgct cgctctcgct ctcgctctct ctcgctgcgt cctcatttcc cctcccaatc | 1500 |
| ctctctcccc tctgcaaccc ccagctcgc tggctttctc tctggcttct ctctttttcct | 1560 |
| cctccaccca cccccttttgg tttgacaatt ttgtcttaag tgtttctcaa aagaggttac | 1620 |
| tttagttagc atgcgcgctg tgggcaattg ttacaagtgt tcttaggttt actgtgaaga | 1680 |

```
gaatgtattc tgtatccgtg aattgcttta tggggggag ggagggctaa ttatatattt    1740
tgttgttcct ctatactttg ttctgttgtc tgcgcctgaa aagggcggaa gagttacaat    1800
aaagtttaca agcgagaacc cgaaaaaaaa aaaa                                1834

<210> SEQ ID NO 20
<211> LENGTH: 2711
<212> TYPE: DNA
<213> ORGANISM: Homo sapiens

<400> SEQUENCE: 20
attttgcaag agagctgag acgggctgct ccactgtact ttgttggctg agaagttgag      60 caggggtgg gggtgggagg gtgggggct ggggggtcg cgtccgaaag ccctcacacc       120
ggtccgggtg ccacctctcc ctgcttgggc gccgccgcg gagcgcttcc cttcccctg      180 caagcgcccg gataatgtct gagaatgtcc atttctggga cgcttagcag ctattatgtc    240
gactcgatca taagtcacga gagtgaggac gcgcctccag ccaagtttcc ttctggccag    300
tacgcgagct cgcggcagcc gggccacgcg gagcacctgg agttcccctc gtgcagcttc    360
cagcccaaag cgccggtgtt cggcgcctcc tgggcgccgc tgagcccgca cgcgtccggg    420
agcctgccgt ccgtctacca cccttacatc cagccccagg gcgtcccgcc ggccgagagc    480
aggtacctcc gcacctggct ggagccggcg ccgcgcggcg aagcggcccc ggggcagggc    540
caggcggcgg tgaaggcgga gccgctgctg ggcgcgcctg gggagctgct caaacagggc    600
acgcccgagt acagtttgga aacttcggcg ggcaggagg ccgtgctgtc taatcaaaga    660
cccggctacg gggacaataa aatttgcgaa ggaagcgagg acaaagagag gccggatcaa    720 accaaccccct ccgccaactg gctgcacgct cgctcttccc ggaaaaagcg ctgtccctac    780
accaaatacc agacgctgga gctagagaag gagtttctgt tcaatatgta cctcaccagg    840
gaccgtaggc acgaagtggc cagactcctc aatctgagtg agagacaagt caaaatctgg    900
tttcagaacc ggcggatgaa aatgaagaaa atgaataagg agcagggcaa agagtaaaga    960
ttaaagatta cccccagtcc tccctagctc ttccccatct cactcttagt tatgtgacga    1020
ctgcaaagcc agtgctgtct gggatgtatt caagtgaatg gggaagggag tctctcttcc    1080
aagtccttta tctgcaccta gaacctcccct ccttcctttt gcccttacct gtctctctct    1140
tctctctagg tgtcaggaga aagttttgtt gatttagaag atagaaatag ttggttccta    1200
agaatgtgat gggccacaag gaaagagaga ccccagtcaa gctcctagta tgccctgtaa    1260 ttttctggg aagtcctagc ccctcacttc cagcttgcct gtttcttctc tacacccacc    1320
caaaagtcac ccagggacac tccaactcta cacagctcag cagacatcca cacacagtaa    1380
tggggtgagc tcacaaccac cattcagtca agtgaggtga cactccagtt gcagaccatc    1440
gcacaccaaa tttggcaaaa cagccctcag actgtcaggc aagcccgggt tctaccccta    1500
atgcaaatac ccaccaggga gatgtctaga ggcagactcc tgagtgaggt gttgcagccc    1560
aaaggctgca gcattgccat accattccca tggagttgcc aactattctc aggccaaggg    1620
ccatggggaa gatggagcaa acctagcccc caagccggtg ggctagaaag tacaagaaaa    1680
ggcagcacgt ggtttatga agctatctta ggtggagcta ctccccacct cccaccaaca    1740
tatacatttt gttgcaggaa atgtttaatt ccgcatgatg tttccctctc cttccaacaa    1800
aagaaggtca aactgtgggt cgtagagcct tgacaatgtt gtcctcctgt tcatctgtgc    1860
accacttgac agactgtagc ttctcttgct ctcgaccggc cctgcattct tccgcaccct    1920
```

```
ccctagctct gaaatcaact ctcttcggtc gtatccacct tgcacccgca agtcaagccg    1980
cccttgtag aaaaatccct ccaccttccg ttccccgcta ggtcaacccc actgtagaca     2040
ggaaagccag gccaggagag tccgaatgag aatttattgt gaatcgattc ccaagctccc    2100
ttccgggaca agtggtctgg gacaggggag agcaacggcc ccagcgcgca acgtctgcg     2160
cgttcctccg aatcccgtcg gcttctcgac ccacgcagag aagcccgggg cttggcggct    2220
ctagccccag cgccaaagga gacccgcccc agggccgggc ttggcctcct gcttcatggg    2280
cctggatgca gatctgcgtg gctggtgcgt gcgcgcgctt ctgggaaaca gtcccgcgtg    2340
caaaggaaag gggcaaaatg gcacctaagc atcagatgga agcttactct ctgcttccgt    2400
tcctccccct gctcccctac ttctcagtcc ccttcaattt gtagactctt gctcctgctt    2460
ctcctgatcc tgcaagggga cattccagta gaagttttttt gctttgtcgg tggctgtcgt  2520
gaaattgtgc ttgtgtttcg tgatttcttt ggggtgatt gtctcgcttg ttttcagttg    2580
tcgattatat gggagggttc tgggtgggag tggggagggc gagggccta gagctctaat    2640
tgtttgtttt ggaagaaaaa aagaaaaaga acaaaaaata tatatcactc tagaaaataa   2700
aaaaaaaaaa a                                                        2711

<210> SEQ ID NO 21
<211> LENGTH: 3047
<212> TYPE: DNA
<213> ORGANISM: Homo sapiens

<400> SEQUENCE: 21
tcttgcgtca agacggccgt gctgagcgaa tgcaggcgac ttgcgagctg ggagcgattt      60
aaaacgcttt ggattccccc ggcctgggtg gggagagcga gctgggtgcc ccctagattc    120
cccgccccg cacctcatga gccgaccctc ggctccatgg agcccggcaa ttatgccacc     180
ttggatggag ccaaggatat cgaaggcttg ctgggagcgg agggggggcg gaatctggtc    240
gcccactccc ctctgaccag ccacccagcg gcgcctacgc tgatgcctgc tgtcaactat    300
gccccccttgg atctgccagg ctcggcggag ccgccaaagc aatgccaccc atgccctggg  360
gtgccccagg ggacgtcccc agctcccgtg ccttatggtt actttggagg cgggtactac    420
tcctgccgag tgtcccggag ctcgctgaaa ccctgtgccc aggcagccac cctggccgcg    480
taccccgcgg agactccac ggccggggaa gagtacccca gccgcccac tgagtttgcc      540
ttctatccgg gatatccggg aacctaccag cctatggcca gttacctgga cgtgtctgtg    600
gtgcagactc tgggtgctcc tggagaaccg cgacatgact ccctgttgcc tgtggacagt    660
taccagtctt gggctctcgc tggtggctgg aacagccaga tgtgttgcca gggagaacag    720
aacccaccag gtccctttttg gaaggcagca tttgcagact ccagcgggca gcaccctcct   780
gacgcctgcg cctttcgtcg cggccgcaag aaacgcattc cgtacagcaa ggggcagttg    840
cgggagctgg agcgggagta tgcggctaac aagttcatca ccaaggacaa gaggcgcaag    900
atctcggcag ccaccagcct ctcggagcgc agattacca tctggtttca gaaccgccgg     960
gtcaaagaga agaaggttct cgccaaggtg aagaacagcg ctacccctta agagatctcc    1020
ttgcctgggt gggaggagcg aaagtggggg tgtcctgggg agaccaggaa cctgccaagc    1080
ccaggctggg gccaaggact ctgctgagag gcccctagag acaacaccct tcccaggcca    1140
ctggctgctg gactgttcct caggagcggc ctgggtaccc agtatgtgca gggagacgga    1200
acccatgtg acagcccact ccaccagggt tcccaaagaa cctggcccag tcataatcat     1260
tcatcctgac agtggcaata atcacgataa ccagtactag ctgccatgat cgttagcctc    1320
```

-continued

```
atatttcta tctagagctc tgtagagcac tttagaaacc gctttcatga attgagctaa    1380
ttatgaataa atttggaagg cgatccctt gcagggaagc tttctctcag accccttcc    1440
attacacctc tcaccctggt aacagcagga agactgagga gaggggaacg ggcagattcg    1500
ttgtgtggct gtgatgtccg tttagcattt ttctcagctg acagctgggt aggtggacaa    1560
ttgtagaggc tgtctcttcc tccctccttg tccaccccat agggtgtacc cactggtctt    1620
ggaagcaccc atccttaata cgatgatttt tctgtcgtgt gaaaatgaag ccagcaggct    1680
gcccctagtc agtccttcct tccagagaaa aagagatttg agaaagtgcc tgggtaattc    1740
accattaatt tcctccccca aactctctga gtcttccctt aatatttctg gtggttctga    1800
ccaaagcagg tcatggtttg ttgagcattt gggatcccag tgaagtagat gtttgtagcc    1860
ttgcatactt agcccttccc aggcacaaac ggagtggcag agtggtgcca accctgtttt    1920
cccagtccac gtagacagat tcacagtgcg gaattctgga agctggagac agacgggctc    1980
tttgcagagc cggggactctg agagggacat gagggcctct gcctctgtgt tcattctctg    2040
atgtcctgta cctgggctca gtgcccggtg ggactcatct cctggccgcg cagcaaagcc    2100
agcgggttcg tgctggtcct tcctgcacct taggctgggg gtgggggcc tgccggcgca    2160
ttctccacga ttgagcgcac aggcctgaag tctggacaac ccgcagaacc gaagctccga    2220
gcagcgggtc ggtggcgagt agtggggtcg gtggcgagca gttggtggtg ggccgcggcc    2280
gccactacct cgaggacatt tccctcccgg agccagctct cctagaaacc ccgcggcggc    2340
cgccgcagcc aagtgtttat ggcccgcggt cgggtgggat cctagccctg tctcctctcc    2400
tgggaaggag tgagggtggg acgtgactta gacacctaca aatctattta ccaaagagga    2460
gcccgggact gagggaaaag gccaaagagt gtgagtgcat gcggactggg ggttcagggg    2520
aagaggacga ggaggaggaa gatgaggtcg atttcctgat ttaaaaaatc gtccaagccc    2580
cgtggtccag cttaaggtcc tcggttacat gcgccgctca gagcaggtca ctttctgcct    2640
tccacgtcct ccttcaagga agccccatgt gggtagcttt caatatcgca ggttcttact    2700
cctctgcctc tataagctca aacccaccaa cgatcgggca agtaaacccc ctccctcgcc    2760
gacttcggaa ctggcgagag ttcagcgcag atgggcctgt ggggagggg caagatagat    2820
gaggggagc ggcatggtgc ggggtgaccc cttggagaga ggaaaaaggc cacaagaggg    2880
gctgccaccg ccactaacgg agatggccct ggtagagacc tttgggggtc tggaacctct    2940
ggactcccca tgctctaact cccacactct gctatcagaa acttaaactt gaggattttc    3000
tctgttttc actcgcaata aattcagagc aaacaaaaaa aaaaaaa                   3047
```

<210> SEQ ID NO 22
<211> LENGTH: 3198
<212> TYPE: DNA
<213> ORGANISM: Homo sapiens

<400> SEQUENCE: 22

```
atttgaggtg ttctgaccag aagaagacag agcggatgat cattcattca ccacgttgac     60
aacctcgcct gtgattgaca gctggagtgg cagaaagcca tgagatttgg tagttgggtc    120
tgagggcgc tctttttttt ccttttcttt ctttctttct ttttttttt ttaaactgat    180
ttttggggga gagaagatct gcttttttt gccccgctg ctgtcttgga aacggagcgc    240
ttttatgctc agtgactcgg gcgctttgct tcaggtcccg tagaccgaag atctgggacc    300
agtagctcac gttgctggag acgttaaggg atttttcgtc gtgctttttt tttttttttt    360
```

```
ttttttttcc gggggagttt gaatatttgt ttcttttcac actggcctta aagaggatat    420
attagaagtt gaagtaggaa gggagccaga gaggccgatg gcgcaaaggt acgacgatct    480 acccccattac gggggcatgg atggagtagg catcccctcc acgatgtatg gggacccgca   540
tgcagccagg tccatgcagc cggtccacca cctgaaccac gggcctcctc tgcactcgca    600
tcagtacccg cacacagctc ataccaacgc catggccccc agcatgggct cctctgtcaa    660
tgacgcttta aagagagata aagatgccat ttatggacac cccctcttcc ctctcttagc    720
actgattttt gagaaatgtg aattagctac ttgtaccccc cgcgagccgg gggtggcggg    780
cggggacgtc tgctcgtcag agtcattcaa tgaagatata gccgtgttcg ccaaacagat    840
tcgcgcagaa aaacctctat tttcttctaa tccagaactg gataacttga tgattcaagc    900
catacaagta ttaaggtttc atctattgga attagagaag gtacacgaat tatgtgacaa    960
tttctgccac cggtatatta gctgtttgaa agggaaaatg cctatcgatt tggtgataga   1020
cgatagagaa ggaggatcaa aatcagacag tgaagatata acaagatcag caaatctaac   1080
tgaccagccc tcttggaaca gagatcatga tgacacggca tctactcgtt caggaggaac   1140
cccaggccct tccagcggtg ccacacgtc acacagtggg gacaacagca gtgagcaagg    1200
tgatggcttg gacaacagtg tagcttcccc cagcacaggt gacgatgatg accctgataa   1260
ggacaaaaag cgtcacaaaa agcgtggcat cttcccaaa gtagccacaa atatcatgag    1320
ggcgtggctg ttccagcatc taacacaccc ttacccttct gaagaacaga aaagcagtt    1380 ggcacaagac acgggactca ccatccttca agtgaacaat tggtttatta atgcccggag   1440
aagaatagtg cagcccatga tagaccagtc caaccgagca gtaagtcaag gaacacctta   1500
taatcctgat ggacagccca tgggaggttt cgtaatggac ggtcagcaac atatgggaat   1560
tagagcacca ggacctatga gtggaatggg catgaatatg ggcatggagg ggcagtggca   1620
ctacatgtaa ccttcatcta gttaaccaat cgcaaagcaa gggggaaggc tgcaaagtat   1680
gccaggggag tatgtagccc ggggtggtcc aatgggtgtg agtatgggac agccaagtta   1740
tacccaaccc cagatgcccc cccatcctgc tcagctgcgt catgggcccc ccatgcatac   1800
gtacattcct ggacaccctc accacccaac agtgatgatg catggaggac cgccccaccc   1860
tggaatgcca atgtcagcat caagccccac agttcttaat acaggagacc caacaatgag   1920
tggacaagtc atggacattc atgctcagta gcttaaggga atatgcattg tctgcaatgg   1980
tgactgattt caaatcatgt ttttctgca atgactgtgg agttccattc ttggcatcta   2040
ctctggacca aggagcatcc ctaattcttc atagggacct ttaaaaagca ggaaatacca   2100
actgaagtca atttggggga catgctaaat aactatataa gacattaaga gaacaaagag   2160
tgaaatattg taaatgctat tatactgtta tccatattac gttgtttctt atagatttt    2220 taaaaaaat gtgaaatttt tccacactat gtgtgttgtt tccatagctc ttcacttcct    2280
ccagaagcct ccttacatta aaagcctta cagttatcct gcaagggaca ggaaggtctg    2340
atttgcagga tttttagagc attaaaataa ctatcaggca gaagaatctt tcttctcgcc   2400
taggatttca gccatgcgcg cgctctctct ctttctctct cttttcctct ctctcctct    2460 ttctagcctg gggcttgaat ttgcatgtct aattcattta ctcaccatat ttgaattggc   2520
ctgaacagat gtaaatcggg aaggatggga aaaactgcag tcatcaacaa tgattaatca   2580
gctgttgcag gcagtgtctt aaggagactg gtaggaggag gcatggaaac caaaaggccg   2640
tgtgtttaga agcctaattg tcacatcaag catcattgtc cccatgcaac aaccaccacc   2700
ttatacatca cttcctgttt taagcagctc taaaacatag actgaagatt tatttttaat   2760
```

```
atgttgactt tatttctgag caaagcatcg gtcatgtgtg tatttttca tagtcccacc    2820 ttggagcatt tatgtagaca ttgtaaataa attttgtgca aaaaggactg aaaaatgaa     2880 ctgtattatt gcaattttt  tttgtaaaag tagcagtttg gtatgagttg gcatgcatac    2940
aagatttact aagtgggata agctaattat acttttgtt  gtggataaac aaatgcttgt    3000
tgatagcctt tttctatcaa gaaaccaagg agctaattat taataacaat cattgcacac    3060
tgagtcttag cgtttctgat ggaaacagtt tggattgtat aataacgcca agcccagttg    3120
tagtcgtttg agtgcagtaa tgaaatctga atctaaaata aaaacaagat tattttgtc     3180 aaaaaaaaaa aaaaaaaa                                                  3198

<210> SEQ ID NO 23
<211> LENGTH: 2911
<212> TYPE: DNA
<213> ORGANISM: Homo sapiens

<400> SEQUENCE: 23
gcggccgcct ccccctcccc ctcccctct  ttcttctcct ccctcgtcgc cgccgccgcc    60
gccgccgcct cagccttcgc ctcagccgcc gcccgctccc gcccgcgcgc ggcgggatgg    120
acgatcaatc caggatgctg cagactctgg ccggggtgaa cctggctggc cactcggtgc    180 agggggcat  ggccctgccg cctccccgc  acggccacga aggggcggac ggcgacggca    240
ggaagcagga catcggcgac atcctccacc agatcatgac catcaccgac cagagcttgg    300
acgaggcgca agcaaagaaa catgccctga actgtcacag aatgaaacca gcgctcttca    360
gcgtcctgtg tgagatcaaa gagaaaacag gtctcagcat cagaggagcc caggaggagg    420
accctcccga tccccagcta atgagactgg acaatatgct tttggcagaa ggggtttcag    480
gtcctgagaa aggtggggga tcggcggcag cagctgcagc cgcggcagcc tctggaggtt    540
cttcagataa ctctattgaa cactcagatt acagagccaa attgacccag atcagacaaa    600
tctatcacac agaactggag aaatatgaac aggcatgtaa tgaatttact acacatgtga    660
tgaaccttct ccgagaacag agtagaacac gtcccatttc tccaaaagag attgaaagaa    720
tggtgggcat catccatcga aaatttagtt ccattcagat gcagctcaaa caaagcactt    780
gtgaagcagt tatgatttta agatcaaggt tccttgatgc cagacggaaa aggcgtaact    840
tcagtaaaca ggccacagaa atcttgaatg aatattttta ctcacacctc agcaaccct     900 accccagtga agaagccaaa gaggagctgg ccaagaaatg cagcatcaca gtgtcacagg    960
tatccaattg gtttggcaac aaacgaatca ggtacaagaa gaacattggc aagtttcagg    1020
aagaagccaa cctctatgct gcaaagacgg ccgtgacagc tgcacacgca gtagcagcag    1080
ctgtgcagaa caaccagacc aattcgccca ccacaccaaa ttccggttct tctggttctt    1140
ttaacctccc aaattctggg gacatgttca tgaacatgca gagtctgaat ggggattctt    1200
accaagggtc ccaagtcgga gccaatgtgc aatcacaggt ggatacccct cgtcatgtta    1260
tcaatcagac gggaggctac agtgatggcc ttggaggaaa ttcactgtac agtccacata    1320
atttaaatgc taatggaggc tggcaggacg caacaactcc atcttctgtg acttctccta    1380 cagaaggcc  aggaagtgtg cactcggata cctctaacta atctctggcc acactttcc     1440 ctgagctaca tgccttgata agtgcattca gagcaatagg aggaaaagga aagcgttttt    1500
gtagcccacc atctacagct ttactgtaaa accttgtctt attcgagaac ttggtaaatc    1560
tgttttttaa ggaatcataa tcatttgtat ttatacttaa aaacacacaa tgttaaaaaa    1620
```

| | | | | |
|---|---|---|---|---|
| aataaagcac | tttatccaat | taggccaaga | tttaacattg | ttgacagtcc tgtagctatt | 1680 |
| ttatcataat | ttattatcaa | tattttacat | taatggtttc | acagttgcca attacttggc | 1740 |
| cttaaggg ta | aaaagtacaa | tatacactaa | acctcaaccg | ttaaagcaga tgcaaaaatt | 1800 |
| cacctcacct | aaattgaact | tcttgcatat | ttccattact | gacttggatt gtctttcttt | 1860 |
| catatcacta | atggagttgg | aataaagagc | tgtttgccta | tccctgttaa tgatggttgt | 1920 |
| gtttaagaat | cttcctcgtc | acgtttgtgt | tcagatctct | tatgttataa ttagatcaga | 1980 |
| gactggtagc | atcgtttctc | tctctgaaag | caccagtgcc | cagagtctgc tcggtaataa | 2040 |
| aattatggat | ccagattgtt | ctgagagacg | aagatacttg | ctgctgatag aggtgaaaac | 2100 |
| gagattgatc | cgtctggggt | tttacggtgt | gcactgggtg | ctgcacagac ttgtcaaggt | 2160 |
| ttgctacgtc | ctctgggcat | ctgcaaaagg | ccctgctctc | tggagtgttg tatatagtgt | 2220 |
| agcaaaagag | tatttataca | tcccaccaat | caaaacacag | ctttattacc tcatgcgaac | 2280 |
| tcatacaaac | caatagaatt | tcaacatgtt | ctgtagctta | gagtgctcac ttactacctc | 2340 |
| tgaacaatac | tcacgctgta | gtttgtctct | ttcttatctt | tttgcatctt gtaattaact | 2400 |
| ctttgtttcc | cttcataaaa | tgtaatgtac | attgtaatct | tttaaaagaa aaatcagggt | 2460 |
| tgcacttgca | acttttaaaa | aaccgagtgt | ggaaacattg | ggtcttaatt caacacagga | 2520 |
| tcggtaaaac | tgttgtaaat | actgagaaac | attttgaatg | ttcttcatct tattactaat | 2580 |
| ccatgcaaaa | aaaaaaaaaa | aagcagcgac | taattgtgat | gcattcagat ttcagtattc | 2640 |
| agtactgtat | atttcaccct | gtgtaatggg | gccccctctc | ctttctctct ttttgtattg | 2700 |
| tatgcgattc | tgaaactgat | tgagtcatga | aaataaattg | tggcggtgat tctaatgtat | 2760 |
| taaaaacgtt | tcgtgttcct | ttctaactgg | attacaccct | ggattgaaaa agtcttcctc | 2820 |
| gtggtagtta | tatgtagttt | caaacatgaa | taaacttttt | gctttcatga ttaaaaaaaa | 2880 |
| aaaaaaaaaa | aaaaaaaaaa | aaaaaaaaaa | a | | 2911 |

<210> SEQ ID NO 24
<211> LENGTH: 2872
<212> TYPE: DNA
<213> ORGANISM: Homo sapiens

<400> SEQUENCE: 24

| | | | | |
|---|---|---|---|---|
| aggaggagga | ggaagatcag | gaggaggagg | aagaagagga | aaaagagaaa aagaagaaa | 60 |
| tatcacagaa | aaaaaaattc | ttcgttgtct | agactgggct | ttttttcccc cctaaaaaat | 120 |
| agcatattgg | agaattggga | gaagtctctt | tggtttggaa | aaaaaaaaaa ggaatcttca | 180 |
| gcctagatca | ctttcttatc | cggactggga | tattaaatat | acgacacatc caggagttta | 240 |
| ttggagcgca | gactgatggc | gcaaaggtac | gatgagctgc | cccattacgg cgggatggac | 300 |
| ggagtagggg | ttcccgcttc | catgtacgga | gaccctcacg | cgccgcggcc gatcccccg | 360 |
| gttcaccacc | tgaaccacgg | gccgccgctc | cacgccacac | agcactacgg cgcgcacgcc | 420 |
| ccgcacccca | atgtcatgcc | ggccagtatg | ggatccgctg | tcaacgacgc cttgaagcgg | 480 |
| gacaaggacg | cgatctatgg | gcacccgttg | tttcctctgt | tagctctggt cttt gagaag | 540 |
| tgcgagctgg | cgacctgcac | tccccgggaa | cctggagtgg | ctggcggaga cgtctgctcc | 600 |
| tccgactcct | tcaacgagga | catcgcggtc | ttcgccaagc | aggttcgcgc cgaaaagcca | 660 |
| ctttttttcct | caaatccaga | gctggacaat | ttgatgatac | aagcaataca agtactaagg | 720 |
| tttcatcttt | tggagttaga | aaaggtccac | gaactgtgcg | ataacttctg ccaccgatac | 780 |
| attagctgtt | tgaaggggaa | aatgcccatc | gacctcgtca | ttgatgaaag agacggcagc | 840 |

```
tccaagtcag atcatgaaga actttcaggc tcctccacaa atctcgctga ccataaccct      900
tcttcttggc gagaccacga tgatgcaacc tcaacccact cagcaggcac cccagggccc      960
tccagtgggg gccatgcttc ccagagcgga gacaacagca gtgagcaagg ggatggttta     1020
gacaacagtg tagcttcacc tggtacaggt gacgatgatg atccggataa ggacaaaaaa     1080
cgccagaaga aaagaggcat tttccccaaa gtagcaacaa atatcatgag agcatggctc     1140
ttccagcatc tcacacatcc gtaccottcc gaagagcaga gaaacagtt agcgcaagac     1200 acaggactta caattctcca gtaaacaac tggtttatta atgccagaag aagaatagta     1260
cagcccatga ttgaccagtc aaatcgagca ggttttcttc ttgatccttc agtgagccaa     1320
ggagcagcat atagtccaga gggtcagccc atggggagct tgtgttgga tggtcagcaa     1380 cacatgggga tccggcctgc aggacctatg agtggaatgg gcatgaatat gggcatggat     1440
gggcaatggc actacatgta accttcatca tgtaaagcaa tcgcaaagca aggggaagt     1500 ttgcagagca tgccagggga ctacgtttct cagggtggtc ctatgggaat gagtatggca     1560
cagccaagtt acactcctcc ccagatgacc ccacacccta ctcaattaag acatggaccc     1620
ccaatgcatt catatttgcc aagccatccc caccacccag ccatgatgat gcacggagga     1680 cccctaccc accctggaat gactatgtca gcacagagcc ccacaatgtt aaattctgta     1740
gatcccaatg ttggcggaca ggttatggac attcatgccc aatagtataa gggaactcaa     1800
gggaaaagga acacacgca aaactatttt taagactttc tgaactttga ccagatgttg     1860
acacttaata tgaaattcca gacagctgtg attattttt actttgtca ttttcatca     1920 agcaacagag gaccaatgca acaagaacac aaatgtgaaa tcatgggctg actgagacaa     1980
ttctgtccat gtaaagatcc tctggaaaaa gactccgaga gttataacta ctgtagtata     2040
aatataggaa ctaagttaaa cttgtacatt tctgttgatc acgccgttat gttgcctcaa     2100
atagttttag aagagaaaaa aaaatatatc cttgttttcc acactatgtg tgttgttccc     2160
aaaagaatga ctgttttggt tcatcagtga attcaccatc caggagagac tgtggtatat     2220
attttaaacc tgttgggcca atgagaaaag aaccacactg gagatcatga tgaacttttg     2280
gctgaacctc atcactcgaa ctccagcttc agaatgtgtt ttcatgcccg gcctttgttc     2340
ctccataaat gtgtccttta gtttcaaaca gatctttata gttcgtgctt cataagccaa     2400
ttcttattat tattttggg ggactcttct tcaaagagct tgccaatgaa gatttaaaga     2460
cagagcagga gcttcttcca ggagttctga gccttggttg tggacaaaac aatcttaagt     2520
tgggcagctt tcctcaacac aaaaaaaagt tattaatggt cattgaacca taactaggac     2580
tttatcagaa actcaaagct tggggataa aaggagcaa gagaatactg taacaaactt     2640
cgtacagagt tcggtctatt aattgtttca tgttagatat tctatgtgtt tacctcaatt     2700
gaaaaaaaaa agaatgtttt tgctagtatc agatctgctg tggaattggt attgtatgtc     2760
catgaattct tctttctca gcacgtgttc ctcactagaa gaaatgctg ttaccttaa     2820 gctttgtcaa atttacatta aaatacttgt atgaggactg tgacgttatg tt           2872
```

<210> SEQ ID NO 25
<211> LENGTH: 500
<212> TYPE: DNA
<213> ORGANISM: Homo sapiens

<400> SEQUENCE: 25

```
tactaccaaa ggtgttgaaa gaggaaatca gcaccaactg ggggaatgaa taagaactcc       60
```

| | |
|---|---|
| cattagcagg tgggtttagc gctgggagag ctttggtcag tgttgttagg tcactgtttg | 120 |
| tgaactgact gcagaacata cataatgaaa cattcctatc catcctgagc agtatcagag | 180 |
| gaagtaattc cttcacatgg aaagtatcaa accatgatga ttccttgagt cagcaaaact | 240 |
| gtaagagaaa ttcaatccca gtgtattttc gcaatatatt caatatgaat tgaacaacta | 300 |
| ggtgagcctt ttaatagtcc gtgtctgggc aggacctgga agacagaagg tggcccaggg | 360 |
| agaatcacag agtctgcagg gacaaggaca tagcctcctt tgcttgcaaa ttaagggagc | 420 |
| cctttcccgg tccagcccag tctctcgtct ccctgtgtag ccttgggcta gtcacttccc | 480 |
| ctctcttggc cccggttccc | 500 |

<210> SEQ ID NO 26
<211> LENGTH: 3705
<212> TYPE: DNA
<213> ORGANISM: Homo sapiens

<400> SEQUENCE: 26

| | |
|---|---|
| tgaagaccag ctgggagccc actgcctgct gccacctcca actccggccc cctcaccatg | 60 |
| cactccctgg acgagccgct cgacctgaag ctgagtatca ccaagctccg ggcggcaaga | 120 |
| gagaagcggg agaggacgct gggtgtggtc cggccccgtg ctctgcacag ggagctgggc | 180 |
| ctggtggatg acagccccac acctggctct ccaggctccc cgccctcagg cttcctgctg | 240 |
| aactccaagt tccccgagaa ggtggaggga cgcttttcag cagcccctct cgtggacctc | 300 |
| agcctgtcac caccatctgg gctggactcc ccaatggca gcagctcgct gtccccgag | 360 |
| cgccagggca cggggacct gcctccagtg cccagtgcct cggacttcca gccactgcgc | 420 |
| tatttggatg gtgtccccag ctccttccag ttcttcctgc ccctcggctc cggggggcc | 480 |
| ctgcacctgc ctgcctcctc cttccttacc cctcccaagg acaagtgcct ctcgccagac | 540 |
| ctgcccctgc ccaagcagct ggtgtgtcgc tgggccaagt gtaaccagct ctttgagctc | 600 |
| ctgcaagacc tggtggacca tgtcaacgat taccatgtca gcccgagaa ggatgcgggg | 660 |
| tactgctgcc actgggaggg ctgcgcccgc catggccgag gtttcaacgc aggtacaag | 720 |
| atgctcatcc acatccgcac acacaccaac gagaagccac accgctgtcc gacctgcagc | 780 |
| aagagcttct cccgcctgga gaacctgaag atccacaacc ggtcgcacac aggtgagaag | 840 |
| ccctacgtct gccccacga gggctgcaac aagcgctatt ccaactccag tgaccgcttt | 900 |
| aagcacacgc gcacccacta tgtggacaag ccctactact gcaagatgcc cggctgccac | 960 |
| aagcgctaca cggaccccag ctcactgcgc aagcacatca ggcccatgg ccactttgtg | 1020 |
| tcccacgagc agcaagagct cctgcagctg cgccaccc caagccgcc actgccgcc | 1080 |
| cccgacggcg gccctatgt cagtggggcc cagatcatca tccccaaccc agctgccctc | 1140 |
| tttggaggcc ctggcctgcc cggcttaccc ctacccctgg ccccggccc ccttgacctc | 1200 |
| agtgccctgg cctgtggcaa cggtggggc agtgggggtg ggggggcat gggccctggg | 1260 |
| ctgccaggcc ccgtcctgcc tctcaatctg gccaagaacc cgctgctgcc ctcgcccttt | 1320 |
| ggggctggcg gactgggctt gctgtggtc tccctccttg ctggcgcagc tggtggcaag | 1380 |
| gccgaggggg agaaggggcg tgggtcggtg ccaccaggg cctgggcat ggagggccac | 1440 |
| aagacgcccc ttgaaaggac ggagagcagc tgctcccggc caagcccga tggactcccc | 1500 |
| ctgctgccag gcaccgtgct ggacctgtcc acgggcgtca actcagctgc cagcagccca | 1560 |
| gaggcgttgg cccctggctg ggtggtcatc ccgccgggct cggtgctgct caaaccggct | 1620 |
| gtggtgaact gagcccatcc tgcggacagt tgtggtgccc cccggcagc tcccggcact | 1680 |

```
gcccccgacg aacggaaact cttctgtgaa atagcaataa tgtcctactg cccgggcagc    1740
cccagcccag cccgccggga gcaaggatgg tgctaggtca ttcatggctg gcctcccagc    1800
ccccgggtgg ggacctggcc tgtcatgcag ggagagctgt gctcctgggt gctgaagcct    1860
cgctcctgtc tgtcccccac cacctggccc tcagcttctg agaggctttc ccctgcccga    1920
cctcctcccg tttccctctc ccaccctggc acctccctca cctagtgacc acccatggca    1980
agttgccctc tccagcagag ggggtgggt ggggtggcat ctgccctccc tgctagcacc    2040
aggctccccc ttcctgagag gagccccag ggaccagagg cctgcccttc cctcctaggc    2100
ttacccagcc cctgccctgg gggtccttg gaccccttc cctctgaccc tgcctccaga    2160
gggaaagcaa gacagatgca ggccctgca aagcccagg tagaagcatg cccccagga    2220 caaggcgcct cccactagtt aggaggaggc ccgctctgca gccgccgtcc tcacccagg    2280 ccaggcctgc agtaccagac gggatagctg gccactccac ccctgcaccc cagggtctcc    2340
tccctctacc ttttgggca ccctgggagc gtgggaagca ggtccgaggg ccctgagct    2400 ggcaaggga ggtgccaggc cagctgtggt gccaagatac tgagtgacct gggccctggc    2460
tcagggagca tgtggggcca ggcccagcgc ccgtcttcc tccttctacc ccgctgggc    2520 ctggcctggg cagcgccccc tgcagaggcc tttgggtcct tggtcctgta acaggaaggg    2580
ggaggctggc tggggacgac cgaccacagg ctgggacaca gctcctggtc tgggggctcc    2640
aagtgacagc atgcagggga gggggctccc agtcagtgct gtgttgggag ctttctggag    2700
gctgtggact gaaggccttg agggaagcag tggctggagg aggtgctgg acccatgaca    2760 cgttgcttcc tctggctttt ccctgctggg ccgctttctc agaggcactt ccccacccct    2820
aacacccagt gggccccccc aggttctgtg ccactcagag ggaccctggc aggggccaga    2880
accacttaag ggtggtgctg gagggccttg tgccccagtc ccatcccagg acgccctgag    2940
ggatggacgc agccatgcac cccccatctg gggcctctcc ctgctccctc tcccacctgg    3000
cagctgggag ttctggcttc taggcctgcc ctgtcaccag gcctctgagt ggccaggccc    3060
ttccacctcc ccatctgtaa aacgaggcag ctgcccggac agccttgggg tccttagtgg    3120
ccctgcaggt cctctggcag ctctgctgac cccaccctct cccggactgc ccttctgtcc    3180
cagaggggtc accctgaccc ggcccacctt gccactgggc tttggactcc agccctgaca    3240
gggcccagcc acactggctc tgcccctcga aggggctatg agcaaggtag gagggagctg    3300
gtctcctttc ttcgggcccc acccaggccc tgagcacccc ccacccctgt gagggcccca    3360
ggccttaagt ccctggcggg gtcatgggtt tgcgacttga gcagagcgga ggaacagggc    3420
actggaaggc cgacgagctc agcatgcgac tcggtgacgg accaggctcg gcagggccgg    3480
tgtacttttt gtggttgtca ttggtgtgtt gttgcacatt ccaggacgtc agtattttaa    3540
caggttctaa gtgcctttct atcgtagctt atgttttcct cctcttggct ccattgctgt    3600
tagcatagag ttttaaaaaa agagataagc taatgactac aacaatatat tcctccatgg    3660
gagaggaagt ttataaagaa acaataaaag tgagttgcaa agatg                   3705
```

<210> SEQ ID NO 27
<211> LENGTH: 3732
<212> TYPE: DNA
<213> ORGANISM: Homo sapiens

<400> SEQUENCE: 27

```
ggccctctgc gcgctgcgcc cgaagcggcg gtcggtggca ggggtggtag cggcggcggc    60
```

-continued

```
gacggtttcg tggggccgc gcgctgctct gtgagcggcg ggtggcagca ggggactcct      120
gacacttccc cttccccacc gaaccgcgct ttctgaaaca aagactcatt ttgaagatgt     180
ttaacaaatc atttggaaca ccctttgggg gtggcacagg tggctttggc acaacttcaa    240
catttggaca gaatactggc tttggcacta ctagtggagg ggcatttgga acatctgcat    300
ttggttctag caacaatact ggaggcctct ttggaaattc acagactaaa ccaggaggat    360
tgtttggaac cagttcattt agccagccag ctacctccac aagcactggc tttgggtttg    420
gtacgtcaac aggaacagca ataccttgt ttggaactgc aagcacaggg accagtctct     480
tctcatccca aaacaatgcc tttgcacaaa ataaaccaac tggctttggc aattttggaa    540
ccagtactag cagtggagga ctctttggaa ccacaaatac cacctctaat ccttttggca    600
gcacatctgg ctccctcttt gggccaagta gttttacagc tgctcctact gggactacta    660
ttaaatttaa ccctccaact ggtacagata ctatggtcaa agctggagtt agcactaaca    720
taagtaccaa gcaccagtgt attactgcta tgaaagaata tgaaagcaag tcactagagg    780
aacttcgttt agaggattat caggctaaca ggaagggccc acagaaccag gtgggagcag    840
gtaccacaac tggcttgttt gggtcttctc cagccacttc cagcgcaaca ggactcttca    900
gctcctccac cactaattca ggctttgcat atggtcagaa caaaactgcc tttgaacta     960
gtacaactgg atttggaaca aatccaggtg gtctctttgg ccaacagaat cagcagacta   1020
ccagcctctt cagcaaacca tttggccagg ctacaaccac ccagaacact ggcttttcct   1080
ttggtaatac cagcaccata ggacagccaa gcaccaacac catgggatta tttggagtaa   1140
cccaagcctc acagcctgga ggtctttttg ggacagctac aaacaccagc actgggacag   1200
catttggaac aggaacaggt ctctttgggc agaccaatac tggatttggt gctgttggtt   1260
cgaccctgtt tggcaataac aagcttacta catttggaag cagcacaacc agtgcacctt   1320
catttggtac aaccagtggc gggctctttg gtaacaaacc aaccctgact ttaggaacca   1380
atacaaacac ttctaatttt ggttttggca caaataccag tgggaatagt attttttggaa  1440
gtaaaccagc acctgggact cttggaactg gcttggtgc aggatttgga acagctcttg    1500
gtgctggaca ggcatctttg tttgggaaca accaacctaa gattggaggg cctcttggta   1560
caggagcctt tgggccct ggatttaata ctacgacagc cactttgggc tttggagccc     1620
cccaggcccc agtagctttg acagatccaa atgcttctgc tgcccagcag gctgttctcc   1680
agcagcacat caatagtcta acatactcac cttttggaga ctctcctctc ttccggaatc   1740
cgatgtcaga ccctaagaag aaggaagaga gattgaaacc aacaaatcca gcagcccaga   1800
aggctcttac tacacctact cattataaac tgacaccccg ccctgccact agagtccggc   1860
caaaggcttt acaaacaaca ggcacagcca agtcacatct cttttgatggg ctggatgacg   1920
atgaaccatc cctagccaat ggagcattca tgcccaagaa gagcattaag aagttggttt   1980
tgaagaacct taataatagc aatctctttt ctcctgttaa tcgtgattca gaaaatctag   2040
cttcaccatc tgaatatcca gaaaatggag agagatttag tttcctaagc aaacctgttg   2100
atgagaatca ccagcaggat ggagatgaag attcccttgt tcacatttt tatactaacc    2160
ctattgccaa acctattcct caaaccccag aaagtgctgg aaataaacac agcaacagca   2220
acagtgtgga tgataccatt gttgcattaa acatgcgtgc tgctttgcga atgggctgg    2280
aaggaagcag tgaagaaacg tcttttcatg atgagtcact tcaggatgac cgagaagaaa   2340
tagaaaataa ttcttaccat atgcacccag caggtattat tctcactaag gttggttact   2400
atactattcc atctatggat gaccttgcta aaattaccaa tgaaaaagga gagtgcattg   2460
```

```
tctctgattt cactattggt cggaaaggtt atggttcaat ctattttgaa ggagatgtga    2520
atttgacaaa tctaaatttg gatgatattg tgcatatccg gaggaaagaa gtagttgtct    2580
acttagatga taaccaaaaa ccacctgtgg gtgaagggct aaataggaag gctgaagtta    2640
cattggatgg agtttggcca acagataaaa catctcgttg tttaataaag agcccagatc    2700
gccttgctga tatcaactat gaaggaagat tggaagcagt ttcaaggaaa caggagctc     2760
aattcaaaga ataccggcct gaaactggtt cttgggtgtt taaggtctcc cattttcta    2820
agtatggcct tcaggattct gatgaagagg aggaggagca tccgtctaaa actagtacaa    2880
agaagttgaa gactgctcct ttgcctcctg caagccagac tacgcccttg cagatggctc    2940
ttaatggcaa acctgcacct ccacctcagg tagagaaaaa aggacagtga atttgaatgg    3000
aatccgtgat accgaagttg aaagcaagtc attcagctaa tacaaagctg ttttatgacc    3060
cttggaactt tgaagagtac aaacattggc aatcacgttg aaacaagtgc aagggagggc    3120
gtgaggtctt gcaggcatct gtcttttac tggagagatt taaagaattc tcttgctgtt    3180
tggattattc ctctacagat tgtcattttt aaacccttt g ttctctctca tttggacttg    3240
ctgaattctc tgctcagtga ttaacttaag atttgctcat gtgggttcat gcacagtaaa    3300
ttctgccttt attgactacc tgatgtgcag tttaatcttt ttctttacct ccatggtttt    3360
ttaaaagtta aattagcttt ctgaaagggt ttttaatctc cattttttta aagttgtttg    3420
cttatacttc gggtaacctt gatatttgta ttttaatagt acataatctt tatgaaaaat    3480
agtttgggaa tgtaaatgaa ttattatttg gcttggggag attagggcct acattgttta    3540
tcgcaattac ttgtatcatt gatacgggat ttctttgtaa agcatcctct acctctcagc    3600
tgctgaaagc tagaccttg gtattttcca tgctataatt cttatggctg ctgaaatgtg    3660
tggttttat gatttattaa ataatctctt aggaggcaaa aaaaaaaaa aaaaaaaaa      3720
aaaaaaaaaa aa                                                         3732

<210> SEQ ID NO 28
<211> LENGTH: 8115
<212> TYPE: DNA
<213> ORGANISM: Homo sapiens

<400> SEQUENCE: 28
ggttgatgcc ggcccaggat ggatcagacc tgtgaactac ccagaagaaa ttgtctgctg      60
cccttttcca atccagtgaa tttagatgcc cctgaagaca aggacagccc tttcggtaat     120
ggtcaatcca attttctga gccacttaat gggtgtacta tgcagttatc gactgtcagt     180
ggaacatccc aaaatgctta tggacaagat tctccatctt gttacattcc actgcggaga     240
ctacaggatt tggcctccat gatcaatgta gagtatttaa atgggtctgc tgatggatca     300
gaatcctttc aagaccctga aaaagtgat tcaagagctc agacgccaat gtttgcact      360
tccttgagtc ctggtggtcc tacagcactt gctatgaaac aggaaccctc ttgtaataac    420
tcccctgaac tccaggtaaa agtaacaaag actatcaaga atggctttct gcactttgag    480
aattttactt gtgtggacga tgcagatgta gattctgaaa tggacccaga acagccagtc    540
acagaggatg agagtataga ggagatcttt gaggaaactc agaccaatgc cacctgcaat   600
tatgagacta atcagagaa tggtgtaaaa gtggccatgg aagtgaaca agacagcaca    660
ccagagagta gacacggtgc agtcaaatcg ccattcttgc cattagctcc tcagactgaa    720
acacagaaaa ataagcaaag aaatgaagtg gacggcagca atgaaaaagc agcccttctc    780
```

```
ccagcccct tttcactagg agacacaaac attacaatag aagagcaatt aaactcaata    840
aatttatctt ttcaggatga tccagattcc agtaccagta cattaggaaa catgctagaa    900
ttacctggaa cttcatcatc atctacttca caggaattgc catttgttcc tcagaaaatt    960
ttgagtaaat gggaagccag tgttggactt gcagaacagt atgatgttcc caagggtca   1020 aagaaccgaa aatgtattcc tggttcaatc aagttggaca gtgaagaaga tatgccattt   1080
gaagactgca caaatgatcc tgagtcagaa catgacctgt tgcttaatgg ctgtttgaaa   1140
tcactggctt ttgattctga acattctgca gatgagaagg aaaagccttg cgctaaatct   1200
cgagccagaa agagctctga taatccaaaa ggactagtg tgaaaaaggg ccacatacaa    1260
tttgaagcac ataagatga acggagggga aagattccag agaaccttgg cctaaacttt    1320
atctctgggg atatatctga tacgcaggcc tctaatgaac tttccaggat agcaaatagc   1380
ctcacagggt ccaacactgc cccaggaagt tttctgtttt cttcctgtgg aaaaaacact   1440
gcaaagaaag aatttgagac ttcaaatggt gactctttat gggcttgcc tgagggtgct    1500 ttgatctcaa agtgttctcg agagaagaat aaacccaac gaagcctggt gtgtggttca    1560
aaagtgaagc tctgctatat tggagcaggt gatgaggaaa agcgaagtga ttccattagt   1620
atctgtacca cttctgatga tggaagcagt gacctggatc ccatagaaca cagctcagag   1680
tctgataaca gtgtccttga aattccagat gctttcgata aacagagaa catgttatct    1740 atgcagaaaa atgaaaagat aaagtattct aggtttgctg ccacaaacac tagggtaaaa   1800
gcaaaacaga agcctctcat tagtaactca catacagacc acttaatggg ttgtactaag   1860
agtgcagagc ctggaaccga gacgtctcag gttaatctct ctgatctgaa ggcatctact   1920
cttgttcaca acccccagtc agattttaca aatgatgctc tctctccaaa attcaacctg   1980
tcatcaagca tatccagtga gaactcgtta ataaagggtg gggcagcaaa tcaagctcta   2040
ttacattcga aaagcaaaca gcccaagttc cgaagtataa agtgcaaaca caagaaaat    2100 ccagttatgg cagaaccccc agttataaat gaggagtgca gttgaaatg ctgctcttct    2160 gataccaaag gctctccttt ggccagcatt tctaaaagtg ggaaagtgga tggtctaaaa   2220
ctactgaaca atatgcatga gaaaccagg gattcaagtg acatagaaac agcagtggtg    2280
aaacatgttt tatccgagtt gaaggaactc tcttacagat ccttaggtga ggatgtcagt   2340
gactctggaa catcaaagcc atcaaaacca ttactttct cttctgcttc tagtcagaat    2400
cacataccta ttgaaccaga ctacaaattc agtacattgc taatgatgtt gaaagatatg   2460
catgatagta agacgaagga gcagcggttg atgactgctc aaaacctggt ctcttaccgg   2520
agtcctggtc gtgggactg ttctactaat agtcctgtag gagtctctaa ggttttggtt    2580
tcaggaggct ccacacacaa ttcagagaaa aaggagatg gcactcagaa ctccgccaat   2640
cctagcccta gtggggtga ctctgcatta tctggcgagt tgtctgcttc cctacctggc    2700
ttactgtccg acaagagaga cctccctgct tctggtaaaa gtcgttcaga ctgtgttact   2760
aggcgcaact gtggacgatc aaagccttca tccaaattgc gagatgcttt ttcagcccaa   2820
atggtaaaga acacagtgaa ccgtaaagcc ttaagaccg agcgcaaaag aaaactgaat    2880
cagcttccaa gtgtgactct tgatgctgta ctgcagggag accgaaacg tggaggttca   2940 ttgagaggtg gggcagaaga tcctagtaaa gaggatcccc ttcagataat gggccactta   3000
acaagtgaag atggtgacca tttttctgat gtgcatttcg atagcaaggt taagcaatct   3060
gatcctggta aatttctga aaaggactc tcttttgaaa acggaaaagg cccagagctg    3120
gactctgtaa tgaacagtga gaatgatgaa ctcaatggtg taaatcaagt ggtgcctaaa   3180
```

```
aagcggtggc agcgtttaaa ccaaaggcgc actaaacctc gtaagcgcat gaacagattt    3240
aaagagaaag aaaactctga gtgtgccttt agggtcttac ttcctagtga ccctgtgcag    3300
gaggggcggg atgagtttcc agagcataga actccttcag caagcatact tgaggaacca    3360
ctgacagagc aaaatcatgc tgactgctta gattcagctg ggccacggtt aaatgtttgt    3420
gataaatcca gtgccagcat tggtgacatg gaaaaggagc caggaattcc cagtttgaca    3480
ccacaggctg agctccctga accagctgtg cggtcagaga gaaacgcct taggaagcca    3540 agcaagtggc ttttggaata tacagaagaa tatgatcaga tatttgctcc taagaaaaaa    3600
caaaagaagg tacaggagca ggtggataag gtaagttccc gctgtgaaga ggaaagcctt    3660
ctagcccgag gtcgatctag tgctcagaac aagcaggtgg acgagaattc tttgatttca    3720
accaaagaag agcctccagt tcttgaaagg gaggctccgt ttttggaggg cccccttggct    3780 cagtcagaac ttggaggtgg acatgctgag ttgccgcagc tgaccttgtc tgtgcctgtg    3840
gctccggaag tctctccacg gcctgccctt gagtctgagg aattgctagt taaaacacaa    3900
ggaaattatg aaagtaaacg tcaaagaaaa ccaactaaga aacttcttga atccaatgat    3960
ttagaccctg gatttatgcc caagaagggg gaccttggcc tttctaaaaa gtgctatgaa    4020
gctggtcacc tggagaatgg cataactgaa tcttgtgcca catcttattc aaaagatttt    4080
ggtggaggca ctaccaagat atttgacaag ccaaggaagc gaaaacgaca gaggcatgct    4140
gtagccaaga tgcagtgcaa aaaagtgaaa aatgatgact cgtcaaaaga gattccaggc    4200
tcagagggag aactaatgcc tcacaggacg gccacaagcc caaggagac tgttgaggaa    4260 ggtgtagaac acgatcccgg gatgcctgcc tctaaaaaaa tgcagggtga acgcggtgga    4320
ggagctgcac tcaaggagaa tgtctgtcag aattgtgaaa aattgggtga gctgctgtta    4380
tgtgaggctc agtgctgtgg ggcttccac ctggagtgcc ttggattgac tgagatgcca    4440
agaggaaaat ttatctgcaa tgaatgtcgc acaggaatcc ataccctgttt tgtatgtaag    4500 cagagtgggg aagatgttaa aaggtgcctt ctacccttgt gtggaaagtt ttaccatgaa    4560
gagtgtgtcc agaagtaccc acccactgtt atgcagaaca agggcttccg gtgctccctc    4620
cacatctgta taacctgtca tgctgctaat ccagccaatg tttctgcatc taaaggtcgg    4680
ttgatgcgct gtgtccgctg tcctgtggca taccacgcca atgacttttg cctggctgct    4740
gggtcaaaga tccttgcatc taatagtatc atctgcccta atcactttac ccctaggcgg    4800
ggctgccgaa atcatgagca tgttaatgtt agctggtgct ttgtgtgctc agaaggaggc    4860
agccttctgt gctgtgattc ttgccctgct gcttttcatc gtgaatgcct gaacattgat    4920
atccctgaag gaaactggta ttgcaatgac tgtaaagcag gcaaaaagcc acactacagg    4980
gagattgtct gggtaaaagt tggacgatac aggtggtggc cagctgagat ctgccatcct    5040
cgagctgttc cttccaacat tgataagatg agacatgatg tgggagagtt cccagtcctc    5100 tttttttggat ctaatgacta tttgtggact caccaggccc gagtcttccc ttacatggag    5160
ggtgacgtga gcagcaagga taagatgggc aaaggagtgg atgggacata taaaaaagct    5220
cttcaggaag ctgcagcaag gtttgaggaa ttaaaggccc aaaaagagct aagacagctg    5280
caggaagacc gaaagaatga caagaagcca ccccttata aacatataaa ggtaaaccgt    5340
cctattggca gggtacagat cttcactgca gacttatctg aaataccccg ttgcaactgt    5400
aaagctactg atgagaaccc ctgtgggata gactctgaat gcatcaaccg catgctgctc    5460
tatgagtgcc accccacagt gtgtcctgcc ggagggcgct gtcaaaacca gtgcttttcc    5520
```

```
aagcgccaat atccagaggt tgaaattttc cgcacattac agcggggttg gggtctacgg    5580
acccaagagg acatcagaaa gggagaattt gttaacgagt acgttgggga gctgatcgac    5640
gaggaggagt gcatggcgag aatcaagcac gcacacgaga acgacatcac ccacttctac    5700
atgctcacta tagacaagga ccgtataata gacgctggcc ccaaaggaaa ctactctcga    5760
tttatgaatc acagctgcca gcccaactgt gagaccctca gtggacagt gaatggggac     5820
actcgtgtgg gcctgtttgc cgtctgtgac attcctgcag ggacggagct gactttaac    5880
tacaacctcg attgtctggg caatgaaaaa acggtctgcc ggtgtggagc ctccaattgc    5940
agtggcttct tgggtgtaag gccaaagaat caacccattg ccacgaaga aaagtcaaag     6000
aaattcaaga agaagcaaca gggaaagcgc aggacccagg gtgaaatcac aaaggagcga    6060
gaagatgagt gttttagttg tggggatgct ggccagctcg tctcctgcaa gaaaccaggc    6120
tgcccaaaag tttaccacgc agactgtctc aatctgacca agcgaccagc agggaaatgg    6180
gaatgtccgt ggcatcagtg tgacatctgc gggaaggaag cagcctcctt ctgtgagatg    6240
tgccccagct cctttgtaa gcagcatcga gaagggatgc ttttcatttc caaactggat    6300
gggcgtctgt cttgtactga gcatgacccc tgtgggccca atcctctgga acctggggag    6360
atccgtgagt atgtgcctcc cccagtaccg ctgcctccag ggccaagcac tcacctggca    6420
gagcaatcaa caggaatggc tgctcaggca cccaaaatgt cagataaacc tcctgctgac    6480
accaaccaga tgctgtcgct ctccaaaaaa gctctggcag ggacttgtca gaggccactg    6540
ctacctgaaa gacctcttga gagaactgac tccaggcccc agcctttaga taggtcaga    6600
gacctcgctg ggtcagggggc ccaatcccaa tccttggttt ccagccagag gccactggac    6660
aggccaccag cagtggcagg accaagaccc cagctaagcg acaaaccctc tccagtgacc    6720
agcccaagct cctcacccctc agtcaggtcc caaccactgg aatcacctct ggggacggct    6780
gacccaaggc tggataaaatc cataggtgct gccagcccaa ggccccagtc actggagaaa    6840
acctcagttc ccactggcct gagacttccg ccgccagaca gactgctcat tactagcagt    6900
cccaaacccc agacttcaga caggcctact gacaaacccc atgcctcttt gtcccagaga    6960
ctcccaccctc ctgagaaagt actatcagct gtggtccaga cccttgtagc taaagaaaaa    7020
gcactgaggc ctgtggacca gaatactcag tcaaaaaata gagctgcttt ggtgatggat    7080
ctcatagacc taactcctcg ccagaaggag cgggcagctt cacctcatca ggtcacacca    7140
caggctgatg agaagatgcc agtgttggag tcaagttcat ggcctgccag caaaggtctg    7200
gggcatatgc cgagagctgt tgagaaaggc tgtgtgtcag atcctcttca gacatctggg    7260
aaagcagcag ccccttcaga ggacccctgg caagctgtta aatcactcac ccaagccaga    7320
ctttcttctc agccttctgc caaagccttt ttatatgagc caaccactca ggcctcagga    7380
agagcttctg caggggctga acagacccag gggttttta ccaaatcccc ggccttggtg    7440
gaaaacaagg gcaaaaccaa atgggtaggg aggccaacaa attacttgca tttggccgcc    7500
aagagttggc aatcttttag gtctctcggg aaggccccac cctcctcccc caatgaagaa    7560
aagaagttgg taaccacaga gcaaagtccc tgggccctgg aaaagcctc atcacgggca    7620
gggctctggc ccatagtggc tggacagaca ctggcacagt cttgctggtc tgctgggagc    7680
acacagacat tggcacagac ttgctggtct cttggaagag ggcaagaccc caaaccagag    7740
caaaatacac ttccagctct taaccaggct ccttccagtc acaagtgtgc agaatcagaa    7800
cagaagtagt accaatcaat gtcacatgaa caaacaagct gccccaggg taccatttgg     7860
ggaggggaaa tcttttcttt ctttccccct taaaaaaaaa cacatctgcc ccgaacactt    7920
```

```
tcccactgtt attctttcct catatcccaa cactcagaac tcttgtgaca ttagccagtg      7980
ggggcttatg gttgtgtgaa ccatgtatga aaatccagtg ggccccaacc aaggagacag      8040
acagacttgg gtctctttcc cccaacttt ccacatggtc atcgtgaaat aaaaagtcca      8100
ctctggaaaa aaaaa                                                       8115

<210> SEQ ID NO 29
<211> LENGTH: 1092
<212> TYPE: DNA
<213> ORGANISM: Homo sapiens

<400> SEQUENCE: 29
ggttgttctc tggagcagcg ttcttttatc tccgtccgcc ttctctccta cctaagtgcg        60
tgccgccacc cgatggaaga ttcgatggac atggacatga gcccctgag gccccagaac       120 tatctttcg gttgtgaact aaaggccgac aaagattatc actttaaggt ggataatgat       180
gaaaatgagc accagttatc tttaagaacg gtcagtttag gggctggtgc aaaggatgag       240
ttgcacattg ttgaagcaga ggcaatgaat tacgaaggca gtccaattaa agtaacactg       300
gcaactttga aaatgtctgt acagccaacg gtttcccttg ggggctttga ataacacca       360 ccagtggtct taaggttgaa gtgtggttca gggccagtgc atattagtgg acagcactta       420
gtagctgtgg aggaagatgc agagtcagaa gatgaagagg aggaggatgt gaaactctta       480
agtatatctg gaaagcggtc tgcccctgga ggtggtagca aggttccaca gaaaaaagta       540
aaacttgctg ctgatgaaga tgatgacgat gatgatgaag aggatgatga tgaagatgat       600
gatgatgatg attttgatga tgaggaagct gaagaaaaag cgccagtgaa gaaatctata       660
cgagatactc cagccaaaaa tgcacaaaag tcaaatcaga atggaaaaga ctcaaaacca       720
tcatcaacac caagatcaaa aggacaagaa tccttcaaga acaggaaaaa actcctaaa       780 acaccaaaag gacctagttc tgtagaagac attaaagcaa aaatgcaagc aagtatagaa       840
aaaggtggtt ctcttcccaa agtggaagcc aaattcatca attatgtgaa gaattgcttc       900
cggatgactg accaagaggc tattcaagat ctctggcagt ccctggagaa agtctcttta       960
agaaaatagt ttaaacaatt tgttaaaaaa ttttccgtct tatttcattt ctgtaacagt      1020
tgatatctgg ctgtcctttt tataatgcag agtgagaact ttccctaccg tgtttgataa      1080
atgttgtcca gg                                                         1092

<210> SEQ ID NO 30
<211> LENGTH: 4258
<212> TYPE: DNA
<213> ORGANISM: Homo sapiens

<400> SEQUENCE: 30
cagtgctgga tgcggggacc cagcgcagaa gcagcgccag gtggagccat cgaagccccc        60
acccacaggc tgacagaggc accgttcacc agagggctca acaccgggat ctatgtttaa       120
gttttaactc tcgcctccaa agaccacgat aattccttcc ccaaagccca gcagcccccc       180
agccccgcgc agccccagcc tgcctcccgg cgcccagatg cccgccatgc cctccagcgg       240
ccccggggac accagcagct ctgctgcgga gcggaggag gaccgaaagg acggagagga       300
gcaggaggag ccgcgtggca aggaggagcg ccaagagccc agcaccacgg cacggaaggt       360
ggggcggcct gggaggaagc gcaagcaccc ccggtggaa agcggtgaca cgccaaagga       420
ccctgcggtg atctccaagt cccatccat ggcccaggac tcaggcgcct cagagctatt       480
```

```
acccaatggg gacttggaga agcggagtga gccccagcca gaggagggga gccctgctgg    540
ggggcagaag ggcggggccc cagcagaggg agagggtgca gctgagaccc tgcctgaagc    600
ctcaagagca gtggaaaatg ctgctgcac ccccaaggag ggccgaggag ccctgcaga     660 agcgggcaaa gaacagaagg agaccaacat cgaatccatg aaaatggagg ctcccggg     720 ccggctgcgg ggtggcttgg gctgggagtc cagcctccgt cagcggccca tgccgaggct    780
caccttccag gcgggggacc cctactacat cagcaagcgc aagcgggacg agtggctggc    840
acgctggaaa agggaggctg agaagaaagc caaggtcatt gcaggaatga atgctgtgga    900
agaaaaccag gggcccgggg agtctcagaa ggtggaggag gccagccctc ctgctgtgca    960
gcagcccact gaccccgcat cccccactgt ggctaccacg cctgagcccg tggggtccga   1020
tgctggggac aagaatgcca ccaaagcagg cgatgacgag ccagagtacg aggacggccg   1080
gggctttggc attgggagc tggtgtgggg gaaactgcgg ggcttctcct ggtggccagg    1140
ccgcattgtg tcttggtgga tgacgggccg gagccgagca gctgaaggca cccgctgggt   1200
catgtggttc ggagacggca aattctcagt ggtgtgtgtt gagaagctga tgccgctgag   1260
ctcgttttgc agtgcgttcc accaggccac gtacaacaag cagcccatgt accgcaaagc   1320
catctacgag gtcctgcagg tggccagcag ccgcgcgggg aagctgttcc cggtgtgcca   1380
cgacagcgat gagagtgaca ctgccaaggc cgtggaggtg cagaacaagc ccatgattga   1440
atgggccctg gggggcttcc agccttctgg ccctaagggc ctggagccac agaagaaga   1500 gaagaatccc tacaaagaag tgtacacgga catgtgggtg aacctgagg cagctgccta    1560 cgcaccacct ccaccagcca aaaagccccg gaagagcaca gcggagaagc ccaaggtcaa   1620
ggagattatt gatgagcgca agagagcg gctggtgtac gaggtgcggc agaagtgccg    1680
gaacattgag gacatctgca tctcctgtgg gagcctcaat gttaccctgg aacacccct    1740 cttcgttgga ggaatgtgcc aaaactgcaa gaactgcttt ctggagtgtg cgtaccagta   1800
cgacgacgac ggctaccagt cctactgcac catctgctgt gggggccgtg aggtgctcat   1860
gtgcggaaac aacaactgct gcaggtgctt ttgcgtggag tgtgtggacc tcttggtggg   1920
gccgggggct gccaggcag ccattaagga agacccctgg aactgctaca gtgcgggca    1980 caagggtacc tacgggctgc tgcggcggcg agaggactgg ccctcccggc tccagatgtt   2040
cttcgctaat aaccacgacc aggaatttga ccctccaaag gtttacccac ctgtcccagc   2100
tgagaagagg aagcccatcc gggtgctgtc tctctttgat ggaatcgcta cagggctcct   2160
ggtgctgaag gacttgggca ttcaggtgga ccgctacatt gcctcggagg tgtgtgagga   2220
ctccatcacg gtgggcatgg tgcggcacca ggggaagatc atgtacgtcg ggacgtccg    2280 cagcgtcaca cagaagcata tccaggagtg gggcccattc gatctggtga ttgggggcag   2340
tccctgcaat gacctctcca tcgtcaaccc tgctcgcaag ggcctctacg agggcactgg   2400
ccggctcttc tttgagttct accgcctcct gcatgatgcg cggcccaagg agggagatga   2460 tcgcccttc ttctggctct tgagaatgt ggtggccatg ggcgttagtg acaagaggga    2520
catctcgcga tttctcgagt ccaaccctgt gatgattgat gccaaagaag tgtcagctgc   2580
acacagggcc cgctacttct ggggtaacct tcccggtatg aacaggccgt ggcatccac    2640 tgtgaatgat aagctggagc tgcaggagtg tctggagcat ggcaggatag ccaagttcag   2700
caaagtgagg accattacta cgaggtcaaa ctccataaag cagggcaaag accagcattt   2760
tcctgtcttc atgaatgaga agagggacat cttatggtgc actgaaatgg aaagggtatt   2820
tggtttccca gtccactata ctgacgtctc caacatgagc cgcttggcga ggcagagact   2880
```

```
gctgggccgg tcatggagcg tgccagtcat ccgccacctc ttcgctccgc tgaaggagta    2940 tttgcgtgt gtgtaaggga catgggggca aactgaggta gcgacacaaa gttaaacaaa    3000
caaacaaaaa acacaaaaca taataaaaca ccaagaacat gaggatggag agaagtatca    3060
gcacccagaa gagaaaaagg aatttaaaac aaaaaccaca gaggcggaaa taccggaggg    3120
ctttgccttg cgaaaagggt tggacatcat ctcctgattt ttcaatgtta ttcttcagtc    3180
ctatttaaaa acaaaaccaa gctcccttcc cttcctcccc cttcccttt tttcggtca     3240 gaccttttat tttctactct tttcagaggg gttttctgtt tgtttgggtt ttgtttcttg    3300
ctgtgactga acaagaagg ttattgcagc aaaaatcagt aacaaaaat agtaacaata     3360 ccttgcagag gaaaggtggg agagaggaaa aaggaaatt ctatagaaat ctatatattg    3420
ggttgttttt ttttttgttt tttgttttt tttttggt ttttttttt actatatatc        3480 tttttttgt tgtctctagc ctgatcagat aggagcacaa gcaggggacg aaagagaga     3540 gacactcagg cggcagcatt ccctcccagc cactgagctg tcgtgccagc accattcctg    3600
gtcacgcaaa acagaaccca gttagcagca gggagacgag aacaccacac aagacatttt    3660
tctacagtat ttcaggtgcc taccacacag gaaaccttga agaaaatcag tttctagaag    3720
ccgctgttac ctcttgttta cagtttatat atatatgata gatatgagat atatatataa    3780
aaggtactgt taactactgt acaacccgac ttcataatgg tgctttcaaa cagcgagatg    3840
agtaaaaaca tcagcttcca cgttgccttc tgcgcaaagg gtttcaccaa ggatggagaa    3900
agggagacag cttgcagatg gcgcgttctc acggtgggct cttccccttg gtttgtaacg    3960
aagtgaagga ggagaacttg ggagccaggt tctccctgcc aaaaagggg ctagatgagg    4020 tggtcgggcc cgtggacagc tgagagtggg attcatccag actcatgcaa taaccctttg    4080
attgttttct aaaaggagac tccctcggca agatggcaga gggtacggag tcttcaggcc    4140
cagtttctca ctttagccaa ttcgagggct ccttgtggtg ggatcagaac taatccagag    4200
tgtgggaaag tgacagtcaa aaccccacct ggagcaaata aaaaaacata caaaacgt      4258
```

<210> SEQ ID NO 31
<211> LENGTH: 1442
<212> TYPE: DNA
<213> ORGANISM: Homo sapiens

<400> SEQUENCE: 31

```
atgtccaaaa aaatcagtgg cggttctgtg gtagagatgc aaggagatga aatgacacga     60
atcatttggg aattgattaa agagaaactc attattccct acgtggaatt ggatctacat    120
agctatgatt taggcataga gaatcgtgat gccaccaacg accaagtcac caaggatgct    180
gcagaagcta taagaagca taatgttggc gtcaaatgtg ccactatcac tcctgatgag    240
aagagggttg aggagttcaa gttgaaacaa atgtggaaat caccaaatgg caccatacga    300
aatattctgg gtggcacggt cttcagagaa gccattatct gcaaaatat cccccggctt    360 gtgagtggat gggtagagcc tatcatcata ggtcgtcatg cttatgggga tcaatacaga    420
gcaactgatt tgttgttcc tgggcctgga aaagtagaga taacctacac accaagtgac    480
ggaacccaaa aggtgacata cctggtacat aactttgaag aaggtggtgg tgttgccatg    540
gggatgtata atcaagataa gtcaattgaa gattttgcac acagttcctt ccaaatggct    600
ctgtctaagg gttggccttt gtatctgagc accaaaaaca ctattctgaa gaaatatgat    660
gggcgtttta agacatctt tcaggagata tatgacaagc agtacaagtc ccagtttgaa    720
```

```
gctcaaaaga tctggtatga gcataggctc atcgacgaca tggtggccca agctatgaaa      780
tcagagggag gcttcatctg ggcctgtaaa aactatgatg gtgacgtgca gtcggactct      840
gtggcccaag ggtatggctc tctcggcatg atgaccagcg tgctggtttg tccagatggc      900
aagacagtag aagcagaggc tgcccacggg actgtaaccc gtcactaccg catgtaccag      960
aaaggacagg agacgtccac caatcccatt gcttccattt ttgcctggac cagagggtta     1020
gcccacagag caaagcttga taacaataaa gagcttgcct tctttgcaaa tgctttggaa     1080
gaagtctcta ttgagacaat tgaggctggc ttcatgacca agggcttggc tgcttgcatt     1140
aaaggtttac ccaatgtgca acgttctgac tacttgaata catttgagtt catggataaa     1200
cttggagaaa acttgaagat caaactagct caggccaaac tttaagttca tacctgagct     1260
aagaaggata ttgtcttttt ggtaactagg tctacaggtt tgcattttc tgtgttacac      1320 tcaaggataa aggcaaaatc aatttttgtaa tttgtttaga agccagagtt tatctttttct   1380 ataagtttac agccttttc ttatatatac agttattgcc acctttgtga acatggcaag      1440
gg                                                                    1442

<210> SEQ ID NO 32
<211> LENGTH: 1740
<212> TYPE: DNA
<213> ORGANISM: Homo sapiens

<400> SEQUENCE: 32
ccagcgttag cccgcggcca ggcagccggg aggagcggcg cgcgctcgga cctctcccgc       60
cctgctcgtt cgctctccag cttgggatgg ccggctacct gcgggtcgtg cgctcgctct      120
gcagagcctc aggctcgcgg ccggcctggg cgccggcggc cctgacagcc cccacctcgc      180
aagagcagcc gcggcgccac tatgccgaca aaaggatcaa ggtggcgaag cccgtggtgg      240
agatggatgg tgatgagatg acccgtatta tctggcagtt catcaaggag aagctcatcc      300
tgccccacgt ggacatccag ctaaagtatt ttgacctcgg gctcccaaac cgtgaccaga      360
ctgatgacca ggtcaccatt gactctgcac tggccaccca gaagtacagt gtggctgtca      420
agtgtgccac catcacccct gatgaggccc gtgtggaaga gttcaagctg aagaagatgt      480
ggaaaagtcc caatggaact atccggaaca tcctgggggg gactgtcttc cgggagccca      540
tcatctgcaa aaacatccca cgcctagtcc ctggctggac caagcccatc accattggca      600
ggcacgccca tggcgaccag tacaaggcca cagactttgt ggcagaccgg gccggcactt      660
tcaaaatggt cttcacccca aaagatggca gtggtgtcaa ggagtgggaa gtgtacaact      720
tccccgcagg cggcgtgggc atgggcatgt acaacaccga cgagtccatc tcaggttttg      780
cgcacagctg cttccagtat gccatccaga gaaatggcc gctgtacatg agcaccaaga      840
acaccatact gaaagcctac gatgggcgtt tcaaggacat cttccaggag atctttgaca      900
agcactataa gaccgacttc gacaagaata agatctggta tgagcaccgg ctcattgatg      960
acatggtggc tcaggtcctc aagtcttcgg gtggctttgt gtgggcctgc aagaactatg     1020
acggagatgt gcagtcagac atcctggccc agggctttgg ctcccttggc ctgatgacgt     1080
ccgtcctggt ctgccctgat gggaagacga ttgaggctga ggcgctcat gggaccgtca      1140 ccgccacta tcgggagcac cagaaggcc ggcccaccag caccaacccc atcgccagca       1200
tctttgcctg gacacgtggc ctggagcacc gggggaagct ggatgggaac caagacctca     1260
tcaggtttgc ccagatgctg gagaaggtgt gcgtggagac ggtggagagt ggagccatga     1320
ccaaggacct ggcgggctgc attcacggcc tcagcaatgt gaagctgaac gagcacttcc     1380
```

```
tgaacaccac ggacttcctc gacaccatca agagcaacct ggacagagcc ctgggcaggc    1440 agtagggga ggcgccaccc atggctgcag tggaggggcc agggctgagc cggcgggtcc    1500
tcctgagcgc ggcagagggt gagcctcaca gcccctctct ggaggccttt ctaggggatg    1560 ttttttata agccagatgt ttttaaaagc atatgtgtgt ttcccctcat ggtgacgtga    1620
ggcaggagca gtgcgtttta cctcagccag tcagtatgtt ttgcatactg taatttatat    1680
tgcccttgga acacatggtg ccatatttag ctactaaaaa gctcttcaca aaaaaaaaa    1740

<210> SEQ ID NO 33
<211> LENGTH: 981
<212> TYPE: DNA
<213> ORGANISM: Homo sapiens

<400> SEQUENCE: 33
agtcagctgg aggagttggc ccctagggtt cttggactat aaggtgctga tcttgggtga      60
tgaccaagtc aaaagactta tgtaataaat tccaaaggat agacccatag caggaacatt     120
tgaaggagaa caggcattat ttcaggtgaa gaccgtagcc ggtgtgcaga ggggtgccct     180
gagaacaatc agtaaaagct gacaagtgcc tttgttcttg agggataagc ttctagaaac     240
cacaagctaa acaagatgcc aagatacctg tgctactctc aatgccttgg agcagaatgt     300
accatgaaaa tattggcatt aatgccaaaa gtaatgtga aaaccaagca cttaagttgg     360
ttttcctatt ttactgtacc acccaagaac actggaaggc agtggttctc acctggggac     420
agttttgccc cttgggaaat ttggcaatgt ctggaaacat tttttattgt cctaactggg     480 gtgagggga tgctattggc atctagaggc caaggatgct gctaaatatt ctccgatgct     540
caggacagac ccccccaac aaagaattat ttggccccaa atgtcaatag tactgccgtt     600
gtgaagctct tagaaggcat tctgtgaagc tctgaacagc agctaaggca tctggtgaaa     660
cctgaagtaa tcacaactgt ttgagagtcg actggaaagt tctgcagaga gggttgtcat     720
gccgctggca cgtccaggtg aaatgggcgt tgctgggtgc acagaaggag aggcaatgga     780
tcccaggtat tggtaggact gatcgtagga ccacggtggg gatggttgga tctgccttgt     840
atcctgcatc tgactctgag gctgagggtt aaaggcagtg gagtggttca aggaggcacg     900
agggttgggc gtgagctgag gtcgtgccat gcactccag cctgggcaac aagagcaaaa     960
ctccatctcc aaaaaaaaaa a                                               981

<210> SEQ ID NO 34
<211> LENGTH: 9795
<212> TYPE: DNA
<213> ORGANISM: Homo sapiens

<400> SEQUENCE: 34
ggcagtggca gcggcgagag cttgggcggc cgccgccgcc tcctcgcgag cgccgcgcgc      60
ccgggtcccg ctcgcatgca agtcacgtcc gccccctcgg cgcggccgcc ccgagacgcc     120
ggccccgctg agtgatgaga acagacgtca aactgcctta tgaatattga tgcggaggct     180
aggctgcttt cgtagagaag cagaaggaag caagatggct gcccttaggg atttgttaga     240
aaggagaccc gactgcaact gctggattgc tgcaaggctg aggacgagag acgaggctgg     300
caaacattca gcagcacacc ctctcaagat tgtttacttg cctttgctcc tgttgagtta     360
caacgcttgg aagcaggaga tgggctcagc agcagccaat aggacatgat ccaggaagag     420
cagtaaggga ctgagctgct gaattcaact agagggcagc cttgtggatg gccccgaagc     480
```

```
aagcctgatg gaacaggata gaaccaacca tgttgagggc aacagactaa gtccattcct    540
gataccatca cctcccattt gccagacaga acctctggct acaaagctcc agaatggaag    600
cccactgcct gagagagctc atccagaagt aaatggagac accaagtggc actctttcaa    660
aagttattat ggaatacect gtatgaaggg aagccagaat agtcgtgtga gtcctgactt    720
tacacaagaa agtagagggt attccaagtg tttgcaaaat ggaggaataa aacgcacagt    780
tagtgaacct tctctctctg ggctccttca gatcaagaaa ttgaaacaag accaaaaggc    840
taatggagaa agacgtaact tcggggtaag ccaagaaaga aatccaggtg aaagcagtca    900
accaaatgtc tccgatttga gtgataagaa agaatctgtg agttctgtag cccaagaaaa    960
tgcagttaaa gatttcacca gttttcaac acataactgc agtgggcctg aaaatccaga    1020
gcttcagatt ctgaatgagc aggaggggaa aagtgctaat taccatgaca agaacattgt    1080
attacttaaa aacaaggcag tgctaatgcc taatggtgct acagtttctg cctcttccgt    1140
ggaacacaca catggtgaac tcctggaaaa aacactgtct caatattatc cagattgtgt    1200
ttccattgcg gtgcagaaaa ccacatctca cataaatgcc attaacagtc aggctactaa    1260
tgagttgtcc tgtgagatca ctcacccatc gcatacctca gggcagatca attccgcaca    1320
gacctctaac tctgagctgc ctccaaagcc agctgcagtg gtgagtgagg cctgtgatgc    1380
tgatgatgct gataatgcca gtaaactagc tgcaatgcta aatacctgtt cctttcagaa    1440
accagaacaa ctacaacaac aaaaatcagt ttttgagata tgcccatctc ctgcagaaaa    1500
taacatccag ggaaccacaa agctagcgtc tggtgaagaa ttctgttcag gttccagcag    1560
caatttgcaa gctcctggtg gcagctctga acggtattta aaacaaaatg aaatgaatgg    1620
tgcttacttc aagcaaagct cagtgttcac taaggattcc ttttctgcca ctaccacacc    1680
accaccacca tcacaattgc ttcttttctcc ccctcctcct cttccacagg ttcctcagct    1740
tccttcagaa ggaaaaagca ctctgaatgg tggagtttta gaagaacacc accactaccc    1800
caaccaaagt aacacaacac ttttaaggga agtgaaaata gagggtaaac ctgaggcacc    1860
accttcccag agtcctaatc catctacaca tgtatgcagc ccttctccga tgctttctga    1920
aaggcctcag aataattgtg tgaacaggaa tgacatacag actgcaggga caatgactgt    1980
tccattgtgt tctgagaaaa caagaccaat gtcagaacac ctcaagcata cccaccaat    2040 ttttggtagc agtggagagc tacaggacaa ctgccagcag ttgatgagaa acaaagagca    2100
agagattctg aagggtcgag acaaggagca aacacgagat cttgtgcccc caacacagca    2160
ctatctgaaa ccaggatgga ttgaattgaa ggccectcgt tttcaccaag cggaatccca    2220
tctaaaacgt aatgaggcat cactgccatc aattcttcag tatcaaccca atctctccaa    2280
tcaaatgacc tccaaacaat acactggaaa ttccaacatg cctggggggc tcccaaggca    2340
agcttacacc cagaaaacaa cacagctgga gcacaagtca caaatgtacc aagttgaaat    2400
gaatcaaggg cagtcccaag gtacagtgga ccaacatctc cagttccaaa acccctcaca    2460
ccaggtgcac ttctccaaaa cagaccattt accaaaagct catgtgcagt cactgtgtgg    2520
cactagattt catttttcaac aaagagcaga ttcccaaact gaaaaactta tgtccccagt    2580
gttgaaacag cacttgaatc aacaggcttc agagactgag ccattttcaa actcacacct    2640
tttgcaacat aagcctcata acaggcagc acaaacacaa ccatcccaga gttcacatct    2700
ccctcaaaac cagcaacagc agcaaaaatt acaaataaag aataaagagg aaatactcca    2760
gacttttcct cacccccaaa gcaacaatga tcagcaaaga gaaggatcat tctttggcca    2820
gactaaagtg gaagaatgtt ttcatggtga aaatcagtat tcaaaatcaa gcgagttcga    2880
```

```
gactcataat gtccaaatgg gactggagga agtacagaat ataaatcgta gaaattcccc      2940
ttatagtcag accatgaaat caagtgcatg caaaatacag gtttcttgtt caaacaatac      3000
acacctagtt tcagagaata agaacagac tacacatcct gaacttttg caggaaacaa       3060
gacccaaaac ttgcatcaca tgcaatattt tccaaataat gtgatcccaa agcaagatct     3120
tcttcacagg tgctttcaag aacaggagca gaagtcacaa caagcttcag ttctacaggg     3180
atataaaaat agaaaccaag atatgtctgg tcaacaagct gcgcaacttg ctcagcaaag     3240
gtacttgata cataaccatg caaatgtttt tcctgtgcct gaccagggag gaagtcacac     3300
tcagacccct ccccagaagg acactcaaaa gcatgctgct ctaaggtggc atctcttaca     3360
gaagcaagaa cagcagcaaa cacagcaacc ccaaactgag tcttgccata gtcagatgca     3420
caggccaatt aaggtggaac ctggatgcaa gccacatgcc tgtatgcaca cagcaccacc     3480
agaaaacaaa acatggaaaa aggtaactaa gcaagagaat ccacctgcaa gctgtgataa     3540
tgtgcagcaa aagagcatca ttgagaccat ggagcagcat ctgaagcagt ttcacgccaa     3600
gtcgttattt gaccataagg ctcttactct caaatcacag aagcaagtaa aagttgaaat     3660
gtcagggcca gtcacagttt tgactagaca accactgct gcagaacttg atagccacac       3720
cccagcttta gagcagcaaa caacttcttc agaaaagaca ccaaccaaaa gaacagctgc     3780
ttctgttctc aataatttta tagagtcacc ttccaaatta ctagatactc ctataaaaaa     3840
tttattggat acacctgtca agactcaata tgatttccca tcttgcagat gtgtagagca     3900
aattattgaa aaagatgaag gtcctttta tacccatcta ggagcaggtc ctaatgtggc      3960
agctattaga gaaatcatgg aagaaaggtt tggacagaag ggtaaagcta ttaggattga     4020
aagagtcatc tatactggta agaaggcaa aagttctcag ggatgtccta ttgctaagtg      4080
ggtggttcgc agaagcagca gtgaagagaa gctactgtgt ttggtgcggg agcgagctgg     4140
ccacacctgt gaggctgcag tgattgtgat tctcatcctg gtgtgggaag gaatcccgct     4200
gtctctggct gacaaactct actcggagct taccgagacg ctgaggaaat acggcacgct     4260
caccaatcgc cggtgtgcct tgaatgaaga gagaacttgc gcctgtcagg gctggatcca     4320
gaaacctgtg gtgcctcctt ctcttttggt tgttcatgga gcatgtacta caatggatgt     4380
aagtttgcca gaagcaagat cccaaggaag tttaagctgc ttggggatga cccaaaagag     4440
gaagagaaac tggagtctca tttgcaaaac ctgtccactc ttatggcacc aacatataag     4500
aaacttgcac ctgatgcata taataatcag attgaatatg aacacagagc accagagtgc     4560
cgtctgggtc tgaaggaagg ccgtccattc tcaggggtca ctgcatgttt ggacttctgt     4620
gctcatgccc acagagactt gcacaacatg cagaatggca gcacattggt atgcactctc     4680
actagagaag acaatcgaga atttggagga aaacctgagg atgagcagct tcacgttctg     4740
cctttataca aagtctctga cgtggatgag tttgggagtg tggaagctca ggaggagaaa     4800
aaacggagtg gtgccattca ggtactgagt tcttttcggc gaaagtcag gatgttagca      4860
gagccagtca agacttgccg acaaaggaaa ctagaagcca agaaagctgc agctgaaaag     4920
ctttcctccc tggagaacag ctcaaataaa atgaaaagg aaaagtcagc cccatcacgt       4980
acaaaacaaa ctgaaaacgc aagccaggct aaacagttgg cagaactttt gcgactttca     5040
ggaccagtca tgcagcagtc ccagcagccc cagcctctac agaagcagcc accacagccc     5100
cagcagcagc agagacccca gcagcagcag ccacatcacc ctcagacaga gtctgtcaac     5160
tcttattctg cttctggatc caccaatcca tacatgagac ggcccaatcc agttagtcct     5220
```

```
tatccaaact cttcacacac ttcagatatc tatggaagca ccagccctat gaacttctat    5280
tccacctcat ctcaagctgc aggttcatat ttgaattctt ctaatcccat gaacccttac    5340
cctgggcttt tgaatcagaa tacccaatat ccatcatatc aatgcaatgg aaacctatca    5400
gtggacaact gctccccata tctgggttcc tattctcccc agtctcagcc gatggatctg    5460
tataggtatc caagccaaga ccctctgtct aagctcagtc taccacccat ccatacactt    5520
taccagccaa ggtttggaaa tagccagagt tttacatcta aatacttagg ttatggaaac    5580
caaaatatgc agggagatgg tttcagcagt tgtaccatta gaccaaatgt acatcatgta    5640
gggaaattgc ctccttatcc cactcatgag atggatggcc acttcatggg agccacctct    5700
agattaccac ccaatctgag caatccaaac atggactata aaaatggtga acatcattca    5760
ccttctcaca taatccataa ctacagtgca gctccgggca tgttcaacag ctctcttcat    5820
gccctgcatc tccaaaacaa ggagaatgac atgctttccc acacagctaa tgggttatca    5880
aagatgcttc cagctcttaa ccatgataga actgcttgtg tccaaggagg cttacacaaa    5940
ttaagtgatg ctaatggtca ggaaaagcag ccattggcac tagtccaggg tgtggcttct    6000
ggtgcagagg acaacgatga ggtctggtca gacagcgagc agagctttct ggatcctgac    6060
attgggggag tggccgtggc tccaactcat gggtcaattc tcattgagtg tgcaaagcgt    6120
gagctgcatg ccacaacccc tttaaagaat cccaatagga atcacccac caggatctcc    6180 ctcgtctttt accagcataa gagcatgaat gagccaaaac atggcttggc tctttgggaa    6240
gccaaaatgg ctgaaaaagc ccgtgagaaa gaggaagagt gtgaaaagta tggcccagac    6300
tatgtgcctc agaaatccca tggcaaaaaa gtgaacggg agcctgctga ccacatgaa    6360 acttcagagc ccacttacct gcgtttcatc aagtctcttg ccgaaaggac catgtccgtg    6420
accacagact ccacagtaac tacatctcca tatgccttca ctcgggtcac agggccttac    6480
aacagatata tatgatatca ccccctttg ttggttacct cacttgaaaa gaccacaacc    6540
aacctgtcag tagtatagtt ctcatgacgt gggcagtggg gaaaggtcac agtattcatg    6600
acaaatgtgg tgggaaaaac ctcagctcac cagcaacaaa agaggttatc ttaccatagc    6660
acttaatttt cactggctcc caagtggtca cagatggcat ctaggaaaag accaaagcat    6720
tctatgcaaa agaaggtgg ggaagaaagt gttccgcaat ttacattttt aaacactggt    6780
tctattattg gacgagatga tatgtaaatg tgatccccc ccccgctta caactctaca    6840 catctgtgac cactttaat aatatcaagt ttgcatagtc atggaacaca atcaaacaa    6900 gtactgtagt attacagtga caggaatctt aaaataccat ctggtgctga atatatgatg    6960
tactgaaata ctggaattat ggcttttga aatgcagttt ttactgtaat cttaactttt    7020
atttatcaaa atagctacag gaaacatgaa tagcaggaaa acactgaatt tgtttggatg    7080
ttctaagaaa tggtgctaag aaaatggtgt ctttaatagc taaaaattta atgcctttat    7140
atcatcaaga tgctatcagt gtactccagt gcccttgaat aatagggta ccttttcatt    7200 caagttttta tcataattac ctattcttac acaagcttag ttttttaaaat gtggacattt    7260 taaaggcctc tggattttgc tcatccagtg aagtccttgt aggacaataa acgtatatat    7320
gtacatatat acacaaacat gtatatgtgc acacacatgt atatgtataa atattttaaa    7380
tggtgtttta gaagcacttt gtctacctaa gctttgacaa cttgaacaat gctaaggtac    7440
tgagatgttt aaaaaacaag tttactttca ttttagaatg caaagttgat ttttttaagg    7500
aaacaaagaa agcttttaaa atattttgc ttttagccat gcatctgctg atgagcaatt    7560
gtgtccattt ttaacacagc cagttaaatc caccatgggg cttactggat tcaagggaat    7620
```

```
acgttagtcc acaaaacatg tttctggtg ctcatctcac atgctatact gtaaaacagt    7680
tttatacaaa attgtatgac aagttcattg ctcaaaaatg tacagtttta agaattttct    7740
attaactgca ggtaataatt agctgcatgc tgcagactca acaaagctag ttcactgaag    7800
cctatgctat tttatggatc ataggctctt cagagaactg aatggcagtc tgcctttgtg    7860
ttgataatta tgtacattgt gacgttgtca tttcttagct taagtgtcct ctttaacaag    7920
aggattgagc agactgatgc ctgcataaga tgaataaaca gggttagttc catgtgaatc    7980
tgtcagttaa aaagaaacaa aaacaggcag ctggtttgct gtggtggttt taaatcatta    8040
atttgtataa agaagtgaaa gagttgtata gtaaattaaa ttgtaaacaa aactttttta    8100
atgcaatgct ttagtatttt agtactgtaa aaaaattaaa tatatacata tatatatata    8160
tatatatata tatatatatg agtttgaagc agaattcaca tcatgatggt gctactcagc    8220
ctgctacaaa tatatcataa tgtgagctaa gaattcatta aatgtttgag tgatgttcct    8280
acttgtcata tacctcaaca ctagtttggc aataggatat tgaactgaga gtgaaagcat    8340
tgtgtaccat cattttttc caagtccttt tttttattgt taaaaaaaaa agcataccctt    8400
ttttcaatac ttgatttctt agcaagtata acttgaactt caacctttt gttctaaaaa    8460
ttcagggata tttcagctca tgctctccct atgccaacat gtcacctgtg tttatgtaaa    8520
attgttgtag gttaataaat atattctttg tcagggattt aacccttta ttttgaatcc    8580
cttctatttt acttgtacat gtgctgatgt aactaaaact aattttgtaa atctgttggc    8640
tcttttatt gtaaagaaaa gcattttaaa agtttgagga atcttttgac tgtttcaagc    8700
aggaaaaaaa aattacatga aaatagaatg cactgagttg ataaagggaa aaattgtaag    8760
gcaggagttt ggcaagtggc tgttggccag agacttactt gtaactctct aaatgaagtt    8820
tttttgatcc tgtaatcact gaaggtacat actccatgtg gacttccctt aaacaggcaa    8880
acacctacag gtatggtgtg caacagattg tacaattaca ttttggccta aatacatttt    8940
tgcttactag tatttaaaat aaattcttaa tcagaggagg cctttgggtt ttattggtca    9000
aatcttgta agctggcttt tgtctttta aaaaatttct tgaatttgtg gttgtgtcca    9060
atttgcaaac atttccaaaa atgtttgctt tgcttacaaa ccacatgatt ttaatgtttt    9120
ttgtatacca taatatctag ccccaaacat ttgattacta catgtgcatt ggtgattttg    9180
atcatccatt cttaatattt gatttctgtg tcacctactg tcatttgtta aactgctggc    9240
caacaagaac aggaagtata gtttgggggg ttggggagag tttacataag gaagagaaga    9300
aattgagtgg catattgtaa atatcagatc tataattgta aatataaaac ctgcctcagt    9360
tagaatgaat ggaaagcaga tctacaattt gctaatatag gaatatcagg ttgactatat    9420
agccatactt gaaaatgctt ctgagtggtg tcaactttac ttgaatgaat ttttcatctt    9480
gattgacgca cagtgatgta cagttcactt ctgaagctag tggttaactt gtgtaggaaa    9540
cttttgcagt ttgacactaa gataacttct gtgtgcattt ttctatgctt ttttaaaaac    9600
tagtttcatt tcattttcat gagatgtttg gtttataaga tctgaggatg gttataaata    9660
ctgtaagtat tgtaatgtta tgaatgcagg ttatttgaaa gctgtttatt attatatcat    9720
tcctgataat gctatgtgag tgttttaat aaaatttata tttatttaat gcactctaaa    9780
aaaaaaaaaa aaaaa                                                     9795
```

<210> SEQ ID NO 35
<211> LENGTH: 9236
<212> TYPE: DNA

<213> ORGANISM: Homo sapiens

<400> SEQUENCE: 35

```
aaacagaagg tgggccgggg cggggagaaa cagaactcgg tcaatttccc agtttgtcgg        60
gtctttaaaa atacaggccc ctaaagcact aagggcatgc cctcggtgaa acaggggagc       120
gcttctgctg aatgagatta aagcgacaga aaagggaaag gagagcgcgg gcaacgggat       180
ctaaagggag atagagacgc gggcctctga gggctggcaa acattcagca gcacaccctc       240
tcaagattgt ttacttgcct ttgctcctgt tgagttacaa cgcttggaag caggagatgg       300
gctcagcagc agccaatagg acatgatcca ggaagagcag taagggactg agctgctgaa       360
ttcaactaga gggcagcctt gtggatggcc ccgaagcaag cctgatggaa caggatagaa       420
ccaaccatgt tgagggcaac agactaagtc cattcctgat accatcacct cccatttgcc       480
agacagaacc tctggctaca aagctccaga atggaagccc actgcctgag agagctcatc       540
cagaagtaaa tggagacacc aagtggcact ctttcaaaag ttattatgga atacctgta       600
tgaagggaag ccagaatagt cgtgtgagtc ctgactttac acaagaaagt agagggtatt       660
ccaagtgttt gcaaaatgga ggaataaaac gcacagttag tgaaccttct ctctctgggc       720
tccttcagat caagaaattg aaacaagacc aaaaggctaa tggagaaaga cgtaacttcg       780
gggtaagcca agaaagaaat ccaggtgaaa gcagtcaacc aaatgtctcc gatttgagtg       840
ataagaaaga atctgtgagt tctgtagccc aagaaaatgc agttaaagat ttcaccagtt       900
tttcaacaca taactgcagt gggcctgaaa atccagagct tcagattctg aatgagcagg       960
aggggaaaag tgctaattac catgacaaga acattgtatt acttaaaaac aaggcagtgc      1020
taatgcctaa tggtgctaca gtttctgcct cttccgtgga acacacacat ggtgaactcc      1080
tggaaaaaac actgtctcaa tattatccag attgtgtttc cattgcggtg cagaaaacca      1140
catctcacat aaatgccatt aacagtcagg ctactaatga gttgtcctgt gagatcactc      1200
acccatcgca tacctcaggg cagatcaatt ccgcacagac ctctaactct gagctgcctc      1260
caaagccagc tgcagtggtg agtgaggcct gtgatgctga tgatgctgat aatgccagta      1320
aactagctgc aatgctaaat acctgttcct ttcagaaacc agaacaacta caacaacaaa      1380
aatcagtttt tgagatatgc ccatctcctg cagaaaataa catccaggga accacaaagc      1440
tagcgtctgg tgaagaattc tgttcaggtt ccagcagcaa tttgcaagct cctggtggca      1500
gctctgaacg gtatttaaaa caaaatgaaa tgaatggtgc ttacttcaag caaagctcag      1560
tgttcactaa ggattccttt tctgccacta ccacaccacc accaccatca caattgcttc      1620
tttctcccc tcctcctctt ccacaggttc ctcagcttcc ttcagaagga aaaagcactc      1680
tgaatggtgg agttttagaa gaacaccacc actacccca ccaaagtaac acaacacttt      1740
taagggaagt gaaaatagag ggtaaacctg aggcaccacc ttcccagagt cctaatccat      1800
ctacacatgt atgcagccct ctccgatgc tttctgaaag gcctcagaat aattgtgtga      1860
acaggaatga catacagact gcagggacaa tgactgttcc attgtgttct gagaaaacaa      1920
gaccaatgtc agaacacctc aagcataacc caccaatttt tggtagcagt ggagagctac      1980
aggacaactg ccagcagttg atgagaaaca aagagcaaga gattctgaag ggtcagagaca      2040
aggagcaaac acgagatctt gtgcccccaa cacagcacta tctgaaacca ggatggattg      2100
aattgaaggc ccctcgtttt caccaagcgg aatcccatct aaaacgtaat gaggcatcac      2160
tgccatcaat tcttcagtat caacccaatc tctccaatca aatgacctcc aaacaataca      2220
ctggaaattc caacatgcct gggggggctcc caaggcaagc ttacacccag aaaacaacac      2280
```

```
agctggagca caagtcacaa atgtaccaag ttgaaatgaa tcaagggcag tcccaaggta   2340
cagtggacca acatctccag ttccaaaaac cctcacacca ggtgcacttc tccaaaacag   2400
accatttacc aaaagctcat gtgcagtcac tgtgtggcac tagatttcat tttcaacaaa   2460
gagcagattc ccaaactgaa aaacttatgt ccccagtgtt gaaacagcac ttgaatcaac   2520
aggcttcaga gactgagcca ttttcaaact cacacctttt gcaacataag cctcataaac   2580
aggcagcaca aacacaacca tcccagagtt cacatctccc tcaaaaccag caacagcagc   2640
aaaaattaca aataaagaat aaagaggaaa tactccagac ttttcctcac ccccaaagca   2700
acaatgatca gcaaagagaa ggatcattct ttggccagac taaagtggaa gaatgttttc   2760
atggtgaaaa tcagtattca aaatcaagcg agttcgagac tcataatgtc caaatgggac   2820
tggaggaagt acagaatata aatcgtagaa attcccctta tagtcagacc atgaaatcaa   2880
gtgcatgcaa aatacaggtt tcttgttcaa acaatacaca cctagtttca gagaataaag   2940
aacagactac acatcctgaa cttttttgcag gaaacaagac ccaaaacttg catcacatgc   3000
aatatttttcc aaataatgtg atcccaaagc aagatcttct tcacaggtgc tttcaagaac   3060
aggagcagaa gtcacaacaa gcttcagttc tacagggata taaaaataga aaccaagata   3120
tgtctggtca acaagctgcg caacttgctc agcaaaggta cttgatacat aaccatgcaa   3180
atgttttttcc tgtgcctgac cagggaggaa gtcacactca gacccctccc cagaaggaca   3240
ctcaaaagca tgctgctcta aggtggcatc tcttacagaa gcaagaacag cagcaaacac   3300
agcaaccccca aactgagtct tgccatagtc agatgcacag gccaattaag gtggaacctg   3360
gatgcaagcc acatgcctgt atgcacacag caccaccaga aaacaaaaca tggaaaaagg   3420
taactaagca agagaatcca cctgcaagct gtgataatgt gcagcaaaag agcatcattg   3480
agaccatgga gcagcatctg aagcagtttc acgccaagtc gttatttgac cataaggctc   3540
ttactctcaa atcacagaag caagtaaaag ttgaaatgtc agggccagtc acagttttga   3600
ctagacaaac cactgctgca gaacttgata gccacacccc agctttagag cagcaaacaa   3660
cttcttcaga aaagacacca accaaaagaa cagctgcttc tgttctcaat aatttatag   3720
agtcaccttc caaattacta gatactccta taaaaaattt attggataca cctgtcaaga   3780
ctcaatatga tttcccatct tgcagatgtg taggtaagtg ccagaaatgt actgagacac   3840
atggcgttta tccagaatta gcaaatttat cttcagatat gggattttcc ttctttttt   3900
aaatcttgag tctggcagca atttgtaaag gctcataaaa atctgaagct tacatttttt   3960
gtcaagttac cgatgcttgt gtcttgtgaa agagaacttc acttacatgc agttttttcca   4020
aaagaattaa ataatcgtgc atgtttattt ttccctctct tcagatcctg taaaatttga   4080
atgtatctgt tttagatcaa ttcgcctatt tagctctttg tatattatct cctggagaga   4140
cagctaggca gcaaaaaaac aatctattaa aatgagaaaa taacgaccat aggcagtcta   4200
atgtacgaac tttaaatatt tttaattca aggtaaaata tattagtttc acaagatttc   4260
tggctaatag ggaaattatt atcttcagtc ttcatgagtt gggggaaatg ataatgctga   4320
cactcttagt gctcctaaag tttccttttc tccatttata catttggaat gttgtgattt   4380
atattcattt tgattcccctt ttctctaaaa tttcatcttt tgattaaaaa aatatgatac   4440
aggcatacct cagagatatt gtgggtttgg ctccatacca caataaaatg aatattacaa   4500
taaagcaagt tgtaaggact ttttggtttc tcactgtatg taaaagttat ttatatacta   4560
tactgtaaca tactaagtgt gcaatagcat tgtgtctaaa aaatatatac tttaaaaata   4620
```

```
atttattgtt aaaaaaatgc caacaattat ctgggccttt agtgagtgct aatcttttg      4680
ctggtggagg gtcgtgcttc agtattgatc gctgtggact gatcatggtg gtagttgctg     4740
aaggttgctg ggatggctgt gtgtgtggca atttcttaaa ataagacaac agtgaagtgc     4800
tgtatcaatt gattttttcca ttcacaaaag atttctctgt agcatgcaat gctgtttgat    4860
agcatttaac ccacagcaga atttctttga aaattggact cagtcctctc aaactgtgct     4920
gctgctttat caactaagtt tttgtaattt tctgaatcct ttgttgtcat ttcagcagtt     4980
tacagcatct tcattggaag tatattccat ctcaaacatt ctttgttcat ccataagaag     5040
caacttctta tcaagttttt tcatgacatt gcagtaactc agccccatct tcaggctcta     5100
cttctaattc tggttctctt gctacatctc cctcatctgc agtgacctct ccacggaagt     5160
cttgaactcc tcaaagtaat ccatgagggt tggaatcaac ttctaaactc ctgttaatgt     5220
tgatatattg acccctccc atgaattatg aatgttctta ataacttcta aatggtgata     5280
ccttcccaga aggctttcaa tgtactttgc ccggatccat cagaagacta tcttggcagc     5340
tgtagactaa caatatattt cttaaatgat aagacttgaa agtcaaaagt actccttaat     5400
ccataggctg cagaatcaat gttgtattaa caggcacgaa aacagcatta atcttgtgca     5460
tctccatcgg agctcttggg tgactaggtg ccttgagcag taatatttg aaaggaggtt       5520
ttggttttgt ttttgtttt ttttttttgt ttttagcag taagtctcaa cactgggctt       5580
aaaatattca gtaaactatg ttgtaaaaag atgtgttatc atccagactt tgttgttcca     5640
ttactctaca caagcagggt acacttagca taattcttaa gggccttgga attttcagaa     5700
tggtaaatga gtatgggctt caacttaaaa tcatcaactg cattagcctg taacaagaga     5760
gtcagcctgt cctttgaagc aaggcattga cttctatcta tgaaagtctt agatggcacc     5820
ttgtttcaat agtaggctgt ttagtacagc caccttcatc agtgatctta gctagatctt     5880
ctgcataact tgctgcagct tctacatcag cacttgctgc ctcaccttgt cctttatgt     5940
tatagagaca gctgcgcttc ttaaacttta taaaccaact tctgctagct tccaacttct    6000
cttctgcagc ttcctcattc tcttcataga actgaaggga gtcaaggcct tgctctggat     6060
taagctttgg cttaaggaat gttgtggctg acgtgatctt ctatccagac cactaaagcg    6120
ctctccatat cagcaataag gccgttttgc tttcttacct ttcatgtgtt cactggagta    6180
atttccttca agaattttc ctttacattc acaacttggc taactggcat gcaaggccta     6240
gctttcagcc tgtcttggct tttgacatgc cttcctcact agctcgtca tatctagctt      6300
ttgatttaaa gtggcaggca tacaactctt cctttcactt gaacacttag aggccactgt     6360
agggttatta attggcctaa tttcaatatt gttgtgtttt agggaataga gaggcccagg    6420
gagagggaga gagcccaaac ggctggttga tagagcaggc agaatgcaca caacatttat    6480
cagattatgt ttgcaccatt taccagatta tgggtacggt ttgtggcacc ccccaaaaat    6540
tagaatagta acatcaaaga tcactgatca cagatcgcca taacataaat aataataaac    6600
tttaaaatac tgtgagaatt accaaaatgt gatacagaga catgaagtga gcacatgctg    6660
ttgaaaaaaa tgacactgat agacatactt aacacgtggg attgccacaa accttcagtt    6720
tgtaaaagtc acagtaactg tgactcacaa aagaacaaag cacaataaaa cgaggtatgc    6780
ctgtattttt aaaaaaagct ttttgttaaa attcaggata tgtaataggt ctgtaggaat    6840
agtgaaatat ttttgctgat ggatgtagat atatacgtgg atagagatga agatcttaat    6900
tatagctatg cagcatagat ttagtcaaag acatttgaaa agacaaatgt taaattagtg    6960
tggctaatga cctacccgtg ccatgttttc cctcttgcaa tgagataccc cacactgtgt    7020
```

```
agaaggatgg agggaggact cctactgtcc ctctttgcgt gtggttatta agttgcctca    7080
ctgggctaaa acaccacaca tctcatagat aatatttggt aagttgtaat cgtcttcact    7140
cttctcttat cacccacccc tatcttccca cttttccatc tttgttggtt tgcaacagcc    7200 ccttctttt  gcctgactct ccaggatttt ctctcatcat aaattgttct aaagtacata    7260
ctaatatggg tctggattga ctattcttat ttgcaaaaca gcaattaaat gttatagga     7320 agtaggaaga aaaaggggta tccttgacaa taaaccaagc aatattctgg gggtgggata    7380
gagcaggaaa ttttatttt  aatcttttaa aatccaagta ataggtaggc ttccagttag    7440
cttaaaatgt ttttttttc  cagctcaaaa aattggattg tagttgatac tacatataat    7500
acattctaat tccctcactg tattctttgt ttagtttcat ttatttggtt taaaataatt    7560
ttttatccca tatctgaaat gtaatatatt tttatccaac aaccagcatg tacatatact    7620
taattatgtg gcacattttc taatagatca gtccatcaat ctactcattt taagaaaaa    7680 aaaatttaa  agtcacttt  agagcccttaa atgtgtagtt gggggttaag ctttgtggat    7740
gtagccttta tatttagtat aattgaggtc taaaataata atcttctatt atctcaacag    7800
agcaaattat tgaaaaagat gaaggtcctt tttatacccaa tctaggagca ggtcctaatg    7860
tggcagctat tagagaaatc atggaagaaa ggtaattaac gcaaaggcac agggcagatt    7920
aacgtttatc cttttgtata tgtcagaatt tttccagcct tcacacacaa agcagtaaac    7980
aattgtaaat tgagtaatta ttagtaggct tagctattct agggttgcca acactacaca    8040
ctgtgctatt caccagagag tcacaatatt tgacaggact aatagtctgc tagctggcac    8100
aggctgccca ctttgcgatg gatgccagaa aacccaggca tgaacaggaa tcggccagcc    8160
aggctgccag ccacaaggta ctggcacagg ctccaacgag aggtcccact ctggctttcc    8220
cacctgataa taaagtgtca aagcagaaag actggtaaag tgtggtataa gaaaagaacc    8280
actgaattaa attcacctag tgttgcaaat gagtacttat ctctaagttt tcttttacca    8340
taaaagagaa gcaagtgtga tatgttgaat agaaagagaa acatactatt tacagctgcc    8400 ttttttttt  ttttcgcta  tcaatcacag gtatacaagt acttgccttt actcctgcat    8460
gtagaagact cttatgagcg agataatgca gagaaggcct tcatataaa  tttatacagc    8520 tctgagctgt tcttcttcta gggtgccttt tcattaagag gtaggcagta ttattattaa    8580
agtacttagg atacattggg gcagctagga catattcagt atcattcttg ctccatttcc    8640
aaattattca tttctaaatt agcatgtaga agttcactaa ataatcatct agtggcctgg    8700
cagaaatagt gaatttccct aagtgccttt ttttttgttgt tttttttgttt tgtttttaa    8760 acaagcagta ggtggtgctt tggtcataag ggaagatata gtctattct  aggactattc    8820 catatttcc  atgtggctgg atactaacta tttgccagcc tccttttcta aattgtgaga    8880
cattcttgga ggaacagttc taactaaaat ctattatgac tccccaagtt ttaaaatagc    8940
taaatttagt aagggaaaaa atagtttatg ttttagaaga ctgaacttag caaactaacc    9000
tgaattttgt gctttgtgaa attttatatc gaaatgagct ttcccatttt cacccacatg    9060
taatttacaa aatagttcat tacaattatc tgtacatttt gatattgagg aaaaacaagg    9120
cttaaaaacc attatccagt ttgcttggcg tagacctgtt taaaaaataa taaaccgttc    9180
atttctcagg atgtggtcat agaataaagt tatgctcaaa tgttcaaata tttaaa        9236

<210> SEQ ID NO 36
<211> LENGTH: 7056
<212> TYPE: DNA
```

<213> ORGANISM: Homo sapiens

<400> SEQUENCE: 36

| | | | | | |
|---|---|---|---|---|---|
| cacacccacg | gcagacacgc | acgcacccgg | gcgccgaagg | gaaagccgcg | tctcgccctc | 60 |
| ccgccccgcc | gtcggtcctg | tctcagtccc | tcagcagagc | gggaaagcgg | aggccggagc | 120 |
| cgtgacctct | gaccccgtgg | ttatgcggag | ccgccgcatt | ccttagcgat | cgcggggcag | 180 |
| ccgccgctgc | cgccgtgggc | gactgacgca | gcgcgggcg | gtggagccgc | cgccgcccct | 240 |
| cccccaccgc | cgctctcgcg | ccagccggtc | cccgcgtgcc | cgcccttct | cccggccgc | 300 |
| acccgagacc | tcgcgcgccg | ccgctgccac | gcgccccccc | caccgccgcc | gccgcccag | 360 |
| ccccgcgcca | ccgcccagc | ccgcccagcc | cggaggtccc | gcgtggagct | gccgccgccg | 420 |
| ccggggagaa | ggatgaagga | caaacagaag | aagaagaagg | agcgcacgtg | ggccgaggcc | 480 |
| gcgcgcctgg | tattagaaaa | ctactcggat | gctccaatga | caccaaaaca | gattctgcag | 540 |
| gtcatagagg | cagaaggact | aaaggaaatg | agaagtggga | cttcccctct | cgcatgcctc | 600 |
| aatgctatgc | tacattccaa | ttcaagagga | ggagaggggt | tgttttataa | actgcctggc | 660 |
| cgaatcagcc | ttttcacgct | caagaaggat | gccctgcagt | ggtctcgcca | tccagctaca | 720 |
| gtggagggag | aggagccaga | ggacacggct | gatgtgagga | gctgtgggtc | taatgaagcc | 780 |
| agcactgtga | gtggtgaaaa | cgatgtatct | cttgatgaaa | catcttcgaa | cgcatcctgt | 840 |
| tctacagaat | ctcagagtcg | acctctttcc | aatcccaggg | acagctacag | agcttcctca | 900 |
| caggcgaaca | aacaaagaa | aaagactggg | gtgatgctgc | ctcgagttgt | cctgactcct | 960 |
| ctgaaggtaa | acggggccca | cgtggaatct | gcatcagggt | tctcgggctg | ccacgccgat | 1020 |
| ggcgagagcg | gcagcccgtc | cagcagcagc | agcggctctc | tggccctggg | cagcgctgct | 1080 |
| attcgtggcc | aggccgaggt | cacccaggac | cctgccccgc | tcctgagagg | cttccggaag | 1140 |
| ccagccacag | gtcaaatgaa | gcgcaacaga | ggggaagaaa | tagattttga | gacacctggg | 1200 |
| tccattcttg | tcaacaccaa | cctccgtgcc | ctgatcaact | ctcggacctt | ccatgcctta | 1260 |
| ccatcacact | tccagcagca | gctcctcttc | ctcctgcctg | aagtagacag | acaggtgggg | 1320 |
| acggatggcc | tgttgcgtct | cagcagcagt | gcactaaata | acgagttttt | tacccatgcg | 1380 |
| gctcagagct | ggcgggagcg | cctggctgat | ggtgaattta | ctcatgagat | gcaagtcagg | 1440 |
| atacgacagg | aaatggagaa | ggaaaagaag | gtggaacaat | ggaaagaaaa | gttctttgaa | 1500 |
| gactactatg | gacagaagct | gggtttgacc | aaagaagagt | cattgcagca | gaacgtgggc | 1560 |
| caggaggagg | ctgaaatcaa | aagtggcttg | tgtgtcccag | gagaatcagt | gcgtatacag | 1620 |
| cgtggtccag | ccacccgaca | gcgagatggg | cattttaaga | aacgctctcg | gccagatctc | 1680 |
| cgaaccagag | ccagaaggaa | tctgtacaaa | aaacaggagt | cagaacaagc | aggggttgct | 1740 |
| aaggatgcaa | aatctgtggc | ctcagatgtt | cccctctaca | aggatgggga | ggctaagact | 1800 |
| gacccagcag | ggctgagcag | tccccatctg | ccaggcacat | cctctgcagc | acccgacctg | 1860 |
| gagggtcccg | aattcccagt | tgagtctgtg | gcttctcgga | tccaggctga | gccagacaac | 1920 |
| ttggcacgtg | cctctgcatc | tccagacaga | attcctagcc | tgcctcagga | aactgtggat | 1980 |
| caggaaccca | aggatcagaa | gaggaaatcc | tttgagcagg | cggcctctgc | atcctttccc | 2040 |
| gaaaagaagc | cccggcttga | agatcgtcag | tcctttcgta | acacaattga | aagtgttcac | 2100 |
| accgaaaagc | cacagcccac | taagagagag | cccaaagtcc | cgcccatccg | gattcaactt | 2160 |
| tcacgtatca | aaccacctg | ggtggttaaa | ggtcagccca | cttaccagat | atgccccgg | 2220 |
| atcatcccca | ccacggagtc | ctcctgccgg | ggttggactg | gcgccaggac | cctcgcagac | 2280 |

```
attaaagccc gtgctctgca ggtccgaggg gcgagaggtc accactgcca tagagaggcg    2340
gccaccactg ccatcggagg gggggtggc ccgggtggag gtggcggcgg ggccaccgat    2400
gagggaggtg gcagaggcag cagcagtggt gatggtggtg aggcctgtgg ccaccctgag    2460
cccaggggag gcccgagcac ccctggaaag tgtacgtcag atctacagcg aacacaacta    2520
ctgccgcctt atcctctaaa tggggagcat acccaggccg gaactgccat gtccagagct    2580
aggagagagg acctgccttc tctgagaaag gaggaaagct gcctactaca gagggctaca    2640
gttggactca cagatgggct aggagatgcc tcccaactcc ccgttgctcc cactggggac    2700
cagccatgcc aggccttgcc cctactgtcc tcccaaacct cagtagctga gagattagtg    2760
gagcagcctc agttgcatcc ggatgttaga actgaatgtg agtctggcac cacttcctgg    2820
gaaagtgatg atgaggagca aggacccacc gttcctgcag acaatggtcc cattccgtct    2880
ctagtgggag atgatacatt agagaaagga actggccaag ctcttgacag tcatcccact    2940
atgaaggatc ctgtaaatgt gacccccagt tccacacctg aatcctcacc gactgattgc    3000
ctgcagaaca gagcatttga tgacgaatta gggcttggtg gctcatgccc tcctatgagg    3060
gaaagtgata ctagacaaga aaacttgaaa accaaggctc tcgtttctaa cagttctttg    3120
cattggatac ccatcccatc gaatgatgag gtagtgaaac agcccaaacc agaatccaga    3180
gaacacatac catctgttga gccccaggtt ggagaggagt gggagaaagc tgctcccacc    3240
cctcctgcat tgcctgggga tttgacagct gaggagggtc tagatcctct tgacagcctt    3300
acttcactct ggactgtgcc atctcgagga ggcagtgaca gcaatggcag ttactgtcaa    3360
caggtggaca ttgaaaagct gaaaatcaac ggagactctg aagcactgag tcctcacggt    3420
gagtccacgg atacagcctc tgactttgaa ggtcacctca cggaggacag cagtgaggct    3480
gacactagag aagctgcagt gacaaaggga tcttcggtgg acaaggatga gaaacccaat    3540
tggaaccaat ctgccccact gtccaaggtg aatggtgaca tgcgtctggt tacaaggaca    3600
gatgggatgg ttgctcctca gagctgggtg tctcgagtat gtgcggtccg ccaaaagatc    3660
ccagattccc tactgctggc cagtactgag taccagccaa gagccgtgtg cctgtccatg    3720
cctgggtcct cagtggaggc cactaaccca cttgtgatgc agttgctgca gggtagcttg    3780
cccctagaga aggttcttcc accagcccac gatgacagca tgtcagaatc cccacaagta    3840
ccacttacaa aagaccagag ccatggctcg ctacgcatgg gatctttaca tggtcttgga    3900
aaaaacagtg gcatggttga tggaagcagc cccagttctt taagggcttt gaaggagcct    3960
cttctgccag atagctgtga aacaggcact ggtcttgcca ggattgaggc cacccaggct    4020
cctggagcac cccaaaagaa ttgcaaggca gtcccaagtt ttgactccct ccatccagtg    4080
acaaatccca ttcatcctc taggaaactg aagaaatgg attccaaaga gcagttctct    4140
tcctttagtt gtgaagatca gaaggaagtc cgtgctatgt cacaggacag taattcaaat    4200
gctgctccag gaaagagccc aggagatctt actacctcga gaacacctcg tttctcatct    4260
ccaaatgtga tctcctttgg tccagagcag acaggtcggg ccctgggtga tcagagcaat    4320
gttacaggcc aagggaagaa gcttttggc tctgggaatg tggctgcaac ccttcagcgc    4380
cccaggcctg cggacccgat gcctcttcct gctgagatcc ctccagtttt tcccagtggg    4440
aagttgggac caagcacaaa ctccatgtct ggtggggtac agactccaag ggaagactgg    4500
gctccaaagc cacatgcctt tgttggcagc gtcaagaatg agaagacttt tgtgggggt    4560 cctcttaagg caaatgccga gaacaggaaa gctactgggc atagtcccct ggaactggtg    4620
```

```
ggtcacttgg aagggatgcc ctttgtcatg gacttgccct tctggaaatt accccgagag    4680
ccagggaagg ggctcagtga gcctctggag ccttcttctc tcccctccca actcagcatc    4740
aagcaggcat tttatgggaa gctttctaaa ctccaactga gttccaccag ctttaattat    4800
tcctctagct ctcccacctt tcccaaaggc cttgctggaa gtgtggtgca gctgagccac    4860
aaagcaaact ttggtgcgag ccacagtgca tcactttcct tgcaaatgtt cactgacagc    4920
agcacggtgg aaagcatctc gctccagtgt gcgtgcagcc tgaaagccat gatcatgtgc    4980
caaggctgcg gtgcgttctg tcacgatgac tgtattggac cctcaaagct ctgtgtattg    5040
tgccttgtgg tgagataata aattatggcc atgggaaaca ttgtatattt agtgtgtgta    5100
ttttgataat gattgatctt aaatctgtat acagaatatc attgatataa tactctttag    5160
gcaggagcac tcttgccttc ccccaaaatt tacactgcta aagccctctg tcacttggcg    5220
acccttctgg tcttgctgga ggggtttcct gggtataacc cattgggctg cccaaggcca    5280
gccagcctga gctctcctgc aagacagagc ctgatgtggc acggagtggg gttgcgggggg   5340
gtgggggggac tgcctgactc ccagagggac ttgaaactga agcaagaagg ttgcattctc   5400
caccaaggga gttaacctac ctgaactaag tagaaatgcc agtcttccac tacccctcc    5460
ctgccatctt ttcttctgct actttgggga gttgatggcc aggaaagaag ccagcacagg    5520
gttaaagtaa ctcctggcat tgcccaccag ggggctggtg cacctgctga cctcagggtc    5580
acagttgagt catttgccag ttgacggagc aagtttgacc ttggttctgt tgctgaagca    5640
aatttggaac ttttctgtct cagtgtgatc cactaaccca caggatcatt tggaaccttg    5700
aatagctctg cttggacaat ggggttgggg aataggggttg tctttcctat gaaaatgcca   5760
tctgtagacc ttgtgagtca gccgtccaga tgtttgcagg tgaattcctc tgcttgacat    5820
cctccctgtc actttggacc ctatgggagt gggcatctcc acgcacctgt gtatgtgaaa    5880
gtcattttac atttcaaagc agtgtgtgtt cttatttttt atatttttaa ctctttattc    5940
ttggatgtat aaagtgaact ttttggcttc tgtaagtatg ctctatgcac ctctaatgtt    6000
ttatcatgta tttatatgtt gtacacagta ctggctgatt ctgtaaatgg atgtattgta    6060
cagagaacat gaacgtctct tcctaatttt acatcttcag catcattgca ttaaagtggt    6120
gtaatctcct tctctacatc tgttgtcaga gccactgagt gctgtgctgc tcgacgtgag    6180
ggtgaaatga ttgacttgtg acctgccagg ttgcccgatg ccctgttggg tcaccggctg    6240
gacctgctgc agcctgcaga gccacagtca gcctgcccac atgccaccga gcaaacgcat    6300
cttgcttttc acatctctcc tcctacagcc ttaatggctg cttgctgcca tatgtgacaa    6360
atcaccacca ccagtgttaa gtgcttctgg attcatgggt gagttccctg ggcagcccc    6420
aggaaggcct tccagatctg gctccagggt caccacctgt cacagcaata cctgggacca    6480
tgctctcctg ggactgtgag gctccttttg acgtactttt gacatcaggc aggtttggga    6540
agaaacaaag ccatgcctgc tcctgcctct ctcccaacat gtttccagca agtagatgcc    6600
cctgtgtgtg ttttcccttg ccttgtttcc tgccttatat cttgtatttc gacttattac    6660
agagttgagg gttcttgctt aatttagatc aagtataaaa tttgtatgac ttcaagtctc    6720
attttatctg aaaggttttt ttctcattta atctgatgtg gcattttcgt catctgaagc    6780
atgagtgaca agttgggaat gatgtggtga tttagaatgc agtattggcc aagtccaagt    6840
tgtcaactta agcgtctgtt taccaaagac cgggaacagg ggcccaaaca tgtccagtcc    6900
tcttcttccc tctgctggaa cctttgggga cactcaaggg tacagtttga cactgatctg    6960
gtccatgagg ctgcccagag aaagcactgc ttctgtatgt ctcttgtggt attggaacaa    7020
```

```
taaacccgta caacctgcaa aaaaaaaaaa aaaaaa                              7056
```

<210> SEQ ID NO 37
<211> LENGTH: 1084
<212> TYPE: DNA
<213> ORGANISM: Homo sapiens

<400> SEQUENCE: 37

```
cacacccacg gcagacacgc acgcacccgg gcgccgaagg gaaagccgcg tctcgccctc      60
ccgccccgcc gtcggtcctg tctcagtccc tcagcagagc gggaaagcgg aggccggagc     120
cgtgacctct gacccgtgg ttatgcggag ccgccgcatt ccttagcgat cgcggggcag      180
ccgccgctgc cgccgtgggc gactgacgca gcgcgggcgc gtggagccgc cgccgcccct    240
ccccaccgc cgctctcgcg ccagccggtc ccgcgtgcc cgccccttct ccccggccgc      300
acccgagacc tcgcgcgccg ccgctgccac gcgcccccc caccgccgcc gccgcccag      360
ccccgcgcca ccgccccagc ccgcccagcc cggaggtccc gcgtggagct gccgccgccg    420
ccggggagaa ggatgaagga caaacagaag aagaagaagg agcgcacgtg ggccgaggcc    480
gcgcgcctgg tattagaaaa ctactcggat gctccaatga caccaaaaca gattctgcag    540
gtcatagagg cagaaggact aaaggaaatg agaagtggga cttcccctct cgcatgcctc    600
aatgctatgc tacattccaa ttcaagagga ggagaggggt tgttttataa actgcctggc    660
cgaatcagcc ttttcacgct caaggtgtga gccactgcac caggcccctt catcttaatt    720
ttaatatatc tttgaataaa caccattgta tgaacctgct gtaagcttgg gagtggtctg    780
ttagtctaca gcttgtgtct gagatgtgct aattgaatat ttgctcagta cctcatctta    840
actgcctttg gctttatgtt gcttatcctt catagtatct tgttcattgg ccttttacat    900
ccataggcat cacttctctg atattcgttg tgctctttta atggattaat ggtttgcttg    960
gttggttcct ctagttagac tgtaaactcc ttgagagcag agtctgtatt ttattaatta   1020
cccacagtac taggtacata gttgccttca ataaatatat atttaatgaa aaaaaaaaaa   1080
aaaa                                                                1084
```

<210> SEQ ID NO 38
<211> LENGTH: 2723
<212> TYPE: DNA
<213> ORGANISM: Homo sapiens

<400> SEQUENCE: 38

```
ggcggcgctt gattgggctg ggggggccaa ataaaagcga tggcgattgg gctgccgcgt      60
ttggcgctcg gtccggtcgc gtccgacacc cggtgggact cagaaggcag tggagccccg    120
gcggcggcgg cggcggcgcg cggggcgac gcgcgggaac aacgcgagtc ggcgcgcggg    180
acgaagaata atcatgggcc agactgggaa gaaatctgag aagggaccag tttgttggcg    240
gaagcgtgta aaatcagagt acatgcgact gagacagctc aagaggttca gacgagctga    300
tgaagtaaag agtatgttta gttccaatcg tcagaaaatt ttggaaagaa cggaaatctt    360
aaaccaagaa tggaaacagc gaaggataca gcctgtgcac atcctgactt ctgtgagctc    420
attgcgcggg actaggagt gttcggtgac cagtgacttg gattttccaa cacaagtcat    480
cccattaaag actctgaatg cagttgcttc agtacccata atgtattctt ggtctcccct    540
acagcagaat tttatggtgg aagatgaaac tgttttacat aacattcctt atatgggaga    600
tgaagtttta gatcaggatg gtactttcat tgaagaacta ataaaaaatt atgatgggaa    660
```

| | |
|---|---|
| agtacacggg gatagagaat gtgggtttat aaatgatgaa attttttgtgg agttggtgaa | 720 |
| tgcccttggt caatataatg atgatgacga tgatgatgat ggagacgatc ctgaagaaag | 780 |
| agaagaaaag cagaaagatc tggaggatca ccgagatgat aaagaaagcc gcccacctcg | 840 |
| gaaatttcct tctgataaaa tttttgaagc catttcctca atgtttccag ataagggcac | 900 |
| agcagaagaa ctaaaggaaa aatataaaga actcaccgaa cagcagctcc caggcgcact | 960 |
| tcctcctgaa tgtaccccca acatagatgg accaaatgct aaatctgttc agagagagca | 1020 |
| aagcttacac tcctttcata cgcttttctg taggcgatgt tttaaatatg actgcttcct | 1080 |
| acatcgtaag tgcaattatt cttttcatgc aacacccaac acttataagc ggaagaacac | 1140 |
| agaaacagct ctagacaaca aaccttgtgg accacagtgt taccagcatt tggagggagc | 1200 |
| aaaggagttt gctgctgctc tcaccgctga gcggataaag accccaccaa acgtccagg | 1260 |
| aggccgcaga agaggacggc ttcccaataa cagtagcagg cccagcaccc ccaccattaa | 1320 |
| tgtgctggaa tcaaaggata cagacagtga tagggaagca gggactgaaa cgggggggaga | 1380 |
| gaacaatgat aaagaagaag aagagaagaa agatgaaact tcgagctcct ctgaagcaaa | 1440 |
| ttctcggtgt caaacaccaa taaagatgaa gccaaatatt gaacctcctg agaatgtgga | 1500 |
| gtggagtggt gctgaagcct caatgtttag agtcctcatt ggcacttact atgacaattt | 1560 |
| ctgtgccatt gctaggttaa ttgggaccaa aacatgtaga caggtgtatg agtttagagt | 1620 |
| caaagaatct agcatcatag ctccagctcc cgctgaggat gtggatactc ctccaaggaa | 1680 |
| aaagaagagg aaacaccggt tgtgggctgc acactgcaga agatacagc tgaaaaagga | 1740 |
| cggctcctct aaccatgttt acaactatca accctgtgat catccacggc agccttgtga | 1800 |
| cagttcgtgc ccttgtgtga tagcacaaaa ttttttgtgaa aagttttgtc aatgtagttc | 1860 |
| agagtgtcaa aaccgctttc cgggatgccg ctgcaaagca cagtgcaaca ccaagcagtg | 1920 |
| cccgtgctac ctggctgtcc gagagtgtga ccctgacctc tgtcttactt gtggagccgc | 1980 |
| tgaccattgg gacagtaaaa atgtgtcctg caagaactgc agtattcagc ggggctccaa | 2040 |
| aaagcatcta ttgctggcac catctgacgt ggcaggctgg gggattttta tcaaagatcc | 2100 |
| tgtgcagaaa aatgaattca tctcagaata ctgtggagag attatttctc aagatgaagc | 2160 |
| tgacagaaga gggaaagtgt atgataaata catgtgcagc tttctgttca acttgaacaa | 2220 |
| tgattttgtg gtggatgcaa cccgcaaggg taacaaaatt cgttttgcaa atcattcggt | 2280 |
| aaatccaaac tgctatgcaa aagttatgat ggttaacggt gatcacagga taggtatttt | 2340 |
| tgccaagaga gccatccaga ctggcgaaga gctgttttttt gattacagat acagccaggc | 2400 |
| tgatgccctg aagtatgtcg gcatcgaaag agaaatggaa atcccttgac atctgctacc | 2460 |
| tcctccccccc tcctctgaaa cagctgcctt agcttcagga acctcgagta ctgtgggcaa | 2520 |
| tttagaaaaa gaacatgcag tttgaaattc tgaatttgca aagtactgta agaataattt | 2580 |
| atagtaatga gtttaaaaat caacttttta ttgccttctc accagctgca aagtgttttg | 2640 |
| taccagtgaa tttttgcaat aatgcagtat ggtacatttt tcaactttga ataaagaata | 2700 |
| cttgaacttg tccttgttga atc | 2723 |

<210> SEQ ID NO 39
<211> LENGTH: 2591
<212> TYPE: DNA
<213> ORGANISM: Homo sapiens

<400> SEQUENCE: 39

| | |
|---|---|
| cggaggtgcg cgggcgcggg cgagcagggt ctccgggtgg gcggcggcga cgccccgcgc | 60 |

```
aggctggagg ccgccgaggc tcgccatgcc gggagaactc taactccccc atggagtcgg    120
ccgacttcta cgaggcggag ccgcggcccc cgatgagcag ccacctgcag agccccccgc    180
acgcgcccag cagcgccgcc ttcggctttc cccggggcgc gggccccgcg cagcctcccg    240
ccccacctgc cgccccggag ccgctgggcg gcatctgcga gcacgagacg tccatcgaca    300
tcagcgccta catcgacccg gccgccttca cgacgagtt cctggccgac ctgttccagc    360
acagccggca gcaggagaag gccaaggcgg ccgtgggccc cacgggcggc ggcggcggcg    420
gcgactttga ctacccgggc gcgcccgcgg gccccggcgg cgccgtcatg cccgggggag    480
cgcacgggcc cccgcccggc tacgctgcg cggccgccgg ctacctggac ggcaggctgg    540
agcccctgta cgagcgcgtc ggggcgccgg cgctgcggcc gctggtgatc aagcaggagc    600
cccgcgagga ggatgaagcc aagcagctgg cgctggccgg cctcttccct taccagccgc    660
cgccgccgcc gccgccctcg caccgcacc cgcaccgcc gccgcgcac ctggccgccc    720
cgcacctgca gttccagatc gcgcactgcg gccagaccac catgcacctg cagcccggtc    780
accccacgcc gccgcccacg cccgtgccca gcccgcaccc cgcgcccgcg ctcggtgccg    840
ccggcctgcc gggccctggc agcgcgctca aggggctggg cgccgcgcac cccgacctcc    900
gcgcgagtgg cggcagcggc gcgggcaagg ccaagaagtc ggtggacaag aacagcaacg    960
agtaccgggt gcggcgcgag cgcaacaaca tcgcggtgcg caagagccgc gacaaggcca   1020
agcagcgcaa cgtggagacg cagcagaagg tgctggagct gaccagtgac aatgaccgcc   1080
tgcgcaagcg ggtggaacag ctgagccgcg aactggacac gctgcggggc atcttccgcc   1140
agctgccaga gagctccttg gtcaaggcca tgggcaactg cgcgtgaggc gcgcggctgt   1200
gggaccgccc tgggccagcc tccggcgggg acccagggag tggtttgggg tcgccggatc   1260
tcgaggcttg cccgagccgt gcgagccagg actaggagat tccggtgcct cctgaaagcc   1320
tggcctgctc cgcgtgtccc ctcccttcct ctgcgccgga cttggtgcgt ctaagatgag   1380
ggggccaggc ggtggcttct ccctgcgagg aggggagaat tcttggggct gagctgggag   1440
cccggcaact ctagtattta ggataaccca tgccttgga aatgcaaact caccgctcca   1500
atgcctactg agtaggggga gcaaatcgtg ccttgtcatt ttatttggag gtttcctgcc   1560
tccttcccga ggctacagca gaccccccatg agagaaggag gggagcaggc ccgtggcagg   1620
aggagggctc agggagctga gatcccgaca agcccgccag ccccagccgc tcctccacgc   1680
ctgtccttag aaaggggtgg aaacataggg acttggggct tggaacctaa ggttgttccc   1740
ctagttctac atgaaggtgg agggtctcta gttccacgcc tctcccacct ccctccgcac   1800
acaccccacc ccagcctgct ataggctggg cttccccttg gggcggaact cactgcgatg   1860
ggggtcacca ggtgaccagt gggagcccccc accccgagtc acaccagaaa gctaggtcgt   1920
gggtcagctc tgaggatgta taccctggt gggagaggga gacctagaga tctggctgtg   1980
gggcgggcat gggggggtgaa gggccactgg gaccctcagc cttgtttgta ctgtatgcct   2040
tcagcattgc ctaggaacac gaagcacgat cagtccatcc cagagggacc ggagttatga   2100
caagctttcc aaatatttg ctttatcagc cgatatcaac acttgtatct ggcctctgtg   2160
ccccagcagt gccttgtgca atgtgaatgt gcgcgtctct gctaaaccac cattttattt   2220
ggtttttgtt ttgttttggt tttgctcgga tacttgccaa aatgagactc tccgtcggca   2280
gctgggggaa gggtctgaga ctccctttcc ttttggtttt gggattactt ttgatcctgg   2340
gggaccaatg aggtgagggg ggttctcctt tgccctcagc tttccccagc cctccggcc   2400
```

| | |
|---|---:|
| tgggctgccc acaaggcttg tcccccagag gccctggctc ctggtcggga agggaggtgg | 2460 |
| cctcccgcca acgcatcact ggggctggga gcagggaagg acggcttggt tctcttcttt | 2520 |
| tggggagaac gtagagtctc actctagatg ttttatgtat tatatctata atataaacat | 2580 |
| atcaaagtca a | 2591 |

<210> SEQ ID NO 40
<211> LENGTH: 4454
<212> TYPE: DNA
<213> ORGANISM: Homo sapiens

<400> SEQUENCE: 40

| | |
|---|---:|
| gaaacgtccc gtgtgggagg ggcgggtctg ggtgcggcct gccgcatgac tcgtggttcg | 60 |
| gaggcccacg tggccgggc ggggactcag gcgcctgggg cgccgactga ttacgtagcg | 120 |
| ggcggggccg gaagtgccgc tccttggtgg gggctgttca tggcggttcc ggggtctcca | 180 |
| acatttttcc cggctgtggt cctaaatctg tccaaagcag aggcagtgga gcttgaggtt | 240 |
| cttgctggtg tgaaatgact gagtacaaac tggtggtggt tggagcaggt ggtgttggga | 300 |
| aaagcgcact gacaatccag ctaatccaga accactttgt agatgaatat gatcccacca | 360 |
| tagaggattc ttacagaaaa caagtggtta tagatggtga aacctgtttg ttggacatac | 420 |
| tggatacagc tggacaagaa gagtacagtg ccatgagaga ccaatacatg aggacaggcg | 480 |
| aaggcttcct ctgtgtattt gccatcaata atagcaagtc atttgcggat attaacctct | 540 |
| acagggagca gattaagcga gtaaaagact cggatgatgt acctatggtg ctagtgggaa | 600 |
| acaagtgtga tttgccaaca aggacagttg atacaaaaca agcccacgaa ctggccaaga | 660 |
| gttacgggat tccattcatt gaaacctcag ccaagaccag acagggtgtt gaagatgctt | 720 |
| tttacacact ggtaagagaa atacgccagt accgaatgaa aaaactcaac agcagtgatg | 780 |
| atgggactca gggttgtatg ggattgccat gtgtggtgat gtaacaagat acttttaaag | 840 |
| ttttgtcaga aaagccac tttcaagctg cactgacacc ctggtcctga cttccctgga | 900 |
| ggagaagtat tcctgttgct gtcttcagtc tcacagagaa gctcctgcta cttccccagc | 960 |
| tctcagtagt ttagtacaat aatctctatt tgagaagttc tcagaataac tacctcctca | 1020 |
| cttggctgtc tgaccagaga atgcacctct tgttactccc tgttattttt ctgccctggg | 1080 |
| ttcttccaca gcacaaacac acctctgcca ccccaggttt ttcatctgaa aagcagttca | 1140 |
| tgtctgaaac agagaaccaa accgcaaacg tgaaattcta ttgaaaacag tgtcttgagc | 1200 |
| tctaaagtag caactgctgg tgatttttt tttcttttta ctgttgaact tagaactatg | 1260 |
| ctaattttg gagaaatgtc ataaattact gttttgccaa gaatatagtt attattgctg | 1320 |
| tttggtttgt ttataatgtt atcggctcta ttctctaaac tggcatctgc tctagattca | 1380 |
| taaatacaaa aatgaatact gaattttgag tctatcctag tcttcacaac tttgacgtaa | 1440 |
| ttaaatccaa ctttcacagt gaagtgcctt tttcctagaa gtggtttgta gacttccttt | 1500 |
| ataatatttc agtggaatag atgtctcaaa aatccttatg catgaaatga atgtctgaga | 1560 |
| tacgtctgtg acttatctac cattgaagga aagctatatc tatttgagag cagatgccat | 1620 |
| tttgtacatg tatgaaattg gttttccaga ggcctgtttt ggggctttcc caggagaaag | 1680 |
| atgaaactga agcacatga ataatttcac ttaataattt ttacctaatc tccactttt | 1740 |
| tcataggtta ctacctatac aatgtatgta atttgtttcc cctagcttac tgataaacct | 1800 |
| aatattcaat gaacttccat ttgtattcaa atttgtgtca taccagaaag ctctacattt | 1860 |
| gcagatgttc aaatattgta aaactttggt gcattgttat ttaatagctg tgatcagtga | 1920 |

-continued

```
ttttcaaacc tcaaatatag tatattaaca aattacattt tcactgtata tcatggtatc   1980
ttaatgatgt atataattgc cttcaatccc cttctcaccc caccctctac agcttccccc   2040
acagcaatag gggcttgatt atttcagttg agtaaagcat ggtgctaatg gaccagggtc   2100
acagtttcaa aacttgaaca atccagttag catcacagag aaagaaattc ttctgcattt   2160
gctcattgca ccagtaactc cagctagtaa ttttgctagg tagctgcagt tagccctgca   2220
aggaaagaag aggtcagtta gcacaaaccc tttaccatga ctggaaaact cagtatcacg   2280
tatttaaaca ttttttttc ttttagccat gtagaaactc taaattaagc caatattctc    2340
atttgagaat gaggatgtct cagctgagaa acgttttaaa ttctctttat tcataatgtt   2400
ctttgaaggg tttaaaacaa gatgttgata aatctaagct gatgagtttg ctcaaaacag   2460
gaagttgaaa ttgttgagac aggaatggaa aatataatta attgataacct atgaggattt   2520 ggaggcttgg cattttaatt tgcagataat accctggtaa ttctcatgaa aaatagactt   2580
ggataacttt tgataaaaga ctaattccaa aatggccact ttgttcctgt ctttaatatc   2640
taaatactta ctgaggtcct ccatcttcta tattatgaat tttcatttat taagcaaatg   2700
tcatattacc ttgaaattca gaagagaaga aacatatact gtgtccagag tataatgaac   2760
ctgcagagtt gtgcttctta ctgctaattc tgggagcttt cacagtactg tcatcatttg   2820
taaatggaaa ttctgctttt ctgtttctgc tccttctgga gcagtgctac tctgtaatt   2880 tcctgaggct tatcacctca gtcatttctt ttttaaatgt ctgtgactgg cagtgattct   2940
ttttcttaaa aatctattaa atttgatgtc aaattaggga gaaagatagt tactcatctt   3000
gggctcttgt gccaatagcc cttgtatgta tgtacttaga gttttccaag tatgttctaa   3060
gcacagaagt ttctaaatgg ggccaaaatt cagacttgag tatgttcttt gaataccta    3120 agaagttaca attagccggg catggtggcc cgtgcctgta gtcccagcta cttgagaggc   3180
tgaggcagga gaatcacttc aacccaggag gtggaggtta cagtgagcag agatcgtgcc   3240
actgcactcc agcctgggtg acaagagaga cttgtctcca aaaaaaagt tacacctagg   3300 tgtgaatttt ggcacaaagg agtgacaaac ttatagttaa aagctgaata acttcagtgt   3360
ggtataaaac gtggttttta ggctatgttt gtgattgctg aaaagaattc tagtttacct   3420
caaaatcctt ctctttcccc aaattaagtg cctggccagc tgtcataaat tacatattcc   3480
ttttggtttt tttaaaggtt acatgttcaa gagtgaaaat aagatgttct gtctgaaggc   3540
taccatgccg gatctgtaaa tgaacctgtt aaatgctgta tttgctccaa cggcttacta   3600
tagaatgtta cttaatacaa tatcatactt attacaattt ttactatagg agtgtaatag   3660
gtaaaattaa tctctatttt agtgggccca tgtttagtct ttcaccatcc tttaaactgc   3720
tgtgaatttt tttgtcatga cttgaaagca aggatagaga aacactttag agatatgtgg   3780
ggttttttta ccattccaga gcttgtgagc ataatcatat ttgctttata tttatagtca   3840
tgaactccta agttggcagc tacaaccaag aaccaaaaaa tggtgcgttc tgcttcttgt   3900
aattcatctc tgctaataaa ttataagaag caaggaaaat tagggaaaat attttatttg   3960
gatggtttct ataaacaagg gactataatt cttgtacatt atttttcatc tttgctgttt   4020
ctttgagcag tctaatgtgc cacacaatta tctaaggtat ttgttttcta taagaattgt   4080
tttaaaagta ttcttgttac cagagtagtt gtattatatt tcaaaacgta agatgatttt   4140
taaaagcctg agtactgacc taagatgaa ttgtatgaac tctgctctgg agggagggga    4200
ggatgtccgt ggaagttgta agacttttat ttttttgtgc catcaaatat aggtaaaaat   4260
```

```
aattgtgcaa ttctgctgtt taaacaggaa ctattggcct ccttggccct aaatggaagg    4320
gccgatattt taagttgatt attttattgt aaattaatcc aacctagttc tttttaattt    4380
ggttgaatgt ttttcttgt taaatgatgt ttaaaaaata aaaactggaa gttcttggct     4440
tagtcataat tctt                                                      4454

<210> SEQ ID NO 41
<211> LENGTH: 5436
<212> TYPE: DNA
<213> ORGANISM: Homo sapiens

<400> SEQUENCE: 41
ggccgcggcg gcggaggcag cagcggcggc ggcagtggcg gcggcgaagg tggcggcggc      60
tcggccagta ctcccggccc ccgccatttc ggactgggag cgagcgcggc gcaggcactg     120
aaggcggcgg cggggccaga ggctcagcgg ctcccaggtg cgggagagag gcctgctgaa     180
aatgactgaa tataaacttg tggtagttgg agctggtggc gtaggcaaga gtgccttgac     240
gatacagcta attcagaatc attttgtgga cgaatatgat ccaacaatag aggattccta    300
caggaagcaa gtagtaattg atggagaaac ctgtctcttg gatattctcg acacagcagg    360
tcaagaggag tacagtgcaa tgagggacca gtacatgagg actggggagg ctttctttg     420 tgtatttgcc ataaataata ctaaatcatt tgaagatatt caccattata gagaacaaat    480
taaaagagtt aaggactctg aagatgtacc tatggtccta gtaggaaata atgtgatttt    540
gccttctaga acagtagaca caaaacaggc tcaggactta gcaagaagtt atggaattcc    600
ttttattgaa acatcagcaa agacaagaca gagagtggag gatgcttttt atacattggt    660
gagggagatc cgacaataca gattgaaaaa aatcagcaaa gaagaaaaga ctcctggctg    720
tgtgaaaatt aaaaaatgca ttataatgta atctgggtgt tgatgatgcc ttctatacat    780
tagttcgaga aattcgaaaa cataaagaaa agatgagcaa agatggtaaa aagaagaaaa    840
agaagtcaaa gacaaagtgt gtaattatgt aaatacaatt tgtactttt tcttaaggca    900 tactagtaca agtggtaatt tttgtacatt acactaaatt attagcatt gttttagcat     960 tacctaattt ttttcctgct ccatgcagac tgttagcttt taccttaaat gcttatttta   1020
aaatgacagt ggaagttttt ttttcctcta agtgccagta ttcccagagt tttggttttt   1080
gaactagcaa tgcctgtgaa aaagaaactg aataccaag atttctgtct tggggtttt    1140 ggtgcatgca gttgattact tcttattttt cttaccaatt gtgaatgttg gtgtgaaaca   1200
aattaatgaa gcttttgaat catccctatt ctgtgttta tctagtcaca taaatggatt    1260
aattactaat ttcagttgag accttctaat tggttttac tgaaacattg agggaacaca    1320
aatttatggg cttcctgatg atgattcttc taggcatcat gtcctatagt ttgtcatccc   1380
tgatgaatgt aaagttacac tgttcacaaa ggttttgtct cctttccact gctattagtc   1440
atggtcactc tccccaaaat attatatttt ttctataaaa agaaaaaaat ggaaaaaaat   1500
tacaaggcaa tggaaactat tataaggcca tttccttttc acattagata aattactata   1560
aagactccta atagcttttc ctgttaaggc agacccagta tgaaatgggg attattatag   1620
caaccatttt ggggctatat ttacatgcta ctaaattttt ataataattg aaaagatttt   1680
aacaagtata aaaaattctc ataggaatta aatgtagtct ccctgtgtca gactgctctt   1740
tcatagtata actttaaatc ttttcttcaa cttgagtctt tgaagatagt tttaattctg   1800
cttgtgacat taaagattta tttgggccag ttatagctta ttaggtgttg aagagaccaa   1860
ggttgcaagg ccaggccctg tgtgaacctt tgagctttca tagagagttt cacagcatgg   1920
```

```
actgtgtccc cacggtcatc cagtgttgtc atgcattggt tagtcaaaat ggggagggac    1980
tagggcagtt tggatagctc aacaagatac aatctcactc tgtggtggtc ctgctgacaa    2040
atcaagagca ttgcttttgt ttcttaagaa aacaaactct ttttaaaaa ttacttttaa     2100 atattaactc aaaagttgag attttggggt ggtggtgtgc caagacatta attttttttt    2160
taaacaatga agtgaaaaag tttacaatc tctaggtttg gctagttctc ttaacactgg     2220
ttaaattaac attgcataaa cacttttcaa gtctgatcca tatttaataa tgctttaaaa    2280
taaaaataaa aacaatcctt ttgataaatt taaaatgtta cttattttaa aataaatgaa    2340
gtgagatggc atggtgaggt gaaagtatca ctggactagg aagaaggtga cttaggttct    2400
agataggtgt cttttaggac tctgattttg aggacatcac ttactatcca tttcttcatg    2460
ttaaaagaag tcatctcaaa ctcttagttt ttttttttta caactatgta atttatattc    2520
catttacata aggatacact tatttgtcaa gctcagcaca atctgtaaat ttttaaccta    2580
tgttacacca tcttcagtgc cagtcttggg caaaattgtg caagaggtga agtttatatt    2640
tgaatatcca ttctcgtttt aggactcttc ttccatatta gtgtcatctt gcctccctac    2700
cttccacatg ccccatgact tgatgcagtt ttaatacttg taattcccct aaccataaga    2760
tttactgctg ctgtggatat ctccatgaag ttttcccact gagtcacatc agaaatgccc    2820
tacatcttat ttcctcaggg ctcaagagaa tctgacagat accataaagg gatttgacct    2880
aatcactaat tttcaggtgg tggctgatgc tttgaacatc tctttgctgc ccaatccatt    2940
agcgacagta ggattttttca aacctggtat gaatagacag aaccctatcc agtggaagga   3000
gaatttaata aagatagtgc tgaaagaatt ccttaggtaa tctataacta ggactactcc    3060
tggtaacagt aatacattcc attgttttag taaccagaaa tcttcatgca atgaaaaata    3120
ctttaattca tgaagcttac ttttttttt tggtgtcaga gtctcgctct tgtcacccag    3180
gctggaatgc agtggcgcca tctcagctca ctgcaacctc catctcccag gttcaagcga    3240
ttctcgtgcc tcggcctcct gagtagctgg gattacaggc gtgtgccact acactcaact    3300 aattttttgta ttttttaggag agacggggtt tcaccctgtt ggccaggctg gtctcgaact   3360
cctgacctca agtgattcac ccaccttggc ctcataaacc tgttttgcag aactcattta    3420
ttcagcaaat atttattgag tgcctaccag atgccagtca ccgcacaagg cactgggtat    3480
atggtatccc caaacaagag acataatccc ggtccttagg tagtgctagt gtggtctgta    3540
atatcttact aaggcctttg gtatacgacc cagagataac acgatgcgta ttttagtttt    3600
gcaaagaagg ggtttggtct ctgtgccagc tctataattg ttttgctacg attccactga    3660
aactcttcga tcaagctact ttatgtaaat cacttcattg ttttaaagga ataaacttga    3720
ttatattgtt ttttatttg gcataactgt gattcttta ggacaattac tgtacacatt     3780
aaggtgtatg tcagatattc atattgaccc aaatgtgtaa tattccagtt ttctctgcat    3840
aagtaattaa aatatactta aaattaata gttttatctg ggtacaaata aacaggtgcc    3900
tgaactagtt cacagacaag gaaacttcta tgtaaaaatc actatgattt ctgaattgct    3960
atgtgaaact acagatcttt ggaacactgt ttaggtaggg tgttaagact tacacagtac    4020
ctcgtttcta cacagagaaa gaaatggcca tacttcagga actgcagtgc ttatgagggg    4080
atatttaggc ctcttgaatt tttgatgtag atgggcattt ttttaaggta gtggttaatt    4140 accctttatgt gaactttgaa tggtttaaca aaagatttgt ttttgtagag attttaaagg    4200
gggagaattc tagaaataaa tgttacctaa ttattacagc cttaaagaca aaaatccttg    4260
```

```
ttgaagtttt tttaaaaaaa gctaaattac atagacttag gcattaacat gtttgtggaa    4320
gaatatagca gacgtatatt gtatcatttg agtgaatgtt cccaagtagg cattctaggc    4380
tctatttaac tgagtcacac tgcataggaa tttagaacct aacttttata ggttatcaaa    4440
actgttgtca ccattgcaca attttgtcct aatatataca tagaaacttt gtggggcatg    4500
ttaagttaca gtttgcacaa gttcatctca tttgtattcc attgattttt tttttcttct    4560 aaacatttt tcttcaaaca gtatataact tttttaggg gatttttttt tagacagcaa      4620
aaactatctg aagatttcca tttgtcaaaa agtaatgatt tcttgataat tgtgtagtaa    4680
tgttttttag aacccagcag ttaccttaaa gctgaattta tatttagtaa cttctgtgtt    4740
aatactggat agcatgaatt ctgcattgag aaactgaata gctgtcataa aatgaaactt    4800
tctttctaaa gaaagatact cacatgagtt cttgaagaat agtcataact agattaagat    4860
ctgtgtttta gtttaatagt ttgaagtgcc tgtttgggat aatgataggt aatttagatg    4920
aatttagggg aaaaaaaagt tatctgcaga tatgttgagg gcccatctct cccccccacac   4980 ccccacagag ctaactgggt tacagtgttt tatccgaaag tttccaattc cactgtcttg    5040
tgttttcatg ttgaaaatac ttttgcattt ttcctttgag tgccaatttc ttactagtac    5100
tatttcttaa tgtaacatgt ttacctgaaa tgtattttaa ctattttgt atagtgtaaa     5160 ctgaaacatg cacattttgt acattgtgct ttcttttgtg ggacatatgc agtgtgatcc    5220
agttgttttc catcatttgg ttgcgctgac ctaggaatgt tggtcatatc aaacattaaa    5280
aatgaccact cttttaattg aaattaactt ttaaatgttt ataggagtat gtgctgtgaa    5340
gtgatctaaa atttgtaata tttttgtcat gaactgtact actcctaatt attgtaatgt    5400
aataaaaata gttacagtga caaaaaaaaa aaaaaa                              5436
```

<210> SEQ ID NO 42
<211> LENGTH: 9784
<212> TYPE: DNA
<213> ORGANISM: Homo sapiens

<400> SEQUENCE: 42

```
aggcctggac gtattctcgc gacatttgcc ggtcgcccgg cttgcactgc ggcgtttccc      60
gcgcgggcta cctcagttct cgggcgtacg gcgcggcctg tcctactgcc gccggcgccg    120
cggccgtcat ggggttcctg aaactgattg agattgagaa cttttaagtcg tacaagggtc    180 gacagattat cggaccattt cagaggttca ccgccatcat tggacccaat ggctctggta    240
agtcaaatct catggatgcc atcagctttg tgctaggtga aaaaaccagc aacctgcggg    300
taaagaccct gcgggacctg atccatggag ctcctgtggg caagccagct gccaaccggg    360
cctttgtcag catggtctac tctgaggagg gtgctgagga ccgtaccttt gcccgtgtca    420
ttgtaggagg ttcttctgag tacaagatca acaacaaagt ggtccaacta catgagtaca    480
gtgaggaatt agagaagttg ggcattctca tcaaagctcg taacttcctc gttttccagg    540
gtgctgtgga atctattgcc atgaagaacc ccaaagagag gacagctcta tttgaagaga    600
ttagtcgttc tggggagctg gcgcaggagt atgacaagcg aaagaaggaa atggtgaagg    660
ctgaagagga cacacagttt aattaccatc gcaagaaaaa tattgcggct gaacgcaagg    720
aagcaaagca ggagaaagaa gaggctgacc ggtaccagcg cctgaaggat gaggtagtac    780
gggctcaggt acagctgcag ctctttaagc tttaccataa tgaagtggaa attgagaagc    840
tcaacaagga actggcctca aagaacaagg agatcgagaa ggacaagaag cgtatggaca    900
aggtggagga tgaactgaag gagaagaaga aggagctggg caaaatgatg cgggagcagc    960
```

-continued

```
agcagattga gaaggagatc aaggagaagg actcagaatt gaaccagaag cggcctcagt   1020
acatcaaagc caaggagaac acctcccaca aaatcaagaa gctggaagca gccaagaagt   1080
ctctgcagaa tgctcagaag cactacaaga agcgtaaagg tgacatggat gagctggaga   1140
aggagatgct gtcagtggag aaggctcggc aggagtttga agaacggatg gaagaagaga   1200
gtcagagtca gggcagagat ttgacgttgg aggagaatca ggtgaagaaa taccaccggt   1260
tgaaagaaga agccagcaag agagcagcta ccctggccca ggagctggag aaattcaatc   1320
gagaccagaa agctgaccag gaccgtctgg atctggaaga acggaagaaa gtagagacag   1380
aggccaagat caagcaaaag ctgcgggaaa ttgaagagaa tcagaagcgg attgagaaac   1440
tggaggaata catcaccact agcaagcagt ccctagaaga gcagaagaag ctagagggg   1500 agctgacaga ggaggtggag atggccaagc ggcgtattga tgaaatcaat aaggagctga   1560
accaggtgat ggagcagcta ggggatgccc gcatcgaccg ccaggagagc agccgccagc   1620
agcgaaaggc agagataatg gaaagcatca agcgccttta ccctggctct gtgtacggcc   1680
gcctcattga cctatgccag cccacacaaa agaagtatca gattgctgta accaaggttt   1740
tgggcaagaa catggatgcc attattgtgg actcggagaa gacaggccgg gactgtattc   1800
agtatatcaa ggagcagcgt ggggagcctg agaccttctt gcctcttgac tacctggagg   1860
tgaagcctac agatgagaaa ctccgggagc tgaaggggc caagctagtg attgatgtga   1920
ttcgctatga gccacctcat atcaaaaagg ccctgcagta tgcttgtggc aatgcccttg   1980
tctgtgacaa cgtggaagat gcccgccgca ttgcctttgg aggccaccag cgccacaaga   2040
cagtggcact ggatggaacc ctattccaga agtcaggagt gatctctggt ggggccagtg   2100
acctgaaggc caaggcacgg cgctgggatg agaaagcagt agacaagttg aaagagaaga   2160
aggagcgctt gacagaggag ctgaaagagc agatgaaggc aaaacggaaa gaggcagagc   2220
tgcgtcaggt gcagtctcag gcccatggac tgcagatgcg gctcaagtac tcccagagtg   2280
acctagaaca gaccaagaca cgacatctag ccctgaatct gcaggaaaaa tccaagctgg   2340
agagtgagct agccaacttt gggcctcgca ttaatgatat caagaggatc attcagagcc   2400
gagagaggga aatgaaagac ttgaaggaga agatgaacca ggtagaggat gaggtgtttg   2460
aagagttttg tcgggagatt ggtgtgcgca acatccggga gtttgaggaa gaaaaggtga   2520
aacggcagaa tgaaatcgcc aagaagcgtt tggagtttga gaatcagaag actcgcttgg   2580
gcattcagtt ggattttgaa aagaaccaac tgaaggagga ccaagataaa gtacacatgt   2640
gggagcagac agtgaaaaaa gatgaaaatg agatagaaaa gctcaaaaag gaggaacaaa   2700
gacacatgaa gatcatagat gagaccatgg ctcagctaca agacctgaag aatcagcatc   2760
tggccaagaa gtcggaagtg aatgacaaga atcatgagat ggaggagatt cgtaagaaac   2820 tcggggcgc caacaaggaa atgacccatt tacagaagga ggtgacagcc attgagacca   2880
agcttgaaca gaagcgcagt gaccgtcaca acttgctaca ggcctgtaag atgcaggaca   2940
ttaagttgcc actgtcaaaa ggcaccatgg atgatattag tcaggaagag ggtagctccc   3000 aggggggagga ctcagtgagt ggttcacaga gaatttccag tatctatgca cgagaggccc   3060
tcattgagat tgactacggt gatctgtgtg aggatctgaa ggatgcccag gctgaggaag   3120
agatcaagca agagatgaac acactgcagc agaagctgaa tgagcagcag agtgtgcttc   3180
agcgtattgc cgcccccaac atgaaggcca tggaaaagct ggaaagtgtc cgagacaagt   3240
tccaggagac ctcagatgag tttgaagcag cccgaaagcg agcaaagaag gccaagcagg   3300
```

```
cattcgaaca gatcaagaag gagcgctttg accgcttcaa tgcttgtttt gaatctgtgg   3360
ctaccaacat tgatgagatc tataaggccc tgtcccgcaa tagcagtgcc caggcattcc   3420
tgggccctga aaccctgaa gagccctact tggatggcat caactacaac tgtgtggctc    3480
```

```
cattcgaaca gatcaagaag gagcgctttg accgcttcaa tgcttgtttt gaatctgtgg   3360
ctaccaacat tgatgagatc tataaggccc tgtcccgcaa tagcagtgcc caggcattcc   3420
tgggccctga gaaccctgaa gagccctact tggatggcat caactacaac tgtgtggctc   3480
ctgggaaacg cttccggcct atggacaact tgtcaggcgg ggagaagaca gtggcagctc   3540
tggccctgct ctttgccatc cacagctaca agccagcccc cttcttcgtc ctggatgaga   3600
ttgatgctgc cttggataac accaacattg gcaaggtggc aaattacatc aaggagcagt   3660
cgacttgcaa cttccaggcc atcgtcatct ctctcaagga ggagttctac accaaggccg   3720
agagcctcat tggagtctat cctgagcaag gggactgtgt gatcagcaaa gtcctgacct   3780
tcgacctcac caagtaccca gatgccaacc ccaaccccaa tgagcagtag cagtattttt   3840
gccctcccgc cctgtctgga tccctaagct gtccctctcc caatctctgg atatttgact   3900
cccaaccttc ccctacctc ctggcccttt ttggtgtagt catgggattt aggcactgct   3960
aatcaagcat gaagaggaac agaggtgatg ttaggtctgg agcaaaaatt cctgaacgac   4020
agggagtatt ctggcctctg aaaggaggtg ctgagctgaa cagggccatc tgttcatcac   4080
acacaccccc ttcctcccc tcatcaccca taatcgtggg cccettgggc ctcttgccca   4140
ctgtgtgtgt gggtatgtat gtgtgtatgt atgtatccgc atgtgtgcat gtgagtatgt   4200
ttgcaaaata ataaaggata ttggagacct gttttagaag gagcctaggc tgaatttgat   4260
tccaagagag cttaggatga cagcaccct gagctgggca aagtactca ggacctcata    4320
ggagtcttag gcagttacct gaaactgcct tcattcactc atttgtgtat tcattcattt   4380
atgtattcat cagacacata ccgaacaccc tctatttgtc aggctctgtg cttggaatac   4440
agagttgaat cagacatgat ctctaccctc ctagtaagga gatacagtgg gttcatgaat   4500
gactatagtt agctgaatgt catatgtact ttgaatttga gaagtgggtg atccctccta   4560
ggcttcctgg aggtcacatt taagctagac cttgacaaat tggtaggatt tggtcaggca   4620
ctaggagtgg agcatgagct ctggggacag acagttatgg gttctggtcc cacttttat   4680
cacttactag ttgtttgacc ttgggcaagt catttgacct tctgtgcctc agtttcctca   4740
tctgtaaaat ggggctaaca atattaccta cctcatagga tttaatgatg tcaagctcct   4800
cactggaggc cttatccctt cgtggagccc actaggtgcc gacccctcag aatataaccc   4860
tcatgcctgg accctgaga gcttctgatc ccagctatta gggacagaag aagcctccaa    4920
atctggaagg tgctgaatgc cctgctgact gggaaagttt cagggcactg atggggtcta   4980
cctggtaagc ggagggcctg aggaaacctg tagcttcaat catgtctggt aaccgggtgc   5040
ctgagcccca atctgggttg tgaggaaata ggggagaggt atcctgggcc acatcccagc   5100
ctaacacctg tgaggttcat tttaggaact aacctcatta gctataagga tcatgcagag   5160
gcagcaaagc cgggtgcgat gagctcagcc tttactcatt cacatacacc atcacacttt   5220
aattccaatc tgtatattgc ttttaaaag ttaagtccat tctaattacc caaatatgca   5280
tgaattcatt ctccttttga gaagttagat tgttaaagat agtctcattc agctaccaac   5340
cactccttga tccttccctt cttagtggct gttgtttgtt gtacttccgt ttagactttg   5400
ttttaatgct tgtacgtaca tatgtgaact cattggaaat attgtgtgtt taatgcaaat   5460
gatatattga attgtttagc aatttgtttt ctttgcttaa cgatgttttt gagatctgtg   5520
catgttactt aatgtagctc aatccatctt ctgtaattgc tgtatagatt gtcatcatat   5580
gattaccaca ttttacttac gcatttcttt tgtgatggac attaagactg ttttaggtt    5640
ttgctattac aaaatactac acaggagcat cactatgcct gtgtgaaagt atatgtatga   5700
```

```
aagtttacct agggttgatt cctagaagtg gaattgcaaa gtcataggat atttatatat    5760
tggtttttaa taatacttcc aaattgccct cctgtactat ttactcagta tttttcttga    5820
ggttgatctg aggtctaaca ttgttatcct atatcatttt catcccaagt agtgatatct    5880
gtgaaatcac aggtttgatg tgtgctaatt atgtattctt ctaatacata ttaaaagaca    5940
taactatcaa aacaaaataa atttgtctgt tttcaaccaa agaagtcacg taccactggt    6000
ggtactgtgt gccataattt ggcaaatgct ggcctttatg gacgagcaca attcgggggt    6060
cagacctggt tcaaattcta gctgtagaaa cttgtgcaag ttacttcacc tctgagccta    6120
agtttccaca tctgtaaaag gagataataa acacctacct tgcagtagtg aagcaaagag    6180
aaaattaaat atatatgaag caatttggct ggcatctaga tcattcacag ccctttaaag    6240
gtcacctttg ctgttctccc cactttacag ataaggaaac tgaggcccaa aaaggtttga    6300
acccaggtct tccaagtcat tcaagtgctt tctccactgt acaggtggtt atcaaccttg    6360
gctgcgcatc agaatcgttt gtaaagcttt ttcttttcc tttttaaaaa gtaaagcaat    6420
atatacacag gtaaaaaaat aaaatagtac agaagggctt ataatgagaa gcagcagttc    6480
cctgcttgca cccccacatc caaggatgt ggagctcttt aaaaataaat tgctctggtc    6540
ccacctctgg aaatctgatt cagccagcat ggataataac ccagataact aaccectacc    6600
tcacaggata aaaaggatta catgagatgc cttaggctaa ggccctggca cacaggaaca    6660
catgtgctac aaaggagctt tggggactta agtcctgagg atccaggagg tgaggtgact    6720
tgtccaagat tccactggtt tagtggcaga gcctagactt ccactcggat ctatttagtg    6780
cttgccccct gctctctcct gtcgtgcccc accacctcct ggcatcacag ggcaaccgtt    6840
gtcaaggcta tgctcacggg aggctgggca ccacagtgtt tccaagagca agctggatcc    6900
gagtagattc cctagggctt gttggaggaa ctagtttgac tcccttatac tgtggacgca    6960
gtagccttgc tgtagggagt tgaagagtac tccacaacag tatcttaagt ttaactgggc    7020
acttccctct ggaaatcaca gtgttgtgca ccaggaacac aaagatgagt caaatcttta    7080
tcctgccttt gaggagctca ctgtttagtt ggggaaacca tttgtaaaac agccattaac    7140
catacagtgt gatcaacact gacaggagca caggaaaaac atctagctta tgtgaagatt    7200
cagagaaggc atcctgtagt ctaggtggtg atacctgaac tgagtcttga gggacgggta    7260
ggaattagcc agttgaggaa gtagaaggaa tttccagata ttggaaacag tatgcatgaa    7320
gacatgaagg caagaaacag caaaacaaat actgaagcat gaagattcct ggggtggggg    7380
gaaagcagca agaaaggta gagaggaacc agattggaag agggtcgtaa atgcatggct    7440
acagaattca gatttgtttt gtaggacagt gtggttccca aactggctgt ataccacaaa    7500
caggtacggc attctgggcc ccggccccta aacattcat taagtctggg gtgaagattt    7560
ggaatcttga atgcttataa aggttaccac atgactaggg tacagccaga tttggaaacc    7620
atagcttgaa ggcagtgagg gagccatgaa atggttttta ataggggac tccagatcag    7680
atgtgaactt aacctgtttc tggctggcta gccaaccagc atggaaaaca gattaggtta    7740
gatgttcatg ctgtatgtgc ccgtgcctgt agcttccctg ttaatcagct tcttacacta    7800
ctatatttgc ttattttgtc tctgaataag ctttaggcac cacaagggtg ggcctgggga    7860
tattttgctt accagtatag cccctgcaaa aaagcacagt gcctgacaca aaacaggcac    7920
ccagtaaagt ttttgaatga atgaatgcat gagtgaatcc atttgtgaga gagcgaatgg    7980
agatgacaag attagctagg agactggaaa aagaccagga ggcctgcact agggcaaagg    8040
```

```
ccagtaggaa tagattggag gtgttaaggt gtgaactgtt aaggtaagat gataacttaa    8100
tgactgatta ttggatgtgg agggtgactg agaggataga atgagtaccc atgaatagcc    8160
atgattccta ccctgtccca gtcatctctt tccttatcca tctctgaaac aatctgctta    8220
catcctcctc agcaactgga attcctcaag ttagttagac attctgtgtg ctgtgtggtc    8280
tctcactgcc cccccactcc ccaccccctcc acaagccatt gattcattca tccagttcaa    8340
taaatcttgg ctaagcacct ccagtgtgca gtaaggctct tccaagccag gactctgact    8400
ccctctttcc tacctcaaga gatgtttttg agggctttcc caggtaagag tcacatctct    8460
tatacaataa cttatagtga gatacccaga atgtcagact tgtaagggaa gactgcccaa    8520 acccccttctg aggtcctcag aggggaatta acttcctaag gtccgactgc taggaagtgt    8580
tggagccaga aatggaagct aggtttcctt tctatgtcat ctctggagtc ttgatcttga    8640
tctatcccat tgtagatcag gacaggcaga ggtggtcagg gagaaggtgg gacttaggtt    8700
gaaccttgaa ggtcaatgta ttggacaggt caaacaagat ggttgccaat tacactgccc    8760
ccttctggaa acccttagca aacctgccat gcttgcagtc ccttctaagg ggtttcctta    8820
gcataagttg ccatgctctg taccatgtga cctcacaatc ctggccacag atagctagat    8880
gtggatagtg tctggttcaa gggcaaccaa tctctaggct ggccagtggc ctgttagctg    8940
gactggcata aggacttcac cttacagggg tggcatgtat caaatggcaa atgtatgaaa    9000
caaccagatc tttcagggag gcagaatgtg agctattcag aagaagtgaa cgttaattag    9060
aatttaatga ggcattagtg gtggtggatg aggggtggcc agaaactaaa cagcaaaagc    9120
aaagagaaag ctgcagaaac cataagtaag cagaggtcat gagacatttg tataatgaga    9180
tcacggagcc acagggtggc agaagccatg aagcagcaag gcaacaatgg gctagaagcc    9240
atgaagcaat aggagccacg aggaacagaa accgtgagac aaaactgact atgagatcca    9300
caaagcagca gaaggcttga atagataaga tcatgagaca gtagaagcga tgagactgca    9360
agaaccacaa ggtagccaga accatgtggc aacatggcaa caggaatgga agaggcagca    9420
ggagctacaa tgcagaaaag ccatggatta ataggaactg aagcgccggg agccatgaag    9480
ctgcaggacc catgaggcag aaaaagccat gggctagcat cgagggggc agaaagaagt    9540 tagtcagtag cagtaggagg agtataaata cagccagaaa ggagttgagt caccaatttg    9600
ggaagcacta gagaagggag caacagatgc ctgcagctga gggggtgaca agataagcca    9660
ggctctagag ctgctttgga tcatgaacca ttttcaagtt tctgttcttc catgaggctg    9720
cctgtgtagc tgttcttgtc ttccttattt ccctgtgaat gctttaataa atccccatca    9780
ctaa                                                                 9784
```

<210> SEQ ID NO 43  
<211> LENGTH: 4131  
<212> TYPE: DNA  
<213> ORGANISM: Homo sapiens

<400> SEQUENCE: 43

```
ttttgtttgg ctgaggggag cgagcggcgc tttgggggag gggtcgcgta ggcgcctcac      60
ctgaccctgc ggccgtgcgg ttgctgctcc ggggcaggtc tccttccagg ccaggggccc     120
ggaatcatgt acataaagca ggtgattatc cagggttttc gaagttacag agatcaaaca     180
attgtagatc ccttcagttc aaaacataat gtgattgtgg gcagaaatgg atctggaaaa     240
agtaactttt tttatgcaat tcagtttgtt ctcagtgatg agtttagtca tcttcgtcca     300
gaacagcggt tggctttatt gcatgaaggt actggtcctc gtgttatttc tgcttttgtg     360
```

```
gagattattt ttgataattc agacaaccgg ttaccaatcg ataaagagga agtttcactt      420
cgaagagtta ttggtgccaa aaaggatcag tatttcttag acaagaagat ggtcacgaaa      480
aatgatgtga tgaacctcct tgaaagcgct ggttttctc gaagcaatcc ttattatatt       540
gttaaacaag gaaagatcaa ccagatggca acagcaccag attctcagag attaaagcta      600
ttaagagaag tagctggtac tagagtgtat gacgaacgaa aggaagaaag catctcctta      660
atgaaagaaa cagagggcaa acgggaaaaa atcaatgagt tgttaaaata cattgaagag      720
agattacata ctctagagga agaaaaggaa gaactagctc agtatcagaa gtgggataaa      780
atgagacgag ccctggaata taccatttac aatcaggaac ttaacgagac tcgtgccaaa      840
cttgatgagc tttctgctaa gcgagagact agtggagaaa aatccagaca attaagagat      900
gctcagcagg atgcaagaga taaaatggag gatatcgaac gccaagttag agaattgaaa      960
acaaaaattt cagctatgaa agaagaaaaa gaacagctta gtgctgaaag acaagagcag     1020
attaagcaga ggactaagtt ggagcttaaa gccaaggatt tacaagatga actagcaggc     1080
aatagtgaac aaaggaaacg tttattaaaa gagaggcaga agctgcttga aaaaatagaa     1140
gaaaagcaga agaactggc agaaacagaa cccaaattca acagtgtgaa agagaaagaa      1200
gaacgaggaa ttgctagatt ggctcaagct acccaggaaa gaacggatct ttatgcaaag     1260
cagggtcgag gaagccagtt tacatcaaaa gaagaaaggg ataagtggat taaaaaggaa     1320
ctcaagtctt tagatcaggc tattaatgac aagaaaagac agattgctgc tatacataag     1380
gatttggaag acactgaagc aaataaagag aaaaatctgg agcagtataa taactggac     1440 caggatctta atgaagtcaa agctcgagta gaagaactgg acagaaaata ttacgaagta     1500
aaaaataaga agatgaact acaaagtgaa agaaactact tgtggagaga agagaatgca      1560
gaacagcaag cacttgctgc taaaagagaa gatcttgaaa agaagcaaca acttcttaga     1620
gcagcaacag gaaaggccat tttaaatgga atagacagca taaacaaagt gctagaccac     1680
ttccgtcgaa aaggaataaa ccagcatgtt caaaatggct atcatggtat tgtaatgaat     1740
aactttgaat gtgaaccagc tttctacaca tgcgtggaag tcactgctgg aaacaggtta     1800
ttttatcaca ttgttgattc agatgaagtc agcacgaaga ttttaatgga gtttaataaa     1860
atgaatcttc ctggagaggt tacttttctg cctcttaaca agttagatgt cagggataca     1920
gcctatcctg aaaccaatga tgctattcct atgatcagca aactgaggta caatcccaga     1980
tttgacaaag cttcaaaca tgtgtttgga aagactctta tttgtcgtag catggaagtt      2040
tcaacccagc tggcccgtgc tttcactatg gactgtatta ctttggaagg tgaccaagtc     2100
agccatcggg gtgctctaac tgggggttat tatgacacaa ggaagtctcg acttgaattg     2160
caaaaagatg ttagaaaagc agaagaagaa ctaggtgaac ttgaagcaaa gctcaatgaa     2220
aacctgcgca gaaatattga aaggattaat aatgaaattg atcagttgat gaaccaaatg     2280
caacagatcg agacccagca aaggaaattt aaagcatcta gagatagcat attatcagaa     2340
atgaagatgc taaagagaa gaggcagcag tcagagaaaa ccttcatgcc taagcaacgt     2400
agcttacaga gtttggaggc aagcttgcat gctatggagt ctaccagaga gtcattgaaa     2460
gcagaactgg gaactgattt gctttctcaa ctgagtttgg aagatcagaa gagagtagat     2520
gcactgaatg atgagattcg tcaacttcag caggaaaaca gacagttgct aaatgaaaga     2580
attaaattag aaggtattat tactcgagta gagacttatc tcaatgagaa tctgagaaaa     2640
cgcttggacc aagtagaaca ggaacttaat gagctgagag agacagaagg gggtactgtt     2700
```

```
ctcacagcca caacatcaga acttgaagcc atcaataaaa gagtaaaaga cactatggca    2760
cgatcagaag atttggacaa ttccattgat aaaacagaag ctggaattaa ggagcttcag    2820
aagagtatgg agcgctggaa aaatatggaa aaagaacata tggatgctat aaatcatgat    2880
actaaagaac tggaaaagat gacaaatcgg caaggcatgc tattgaagaa gaaagaagag    2940
tgtatgaaga aaattcgaga acttggatca cttccccagg aagcatttga aaagtaccag    3000
acactgagcc tcaaacagtt gtttcgaaaa cttgagcagt gcaacacaga attaaagaag    3060
tacagccatg ttaacaaaaa ggctttggat cagtttgtaa atttctccga gcagaaagaa    3120
aagttaataa agcgtcaaga agagttagat aggggttaca aatcaatcat ggaactgatg    3180
aatgtacttg aacttcggaa atatgaagct attcagttaa ctttcaaaca ggtatctaag    3240
aacttcagtg aagtattcca gaagttagta cctggtggca aagctacttt ggtgatgaag    3300
aaaggagatg tggagggcag tcagtctcaa gatgaaggag aagggagtgg tgagagtgag    3360
aggggttctg gctcacaaag cagtgtccca tcagttgacc agtttactgg agttggaatt    3420
agggtgtcat ttacaggaaa acaaggtgaa atgagagaaa tgcaacagct ttcaggtgga    3480
cagaaatcct tggtagccct tgctctgatt tttgccattc agaaatgtga cccggctcca    3540
ttttacttgt ttgatgaaat tgaccaggct ctggatgctc agcacagaaa ggctgtgtca    3600
gatatgatta tggaacttgc tgtacatgct cagtttatta caactacttt taggcctgaa    3660
ctgcttgagt cagctgacaa attctatggt gtaaagttca gaaataaggt tagtcatatt    3720
gatgtgatca cagcagagat ggccaaagac tttgtagaag atgataccac acatggttaa    3780
ttggaaaata ctacctactg gtttgggaga tgtatatagt aatatgattc tcatacccag    3840
gaactgtaaa tttaaaccta aatatttggc caatagtttt cagacttaaa gcatcatagt    3900 cctttatat ttgtctttgt attttataag atactctgta atgtcatgtt tgtactgata    3960
gtttaagaat ttaatttcct gtacaacttt ttgtaaaatg ttctgctcct attttaaatg    4020
ttttgaaaca tgctaaatat tctttcctaa ttattttatc acttatacta ccttttttat    4080
agcttcaatt aaataatcgg ttttatgact aaaaaaaaaa aaaaaaaaa a              4131
```

<210> SEQ ID NO 44
<211> LENGTH: 6277
<212> TYPE: DNA
<213> ORGANISM: Homo sapiens

<400> SEQUENCE: 44

```
aaaaaaaaaa aaaaaaaaag aaaaaaaacc ccgccggatc cgaccgccac tttcaaaacc      60
ccccaccgct ctagaaccgc gggagcttcc gtccctgagt agaattcgag ggtgtaaaga     120
agaggaaggg gaaaaatatc ttgtaccagc ccaggggtga agaagccccc ggcctgagaa     180
agaaggagga gtgggggagg cgaacagtct cgttgctgcc tctgtgtacg ctgaggggg      240 aggtggccac cgagtactaa attcacttgg gaataaaaga aaacataag aaaattataa      300 gagaaaggaa ttgtcttaga agaagaagg caagccacca ttttacccac gtaaatatat      360
gaatatattt ctgacattga ggtgttccag aagatgataa agaaatgata gcagctccag     420
aaataccaac tgattttaat ctactacagg agtcagaaac acattttct tctgacacag      480 attttgaaga tatcgaagga aaaaaccaaa agcaaggcaa aggcaaaact tgtaaaaaag     540
gcaaaagggg cccagcagaa aagggcaaag gtggaaatgg aggaggaaaa cctccttctg     600
gtccaaaccg aatgaatggt catcaccaac agaatggagt ggaaaacatg atgttgtttg     660
aagttgttaa aatgggcaag agtgctatgc agtcggtggt agatgattgg atagaatcat     720
```

```
acaagcatga ccgagatata gcacttcttg accttatcaa cttttttatt cagtgttcag    780
gctgtaaagg agttgtcaca gcagaaatgt ttagacatat gcagaactct gagataattc    840
gaaaaatgac tgaagaattc gatgaggata gtggagatta ccacttacc atggctggtc     900
ctcagtggaa gaagttcaaa tccagttttt gtgaattcat tggcgtgtta gtacggcaat    960
gtcaatatag tatcatatat gatgagtata tgatggatac agtcatttca cttcttacag   1020
gattgtctga ctcacaagtc agagcatttc gacatacaag caccctggca gctatgaagt   1080
tgatgacagc tttggtgaat gtggcactaa atcttagcat taatatggat aatacacaaa   1140
gacaatatga agcagaacgg aataaaatga ttggaaaacg agccaatgag aggctagaac   1200
tcctgctaca aaagcggaaa gagcttcagg aaaatcaaga tgaaatagaa atatgatga    1260
atgcaatatt taaggagtg tttgtacata gataccgtga tgcgatagct gaaattcgag    1320
ctatttgcat tgaagagatt ggcatttgga tgaagatgta tagtgatgcc tttcttaatg   1380
acagttattt aaaatatgtt ggttggacta tgcatgataa gcaaggtgaa gtaagactca   1440
aatgtcttac tgctctacaa gggctttatt ataacaaaga gcttaattcc aaactggaac   1500
tttttaccag tcggttcaag gatagaattg tgtctatgac ccttgacaaa gaatatgatg   1560
ttgcagtaca agcaataaaa ttactcactc ttgttttaca gagtagtgaa gaagttctca   1620
ctgcagaaga ttgtgaaaat gtctatcatc tggtttattc agctcaccgg ccagtagcag   1680
tagcagctgg agaatttctc tacaaaaagc tcttcagtcg tagagatcca gaggaggatg   1740
gaatgatgaa aagaagagga agacaaggtc caaatgccaa ccttgttaag acattggttt   1800
ttttctttct agaaagtgag ttacatgagc atgcagcata ccttgtggat agcatgtggg   1860
actgtgctac tgagctgctg aaagactggg aatgtatgaa tagcttgtta ctggaagagc   1920
cacttagtgg agaggaagca ctaacagata ggcaagagag tgctctgatt gaaataatgc   1980
tttgtaccat tagacaagcg gctgaatgtc atcctcccgt gggaagaggg acaggaaaaa   2040
gggtgcttac agcaaaggag aagaagacac agttggatga taggacaaaa atcactgagc   2100
ttttttgccgt ggcccttcct cagttattag caaaatactc tgtagatgca gaaaaggtga   2160
ctaacttgtt gcagttgcct cagtactttg atttggaaat atataccact ggacgattag   2220
aaaagcattt ggatgcctta ttgcgacaga tccggaatat tgtagagaag cacacagata   2280
cagatgtttt ggaagcatgt tctaaaactt accatgcact ctgtaatgaa gagttcacaa   2340
tcttcaacag agtagatatt tcaagaagtc aactgataga tgaattggca gataaattta   2400
accggcttct tgaagatttt ctgcaagagg gtgaagaacc tgatgaagat gatgcatatc   2460
aggtattgtc aacattgaag aggatcactg cttttcataa tgcccatgac ctttcaaagt   2520
gggatttatt tgcttgtaat tacaaactct gaaaactgg aatcgaaaat ggagacatgc    2580
ctgagcagat tgttattcac gcactgcagt gtactcacta tgtaatcctt tggcaacttg   2640
ctaagataac tgaaagcagc tctacaaagg aggacttgct gcgttaaag aaacaaatga    2700
gagtattttg tcagatatgt caacattacc tgaccaacgt gaatactact gttaaggaac   2760
aggccttcac tattctgtgt gatattttga tgatcttcag ccatcagatt atgtcaggag   2820
ggcgtgacat gttagagcca ttagtgtata ccccctgattc ttcattgcag tctgagttgc   2880
tcagctttat tttggatcat gtcttcattg aacaggatga tgataataat agtgcagatg   2940
gtcagcaaga ggatgaagcc agtaaaattg aagctctgca caagagaaga aatttacttg   3000
cagcattttg taagctaatt gtatatactg tggtggagat gaatacagct gcagatatct   3060
```

```
tcaaacagta tatgaagtat tataatgact atggagatat catcaaagaa acaatgagta      3120
aaacaaggca gatagacaaa attcagtgtg ctaagaccct tattctcagt ctgcaacagc      3180
tttttaatga aatgatacaa gaaatggct ataattttga tagatcatcc tctacattta       3240
gtggcataaa agaacttgct cgacgttttg ctttaacttt tggacttgat cagttgaaaa      3300
caagagaagc cattgccatg ctacacaaag atggcataga atttgctttt aaagagccta      3360
atccgcaagg ggagagccat ccacctttaa atttggcatt tcttgatatt ctgagtgaat      3420
tttcttctaa actacttcga caagacaaaa gaacagtgta tgtttacttg gaaaagttca      3480
tgacctttca gatgtcactc cgaagagagg atgtgtggct tccactgatg tcttaccgaa      3540
attctttgct agctggtggt gatgatgaca ccatgtcagt cattagtgga atcagcagcc      3600
gggggtcaac agtacggagt aaaaaatcaa aaccatctac aggaaaacgg aaagtggttg      3660
agggcatgca gctttcactc actgaagaaa gtagtagtag tgacagtatg tggttaagca      3720
gagaacaaac actgcacacc cctgttatga tgcagacacc acaactcacc tccactatta      3780
tgagagagcc caaaagatta cggcctgagg atagcttcat gagtgtttat ccaatgcaga      3840
ctgaacatca tcaaacacct cttgattata acacgcaggt aacatggatg ttagctcaaa      3900
gacaacaaga ggaagcaagg caacagcagg agagagcagc aatgagctat gttaaactgc      3960
gaactaatct tcagcatgcc attcggcgtg cacaagcct aatggaagat gatgaagagc       4020
caattgtgga agatgttatg atgtcctcag aagggaggat tgaggatctt aatgagggaa      4080
tggattttga caccatggat atagatttgc caccatcaaa gaacagacga gagagaacag      4140
aactgaagcc tgatttcttt gatccagctt caattatgga tgaatcagtt cttggagtgt      4200
caatgtttta ataccagtac acaattaaat ctgtggtgaa gtcattttct aagtggaaga      4260
ggaaatttta aagtgtggta gatacagtga aattctgtac agattttttct ctaaggagaa     4320 tatgacatgc ttatgcttac caagatcaag tgcattgagg ggcagttttg tttgcctgaa      4380
taaacgtaaa ggacaagtaa acaatttgat gataagctac agttttttctt agaaagtaaa    4440 tatttatttt atgcgctgtt agttggcttt tgaatcgatt atttcatgct ttttttttaaa    4500 aaaaaaaaa aacaaaataa caatctgaag aggcatttgg tacagatatg aattctctta      4560 cattttattta ctggttgtac taaataatga tgacctctgc tggatttctg tttacatcca     4620
gaaaacaatt ttaaggatgt atttattccc ctaccctgaa gaaagtgtag gatagaattg      4680 ttttagcat tctaaattta aatgcttaaa acgtcaatca acaaaacttt gttttaaata       4740
ttgtaattgt gggagaaaagt aaacttataa gcagaacttt tacaatttttt tcatctaaaa    4800 gtatttaag atattttaa aatccaagag cttctctata cttttcagaa atatccagat        4860
gcagtgaact gccagaaggt aaccagtctc aaacatgctt atcccattat caaccctgaa      4920
agtttgcttg tcctttaaga taaaaatgta atgttgtgat attccttcca gtaatgccac      4980
tgtattttgt ctccaaataa aagaagctta ttgtagtatg tttgcagaaa aattctaaac      5040
aaaaattata cagcttatta gagtgtggga atagggatct aaattttaaa taaaattata      5100
tatatatata aattggtgct gattttataa ttgcgcagtt tgtttagttt tttcttactt      5160
ttaaattcca acttaaaatt atgaggtttc agaaatatat tgaaagttta acaatgttta      5220
aaaatagaaa agcatgagtg ttcatgcttt aaaatgattt ttaaatttgt attttatatt      5280
gttttatcta tctgtctttg caagcagtct tcaggttaaa gatacttcta acaggttaca      5340 gtacattttcc tctgtatgta aattagatgg gataatagaa ttcataaccc ataatattct     5400
ttgaaagcta agctttaaac ttcatttttat gtcctttcac aaataaatta gtttaaaaca     5460
```

| | | | | |
|---|---|---|---|---|
| gaaagtggct | acttgccatt | ttgacatcaa | ctcattttgc | gaggcttagg cagctagaca | 5520 |
| tcgtttaaaa | caaatatta | acttatatta | catgtgtatc | tatctattgt cagtcgtctc | 5580 |
| tcagttcttg | aggtatatta | ttttaatcat | tccatgcctt | aatatgcttg caatacaaga | 5640 |
| atatcttcag | atgggtgaat | accaaaaggc | tttcagtttt | tagtcagaaa tcaagcattg | 5700 |
| ggctgtggta | gccaaaaacc | ataggttagc | taaaagatc | atgatacaat tattttatta | 5760 |
| agtcatggtt | aataacaaat | gaatccagac | ttgtctaaca | gattttccat caacaaatat | 5820 |
| tgttatgtgc | aaagtattg | cctatgttgt | tttacacacc | actgcattaa ctagaactgc | 5880 |
| tgagaggact | gtatatatga | ttttaaacct | aagttgattt | tttttctcac tcttgaaagg | 5940 |
| agtacttctt | tgtgaaagca | gttcttacag | ctttgttttc | aaccagctaa aaatgtttta | 6000 |
| tatattactc | taacctgttg | tcctccacat | tctattgtcc | taattgtact gttttctgat | 6060 |
| ttgtatttat | gtcttgagac | agtaacttt | tgaataaaaa | taaacctaca gtatgttgta | 6120 |
| tgttttctct | tgtactcaaa | gggggagggt | ggctataaat | ggtttgcaaa tttatatcta | 6180 |
| ttatcacatc | ttttaatgtg | tttggggaat | aatttataga | gaataccatc agtttatatt | 6240 |
| tttaataaat | catatgtatt | tacaatgaaa | aaaaaaa | | 6277 |

<210> SEQ ID NO 45
<211> LENGTH: 3773
<212> TYPE: DNA
<213> ORGANISM: Homo sapiens

<400> SEQUENCE: 45

| | | | | |
|---|---|---|---|---|
| aggcgcacag | gtaccatttt | gaccgtaaac | atcctgccga | tttgaaccga ggatttgggc | 60 |
| ggcaggaaga | gccgcggcgt | aacggcagcc | atcttgtttg | tttgagtgaa tcggaaagga | 120 |
| ggcgccggct | gtggcggcgg | cgggagctgc | tcggaagcta | cacctcgcaa gggctccccc | 180 |
| ctttccccac | cccctccccc | gaccctttc | ccctccccgg | gccacccagc ccgcccaact | 240 |
| cccagcggag | agcaaggttt | tcttctgttt | tcatagccag | ccagaacaat gttctacgca | 300 |
| cattttgttc | tcagtaaaag | agggcctctg | gccaaaattt | ggctagcggc ccattgggat | 360 |
| aagaagctaa | ccaaagccca | tgtgttcgag | tgtaatttag | agagcagcgt ggagagtatc | 420 |
| atctcaccaa | aggtgaaaat | ggcattacgg | acatcaggac | atctcttact gggagtagtt | 480 |
| cgaatctatc | acaggaaagc | caaataccctt | cttgcagact | gtaatgaagc attcattaag | 540 |
| ataaagatgg | cttttcggcc | aggtgtggtt | gacctgcctg | aggaaaatcg ggaagcagct | 600 |
| tataatgcca | ttactttacc | tgaagaattt | catgactttg | atcagccact gcctgactta | 660 |
| gatgacatcg | atgtggccca | gcagttcagc | ttgaatcaga | gtagagtgga agagataacc | 720 |
| atgagagaag | aagttgggaa | catcagtatt | ttacaagaaa | atgattttgg tgattttgga | 780 |
| atggatgatc | gtgagataat | gagagaaggc | agtgcttttg | aggatgacga catgttagta | 840 |
| agcactacta | cttctaacct | cctattagag | tctgaacaga | gcaccagcaa tctgaatgag | 900 |
| aaaattaacc | atttagaata | tgaagatcaa | tataaggatg | ataattttgg agaaggaaat | 960 |
| gatggtggaa | tattagatga | caaacttatt | agtaataatg | atggcggtat ctttgatgat | 1020 |
| cccccctgccc | tctctgaggc | aggggtgatg | ttgccagagc | agcctgcaca tgacgatatg | 1080 |
| gatgaggatg | ataatgtatc | aatgggtggg | cctgatagtc | ctgattcagt ggatccgtt | 1140 |
| gaaccaatgc | caaccatgac | tgatcaaaca | acacttgttc | caaatgagga agaagcattt | 1200 |
| gcattggagc | ctattgatat | aactgttaaa | gaaacaaaag | ccaagaggaa gaggaagcta | 1260 |

```
attgttgaca gtgtcaaaga gttggatagc aagacaatta gagcccaact tagtgattat    1320
tcagatattg ttactacttt ggatctggca ccgcccacca agaaattgat gatgtggaaa    1380
gagacaggag gagtagaaaa actgttttct ttacctgctc agcctttgtg aataacaga     1440
ctactgaagc tctttacacg ctgtcttaca ccgcttgtac cagaagacct tagaaaaagg   1500
aggaaaggag gagaggcaga taatttggat gaattcctca agaatttga aaatccagag    1560
gttcctagag aggaccagca acagcagcat cagcagcgtg atgttatcga tgagcccatt   1620
attgaagagc caagccgcct ccaggagtca gtgatggagg ccagcagaac aaacatagat   1680
gagtcagcta tgcctccacc accacctcag ggagttaagc gaaaagctgg acaaattgac   1740
ccagagcctg tgatgcctcc tcagcaggta gagcagatgg aaataccacc tgtagagctt   1800
cccccagaag aacctccaaa tatctgtcag ctaataccag agttagaact tctgccagaa   1860
aaagagaagg agaagagaa ggaaaaagaa gatgatgaag aggaagagga tgaagatgca    1920
tcaggggcg atcaagatca ggaagaaaga agatggaaca aaggactca gcagatgctt     1980
catggtcttc agcgtgctct tgctaaaact ggagctgaat ctatcagttt gcttgagtta   2040
tgtcgaaata cgaacagaaa acaagctgcc gcaaagttct acagcttctt ggttcttaaa   2100
aagcagcaag ctattgagct gacacaggaa gaaccgtaca gtgacatcat cgcaacacct   2160
ggaccaaggt tccatattat ataaggagct agaagcatta tagctagtgt ttgattcact   2220
agtgcttaca aattgccccc atgtgtaggg gacacagaac cctttgagaa aacttagatt   2280
tttgtctgta caaagtcttt gccttttttcc ttcttcattt ttttccagta cattaaattt   2340
gtcaatttca tctttgaggg aaactgatta gatgggttgt gtttgtgttc tgatggagaa   2400
aacagcaccc caaggactca gaagatgatt ttaacagttc agaacagatg tgtgcaatat   2460
tggtgcatgt aataatgttg agtggcagtc aaagtcatg attttttatct tagttcttca   2520
ttactgcatt gaaaggaaa acctgtctga gaaaatgcct gacagtttaa tttaaaacta   2580
tggtgtaagt ctttgacaag aaaaaaaaac aaacaaacac ttctttccat cagtaacact   2640
ggcaatcttc ctgttaacca ctctccttag ggatggtatc tgaaacaaca atggtcaccc   2700
tcttgagatt cgttttaagt gtaattccat aatgagcaga ggtgtacgcg aaattgtgtt   2760
atgactgata gccttcagct acaaaaagat aggactgacc tggtttaaag tgttctatt t   2820
tgtaaatcat tccatttgag tctttctgat gaacttggct atactgaaat ctgttatttt   2880
agtgaggctc caaaatgagc aaagctaggc ctgattagag tagagtgact attaaaaaac   2940
ataactttct aggagctata aatcaaagtt ttaaaaagat gtttggatat atttgagtat   3000
tccgatcatg aaaacagaaa ttgccctgcc tactacaagg acagactgat gggaaattat   3060
gcacctggtc aacttagctt ttaagcagac gatgctgtaa aaactaacgg cttctctgat   3120
atttattgta agttttagta ctgatctcct tttccagtgc tgcacactcc tggtttggaa   3180
ctttaatagc gttgcaacga aatcctatat ccagtttcct gtaatttaat tgaagaaaaa   3240
tacatccaaa taaagacttt attattaaca gaccagatag catcagaaat catgtgactg   3300
ttatgattat cagaatgtct taacttttta gggcaaagtt aacactgaaa gttctagctt   3360
aagtgttgaa acttttgtgg gaaaaaaaaa tcacttttga aactcagact tcagtgtata   3420
cccaataatt taaaattatg tgaaatgttt taaatttgtg aactcgtaat tactgtttta   3480
atgattcagt tcttcagag tggtaattgt ataaaattgc tattgcagct ttacattcaa    3540
tatgatgtgc ctgtaaacca aggagttttc cccgttgta aaaagacatt gtagataatt    3600
gaatgtttga ttttagaaag gtcattagtt tcttgttaca cattttgtta gtctggtttt   3660
```

<210> SEQ ID NO 46
<211> LENGTH: 2235
<212> TYPE: DNA
<213> ORGANISM: Homo sapiens

<400> SEQUENCE: 46

```
tgttgcttat cgggtttaat attgttcttg aaaatagttg atgctatgtt atgtataact   3720
tttctaataa aagttgtgtt ataagctgta aaaaaaaaa aaaaaaaaa aaa            3773 gtggagcaga agccacagtc acttcctgaa ggcagcggcc ccagctcggg tcccactcat     60
cccatggccc atcacctgcc tgcagccatg gagagccatc aggacttccg gagcatcaaa    120
gcaaagttcc aggcctctca gccggagccc agcgacctgc caaaaaaacc tccgaagcct    180
gagtttggta aactgaagaa gttctcccag cctgagctaa gcgagcaccc caagaaggcc    240
ccgctgcctg agtttggtgc agtgtccttg aagccccgc cgcctgaggt cactgacctc     300
cccaagaagc cccgccgcc tgaggtcact gacctcccca agaagccccc gccgcctgag    360
gtcactgacc tccccaagaa gccccgccg cctgaggtca ctgacctccc caagaagccg    420
tccaaactgg agttgagtga cctctccaag aagttcccac agctggggc cactccgttt    480
ccaaggaagc ccctgcagcc tgaggtcggt gaggcccctt tgaaggcctc gctgccggag    540
cctggtgcgc cggccggaa acccctgcag cccgacgaac tcagtcaccc cgccagaccc    600
ccctccgaac ccaaatccgg cgcattcccc aggaagctct ggcaacccga ggccggtgag    660
gctaccccga ggtccccgca gcctgagttg agtacctttc caagaagcc tgcgcagcct    720
gagttcaacg tgtaccccaa aaagcctccg cagcctcagg tcggtggcct ccctaagaag    780
tccgtgccgc agcctgagtt cagcgaggcc gctcagactc ccctctggaa gcctcagtcc    840
agcgagccga agcgcgactc cagcgccttt cccaaaaagg cctcccagcc tccgctgagt    900
gactttccca gaagcctcc gcagcctgag cttggggacc tcaccaggac ctcctcagag    960
cccgaagtca gcgtgcttcc caagaggccg cggccggccg aattcaaagc gctctccaag   1020
aagcccccgc agcccgagct gggcggcctc cccaggacct cctcagagcc cgagttcaac   1080
tcactcccca ggaagctgct gcagccggag cgccgggggc caccccgcaa gttctcacag   1140
cctgagccca gcgctgtcct caagagacac ccgcagcctg agttcttcgg tgatctccct   1200
cgaaagcctc cactcccag ctccgcttcc gagagctcac tgcctgcggc cgtgccggc   1260
ttcagctccc ggcacccgct cagccctggg tttggagcgg ctgggacacc ccgctggagg   1320
tcaggaggcc tggttcacag tggaggggcc aggccaggcc tcagacccag ccatccaccc   1380
cggcggaggc ctctgccccc tgccagcagc ctgggacacc ctccagccaa gccccgctg    1440
cccccgggc ccgtggatat gcagagcttt cggagaccct ctgcagcatc catagatcta   1500
cggaggaccc gctcggccgc tgggctccac ttccaggacc gacagcctga agacatcccg   1560
caggtcccag atgagatcta cgagctgtat gacgatgtgg aacccagaga tgactccagc   1620
cccagcccca agggcagaga tgaagcgccc tcagttcagc aagccgccag gaggccacca   1680
caagacccag cgctcaggaa ggagaaggat ccccagccac agcagttgcc acccatggac   1740
ccaaagttgc tgaagcagct gaggaaggca gagaaggccg agagggagtt ccggaagaag   1800
ttcaagtttg aaggggagat cgtggttcac acgaagatga tgatcgaccc caacgctaag   1860
acacgtcgcg gggtggcaa gcacctcggg atcggcgcg gggagatcct ggaggtgatc   1920
gagttcacca gcaatgagga gatgctgtgc cgggaccca aaggcaaata tggctacgtg   1980
```

| | |
|---|---|
| cccagaacag cgctcctgcc cctggagacg gaggtgtacg atgatgtcga cttctgcgat | 2040 |
| cccctggaaa accaaccact cccctggga cggtaagacc ggtaggcgtg gggccaggac | 2100 |
| agccagccag cccagcgccc gctcacccag gagccctgga tcccggcgcg ggaaagtcac | 2160 |
| agagctgcct gggcttgtac ctggccacat aaagccccag tttaaagcaa aaaaaaaaa | 2220 |
| aaaaaaaaaa aaaaa | 2235 |

<210> SEQ ID NO 47
<211> LENGTH: 2217
<212> TYPE: DNA
<213> ORGANISM: Homo sapiens

<400> SEQUENCE: 47

| | |
|---|---|
| gccatcaaaa tcacagtgga tgggccccga gaacctcgaa atcgtactga gaagcactcc | 60 |
| acaatgccag actcacctgt ggatgtgaag acgcaatcta ggctgactcc tccaacaatg | 120 |
| ccacctcccc caactactca aggagctcca agaaccagtt catttacacc gacaacgtta | 180 |
| actaatggca cgagccattc tcctacagcc ttgaatggcg ccccctcacc acccaatggc | 240 |
| ttcagcaatg ggccttcctc ttcttcctcc tcctctctgg ctaatcaaca gctgccccca | 300 |
| gcctgtggtg ccaggcaact cagcaagctg aaaaggttcc ttactaccct gcagcagttt | 360 |
| ggcaatgaca tttcacccga dataggagaa agagttcgca ccctcgttct gggactagtg | 420 |
| aactccactt tgacaattga gaatttcat tccaaactgc aagaagctac taacttccca | 480 |
| ctgagacctt ttgtcatccc atttttgaag gccaacttgc ccctgctgca gcgtgagctc | 540 |
| ctccactgcg caagactggc caaacagaac cctgcccagt acctcgccca gcatgaacag | 600 |
| ctgcttctgg atgccagcac cacctcacct gttgactcct cagagctgct tctcgatgtg | 660 |
| aacgaaaacg ggaagaggcg aactccagac agaaccaaag aaaatggctt tgacagagag | 720 |
| cctttgcact cagaacatcc aagcaagcga ccatgcacta ttagcccagg ccagcggtac | 780 |
| agtccaaata cggcttatc ctaccagccc aatggcctgc ctcaccctac cccacctcca | 840 |
| cctcagcatt accgtttgga tgatatggcc attgcccacc actacaggga ctcctatcga | 900 |
| cacccccagcc acaggacct cagggacaga aacagaccta tggggttgca tggcacacgt | 960 |
| caagaagaaa tgattgatca cagactaaca gacagagaat gggcagaaga gtggaaacat | 1020 |
| cttgaccatc tgttaaactg cataatggac atggtagaaa aaacaaggcg atctctcacc | 1080 |
| gtactaaggc ggtgtcaaga agcagaccgg gaagaattga attactggat ccggcggtac | 1140 |
| agtgacgccg aggacttaaa aaaaggtggc ggcagtagca gcagccactc taggcagcag | 1200 |
| agtcccgtca acccagaccc agttgcacta gacgcgcatc gggaattcct tcacaggcct | 1260 |
| gcgtctggat acgtgccaga ggagatctgg aagaaagctg aggaggccgt caatgaggtg | 1320 |
| aagcgccagg cgatgacgga gctgcagaag gccgtgtctg aggcggagcg gaaagcccac | 1380 |
| gacatgatca caacagagag ggccaagatg gagcgcacgg tcgccgaggc caaacggcag | 1440 |
| gcggcggagg acgcactggc agttatcaat cagcaggagg attcaagcga gagttgctgg | 1500 |
| aattgtggcc gtaaagcgag tgaaacctgc agtggctgta acacagcccg atactgtggc | 1560 |
| tcattttgcc agcacaaaga ctgggagaag caccatcaca tctgtggaca gaccctgcag | 1620 |
| gcccagcagc agggagacac acctgcagtc agctcctctg tcacgcccaa cagcggggct | 1680 |
| gggagcccga tggacacacc accagcagcc actccgaggt caaccaccc gggaacccct | 1740 |
| tccaccatag agacaaccc tcgctagacg tgaactcaga actgtcggag gaaagacaac | 1800 |
| acaaccaacg cgaaaccaat tcctcatcct cagatgctca aagttgtttt ttttgtttgt | 1860 |

```
ttgtttatta gatgaattat cctatttcag tacttcagca agagagaacc taactgtatc    1920
ttgaggtggt agtaaaacac agagggccag taacgggtca taatgactta ttgtggataa    1980
caaagatatc ttttctttag agaactgaaa agagagcaga gaatataaca tgaaatgata    2040
gatttgacct cctccctgaa attttcaagt agctgggatt ttaaactaga tgacctcatt    2100
aaccgatgct ttaccaaaca ccaaaccaag agattgctaa ttgctgttga agcaaaaat     2160 gctaatatta aaagtcacaa tgttctttat atacaataat ggaaaaaaaa aaaaaaa       2217

<210> SEQ ID NO 48
<211> LENGTH: 4372
<212> TYPE: DNA
<213> ORGANISM: Homo sapiens

<400> SEQUENCE: 48
acagctggct gcctcacccg caggctgcag ggagaccttc cccagcctgc agccccaggc      60
ccgccccgcg tcacatgagc cccagggctc caccccctc cccagggcag aggacaccca     120
gttggtggcc gggagggcct cggctttcca gggacagagg cccaactcca ggacgcccca    180
gctggcccag cccctcctct ttccctcaag gctgcaggag gtcgggaaag gcagtcctgg    240
tagaggcctg tcctgggctc caggttggcc cctgagggtg gccctcctca tgccggcttc    300
aagactgagg gacagggcag ccagttcagc ctcgggatcc acctgtggct ccatgtccca    360
gacgcaccct gtgctggaga gcggcctcct ggcatctgcc ggctgctccg caccccgggg    420
tcccaggaag ggcggcccag ccccagtgga caggaaagct aaggcctcag cgatgccgga    480
ctccccagcg gaggtgaaga cgcagccccg gtccacaccc ccagcatgc cgcccccacc     540 gcctgccgca tcccagggg ccacacgccc cccctccttc acgccacaca cacatcgaga     600
ggacgggcct gcgacgctgc cccacggccg ttttcatggc tgcttaaaat ggtctatggt    660
ctgtctcttg atgaacggca gcagccactc accaacagcc atcaatggtg caccgtgcac    720
acccaacggc ttcagcaatg gcccggccac ctcgtccaca gcctccttgt ccacacagca    780
cctgccccca gcctgcgggg cccggcagct cagcaagctc aagcgcttcc tcaccacact    840
gcagcagttt ggcagcgaca tctccccaga gattggggag cgcgtgcgca cactggtgct    900
gggcctggtg aactcgacat tgacgatcga ggagtttcat tccaagcttc aggaggccac    960
caacttccct ctgcggccgt ttgtcattcc cttcctgaag gcaaacctgc ccttgctgca   1020
gcgggagctc ctgcactgtg cacgcctggc caagcagacg cccgcccagt acttggccca   1080
gcatgagcag ctcctgctgg acgccagcgc ctcctccccc atcgactcct cagagctgct   1140
actggaagtc aacgagaacg gcaagaggag gacgcccgac aggaccaaag gaacgggtc    1200 agaccgcgac ccgctgcacc ccgagcacct cagcaaacgg ccatgcaccc tgaaccctgc   1260
ccagcgctac agccccagca acgggccacc gcagcccaca ccgccgccgc actaccgcct   1320
ggaggacata gccatggccc accacttccg agatgcctac cgccacccag accccggga    1380 gctacgagag cgccatcggc cgcttgtggt gcctgggtcc cggcaggaag aagtgatcga   1440
ccacaagctc acagagcgtg agtgggcaga agagtggaag cacctcaaca acctcctgaa   1500
ctgcatcatg gacatggtgg agaagacgcg gcgctcgctc acggtgctgc gcaggtgcca   1560
ggaggccgac cgcgaggagc tcaaccactg ggcgcggcgc tacagcgacg ccgaggacac   1620
aaagaagggc cccgctcccg ccgcggcccg gccccgcagc agctccgccg gtcccgaagg   1680
gcctcagcta gacgtgcctc gcgagttcct gccgaggacc ctcaccggct acgtgcctga   1740
```

```
ggacatctgg aggaaggctg aagaggccgt gaatgaggtg aagcggcagg ccatgtcgga   1800
gctgcagaaa gccgtgtcgg acgcggagcg caaagcgcac gagctcatca ccacggagcg   1860
tgccaagatg gagcgggccc tggccgaggc gaagcggcag gcctccgagg acgccctgac   1920
ggtcatcaac cagcaggagg actccagcga gagctgctgg aactgcgggc ggaaagccag   1980
tgagacgtgc agcggctgca acgcggcacg ctactgcggg tccttctgcc agcatcggga   2040
ctgggagaag catcaccacg tgtgtggcca gagcctgcag gccccacag ccgtggtggc   2100 cgacccggtg cctggaccgc cgaagccgc ccacagcctg ggccctccc tgcctgtggg   2160 tgctgccagc cccagcgaag ccggctctgc ggggccttct cgcccggct ccccagccc   2220 acctggccca ctggacaccg tgcccgctg accccactgg ccctggcct gccggacaca   2280 gcaccgtgcc aaccccaccc agctccaggc ccaccggatg ctgtgcctgg cctccgatgc   2340
ctggcctgcc agacactgcg ccccgcctga cctgggggag ccgaccaatt agtcactgct   2400
gctactgccc ctctccgaaa gaagacacag aaccaacaaa accgcattca gtgcacctgc   2460
ctcagctacc taatgattcc gcgcggagac ctcctgacaa cgtctcttca gcatcctca   2520 gaagcctcga ctgagcttta cacagcagag cagatgccgc aggcgcggcg gctctgccca   2580
cctctctttt cctctctgtc tgtctctccc cctctgtctt ctctatcctc tctctctcta   2640
tgactatcac acactttctc ttcaatgaaa aaatcgaatt ggtggcttat attttcagca   2700
aagaattttg gggggttttg tgtgttggca aaagagctac tcagaaatgg acaaagaaaa   2760
cgggggggtt ctcccctcc tgattaaaaa gggagaaaga aaactgcgat tttatagctg   2820
gagatctgaa cccagctgtg cccctccccc aggggcgtga ggctgatcag cgaagacggg   2880
aggaaagatt tcgatttctg actcaagatg cattttggt ttcagattt ttttttcctgt   2940 aatgttaaac tctttggctt taagtaaaa tccaaaaagt tttttaaaaa agcaaagga   3000 agcatacttg tgaactacct tgctagctag ccagccaagg ataccggaca cacctctgct   3060
ccaaaggaaa tccaaaaaag caaacacaag aaatcaaat ccaaaatttg tttgtcactg   3120
ccaaagtatt ttttcactg tttcacttgc tcttgggttt gtttggatgt gggtcttttt   3180
ctcttctgtt ctgattttgt ttgtgggtgt cgggatattt gggtgcagag ggtttgtgcc   3240
cagttagaag cgacttttgt tctcttctgc gtaggcgttg gtgcgtccgc cgcgtgtgcg   3300
tggtccgtgt gccgttgctc cggcctgcgt ctccatatgt gtaggaaagg acacgccgtc   3360
tgtcctcacg cccctgtga cttttcatat ttccgttttc cacttgtgga aaaaaagtgc   3420
taaagttttc ttcccagaga gagcataatt ccgaaacaaa actgtgacaa tcttttgggt   3480
tgattctcga ctgcttttcg agcatgcgga gccagcaggc ctccctgaaa cactgcttct   3540
cggccagccc gtcctcctct acctctctcc tctccgcgcc ctccgacctc tctcggcccc   3600
ctcaccccag ctccgacctc tctcagcccc atcgccccaa ctccaacctc tcggcccat   3660 cgccccaccg cagctactcc cctttcttcc aaacttttgc agaaaaaaca aaaaaactac   3720
aaacaaaagc agccctctgc ctcctcccca gggaagaccc tgaccgtgta catagccctg   3780
gtgctcctgc ccagccaccc ctcagatgcg ttcgcctctg gcctggggt gtgtctcggt   3840 gacgttttct atcagacgtg ctccctccca tcctccagcc ctgccaccc tcctccact   3900 cctctcaact gcctcagcga tttcaagaag gaaataaagg gataaagaaa ttcatgcttg   3960
caccgagtac aaggacagac agcaggcacg gccgcagcc tggcatctgt gcgtgtggcg   4020
tggcccgtgg cttggcatct gtgtgcgtgg tgtggcccgt ggcctggcat ctgtgtgcgt   4080
ggcgtggccc gtgcctggc atctgtgtgt gtggcgtggc ccgtggcctg gcatctgtgc   4140
```

```
gcgtggcgtg gcccgtggcc tggcatctgt gtgcgtggct atcaggagtt ctaggaactc    4200
agtgcaatac gggagtgacc cagctactga accagccacg aacagcccgc cagaggcctg    4260
aagctgagcg tgtacgttaa tgtgaatgta tatagtcttt gcagaggtcc aaatgatatt    4320
catgatggta ataaacgaga tgtttgccaa ataaaaaaca gaaaccgcag ga            4372
```